US010442846B2

(12) United States Patent
Smythe et al.

(10) Patent No.: US 10,442,846 B2
(45) Date of Patent: *Oct. 15, 2019

(54) HEPCIDIN ANALOGUES AND USES THEREOF

(71) Applicant: Protagonist Therapeutics, Inc., Newark, CA (US)

(72) Inventors: Mark Leslie Smythe, Bardon (AU); Gregory Thomas Bourne, Brisbane (AU); Simone Vink, Taringa (AU); Brian Troy Frederick, Ben Lomand, CA (US); Praveen Madala, Brisbane (AU); Anne Pernille Tofteng Shelton, Valby (DK); Jacob Ulrik Fog, Bagsvaerd (DK)

(73) Assignee: Protagonist Therapeutics, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/037,982

(22) Filed: Jul. 17, 2018

(65) Prior Publication Data

US 2019/0185535 A1 Jun. 20, 2019

Related U.S. Application Data

(63) Continuation of application No. 15/828,214, filed on Nov. 30, 2017, now Pat. No. 10,030,061, which is a continuation of application No. 15/720,333, filed on Sep. 29, 2017, now abandoned, which is a continuation of application No. 14/775,469, filed as application No. PCT/US2014/030352 on Mar. 17, 2014, now Pat. No. 9,822,157.

(60) Provisional application No. 61/800,048, filed on Mar. 15, 2013, provisional application No. 61/800,284, filed on Mar. 15, 2013.

(51) Int. Cl.
| | | |
|---|---|---|
| *A61K 38/10* | (2006.01) | |
| *A61K 38/08* | (2019.01) | |
| *A61K 38/04* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *C07K 14/575* | (2006.01) | |
| *A61K 38/00* | (2006.01) | |

(52) U.S. Cl.
CPC ............ *C07K 14/575* (2013.01); *A61K 38/00* (2013.01)

(58) Field of Classification Search
None
See application file for complete search history.

(56) References Cited

U.S. PATENT DOCUMENTS

| | | |
|---|---|---|
| 4,684,620 A | 8/1987 | Hruby et al. |
| 4,724,229 A | 2/1988 | Ali |
| 5,192,746 A | 3/1993 | Lobl et al. |
| 5,990,084 A | 11/1999 | Richter et al. |
| 6,087,334 A | 7/2000 | Beeley et al. |
| 6,235,711 B1 | 5/2001 | Dutta |
| 6,818,617 B1 | 11/2004 | Niewiarowski |
| 7,534,764 B2 | 5/2009 | Ganz et al. |
| 8,313,950 B2 | 11/2012 | Rovin et al. |
| 8,435,941 B2 | 5/2013 | Ganz et al. |
| 8,536,140 B2 | 9/2013 | Clandinin et al. |
| 8,568,706 B2 | 10/2013 | Grabstein et al. |
| 8,796,418 B2 | 8/2014 | Walensky et al. |
| 8,946,150 B2 | 2/2015 | Gallagher et al. |
| 8,999,935 B2 | 4/2015 | Huang |
| 9,169,292 B2 | 10/2015 | Gallagher et al. |
| 9,273,093 B2 | 3/2016 | Bhandari et al. |
| 9,518,091 B2 | 12/2016 | Bhandari et al. |
| 9,624,268 B2 | 4/2017 | Bourne et al. |
| 9,714,270 B2 | 7/2017 | Bhandari et al. |
| 9,809,623 B2 | 11/2017 | Bhandari et al. |
| 9,822,157 B2 | 11/2017 | Smythe et al. |
| 10,023,614 B2 | 7/2018 | Bhandari et al. |
| 10,030,061 B2 | 7/2018 | Smythe et al. |
| 10,035,824 B2 | 7/2018 | Bhandari et al. |
| 10,059,744 B2 | 8/2018 | Bhandari et al. |
| 10,196,424 B2 | 2/2019 | Bourne et al. |
| 10,301,371 B2 | 5/2019 | Bhandari et al. |
| 2003/0166138 A1 | 9/2003 | Kinsella et al. |
| 2003/0166514 A1 | 9/2003 | Jones et al. |

(Continued)

FOREIGN PATENT DOCUMENTS

| | | |
|---|---|---|
| DE | 10107707 A1 | 8/2002 |
| JP | 2011-231085 A | 11/2011 |

(Continued)

OTHER PUBLICATIONS

Li et al., "Cyclization strategies in peptide derived drug design," Curr. Topics Med. Chem. 2:325-341 (2002) (Year: 2002).*

(Continued)

*Primary Examiner* — Julie Ha
*Assistant Examiner* — Kristina M Hellman
(74) *Attorney, Agent, or Firm* — Cooley LLP

(57) ABSTRACT

The present invention relates, inter alia, to certain hepcidin peptide analogs, including peptides and dimers thereof, and to the use of the peptides and peptide dimers in the treatment and/or prevention of a variety of diseases, conditions or disorders, including treatment and/or prevention of iron overload diseases, which include hereditary hemochromatosis and iron-loading anemias, and other conditions and disorders described herein.

19 Claims, 7 Drawing Sheets

Specification includes a Sequence Listing.

(56) References Cited

U.S. PATENT DOCUMENTS

| | | | |
|---|---|---|---|
| 2004/0052785 A1 | 3/2004 | Goodman et al. | |
| 2004/0176293 A1 | 9/2004 | Peterson et al. | |
| 2006/0183884 A1 | 8/2006 | Blaschuk et al. | |
| 2007/0032417 A1 | 2/2007 | Baell | |
| 2007/0166308 A1 | 7/2007 | Pullen et al. | |
| 2007/0197430 A1 | 8/2007 | Baell et al. | |
| 2008/0019913 A1 | 1/2008 | Polt et al. | |
| 2008/0213277 A1* | 9/2008 | Sasu | A61K 39/3955 424/141.1 |
| 2008/0260820 A1 | 10/2008 | Borrelly et al. | |
| 2008/0300180 A1 | 12/2008 | Schambye et al. | |
| 2009/0053819 A1 | 2/2009 | Seymour et al. | |
| 2009/0257952 A1 | 10/2009 | Cochran et al. | |
| 2010/0151487 A1 | 6/2010 | Rovin et al. | |
| 2010/0190710 A1 | 7/2010 | Chemtob et al. | |
| 2010/0196441 A1 | 8/2010 | Sondermeijer et al. | |
| 2010/0272731 A1 | 10/2010 | Presta et al. | |
| 2010/0280098 A1 | 11/2010 | Juliano et al. | |
| 2011/0059087 A1 | 3/2011 | Lewis et al. | |
| 2011/0086024 A1 | 4/2011 | Arthos et al. | |
| 2011/0118186 A1 | 5/2011 | Schteingart et al. | |
| 2011/0282029 A1 | 11/2011 | Holmes et al. | |
| 2012/0021975 A1 | 1/2012 | Hoffman et al. | |
| 2012/0071422 A1 | 3/2012 | Gallagher et al. | |
| 2012/0115930 A1 | 5/2012 | Monia et al. | |
| 2013/0029907 A1 | 1/2013 | Gallagher et al. | |
| 2013/0172272 A1 | 7/2013 | Gallagher et al. | |
| 2013/0183755 A1 | 7/2013 | Gallagher et al. | |
| 2013/0310303 A1 | 11/2013 | Eldar-Finkelman et al. | |
| 2014/0005128 A1 | 1/2014 | Mo et al. | |
| 2014/0193465 A1 | 7/2014 | Bhandari et al. | |
| 2014/0286953 A1 | 9/2014 | Sasu et al. | |
| 2014/0294901 A1 | 10/2014 | Bhandari et al. | |
| 2014/0294902 A1 | 10/2014 | Bhandari et al. | |
| 2014/0336110 A1 | 11/2014 | Ganz et al. | |
| 2015/0056301 A1 | 2/2015 | Kawabe et al. | |
| 2015/0157692 A1 | 6/2015 | Fu | |
| 2015/0203555 A1 | 7/2015 | Gellman et al. | |
| 2015/0284429 A1 | 10/2015 | Merutka | |
| 2016/0031944 A1 | 2/2016 | Bhandari et al. | |
| 2016/0039878 A1 | 2/2016 | Gallagher et al. | |
| 2016/0145306 A1 | 5/2016 | Bourne et al. | |
| 2016/0152664 A1 | 6/2016 | Bhandari et al. | |
| 2016/0159862 A1 | 6/2016 | Bhandari et al. | |
| 2016/0222076 A1 | 8/2016 | Smythe et al. | |
| 2016/0368966 A1 | 12/2016 | Bhandari et al. | |
| 2017/0313754 A1 | 11/2017 | Bourne et al. | |
| 2017/0327541 A1 | 11/2017 | Bhandari et al. | |
| 2018/0022778 A1 | 1/2018 | Bourne et al. | |
| 2018/0079782 A1 | 3/2018 | Bhandari et al. | |
| 2018/0079783 A1 | 3/2018 | Bhandari et al. | |
| 2018/0099995 A1 | 4/2018 | Bhandari et al. | |
| 2018/0100004 A1 | 4/2018 | Smythe et al. | |
| 2018/0105572 A1 | 4/2018 | Bhandari et al. | |
| 2018/0148477 A1 | 5/2018 | Bhandari et al. | |
| 2019/0002500 A1 | 1/2019 | Bhandari et al. | |
| 2019/0002503 A1 | 1/2019 | Bourne et al. | |
| 2019/0016756 A1 | 1/2019 | Bhandari et al. | |
| 2019/0076400 A1 | 3/2019 | Anandan et al. | |
| 2019/0185536 A1 | 6/2019 | Smythe et al. | |

FOREIGN PATENT DOCUMENTS

| | | |
|---|---|---|
| WO | WO 1992/017492 A1 | 10/1992 |
| WO | WO 1997/025351 A2 | 7/1997 |
| WO | WO 1998/008871 A1 | 3/1998 |
| WO | WO 2000/055184 A1 | 3/1998 |
| WO | WO 1999/002194 A1 | 1/1999 |
| WO | WO 1999/026615 A1 | 6/1999 |
| WO | WO 2000/006243 A2 | 2/2000 |
| WO | WO 2000/009560 A1 | 2/2000 |
| WO | WO 2000/018789 A1 | 4/2000 |
| WO | WO 2000/018790 A1 | 4/2000 |
| WO | WO 2000/023474 A1 | 4/2000 |
| WO | WO 2000/055119 A1 | 9/2000 |
| WO | WO 2000/061580 A1 | 10/2000 |
| WO | WO 2001/068586 A2 | 9/2001 |
| WO | WO 2003/066678 A1 | 8/2003 |
| WO | WO 2004/011650 A2 | 2/2004 |
| WO | WO 2004/092405 A2 | 10/2004 |
| WO | WO 2006/032104 A1 | 3/2006 |
| WO | WO 2007/138291 A2 | 12/2007 |
| WO | WO 2008/097461 A2 | 8/2008 |
| WO | WO 2008/134659 A2 | 11/2008 |
| WO | WO 2008/140602 A2 | 11/2008 |
| WO | WO 2009/002947 A2 | 12/2008 |
| WO | WO 2009/027752 A2 | 3/2009 |
| WO | WO 2010/065815 A2 | 6/2010 |
| WO | WO 2010/116752 A1 | 10/2010 |
| WO | WO 2010/124874 A1 | 11/2010 |
| WO | WO 2011/091357 A1 | 7/2011 |
| WO | WO 2011/149942 A2 | 12/2011 |
| WO | WO 2012/052205 A1 | 4/2012 |
| WO | WO 2013/086143 A1 | 6/2013 |
| WO | WO 2014/059213 A1 | 4/2014 |
| WO | WO 2014/127316 A2 | 8/2014 |
| WO | WO 2014/145561 A2 | 9/2014 |
| WO | WO 2014/165448 A1 | 10/2014 |
| WO | WO 2014/165449 A1 | 10/2014 |
| WO | WO 2015/157283 A9 | 10/2015 |
| WO | WO 2015/176035 A1 | 11/2015 |
| WO | WO 2015/200916 A2 | 12/2015 |
| WO | WO 2016/011208 A1 | 1/2016 |
| WO | WO 2016/054411 A1 | 4/2016 |
| WO | WO 2016/054445 A1 | 4/2016 |
| WO | WO 2016/109363 A1 | 7/2016 |
| WO | WO 2017/011820 A2 | 1/2017 |
| WO | WO 2017/117411 A1 | 7/2017 |
| WO | WO 2018/022937 A1 | 2/2018 |
| WO | WO 2018/136646 A1 | 7/2018 |

OTHER PUBLICATIONS

U.S. Appl. No. 15/486,684, filed Apr. 13, 2017, Bhandari et al.
U.S. Appl. No. 15/493,471, filed Apr. 21, 2017, Bhandari et al.
U.S. Appl. No. 15/831,099, filed Dec. 4, 2017, Bhandari et al.
U.S. Appl. No. 15/831,120, filed Dec. 4, 2017, Bhandari et al.
U.S. Appl. No. 15/745,371, filed Jan. 16, 2018, Bhandari et al.
U.S. Appl. No. 16/035,060, filed Jul. 13, 2018, Bhandari et al.
U.S. Appl. No. 16/113,072, filed Aug. 27, 2018, Bhandari et al.
U.S. Appl. No. 16/128,352, filed Sep. 11, 2018, Anandan et al.
U.S. Appl. No. 16/217,864, filed Dec. 12, 2018, Bourne et al.
U.S. Appl. No. 16/282,908, filed Feb. 22, 2019, Bhandari et al.
U.S. Appl. No. 16/282,920, filed Feb. 22, 2019, Bhandari et al.
U.S. Appl. No. 16/319,958, filed Jan. 23, 2019, Bhandari.
Adams and Macmillan, "Investigation of peptide thioester formation via N→Se acyl transfer." Journal of Peptide Science (2013); 19 (2): 65-73.
Ashby, et al., "Plasma hepcidin levels are elevated but responsive to erythropoietin therapy in renal disease." Kidney International (2009); 75 (9): 976-981.
Boer, J., et al., "Design and Synthesis of Potent and Selective $\alpha_4\beta_7$ Integrin Antagonists." J. Med. Chem. (2001); 44 (16): 2586-2592.
Bowie, et al., " Deciphering the Message in Protein Sequences: Tolerance to Amino Acid Substitutions." Science (1990); 247: 1306-1310.
Chatterjee, J. et al., "N-Methylation of Peptides: a New Perspective in Medicinal Chemistry", Accounts of Chemical Research, 41(10): 1331-1342 (2008).
Clark, Richard J., et al. "Design, synthesis, and characterization of cyclic analogues of the iron regulatory peptide hormone hepcidin." Peptide Science (2013); 100.5: 519-526.
Database EPO Proteins [Online] Dec. 3, 2010 (Dec. 3, 2010), "Sequence from Patent WO2010124874." XP002761649, retrieved from EBI accession No. EPOP:HI656765 Database accession No. HI656765, 1 page.
Database USPTO Proteins [Online] Dec. 17, 2012 (Dec. 17, 2012), "Sequence from U.S. Pat. No. 8,313,950.", XP002761650, retrieved from EBI accession No. USPOP:AGA36544 Database accession No. AGA36544, 1 page.

(56) References Cited

OTHER PUBLICATIONS

De Mast, et al., "Increased serum hepcidin and alterations in blood iron parameters associated with asymptomatic P. falciparum and P. vivax malaria." Haematologica (2010); 95 (7): 1068-1074.
Definition of Isostere, Medical Definition and More from Merriam-Webster Dictionary, 3 pages, www.merriam-webster.com/medical/isostere accessed on Feb. 5, 2015.
Desbenoit, N., et al. "Reversible metalation of a bis-disulfide analogue of the Cys*-X-Cys* hepcidin binding site: structural characterisation of the related copper complex]." Annales Pharmaceutiques Francaises (2010); 68(6): 388-396. (with English summary).
Dolain, Christel, et al. "Inducing α-Helices in Short Oligopeptides through Binding by an Artificial Hydrophobic Cavity." Journal of the American Chemical Society (2010); 132.16: 5564-5565.
Dubree, Nathan J.P. et al., "Selective α4 β7 Integrin Antagonists and Their Potential as Antiinflammatory Agents", J. Med. Chem., 45: 3451-3457 (2002).
Dutta, Anand S., "Potent Cyclic Monomeric and Dimeric Peptide Inhibitors of VLA-4 (a4b1 Integrin)—Mediated Cell Adhesion Based on the Ile-Leu-Asp-Val Tetrapeptide", J. Peptide Sci. (2000); 6: 321-341.
European Application No. 13845982.1, Extended European Search Report dated May 13, 2016.
European Application No. 14763104.8, Extended European Search Report dated Sep. 23, 2016, 10 pages.
European Application No. 14779463.0, Extended European Search Report dated Nov. 9, 2016, 9 pages.
European Application No. 14780207.8, Extended European Search Report dated Feb. 17, 2017, 9 pages.
European Application No. 14780207.8, Partial Supplementary European Search Report dated Nov. 16, 2016, 6 pages.
European Application No. 15792950.6, Extended European Search Report dated May 2, 2018, 10 pages.
European Application No. 15812513.8, Extended European Search Report dated Apr. 12, 2018, 11 pages.
European Application No. 15821351.2, Extended European Search Report dated Jan. 3, 2018, 6 pages.
European Application No. 15846131.9, Extended European Search Report dated Jan. 25, 2018, 8 pages.
European Application No. 15846983.3, Extended European Search Report dated Jun. 19, 2018, 10 pages.
European Application No. 15846983.3, Partial European Search Report dated Mar. 2, 2018, 11 pages.
European Application No. 16825301.1, Extended European Search Report dated Jan. 21, 2019, 6 pages.
Ganz and Nemeth, "Hepcidin and iron homeostasis." Biochimica et Biophysica Acta (BBA)—Molecular Cell Research (Sep. 2012); 1823 (9): 1434-1443.
Gee et al. "Cyclic Peptides as Non-carboxyl-terminal Ligands of Syntrophin PDZ Domains," The Journal of Biological Chemistry, 273(34): 21980-21987 (1998).
Girelli, Domenico, et al. "Hepcidin in the diagnosis of iron disorders." Blood (2016); 127.23: 2809-2813.
Haanstra, et al., "Antagonizing the a4B1 Integrin, but no a4B7, Inhibits Leukocytic Infiltration of the Central Nervous System in Rhesus Monkey Experimental Autoimmune Encephalomyelitis", Journal of Immunology, 90(5): 1961-1973 (2013).
Ilyin, Gennady, et al. "Comparative analysis of mouse hepcidin 1 and 2 genes: evidence for different patterns of expression and co-inducibility during iron overload 1." FEBS Letters (2003); 542.1-3 : 22-26.
Jackson, D.Y., "Alpha 4 integrin antagonists." Current Pharmaceutical Design (8)14: 1229-1253 (2002).
Janssen et al., "Comparison of a Monomeric and Dimeric Radiolabeled RGD-Peptide for Tumor Targeting", Cancer Biotherapy and Radiopharmaceuticals, 17(6): 641-646 (2002).
Jordan, John B., et al. "Hepcidin revisited, disulfide connectivity, dynamics, and structure." Journal of Biological Chemistry (2009); 284.36: 24155-24167.

Kelleman, A. et al., "Incorporation of thioether building blocks into an $α_vβ_3$-specific RGD peptide: Synthesis and biological activity", Biopolymers (Peptide Science), 71(6): 686-695 (2003).
Kitazume and Yamazaki, Experimental Methods in Organic Fluorine Chemistry, Gordon and Breach Science Publishers, 1998, page 9, 3 pages.
Kluskens, L.D. et al., "Angiotensin-(1-7) with Thioether Bridge: An Angiotensin-Converting Enzyme-Resistant, Potent Angiotensin-(1-7) Analog", The Journal of Pharmacology and Experimental Therapeutics, 328(3): 849-855 (2009).
Knudsen, Lotte B., et al. "Potent derivatives of glucagon-like peptide-1 with pharmacokinetic properties suitable for once daily administration." Journal of Medicinal Chemistry (2000); 43.9: 1664-1669.
Krause, Alexander, et al. "LEAP-1, a novel highly disulfide-bonded human peptide, exhibits antimicrobial activity." FEBS Letters (2000); 480.2-3 : 147-150.
Ley, Klaus, et al. "Integrin-based therapeutics: biological basis, clinical use and new drugs." Nature Reviews Drug Discovery (2016); 15.3: 173-183.
Li and Roller, "Cyclization Strategies in Peptide Derived Drug Design." Curr. Topics Med. Chem. (2002); 2: 325-341.
Liu, Shuang, "Radiolabeled Cyclic RGD Peptides as Integrin $α_vβ_3$-Targeted Radiotracers: Maximizing Binding Affinity via Bivalency." Bioconjugate Chem. (2009); 20 (12): 2199-2213.
Liu, Shuang, "Radiolabeled Multimeric Cyclic RGD Peptides as Integrin avB3 Targeted Radiotracers for Tumor Imaging", School of Health Science, Purdue University, Molecular Pharmaceuticals, 3(5): 472-487 (2006).
Madsen, Kjeld, et al. "Structure—activity and protraction relationship of long-acting glucagon-like peptide-1 derivatives: importance of fatty acid length, polarity, and bulkiness." Journal of Medicinal Chemistry (2007); 50.24: 6126-6132.
Methods in Molecular Biology, vol. 35 Peptide Synthesis Protocols, Edited by M.W Pennington and B. M. Dunn Copyright, 1994 Humana Press Inc, Totowa, NJ, pp. 201-241.
Muñoz, Manuel, et al. "Disorders of iron metabolism. Part II: iron deficiency and iron overload." Journal of Clinical Pathology (2011); 64.4: 287-296.
Nemeth, Elizabeta, et al. "The N-terminus of hepcidin is essential for its interaction with ferroportin: structure-function study." Blood (2006); 107.1: 328-333.
Park, C.H., et al., "Hepcidin, a urinary antimicrobial peptide synthesized in the liver." J Biol Chem. (2001); 276(11): 7806-7810. Epub Dec. 11, 2000.
Parrow, et al., "Prospects for a hepcidin mimic to treat β-thalassemia and hemochromatosis." Expert Review of Hematology (2011); 4 (3): 233-235.
PCT/US2013/064439, International Preliminary Report on Patentability, dated Apr. 14, 2015, 8 pages.
PCT/US2013/064439, International Search Report and Written Opinion, dated Jan. 24, 2014, 15 pages.
PCT/US2014/030352, Invitation to Pay Additional Fees, dated Sep. 10, 2014, 2 pages.
PCT/US2014/030352, International Preliminary Report on Patentability, dated Sep. 15, 2015, 7 pages.
PCT/US2014/030352, International Search Report and Written Opinion, dated Nov. 28, 2014, 12 pages.
PCT/US2014/032391, International Preliminary Report on Patentability, dated Oct. 6, 2015, 8 pages.
PCT/US2014/032391, International Search Report, dated Aug. 7, 2014, 5 pages.
PCT/US2014/032391, Written Opinion, dated Aug. 7, 2014, 7 pages.
PCT/US2014/032392, International Preliminary Report on Patentability, dated Oct. 6, 2015, 10 pages.
PCT/US2014/032392, International Search Report and Written Opinion, dated Sep. 15, 2014, 15 pages.
PCT/US2015/031243, International Preliminary Report on Patentability, dated Nov. 22, 2016, 8 pages.
PCT/US2015/031243, International Search Report and Written Opinion, dated Aug. 5, 2015, 14 pages.

(56) References Cited

OTHER PUBLICATIONS

PCT/US2015/038370, International Preliminary Report on Patentability, dated Dec. 27, 2016, 4 pages.
PCT/US2015/038370, International Search Report and Written Opinion, dated Sep. 14, 2015, 5 pages.
PCT/US2015/040658, International Preliminary Report on Patentability, dated Jan. 17, 2017, 5 pages.
PCT/US2015/040658, International Search Report and Written Opinion, dated Oct. 28, 2015, 12 pages.
PCT/US2015/053558, Invitation to Pay Additional Fees, dated Dec. 16, 2015, 3 pages.
PCT/US2015/053558, International Preliminary Report on Patentability, dated Apr. 4, 2017, 9 pages.
PCT/US2015/053558, International Search Report and Written Opinion, dated Feb. 19, 2016, 16 pages.
PCT/US2015/053603, Invitation to Pay Additional Fees, dated Dec. 10, 2015, 3 pages.
PCT/US2015/053603, International Preliminary Report on Patentability, dated Apr. 4, 2017, 8 pages.
PCT/US2015/053603, International Search Report and Written Opinion, dated Feb. 12, 2016, 13 pages.
PCT/US2016/042680, (2nd) International Search Report and Written Opinion, dated Apr. 17, 2017, 13 pages.
PCT/US2016/042680, International Search Report and Written Opinion, dated Jan. 13, 2017, 12 pages.
PCT/US2016/069255, Invitation to Pay Additional Fees, dated Mar. 30, 2017, 2 pages.
PCT/US2016/069255, International Search Report and Written Opinion dated Jun. 1, 2017, 11 pages.
PCT/US2017/044249, International Preliminary Report on Patentability, dated Jan. 29, 2019, 9 pages.
PCT/US2017/044249, Invitation to Pay Additional Fees, dated Sep. 14, 2017, 3 pages.
PCT/US2017/044249, International Search Report and Written Opinion, dated Nov. 21, 2017, 14 pages.
PCT/US2018/014257, International Search Report and Written Opinion, dated May 14, 2018, 13 pages.
PCT/US2018/014257, Invitation to Pay Additional Fees, dated Mar. 22, 2018, 2 pages.
PCT/US2018/050480, Invitation to Pay Additional Fees, dated Nov. 6, 2018, 3 pages.
PCT/US2018/050480, International Search Report and Written Opinion, dated Jan. 29, 2019, 13 pages.
Pelton, J.T. et al., "Somatostatin Analogs with Affinity for Opiate Receptors in Rat Brain Binding Assay", Peptides, 6(Suppl 1): 159-163 (1985).
Preza, G., et al., "Minihepcidins are rationally designed small peptides that mimic hepcidin activity in mice and may be useful for the treatment of iron overload", J Clin Invest (2011); 121(12): 4880-4888.
Ramos, E., et al., "Minihepcidins prevent iron overload in a hepcidin-deficient mouse model of severe hemochromatosis." Blood (Nov. 2012); 120(18): 3829-3836. Epub Sep. 18, 2012.
Rivera, Seth, et al. "Synthetic hepcidin causes rapid dose-dependent hypoferremia and is concentrated in ferroportin-containing organs." Blood (2005); 106.6: 2196-2199.
Sasaki, et al., "D-Arg2-dermorphin tetrapeptide analogs: a potent and long-lasting analgesic activity after subcutaneous administration." Biochem Biophys Res Commun. (1984); 120 (1): 214-218.
Search Report and Written Opinion in Singaporean Application No. 11201609614Q, dated Mar. 12, 2018, 9 pages.
Search Report and Written Opinion in Singaporean Application No. 11201610799W, dated May 31, 2018, 4 pages.
Search Report and Written Opinion in Singaporean Application No. 11201700327W, dated Mar. 16, 2018, 10 pages.
Shahidi, Neal, et al. "Vedolizumab for the treatment of ulcerative colitis." Expert Opinion on Biological Therapy (2016); 16.1 : 129-135.
SID 24885660, National Center for Biotechnology Information, PubChem Substance Database; SID=24885660, 5 pages. https://pubchem.ncbi.nlm.nih.gov/substance/24885660, available date: Jul. 16, 2007, accessed Jul. 21, 2016.
Soler-Ferran and Briskin, "Integrin $\alpha_4\beta_7$ Antagonists: Activities, Mechanisms of Action and Therapeutic Prospects", Current Immunology Reviews (2012), 8(2): 118-134.
Tandara, Leida, and Salamunic, Ilza . "Iron metabolism: current facts and future directions." Biochemia Medica (2012); 22.3: 311-328.
Temming, K. et al. "Rational Design of RGD-Albumin Conjugates for targeted Delivery of the VEGF-R Kinase Inhibitor PTK787 to Angiogenic Endothelium", ChemMedChem, 1: pp. 1200-1203 (2006).
Thermo Electron Corporation, Technical Information, "N-terminal and C-terminal Amidation of Peptides", 2 pages (2004).
Thumshirn, G. et al., "Multimeric Cyclic RGD Peptides as Potential Tools for Tumor Targeting: Solid Phase Peptide Synthesis and Chemoselective Oxime Ligation", Chem. Eur. J., 9: 2717-2725 (2003).
U.S. Appl. No. 14/050,349, Final Office Action dated Sep. 9, 2015, 17 pages.
U.S. Appl. No. 14/050,349, Non-Final Office Action dated Feb. 27, 2015, 14 pages.
U.S. Appl. No. 14/050,349, Notice of Allowance dated Jan. 12, 2016, 9 pages.
U.S. Appl. No. 14/229,784, Non-Final Office Action dated Aug. 13, 2015, 16 pages.
U.S. Appl. No. 14/229,784, Office Action dated Mar. 8, 2016, 6 pages.
U.S. Appl. No. 14/229,799, Non-Final Office Action dated Jul. 24, 2015, 19 pages.
U.S. Appl. No. 14/229,799, Office Action dated Mar. 4, 2016, 18 pages.
U.S. Appl. No. 14/714,198, Notice of Allowance dated Mar. 17, 2017, 3 pages.
U.S. Appl. No. 14/714,198, Office Action dated Nov. 7, 2016, 6 pages.
U.S. Appl. No. 14/775,469, Notice of Allowance dated Aug. 10, 2017, 11 pages.
U.S. Appl. No. 14/775,469, Notice of Allowance dated Sep. 5, 2017, 9 pages.
U.S. Appl. No. 14/775,469, Office Action dated Apr. 11, 2017, 22 pages.
U.S. Appl. No. 14/800,627, Notice of Allowance dated Feb. 15, 2017, 9 pages.
U.S. Appl. No. 14/800,627, Office Action dated Aug. 25, 2016, 11 pages.
U.S. Appl. No. 14/872,975, Notice of Allowance dated Aug. 16, 2017, 9 pages.
U.S. Appl. No. 14/872,975, Office Action dated Dec. 27, 2016, 14 pages.
U.S. Appl. No. 15/046,325, Office Action dated Aug. 1, 2016, 13 pages.
U.S. Appl. No. 15/442,229, Notice of Allowance dated Sep. 12, 2018, 9 pages.
U.S. Appl. No. 15/442,229, Office Action dated Apr. 20, 2018, 12 pages.
U.S. Appl. No. 15/614,047, Notice of Allowance dated Jun. 7, 2018, 8 pages.
U.S. Appl. No. 15/720,333, Office Action dated Aug. 28, 2018, 24 pages.
U.S. Appl. No. 15/828,214, Notice of Allowance dated Jun. 11, 2018, 9 pages.
U.S. Appl. No. 15/828,214, Office Action dated May 15, 2018, 12 pages.
U.S. Appl. No. 15/831,087, Notice of Allowance dated May 11, 2018, 8 pages.
U.S. Appl. No. 15/831,087, Office Action dated Apr. 12, 2018, 10 pages.
U.S. Appl. No. 15/831,100, Notice of Allowance dated May 8, 2018, 8 pages.
U.S. Appl. No. 15/831,100, Office Action dated Apr. 12, 2018, 11 pages.
U.S. Appl. No. 15/514,983, Office Action dated Nov. 2, 2018, 8 pages.

(56) References Cited

OTHER PUBLICATIONS

U.S. Appl. No. 15/836,648, Office Action dated Nov. 6, 2018, 7 pages.
U.S. Appl. No. 16/128,352, Notice of Allowance dated Feb. 6, 2019, 5 pages.
U.S. Appl. No. 16/128,352, Notice of Allowability dated Feb. 21, 2019, 2 pages.
Waitemata District Health Board, "Crushing Guide for Oral Medication in Residential Aged Care", 2 pages (2011).
Xie, Youmei et al., "Nerve Growth Factor (NGF) Loop 4 Dimeric Mimetics Activate ERK and AKT and Promote NGF-like Neurotrophic Effects", The Journal of Biological Chemistry, 275(38): 29868-29874 (2000).
Yu and Gallagher, "A Naturally Occurring, Soluble Antagonist of Human IL-23 Inhibits the Development and in Vitro Function of Human Th17 Cells", The Journal of Immunology, 185: 7302-7308 (2010).
Clark, et al., "Understanding the Structure/Activity Relationships of the Iron Regulatory Peptide Hepcidin." Chem Biol. (Mar. 2011); 18(3): 336-343.
PCT/US2019/017192, International Search Report and Written Opinion, dated Jun. 11, 2019, 13 pages.
Legge and Morieson, "On the prediction of partition coefficients and $R_F$ values of peptides." Aust. J. Biol. Sci. (1964); 17: 561-571.
Pattarawarapan, "Selective Formation of Homo- and Heterobivalent Peptidomimetics." J. Med. Chem. (Aug. 2003); 46 (17): 3565-3567.
PCT/US2019/017192, Invitation to Pay Additional Fees, dated Apr. 16, 2019, 2 pages.
U.S. Appl. No. 15/467,810, Notice of Allowability dated Mar. 13, 2019, 8 pages.
U.S. Appl. No. 15/698,407, Office Action dated Apr. 25, 2019, 15 pages.
U.S. Appl. No. 15/514,983, Notice of Allowance dated Jan. 7, 2019, 6 pages.
U.S. Appl. No. 16/289,451, Office Action dated Mar. 21, 2019, 21 pages.
U.S. Appl. No. 16/039,813, Office Action dated Apr. 19, 2019, 11 pages.

\* cited by examiner

HEPCIDIN ANALOGUES AND USES THEREOF

CROSS REFERENCE TO RELATED APPLICATIONS

This application is a Continuation of U.S. application Ser. No. 15/828,214, filed Nov. 30, 2017; which is a Continuation of U.S. application Ser. No. 15/720,333, filed Sep. 29, 2017; which is a Continuation of U.S. application Ser. No. 14/775,469, filed Sep. 11, 2015, now U.S. Pat. No. 9,822,157; which is a U.S. National Phase application of International Patent Application No. PCT/US2014/030352, filed Mar. 17, 2014; which claims the benefit under 35 U.S.C. § 119(e) of U.S. Provisional Application No. 61/800,048, filed on Mar. 15, 2013, and U.S. Provisional Application No. 61/800,284, filed on Mar. 15, 2013, each of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is PRTH_001_04US_ST25.txt. The text file is 128 KB, was created on Jul. 16, 2018, and is being submitted electronically via EFS-Web.

FIELD OF THE INVENTION

The present invention relates, inter alia, to certain hepcidin peptide analogues, including peptides and dimers thereof, as well as compositions comprising the peptides and peptide dimers, and to the use of the peptides and peptide dimers in the treatment and/or prevention of a variety of diseases, conditions or disorders, including treatment and/or prevention of iron overload diseases including hereditary hemochromatosis, iron-loading anemias, and other conditions and disorders described herein.

BACKGROUND

Hepcidin (also referred to as LEAP-1), a peptide hormone produced by the liver, is a regulator of iron homeostasis in humans and other mammals. Hepcidin acts by binding to its receptor, the iron export channel ferroportin, causing its internalization and degradation. Human hepcidin is a 25-amino acid peptide (Hep25). See Krause et al. (2000) FEBS Lett 480:147-150, and Park et al. (2001) J Biol Chem 276:7806-7810. The structure of the bioactive 25-amino acid form of hepcidin is a simple hairpin with 8 cysteines that form 4 disulfide bonds as described by Jordan et al. J Biol Chem 284:24155-67. The N terminal region is required for iron-regulatory function, and deletion of 5 N-terminal amino acid residues results in a loss of iron-regulatory function. See Nemeth et al. (2006) Blood 107:328-33.

Abnormal hepcidin activity is associated with iron overload diseases, including hereditary hemochromatosis (HH) and iron-loading anemias. Hereditary hemochromatosis is a genetic iron overload disease that is mainly caused by hepcidin deficiency, or in some cases by hepcidin resistance. This allows excessive absorption of iron from the diet and development of iron overload. Clinical manifestations of HH may include liver disease (e.g., hepatic cirrhosis and hepatocellular carcinoma), diabetes, and heart failure. Currently, the only treatment for HH is regular phlebotomy, which is very burdensome for the patients. Iron-loading anemias are hereditary anemias with ineffective erythropoiesis such as β-thalassemia, which are accompanied by severe iron overload. Complications from iron overload are the main cause of morbidity and mortality for these patients. Hepcidin deficiency is the main cause of iron overload in non-transfused patients, and contributes to iron overload in transfused patients. The current treatment for iron overload in these patients is iron chelation which is very burdensome, sometimes ineffective, and accompanied by frequent side effects.

Hepcidin has a number of limitations which restrict its use as a drug, including a difficult synthesis process due in part to aggregation and precipitation of the protein during folding, which in turn leads to high cost of goods. What are needed in the art are compounds having hepcidin activity and also possessing other beneficial physical properties such as improved solubility, stability, and/or potency, so that hepcidin-like biologics might be produced affordably, and used to treat hepcidin-related diseases and disorders such as, e.g., those described herein.

The present invention addresses such needs, providing novel peptide analogues, and dimers thereof, having hepcidin activity and also having other beneficial properties making the peptides of the present invention suitable alternatives to hepcidin.

BRIEF SUMMARY OF THE INVENTION

The present invention generally relates to peptides exhibiting hepcidin activity and methods of using the same.

In some embodiments, the invention provides peptides, which may be isolated and/or purified, comprising, consisting essentially of, or consisting of, the following structural formula I:

$$R^1\text{-}X\text{-}Y\text{-}R^2 \qquad \text{(I) (SEQ ID NO:12)}$$

or a pharmaceutically acceptable salt or solvate thereof, wherein
$R^1$ is hydrogen, an C1-C6 alkyl, C6-C12 aryl, C6-C12 aryl C1-C6 alkyl, C1-C20 alkanoyl (e.g. methyl, acetyl, formyl, benzoyl or trifluoroacetyl, isovaleric acid, isobutyric acid, octanoic acid, lauric acid and hexadecanoic acid), γ-Glu-hexadecanoic acid) or pGlu, appended to the N-terminus, and including PEGylated versions (e.g. PEG3 to PEG11), alone or as spacers of any of the foregoing;
$R^2$ is —NH$_2$ or —OH;
X is a peptide sequence having the formula (Ia)

$$X1\text{-}X2\text{-}X3\text{-}X4\text{-}X5\text{-}X6\text{-}X7\text{-}X8\text{-}X9\text{-}X10 \qquad \text{(Ia) (SEQ ID NO:1)}$$

wherein
X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Lys, Ala, or D-His;
X4 is Phe, Ala, Dpa, bhPhe, of D-Phe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg, or Dapa;
X9 is Phe, Ala, Ile, Tyr, Lys, Arg, bhPhe or D-Phe; and
X10 is Lys, Phe or absent;
Y is absent or Y is a peptide having the formula (IIa)

$$Y1\text{-}Y2\text{-}Y3\text{-}Y4\text{-}Y5\text{-}Y6\text{-}Y7\text{-}Y8\text{-}Y9\text{-}Y10\text{-}Y11\text{-}Y12\text{-}Y13\text{-}Y14\text{-}Y15 \qquad \text{(IIa) (SEQ ID NO:5)}$$

wherein

Y1 is Gly, Cys, Ala, Phe, Pro, Glu, Lys, D-Pro, Val, Ser or absent;
Y2 is Pro, Ala, Cys, Gly or absent;
Y3 is Arg, Lys, Pro, Gly, His, Ala, Trp or absent;
Y4 is Ser, Arg, Gly, Trp, Ala, His, Tyr or absent;
Y5 is Lys, Met, Arg, Ala or absent;
Y6 is Gly, Ser, Lys, Ile, Arg, Ala, Pro, Val or absent;
Y7 is Trp, Lys, Gly, Ala Ile, Val or absent;
Y8 is Val, Thr, Gly, Cys, Met, Tyr, Ala, Glu, Lys, Asp, Arg or absent;
Y9 is Cys, Tyr or absent;
Y10 is Met, Lys, Arg, Tyr or absent;
Y11 is Arg, Met, Cys, Lys or absent;
Y12 is Arg, Lys, Ala or absent;
Y13 is Arg, Cys, Lys, Val or absent;
Y14 is Arg, Lys, Pro, Cys, Thr or absent; and
Y15 is Thr, Arg or absent;
wherein if Y is absent from the peptide of formula (I), X7 is Ile; and
wherein said compound of formula (I) is optionally PEGylated on $R^1$, X, or Y.

In some embodiments, the compound of formula (I) comprises two or more cysteine residues, wherein at least two of said cysteine residues are linked via a disulfide bond.

In some embodiments, the invention provides peptides, which may be isolated and/or purified, comprising, consisting essentially of, or consisting of the following structural formula I':

$$X^{1'}\text{-}Y'\text{-}R^{2'} \quad (I') \text{ (SEQ ID NO:21)}$$

or a pharmaceutically acceptable salt or solvate thereof, wherein $R^{1'}$ is hydrogen, an $C_1$-$C_6$ alkyl, $C_6$-$C_{12}$ aryl, $C_6$-$C_{12}$ aryl $C_1$-$C_6$ alkyl, $C_1$-$C_{20}$ alkanoyl (e.g. methyl, acetyl, formyl, benzoyl or trifluoroacetyl, isovaleric acid, isobutyric acid, octanoic acid, lauric acid and hexadecanoic acid), γ-Glu-hexadecanoic acid) or pGlu, appended to the N-terminus, and including PEGylated versions (e.g. PEG3 to PEG11), alone or as spacers of any of the foregoing;
$R^{2'}$ is —$NH_2$ or —OH;
X' is a peptide sequence having the formula Ia'

$$X1\text{-}X2\text{-}X3\text{-}X4\text{-}X5\text{-}X6\text{-}X7\text{-}X8\text{-}X9\text{-}X10 \quad (Ia') \text{ (SEQ ID NO:13)}$$

wherein
X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Ala, D-His or Lys;
X4 is Phe, Ala, Dpa, bhPhe or D-Phe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg, or Dapa;
X9 is Phe, Ala, Ile, Tyr, Lys, Arg, bhPhe or D-Phe; and
X10 is Lys, Phe or absent;
and provided that if Y' is absent, X7 is Ile;
Y' is a peptide having the formula IIa'

$$Y1\text{-}Y2\text{-}Y3\text{-}Y4\text{-}Y5\text{-}Y6\text{-}Y7\text{-}Y8\text{-}Y9\text{-}Y10\text{-}Y11\text{-}Y12\text{-}Y13\text{-}Y14\text{-}Y15 \quad (IIa') \text{ (SEQ ID NO:16)}$$

wherein
Y1 is Gly, Cys, Ala, Phe, Pro, Glu, Lys, D-Pro, Val, Ser or absent;
Y2 is Pro, Ala, Cys, Gly or absent;
Y3 is Arg, Lys, Pro, Gly, His, Ala, Trp or absent;
Y4 is Ser, Arg, Gly, Trp, Ala, His, Tyr or absent;
Y5 is Lys, Met, Arg, Ala or absent;
Y6 is Gly, Ser, Lys, Ile, Ala, Pro, Val or absent;
Y7 is Trp, Lys, Gly, Ala, Ile, Val or absent;
Y8 is Val, Thr, Gly, Cys, Met, Tyr, Ala, Glu, Lys, Asp, Arg or absent;
Y9 is Cys, Tyr or absent;
Y10 is Met, Lys, Arg, Tyr or absent;
Y11 is Arg, Met, Cys, Lys or absent;
Y12 is Arg, Lys, Ala or absent;
Y13 is Arg, Cys, Lys, Val or absent;
Y14 is Arg, Lys, Pro, Cys, Thr or absent; and
Y15 is Thr, Arg or absent;
wherein said compound of formula I' is optionally PEGylated on $R^{1'}$, X', or Y'; and wherein when said compound of formula I' comprises two or more cysteine residues, at least two of said cysteine residues being linked via a disulfide bond.

In some embodiments, the compound of formula I' comprises an moiety that is hydrogen, isovaleric acid, isobutyric acid, or acetyl.

In some embodiments, the compound of formula I' comprises an X' peptide of formula Ia' as described herein, wherein
X1 is Asp, Ala, Ida, pGlu, bhAsp, Leu, D-Asp or absent;
X2 is Thr, Ala, or D-Thr;
X3 is His, Lys, D-His or Lys;
X4 is Phe, Ala, Dpa or D-Phe;
X5 is Pro, Gly, Arg, Lys, Ala, D-Pro or bhPro;
X6 is Ile, Cys, Arg, Lys, D-Ile or D-Cys;
X7 is Cys, Ile, Leu, Val, Phe, D-Ile or D-Cys;
X8 is Ile, Arg, Phe, Gln, Lys, Glu, Val, Leu or D-Ile;
X9 is Phe or bhPhe; and
X10 is Lys, Phe or absent.

In some embodiments, the compound of formula I' comprises an X' peptide of formula Ib':

$$X1\text{-}Thr\text{-}His\text{-}X4\text{-}X5\text{-}X6\text{-}X7\text{-}X8\text{-}Phe\text{-}X10 \quad (Ib')$$

wherein
X1 is Asp, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile Lys, Glu, Phe, Gln or Arg; and
X10 is Lys or absent.

In some embodiments, the compound of formula I' comprises an X' peptide of formula Ic':

$$X1\text{-}Thr\text{-}His\text{-}X4\text{-}X5\text{-}Cys\text{-}Ile\text{-}X8\text{-}Phe\text{-}X10 \quad (Ic')$$

wherein
X1 is Asp, Ida, pGlu, bhAsp or absent;
X4 is Phe or Dpa;
X5 is Pro or bhPro;
X8 is Ile Lys, Glu, Phe, Gln or Arg; and
X10 is Lys or absent.

In some embodiments, the compound of formula I' comprises a Y' peptide of formula IIb'.

$$Y1\text{-}Y2\text{-}Y3\text{-}Y4\text{-}Y5\text{-}Y6\text{-}Y7\text{-}Y8\text{-}Cys\text{-}Y10 \quad (IIb')$$

wherein
Y1 is Gly, Ala, Lys, Pro or D-Pro;
Y2 is Pro, Ala or Gly;
Y3 is Arg, Ala, Lys or Trp;
Y4 is Ser, Gly or Ala;

Y5 is Lys, Met, Arg or Ala;
Y6 is Gly, Arg or Ala;
Y7 is Trp or Ala;
Y8 is Val, Thr, Ala or Glu; and
Y10 is Met, Lys or absent.

In some embodiments, the compound of formula I' comprises a Y' peptide of formula IIc'.

Y1-Y2-Y3-Ser-Lys-Gly-Trp-Y8-Cys-Y10 (IIc')

wherein
Y1 is Gly, Pro or D-Pro;
Y2 is Pro or Gly;
Y3 is Arg or Lys;
Y8 is Val or Thr; and
Y10 is Met, Lys or absent.

In some embodiments, the compound of formula I' comprises a Y' peptide of formula IId':

Cys-Y3-Y4-Arg-Y6-Y7-Y8-Cys-Y10-Y11-Y12-Y13-Y14-Y15 (IId')

wherein
Y1 is Val or Ala or absent;
Y3 is Gly, Pro or absent;
Y4 is His, Trp or Tyr; Y6 is Ser, Gly or Pro;
Y7 is Ile, Gly or Lys;
Y8 is Gly, Met or absent;
Y10 is Tyr or Cys;
Y11 is Arg, Lys, Met or Ala;
Y12 is Arg or Ala;
Y13 is Cys or Val or absent;
Y14 is Cys, Lys, Pro, Arg, Thr or absent; and
Y15 is Arg, Thr or absent.

In some embodiments, the compound of formula I' comprises a Y' peptide of formula IIe':

Val-Cys-Y3-His-Arg-Y6-Y7-Y8-Cys-Tyr-Arg-Y12-Y13-Y14-Y15 (IIe')

wherein
Y3 is Gly or absent;
Y6 is Ser or Pro;
Y7 is Ile or Lys;
Y8 is Gly or absent;
Y12 is Arg or Ala;
Y13 is Cys or Val or absent;
Y14 is Cys, Arg, Thr or absent; and
Y15 is Arg or absent.

In some embodiments, the invention provides peptides, which may be isolated and/or purified, comprising, consisting essentially of, or consisting of the following structural formula I":

$R^{1''}$-X"-Y"-$R^{2''}$ (I") (SEQ ID NO:27)

or a pharmaceutically acceptable salt or solvate thereof, wherein
$R^{1''}$ is hydrogen, an $C_1$-$C_6$ alkyl, $C_6$-$C_{12}$ aryl, $C_6$-$C_{12}$ aryl $C_1$-$C_6$ alkyl, $C_1$-$C_{20}$ alkanoyl (e.g. methyl, acetyl, formyl, benzoyl or trifluoroacetyl, isovaleric acid, isobutyric acid, octanoic acid, lauric acid and hexadecanoic acid), γ-Glu-hexadecanoic acid) or pGlu, appended to the N-terminus, and including PEGylated versions (e.g. PEG3 to PEG11), alone or as spacers of any of the foregoing;
$R^{2''}$ is —$NH_2$ or —OH;
X" is a peptide sequence having the formula Ia"

X1-X2-X3-X4-X5-X6-X7-X8-X9-X10 (Ia") (SEQ ID NO:22)

wherein
X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Ala, D-His or Lys;
X4 is Phe, Ala, Dpa, bhPhe or D-Phe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg, or Dapa;
X9 is Phe, Ala, Ile, Tyr, Lys, Arg, bhPhe or D-Phe; and
X10 is Lys, Phe or absent;
and provided that if Y" is absent, X7 is Ile.

In some embodiments, the compound of formula I" is PEGylated on $R^{1''}$, X", or Y".

In some embodiments, the compound of formula I" comprises two or more cysteine residues, at least two of said cysteine residues being linked via a disulfide bond.

In some embodiments, the compound of formula I" comprises an $R^{1''}$ that is hydrogen, isovaleric acid, iso-butyric acid or acetyl.

In some embodiments, the compound of formula I" comprises an X" peptide according to formula Ia", disclosed herein,
wherein
X1 is Asp, Ala, Ida, pGlu, bhAsp, Leu, D-Asp or absent;
X2 is Thr, Ala, or D-Thr;
X3 is His, Lys, D-His or Lys;
X4 is Phe, Ala, or Dpa;
X5 is Pro, Gly, Arg, Lys, Ala, D-Pro or bhPro;
X6 is Ile, Cys, Arg, Lys, D-Ile or D-Cys;
X7 is Cys, Ile, Leu, Val, Phe, D-Ile or D-Cys;
X8 is Ile, Arg, Phe, Gln, Lys, Glu, Val, Leu or D-Ile;
X9 is Phe or bhPhe; and
X10 is Lys or absent.

In some embodiments, the compound of formula I" comprises an X" peptide of formula Ib":

X1-Thr-His-X4-X5-X6-X7-X8-Phe-X10 (Ib")

wherein
X1 is Asp, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile, Lys, Glu, Phe, Gln or Arg; and
X10 is Lys, Phe or absent.

In some embodiments, the compound of formula I" comprises an X" peptide of formula Ic":

X1-Thr-His-X4-X5-Cys-Ile-X8-Phe-X10 (Ic")

wherein
X1 is Asp, Ida, pGlu, bhAsp or absent;
X4 is Phe or Dpa;
X5 is Pro or bhPro;
X8 is Ile, Lys, Glu, Phe, Gln or Arg; and
X10 is Lys or absent.

In some embodiments, the compound of formula I" comprises a Y" peptide of formula IIa":

Y1-Y2-Y3-Y4-Y5-Y6-Y7-Y8-Cys-Y10 (IIa") (SEQ ID NO:25)

wherein
Y1 is Gly, Ala, Lys, Pro or D-Pro;
Y2 is Pro, Ala or Gly;
Y3 is Arg, Ala, Lys or Trp;
Y4 is Ser, Gly or Ala;
Y5 is Lys, Met, Arg or Ala;

Y6 is Gly, Arg or Ala;
Y7 is Trp, Ala or absent;
Y8 is Val, Thr, Lys, Ala, Glu or absent; and
Y10 is Met, Lys or absent.

In some embodiments, the compound of formula I" comprises a Y" peptide of formula IIb":

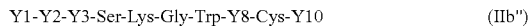

wherein
Y1 is Gly, Pro or D-Pro;
Y2 is Pro, Gly;
Y3 is Arg, Lys;
Y8 is Val or Thr; and
Y10 is Met, Lys or absent.

In related embodiments, the present invention includes dimers, e.g., homodimers, of any of the peptides of the present invention.

In some embodiments, the peptides or dimers of the present invention exhibit hepcidin activity. In some embodiments, the peptides or dimers bind ferroportin, e.g., human ferroportin.

In some embodiments, the present invention provides methods of binding a ferroportin or inducing ferroportin internalization and degradation which comprise contacting the ferroportin with at least one peptide, dimer or composition as disclosed herein.

In some embodiments, the present invention provides compositions and medicaments comprising at least one peptide or dimer as disclosed herein.

In some embodiments, the present invention provides a method of manufacturing medicaments comprising at least one peptide or dimer as disclosed herein for the treatment of diseases of iron metabolism, such as iron overload diseases.

Also provided are methods of treating a disease of iron metabolism in a subject, such as a mammalian subject, e.g., a human subject, comprising administering at least one peptide, dimer or composition as disclosed herein to the subject. In some embodiments, the peptide or dimer is administered in a therapeutically effective amount. In some embodiments, the disease of iron metabolism is an iron overload disease.

In some embodiments, the present invention provides a method of manufacturing a peptide or peptide dimer of the present invention synthetically. In some embodiments, the present invention provides a method of manufacturing a peptide or peptide dimer of the present invention recombinantly.

In some embodiments, the present invention provides a pharmaceutical composition comprising a peptide analogue (e.g., a peptide or dimer of the present invention), or pharmaceutically acceptable salt or solvate thereof, as described herein, in combination with one or more peptide analogue (e.g., a peptide or dimer of the present invention) or pharmaceutically acceptable salt or solvate thereof, as described herein together with a pharmaceutically acceptable carrier, excipient or vehicle.

In some embodiments, the invention provides a process for manufacturing a compound or a pharmaceutical composition as disclosed herein.

In some embodiments, the invention provides a device comprising at least one peptide analogue (e.g., a peptide or dimer of the present invention), or pharmaceutically acceptable salt or solvate thereof for delivery of the peptide analogue to a subject.

In some embodiments, the present invention provides kits comprising at least one peptide, dimer, or composition as disclosed herein packaged together with a reagent, a device, instructional material, or a combination thereof.

In some embodiments, the present invention provides complexes which comprise at least one peptide or dimer as disclosed herein bound to a ferroportin, e.g., a human ferroportin, or an antibody, such as an antibody which specifically binds a peptide as disclosed herein, Hep25, or a combination thereof.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DETAILED DESCRIPTION OF THE INVENTION

Figure 1:
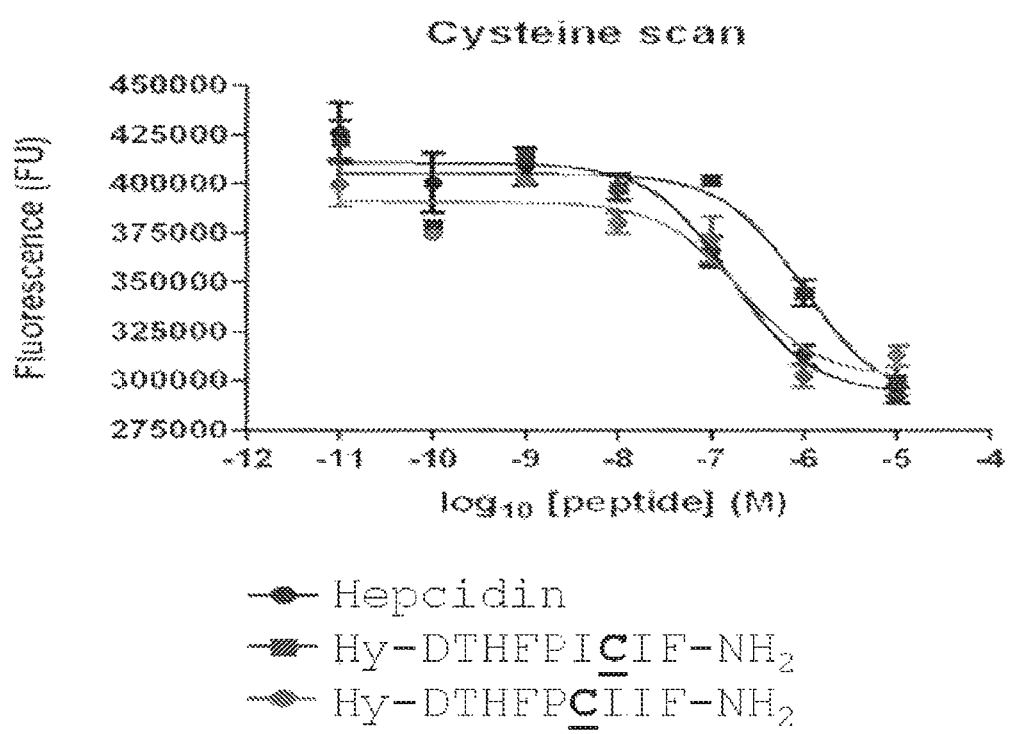
FIG. 1 shows the results of an in vitro activity assay measuring the induction of degradation of the human ferroportin protein. Presented are dose response curves for Compound No. 1 as compared to Hepcidin and the Mini-Hepcidin control.

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well-known and commonly used in the art.

All publications, patents and published patent applications referred to in this application are specifically incorporated by reference herein. In case of conflict, the present specification, including its specific definitions, will control.

Each embodiment of the invention described herein may be taken alone or in combination with one or more other embodiments of the invention.

Definitions

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

The term formula (I), is used herein interchangeably with the term formula I (i.e., without the parentheses). The term formula (I'), is used herein interchangeably with the term formula I' (i.e., without the parentheses). The term formula (I"), is used herein interchangeably with the term formula I" (i.e., without the parentheses).

The recitations "sequence identity", "percent identity", "percent homology", or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Calculations of sequence similarity or sequence identity between sequences (the terms are used interchangeably herein) can be performed as follows. To determine the percent identity of two amino acid sequences, or of two nucleic acid sequences, the sequences can be aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two amino acid sequences is determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using an NWSgapdna.CMP matrix and a gap weight of 40, 50, 60, 70, or 80 and a length weight of 1, 2, 3, 4, 5, or 6. Another exemplary set of parameters includes a Blossum 62 scoring matrix with a gap penalty of 12, a gap extend penalty of 4, and a frameshift gap penalty of 5. The percent identity between two amino acid or nucleotide sequences can also be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

The peptide sequences described herein can be used as a "query sequence" to perform a search against public databases to, for example, identify other family members or related sequences. Such searches can be performed using the NBLAST and XBLAST programs (version 2.0) of Altschul, et al., (1990, J. Mol. Biol, 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al. (Nucleic Acids Res. 25:3389-3402, 1997). When utilizing BLAST and Gapped BLAST programs, the default parameters of the respective programs (e.g., XBLAST and NBLAST) can be used.

As used herein, the term "pharmaceutically acceptable salt" is intended to indicate a salt which is not harmful to a patient or subject to which the salt in question is administered. It may suitably be a salt chosen, e.g., among acid addition salts and basic salts. Examples of acid addition salts include chloride salts, citrate salts and acetate salts. Examples of basic salts include salts where the cation is selected among alkali metal cations, such as sodium or potassium ions, alkaline earth metal cations, such as calcium or magnesium ions, as well as substituted ammonium ions, such as ions of the type N(R1)(R2)(R3)(R4)+, where R1, R2, R3 and R4 independently will typically designate hydrogen, optionally substituted C1-6-alkyl or optionally substituted C2-6-alkenyl. Examples of relevant C1-6-alkyl groups include methyl, ethyl, 1-propyl and 2-propyl groups. Examples of C2-6-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in *J. Pharm. Sci.* 66: 2 (1977). Also, for a review on suitable salts, see *Handbook of Pharmaceutical Salts: Properties, Selection, and Use* by Stahl and Wermuth (Wiley-VCH, 2002). Other suitable base salts are formed from bases which form non-toxic salts. Representative examples include the aluminum, arginine, benzathine, calcium, choline, diethylamine, diolamine, glycine, lysine, magnesium, meglumine, olamine, potassium, sodium, tromethamine, and zinc salts. Hemisalts of acids and bases may also be formed, e.g., hemisulphate and hemicalcium salts. Compositions to be used in the invention suitable for parenteral administration may comprise sterile aqueous solutions and/or suspensions of the pharmaceutically active ingredients preferably made isotonic with the blood of the recipient, generally using sodium chloride, glycerin, glucose, mannitol, sorbitol, and the like. Organic acids suitable for forming pharmaceutically acceptable acid addition salts include, by way of example and not limitation, acetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl) benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo(2.2.2)-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

The term "solvate" in the context of the present invention refers to a complex of defined stoichiometry formed between a solute (in casu, a peptide analogue or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

The term "agonist" as employed in the context of the invention refers to a substance (ligand) that causes internalization of the ferroportin protein.

As used herein, a "disease of iron metabolism" includes diseases where aberrant iron metabolism directly causes the disease, or where iron blood levels are dysregulated causing disease, or where iron dysregulation is a consequence of another disease, or where diseases can be treated by modulating iron levels, and the like. More specifically, a disease of iron metabolism according to this disclosure includes iron overload diseases, iron deficiency disorders, disorders of iron biodistribution, other disorders of iron metabolism and other disorders potentially related to iron metabolism, etc. Diseases of iron metabolism include hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia *intermedia*, alpha thalassemia, sideroblastic anemia, *porphyria, porphyria* cutanea *tarda*, African iron overload, hyperferritinemia, ceruloplasmin deficiency, atransferrinemia, congenital dyserythropoietic anemia, anemia of chronic disease, anemia of inflammation, anemia of infection, hypochromic microcytic anemia, iron-deficiency anemia, iron-refractory iron deficiency anemia, anemia of chronic kidney disease, erythropoietin resistance, iron deficiency of obesity, other anemias, benign or malignant tumors that overproduce hepcidin or induce its overproduction, conditions with hepcidin excess, Friedreich ataxia, *gracile* syndrome, Hallervorden-Spatz disease, Wilson's disease, pulmonary hemosiderosis, hepatocellular carcinoma, cancer, hepatitis, cirrhosis of liver, pica, chronic renal failure, insulin resistance, diabetes, atherosclerosis, neurodegenerative disorders, multiple sclerosis, Parkinson's disease, Huntington's disease, and Alzheimer's disease.

In some embodiments, the disease and disorders are related to iron overload diseases such as iron hemochromatosis, HFE mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, neonatal hemochromatosis, hepcidin deficiency, transfusional iron overload, thalassemia, thalassemia *intermedia*, alpha thalassemia.

In some embodiments, the peptides of the invention are used to treat diseases and disorders that are not typically identified as being iron related. For example, hepcidin is highly expressed in the murine pancreas suggesting that diabetes (Type I or Type II), insulin resistance, glucose intolerance and other disorders may be ameliorated by treating underlying iron metabolism disorders. See Ilyin, G. et al. (2003) FEBS Lett. 542 22-26, which is herein incorporated by reference. As such, peptides of the invention may be used to treat these diseases and conditions. Those skilled in the art are readily able to determine whether a given disease can be treated with a peptide according to the present invention using methods known in the art, including the assays of WO 2004092405, which is herein incorporated by reference, and assays which monitor hepcidin, hemojuvelin, or iron levels and expression, which are known in the art such as those described in U.S. Pat. No. 7,534,764, which is herein incorporated by reference.

In certain embodiments of the present invention, the diseases of iron metabolism are iron overload diseases, which include hereditary hemochromatosis, iron-loading anemias, alcoholic liver diseases and chronic hepatitis C.

As used herein, the terms "protein", "polypeptide" and "peptide" are used interchangeably to refer to two or more amino acids linked together. Except where indicated otherwise, e.g., for the abbreviations for the uncommon or unnatural amino acids set forth herein, the three-letter and one-letter abbreviations, as used in the art, are used herein to represent amino acid residues. Except when preceded with "D-", the amino acid is an L-amino acid. Groups or strings of amino acid abbreviations are used to represent peptides. Except when specifically indicated, peptides are indicated with the N-terminus on the left and the sequence is written from the N-terminus to the C-terminus.

The term "peptide analogue" in the context of the present invention refers to a molecule in which a first peptide moiety is attached (i.e. coupled or linked), either directly or via a linking (i.e. bridging or spacing) chemical moiety, to a second peptide moiety, by means of covalent chemical bonding. In certain embodiments, a peptide analogue is a peptide described herein comprising an X peptide sequence and a Y peptide sequence. In certain embodiments, a peptide analogue is a peptide described herein comprising an X' peptide sequence and a Y' peptide sequence. In certain embodiments, a peptide analogue is a peptide described herein comprising an X" peptide sequence and a Y" peptide sequence. In certain embodiments, a peptide analogue is a peptide described herein comprising an X peptide sequence and/or a Y peptide sequence conjugated to an additional chemical moiety. In certain embodiments, a peptide analogue is a peptide described herein comprising an X' peptide sequence and/or a Y' peptide sequence conjugated to an additional chemical moiety. In certain embodiments, a peptide analogue is a peptide described herein comprising an X" peptide sequence and/or a Y" peptide sequence conjugated to an additional chemical moiety. The peptides of the present invention described herein are peptide analogues. Peptide analogues also include any of the peptide dimers described herein.

Peptides and peptide dimers of the present invention may also be referred to herein as compounds or peptide analogues.

The term "conservative substitution" as used herein denotes that one or more amino acids are replaced by another, biologically similar residue. Examples include substitution of amino acid residues with similar characteristics, e.g., small amino acids, acidic amino acids, polar amino acids, basic amino acids, hydrophobic amino acids and aromatic amino acids. See, for example, the table below. In some embodiments of the invention, one or more Met residues are substituted with norleucine (Nle) which is a bioisostere for Met, but which, as opposed to Met, is not readily oxidized. Another example of a conservative substitution with a residue normally not found in endogenous, mammalian peptides and proteins is the conservative substitution of Arg or Lys with, for example, ornithine, canavanine, aminoethylcysteine or another basic amino acid. In some embodiments, one or more cysteines of a peptide analogue of the invention may be substituted with another residue, such as a serine. For further information concerning phenotypically silent substitutions in peptides and proteins, see, for example, Bowie et. al. Science 247, 1306-1310, 1990. In the scheme below, conservative substitutions of amino acids are grouped by physicochemical properties. I: neutral, hydrophilic, II: acids and amides, III: basic, IV: hydrophobic, V: aromatic, bulky amino acids.

| I | II | III | IV | V |
|---|----|-----|----|----|
| A | N | H | M | F |
| S | D | R | L | Y |
| T | E | K | I | W |
| P | Q |   | V |   |
| G |   |   | C |   |

In the scheme below, conservative substitutions of amino acids are grouped by physicochemical properties. VI: neutral or hydrophobic, VII: acidic, VIII: basic, IX: polar, X: aromatic.

| VI | VII | VIII | IX | X |
|----|-----|------|----|----|
| A | E | H | M | F |
| L | D | R | S | Y |
| I |   | K | T | W |
| P |   |   | C |   |
| G |   |   | N |   |
| V |   |   | Q |   |

In certain embodiments, the present invention provides peptides which are useful in the study and treatment of diseases of iron metabolism.

Throughout the present specification, unless naturally occurring amino acids are referred to by their full name (e.g. alanine, arginine, etc.), they are designated by their conventional three-letter or single-letter abbreviations (e.g. Ala or A for alanine, Arg or R for arginine, etc.). In the case of less common or non-naturally occurring amino acids, unless they are referred to by their full name (e.g. sarcosine, ornithine, etc.), frequently employed three- or four-character codes are employed for residues thereof, including, Sar or Sarc (sarcosine, i.e. N-methylglycine), Aib (α-aminoisobutyric acid), Dab (2,4-diaminobutanoic acid), Dapa (2,3-diaminopropanoic acid), γ-Glu (γ-glutamic acid), Gaba (γ-aminobutanoic acid), β-Pro (pyrrolidine-3-carboxylic acid), and 8Ado (8-amino-3,6-dioxaoctanoic acid), Abu (4-amino butyric acid), bhPro (β-homoproline), bhPhe (β-homophenylalanine) and Dpa (β,β diphenylalanine), and Ida (Iminodiacetic acid).

As is clear to the skilled artisan, the peptide sequences disclosed herein are shown proceeding from left to right, with the left end of the sequence being the N-terminus of the peptide and the right end of the sequence being the C-terminus of the peptide. Among sequences disclosed herein are sequences incorporating a "Hy-" moiety at the amino terminus (N-terminus) of the sequence, and either an "—OH" moiety or an "—NH$_2$" moiety at the carboxy terminus (C-terminus) of the sequence. In such cases, and unless otherwise indicated, a "Hy-" moiety at the N-terminus of the sequence in question indicates a hydrogen atom [e.g., $R^1$, $R^{1'}$, or $R^{1''}$=hydrogen (Hy—) in formula I, I', or I", respectively, corresponding to the presence of a free primary or secondary amino group at the N-terminus], while an "—OH" or an "—NH$_2$" moiety at the C-terminus of the sequence indicates a hydroxy group [e.g., $R^2$, $R^{2'}$, or $R^{2''}$=OH in formula I, I', or I", respectively, corresponding to the presence of a carboxy (COOH) group at the C-terminus] or an amino group [e.g., $R^2$, $R^{2'}$, or $R^{2''}$=NH$_2$ in formula I, I', or I", respectively, corresponding to the presence of an amido (CONH$_2$) group at the C-terminus], respectively. In each sequence of the invention, a C-terminal "—OH" moiety may be substituted for a C-terminal "—NH$_2$" moiety, and vice-versa. Furthermore, $R^1$, $R^{1'}$, or $R^{1''}$ can in all sequences be substituted with isovaleric acids or equivalent. In some embodiments, wherein a peptide of the present invention is conjugated to an acidic compound such as, e.g., isovaleric acid, isobutyric acid, valeric acid, and the like, the presence of such a conjugation is referenced in the acid form. So, for example, but not to be limited in any way, instead of indicating a conjugation of isovaleric acid to a peptide DTHFPCIKFCK (SEQ ID NO:215) by referencing isovaleroyl (e.g., isovaleroyl-DTHFPCIKFCK [SEQ ID NO:215]), in some embodiments, the present application references such a conjugation as isovaleric acid-DTHFPCIKFCK (SEQ ID NO:215). Unless otherwise indicated, reference is made to the L-isomeric forms of the amino acids in question. Where appropriate, the D-isomeric form of an amino acid is indicated in the conventional manner by the prefix "D" before the conventional three-letter code (e.g., DAsp or D-Asp; DPhe or D-Phe).

In some embodiments, the invention provides peptides, which may be isolated and/or purified, comprising, consisting essentially of, or consisting of, the following structural formula:

$$R^1\text{-}X\text{-}Y\text{-}R^2 \qquad \text{(I) (SEQ ID NO:12)}$$

or a pharmaceutically acceptable salt or solvate thereof, wherein $R^1$ is hydrogen, an C1-C6 alkyl, C6-C12 aryl, C6-C12 aryl C1-C6 alkyl, C1-C20 alkanoyl (e.g., methyl, acetyl, formyl, benzoyl or trifluoroacetyl, isovaleric acid, isobutyric acid, octanoic acid, lauric acid and hexadecanoic acid), γ-Glu-hexadecanoic acid) or pGlu, appended to the N-terminus, and including PEGylated versions (e.g., PEG3 to PEG11), alone or as spacers of any of the foregoing;

$R^2$ is —NH$_2$ or —OH;

X is a peptide sequence having the formula (Ia)

X1-X2-X3-X4-X5-X6-X7-X8-X9-X10   (Ia) (SEQ ID NO:1)

wherein

X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Lys, Ala, or D-His;
X4 is Phe, Ala, Dpa, bhPhe, or D-Phe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg, or Dapa;
X9 is Phe, Ala, Ile, Tyr, Lys, Arg, bhPhe or D-Phe; and
X10 is Lys, Phe or absent;
Y is absent or Y is a peptide having the formula (IIa)

Y1-Y2-Y3-Y4-Y5-Y6-Y7-Y8-Y9-Y10-Y11-Y12-Y13-Y14-Y15   (IIa) (SEQ ID NO:5)

wherein

Y1 is Gly, Cys, Ala, Phe, Pro, Glu, Lys, D-Pro, Val, Ser or absent;
Y2 is Pro, Ala, Cys, Gly or absent;
Y3 is Arg, Lys, Pro, Gly, His, Ala, Trp or absent;
Y4 is Ser, Arg, Gly, Trp, Ala, His, Tyr or absent;
Y5 is Lys, Met, Arg, Ala or absent;
Y6 is Gly, Ser, Lys, Ile, Arg, Ala, Pro, Val or absent;
Y7 is Trp, Lys, Gly, Ala Ile, Val or absent;
Y8 is Val, Thr, Gly, Cys, Met, Tyr, Ala, Glu, Lys, Asp, Arg or absent;
Y9 is Cys, Tyr or absent;
Y10 is Met, Lys, Arg, Tyr or absent;
Y11 is Arg, Met, Cys, Lys or absent;
Y12 is Arg, Lys, Ala or absent;
Y13 is Arg, Cys, Lys, Val or absent;
Y14 is Arg, Lys, Pro, Cys, Thr or absent; and
Y15 is Thr, Arg or absent;
wherein if Y is absent from the peptide of formula (I), X7 is Ile; and
wherein said compound of formula (I) is optionally PEGy-lated on R', X, or Y.

In some embodiments, the compound or peptide of formula (I) comprises two or more cysteine residues, wherein at least two of said cysteine residues are linked via a disulfide bond.

In some embodiments, X is a peptide sequence according to formula (Ia), described herein,
wherein
X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Lys, Ala, or D-His;
X4 is Phe, Ala, Dpa, or bhPhe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg, or Dapa;
X9 is Phe, Ala, Ile, Tyr, Lys, Arg, bhPhe or D-Phe; and
X10 is Lys, Phe or absent.

In some embodiments, X is a peptide sequence according to formula (Ia), described herein, wherein
X1 is Asp, Ala, Ida, pGlu, bhAsp, Leu, D-Asp or absent;
X2 is Thr, Ala, or D-Thr;
X3 is His, Lys, or D-His;
X4 is Phe, Ala, or Dpa;
X5 is Pro, Gly, Arg, Lys, Ala, D-Pro or bhPro;
X6 is Ile, Cys, Arg, Lys, D-Ile or D-Cys;
X7 is Cys, Ile, Leu, Val, Phe, D-Ile or D-Cys;
X8 is Ile, Arg, Phe, Gln, Lys, Glu, Val, Leu or D-Ile;
X9 is Phe or bhPhe; and
X10 is Lys, Phe or absent.

In some embodiments, X is a peptide sequence having the formula (Ib)

X1-Thr-His-X4-X5-X6-X7-X8-Phe-X10   (Ib) (SEQ ID NO:2)

wherein
X1 is Asp, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile, Lys, Glu, Phe, Gln or Arg; and
X10 is Lys, Phe or absent;

In some embodiments, X is a peptide sequence according to formula (Ib), as described herein, wherein
X1 is Asp, Glu, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile, Lys, Glu, Phe, Gln or Arg; and
X10 is Lys or absent.

In some embodiments, X is a peptide sequence having the formula (Ic)

X1-Thr-His-X4-X5-Cys-Ile-X8-Phe-X10   (Ic) (SEQ ID NO:3)

wherein
X1 is Asp, Glu, Ida, pGlu, bhAsp or absent;
X4 is: Phe or Dpa;
X5 is Pro or bhPro;
X8 is Ile Lys, Glu, Phe, Gln or Arg; and
X10 is Lys or absent.

In some embodiments, X is a peptide sequence having the formula (Id)

X1-Thr-His-Phe-X5-Cys-Ile-X8-Phe-X10   (Id) (SEQ ID NO:4)

wherein
X1 is Asp, Glu, or Ida;
X4 is: Phe;
X5 is Pro or bhPro;
X8 is Ile, Lys or Phe; and
X10 is absent.

In some embodiments, Y is a peptide sequence having the formula IIb

Y1-Y2-Y3-Y4-Y5-Y6-Y7-Y8-Cys-Y10   (IIb) (SEQ ID NO:6)

wherein
Y1 is Gly, Ala, Lys, Pro or D-Pro;
Y2 is Pro, Ala or Gly;
Y3 is Arg, Ala, Lys or Trp;
Y4 is Ser, Gly or Ala;
Y5 is Lys, Met, Arg or Ala;
Y6 is Gly, Arg or Ala;
Y7 is Trp, Ala or absent;
Y8 is Val, Thr, Lys, Ala, Glu or absent; and
Y10 is Met, Lys or absent.

In some embodiments, Y is a peptide sequence according to formula (IIb), as described herein,
wherein
Y1 is Gly, Ala, Lys, Pro or D-Pro;
Y2 is Pro, Ala or Gly;
Y3 is Arg, Ala, Lys or Trp;
Y4 is Ser, Gly or Ala;
Y5 is Lys, Met, Arg or Ala;
Y6 is Gly, Arg or Ala;
Y7 is Trp or Ala;
Y8 is Val, Thr, Ala, or Glu; and
Y10 is Met, Lys or absent.

In some embodiments, Y is a peptide sequence having the formula (IIc)

Y1-Y2-Y3-Ser-Lys-Gly-Trp-Y8-Cys-Y10    (IIc) (SEQ ID NO:7)

wherein
Y1 is Gly, Pro or D-Pro;
Y2 is Pro or Gly;
Y3 is Arg or Lys;
Y8 is Val or Thr; and
Y10 is Met, Lys or absent.

In some embodiments, Y is a peptide sequence having the formula (IId)

Y1-Cys-Y3-Y4-Arg-Y6-Y7-Y8-Cys-Y10-Y11-Y12-
    Y13-Y14-Y15    (IId) (SEQ ID NO:8)

wherein
Y1 is Val, Ala or absent;
Y3 is Gly, Pro or absent;
Y4 is His, Trp or Tyr;
Y6 is Ser, Gly or Pro;
Y7 is Ile, Gly or Lys;
Y8 is Gly, Met or absent;
Y10 is Tyr or Cys;
Y11 is Arg, Lys, Met or Ala;
Y12 is Arg or Ala;
Y13 is Cys or Val or absent;
Y14 is Cys, Lys, Pro, Arg, Thr or absent; and
Y15 is Arg, Thr or absent.

In some embodiments, Y is a peptide sequence having the formula (IIe)

Val-Cys-Y3-His-Arg-Y6-Y7-Y8-Cys-Tyr-Arg-Y12-
    Y13-Y14-Y15    (IIe) (SEQ ID NO:9)

wherein
Y3 is Gly or absent;
Y6 is Ser or Pro;
Y7 is Ile or Lys;
Y8 is Gly or absent;
Y12 is Arg or Ala;
Y13 is Cys, Val or absent;
Y14 is Cys, Arg, Thr or absent; and
Y15 is Arg or absent.

In some embodiments, Y is a peptide sequence having the formula (IIf)

Y1-Pro-Y3-Ser-Y5-Y6-Y7-Y8-Cys-Y10    (IIf) (SEQ ID NO:10)

wherein
Y1 is Gly, Glu, Val, or Lys;
Y3 is Arg or Lys;
Y5 is Arg or Lys;
Y6 is Gly, Ser, Lys, Ile or Arg;
Y7 is Trp or absent;
Y8 is Val, Thr, Asp, Glu or absent; and
Y10 is Lys or absent.

In some embodiments, Y is a peptide sequence having the formula (IIg)

Y1-Pro-Y3-Ser-Y5-Y6-Y7-Y8-Cys-Y10    (IIg) (SEQ ID NO:11)

wherein
Y1 is Glu or Lys;
Y3 is Arg or Lys;
Y5 is Arg or Lys;
Y6 is Gly, Ser, Lys, Ile or Arg;
Y7 is Trp or absent;
Y8 is Val or absent; and
Y10 is Lys or absent.

In some embodiments, the peptide of formula (I) comprises at least three, at least four, at least five, at least six, at least seven, at least eight, at least nine, at least ten, at least eleven, at least twelve, at least thirteen, at least fourteen or at least fifteen Y residues in Y.

In some embodiments, Y1 to Y3 are present and Y4 to Y15 are absent.
In some embodiments, Y1 to Y11 are present and Y12 to Y15 are absent.
In some embodiments, Y1 to Y10 are present and Y11 to Y15 are absent.
In some embodiments, Y8 and Y15 are absent.
In some embodiments, Y3 and Y15 are absent
In some embodiments, Y3, Y14 and Y15 are absent.
In some embodiment Y5 is absent.
In some embodiments Y1, Y5, Y7, Y12, Y13, Y14 and Y15 are absent.

In some embodiments Y1, Y5, and Y7 are absent. In some embodiments, Y8 is absent. In some embodiments, Y3 is absent. In some embodiments Y1, Y5, Y7, and Y11-Y15 are absent. In some embodiments, Y8 and Y11-Y15 are absent. In some embodiments, Y3 and Y11-Y15 are absent.

In some embodiments, the present invention provides a compound of formula (I), wherein the compound comprises any one of the X/Y peptide sequence formula combinations presented in Table 1 below.

TABLE 1

Illustrative combinations of X and Y peptides of a compound of Formula (I)
Formula I combinations

| Combination Number | X Peptide Sequence Formula | Y Peptide Sequence Formula |
|---|---|---|
| 1 | Ia | IIa |
| 2 | Ia | IIb |
| 3 | Ia | IIc |
| 4 | Ia | IId |
| 5 | Ia | IIe |
| 6 | Ia | IIf |
| 7 | Ia | IIg |
| 8 | Ib | IIa |
| 9 | Ib | IIb |
| 10 | Ib | IIc |
| 11 | Ib | IId |
| 12 | Ib | IIe |
| 13 | Ib | IIf |

TABLE 1-continued

Illustrative combinations of X and Y peptides of
a compound of Formula (I)
Formula I combinations

| Combination Number | X Peptide Sequence Formula | Y Peptide Sequence Formula |
| --- | --- | --- |
| 14 | Ib | IIg |
| 15 | Ic | IIa |
| 16 | Ic | IIb |
| 17 | Ic | IIc |
| 18 | Ic | IId |
| 19 | Ic | IIe |
| 20 | Ic | IIf |
| 21 | Ic | IIg |
| 22 | Id | IIa |
| 23 | Id | IIb |
| 24 | Id | IIc |
| 25 | Id | IId |
| 26 | Id | IIe |
| 27 | Id | IIf |
| 28 | Id | IIg |

In some embodiments, the invention provides peptides, which may be isolated and/or purified, comprising, consisting essentially of, or consisting of, the following structural formula:

$$R^{1\prime}\text{-}X'\text{-}Y'\text{-}R^{2\prime} \quad \text{(I') (SEQ ID NO:21)}$$

or a pharmaceutically acceptable salt or solvate thereof, wherein
$R^{1\prime}$ is hydrogen, an $C_1$-$C_6$ alkyl, $C_6$-$C_{12}$ aryl, $C_6$-$C_{12}$ aryl $C_1$-$C_6$ alkyl, $C_1$-$C_{20}$ alkanoyl (e.g., methyl, acetyl, formyl, benzoyl or trifluoroacetyl, isovaleric acid, isobutyric acid, octanoic acid, lauric acid and hexadecanoic acid), γ-Glu-hexadecanoic acid) or pGlu, appended to the N-terminus, and including PEGylated versions (e.g., PEG3 to PEG11), alone or as spacers of any of the foregoing;
$R^{2\prime}$ is —$NH_2$ or —OH;
X' is a peptide sequence having the formula (Ia')

$$X1\text{-}X2\text{-}X3\text{-}X4\text{-}X5\text{-}X6\text{-}X7\text{-}X8\text{-}X9\text{-}X10 \quad \text{(Ia') (SEQ ID NO:13)}$$

wherein
X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Lys, Ala, or D-His;
X4 is Phe, Ala, Dpa, bhPhe or D-Phe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg or Dapa;
X9 is Phe, Ala, Ile, Tyr, Lys, Arg, bhPhe or D-Phe; and
X10 is Lys, Phe or absent;
and provided that if Y' is absent, X7 is Ile; and
Y' is a peptide having the formula (IIa')

$$Y1\text{-}Y2\text{-}Y3\text{-}Y4\text{-}Y5\text{-}Y6\text{-}Y7\text{-}Y8\text{-}Y9\text{-}Y10\text{-}Y11\text{-}Y12\text{-}Y13\text{-}Y14\text{-}Y15 \quad \text{(IIa') (SEQ ID NO:16)}$$

wherein
Y1 is Gly, Cys, Ala, Phe, Pro, Glu, Lys, D-Pro, Val, Ser or absent;
Y2 is Pro, Ala, Cys, Gly or absent;
Y3 is Arg, Lys, Pro, Gly, His, Ala, Trp or absent;
Y4 is Ser, Arg, Gly, Trp, Ala, His, Tyr or absent;
Y5 is Lys, Met, Arg, Ala or absent;
Y6 is Gly, Ser, Lys, Ile, Arg, Ala, Pro, Val or absent;
Y7 is Trp, Lys, Gly, Ala Ile, Val or absent;
Y8 is Val, Thr, Gly, Cys, Met, Tyr, Ala, Glu, Lys, Asp, Arg or absent;
Y9 is Cys, Tyr or absent;
Y10 is Met, Lys, Arg, Tyr or absent;
Y11 is Arg, Met, Cys, Lys or absent;
Y12 is Arg, Lys, Ala or absent;
Y13 is Arg, Cys, Lys, Val or absent;
Y14 is Arg, Lys, Pro, Cys, Thr or absent; and
Y15 is Thr, Arg or absent;
wherein said compound of formula (I') is optionally PEGylated on $R^{1\prime}$, X', or Y'; and wherein when said compound of formula (I') comprises two or more cysteine residues, at least two of said cysteine residues being linked via a disulfide bond.

In some embodiments, $R^{1\prime}$ is hydrogen, isovaleric acid, isobutyric acid or acetyl.

In some embodiments of the peptide compound of formula (I'), X' is a peptide sequence according to formula (Ia'), wherein
X1 is Asp, Ala, Ida, pGlu, bhAsp, Leu, D-Asp or absent;
X2 is Thr, Ala, or D-Thr;
X3 is His, Lys, D-His or Lys;
X4 is Phe, Ala, Dpa or D-Phe;
X5 is Pro, Gly, Arg, Lys, Ala, D-Pro or bhPro;
X6 is Ile, Cys, Arg, Lys, D-Ile or D-Cys;
X7 is Cys, Ile, Leu, Val, Phe, D-Ile or D-Cys;
X8 is Ile, Arg, Phe, Gln, Lys, Glu, Val, Leu or D-Ile;
X9 is Phe or bhPhe; and
X10 is Lys, Phe or absent.

In some embodiments of the peptide compound of formula I', X' is a peptide sequence having the formula (Ib')

$$X1\text{-}Thr\text{-}His\text{-}X4\text{-}X5\text{-}X6\text{-}X7\text{-}X8\text{-}Phe\text{-}X10 \quad \text{(Ib') (SEQ ID NO:14)}$$

wherein
X1 is Asp, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile Lys, Glu, Phe, Gln or Arg; and
X10 is Lys or absent.

In some embodiments of the peptide compound of formula I', X' is a peptide sequence having the formula (Ic')

$$X1\text{-}Thr\text{-}His\text{-}X4\text{-}X5\text{-}Cys\text{-}Ile\text{-}X8\text{-}Phe\text{-}X10 \quad \text{(Ic') (SEQ ID NO:15)}$$

wherein
X1 is Asp, Ida, pGlu, bhAsp or absent;
X4 is: Phe or Dpa;
X5 is Pro or bhPro;
X8 is Ile Lys, Glu, Phe, Gln or Arg; and
X10 is Lys or absent;

In some embodiments of the peptide compound of formula I', X' is a peptide sequence having the formula (Id')

$$X1\text{-}Thr\text{-}His\text{-}Phe\text{-}X5\text{-}Cys\text{-}Ile\text{-}X8\text{-}Phe\text{-}X10 \quad \text{(Id') (SEQ ID NO:4)}$$

wherein
X1 is Asp, Glu, or Ida;
X4 is: Phe;
X5 is Pro or bhPro;
X8 is Ile, Lys, or Phe; and
X10 is absent;

In some embodiments of the peptide compound of formula I', Y' is a peptide sequence having the formula (IIb')

$$Y1\text{-}Y2\text{-}Y3\text{-}Y4\text{-}Y5\text{-}Y6\text{-}Y7\text{-}Y8\text{-}Cys\text{-}Y10 \quad \text{(IIb') (SEQ ID NO:17)}$$

wherein
Y1 is Gly, Ala, Lys, Pro or D-Pro;
Y2 is Pro, Ala or Gly;
Y3 is Arg, Ala, Lys or Trp;
Y4 is Ser, Gly or Ala;
Y5 is Lys, Met, Arg or Ala;
Y6 is Gly, Arg or Ala;
Y7 is Trp or Ala;
Y8 is Val, Thr, Ala or Glu; and
Y10 is Met, Lys or absent.

In some embodiments of the peptide compound of formula I', Y' is a peptide sequence having the formula (IIc')

Y1-Y2-Y3-Ser-Lys-Gly-Trp-Y8-Cys-Y10    (IIc') (SEQ ID NO:18)

wherein
Y1 is Gly, Pro or D-Pro;
Y2 is Pro or Gly;
Y3 is Arg or Lys;
Y8 is Val or Thr; and
Y10 is Met, Lys or absent.

In some embodiments of the peptide compound of formula I', Y' is a peptide sequence having the formula (IId')

Y1-Cys-Y3-Y4-Arg-Y6-Y7-Y8-Cys-Y10-Y11-Y12-
     Y13-Y14-Y15    (IId') (SEQ ID NO:19)

wherein
Y1 is Val or Ala or absent;
Y3 is Gly, Pro or absent;
Y4 is His, Trp or Tyr;
Y6 is Ser, Gly or Pro;
Y7 is Ile, Gly or Lys;
Y8 is Gly, Met or absent;
Y10 is Tyr or Cys;
Y11 is Arg, Lys, Met or Ala;
Y12 is Arg or Ala;
Y13 is Cys or Val or absent;
Y14 is Cys, Lys, Pro, Arg, Thr or absent; and
Y15 is Arg, Thr or absent.

In some embodiments of the peptide compound of formula I', Y' is a peptide sequence having the formula (IIe')

Val-Cys-Y3-His-Arg-Y6-Y7-Y8-Cys-Tyr-Arg-Y12-
     Y13-Y14-Y15    (IIe') (SEQ ID NO:20)

wherein
Y3 is Gly or absent;
Y6 is Ser or Pro;
Y7 is Ile or Lys;
Y8 is Gly or absent;
Y12 is Arg or Ala;
Y13 is Cys, Val or absent;
Y14 is Cys, Arg, Thr or absent; and
Y15 is Arg or absent.

In some embodiments of the peptide compound of formula I', Y' is a peptide sequence having the formula (IIf')

Y1-Pro-Y3-Ser-Y5-Y6-Y7-Y8-Cys-Y10    (IIf') (SEQ ID NO:10)

wherein
Y1 is Gly, Glu, Val, or Lys;
Y3 is Arg or Lys;
Y5 is Arg or Lys;
Y6 is Gly, Ser, Lys, Ile or Arg;
Y7 is Trp or absent;
Y8 is Val, Thr, Asp, Glu or absent; and
Y10 is Lys or absent.

In some embodiments of the peptide compound of formula I', Y' is a peptide sequence having the formula (IIg')

Y1-Pro-Y3-Ser-Y5-Y6-Y7-Y8-Cys-Y10    (IIg') (SEQ ID NO:11)

wherein
Y1 is Glu or Lys;
Y3 is Arg or Lys;
Y5 is Arg or Lys;
Y6 is Gly, Ser, Lys, Ile or Arg;
Y7 is Trp or absent;
Y8 is Val or absent; and
Y10 is Lys or absent.

In some embodiments, the peptide of formula I' comprises at least three, at least four, at least five, at least six, at least seven, at least eight, at least nine, at least ten, at least eleven, at least twelve, at least thirteen, at least fourteen or at least fifteen Y residues in Y'.

In some embodiments, Y1 to Y3 are present and Y4 to Y15 are absent.

In some embodiments, Y1 to Y11 are present and Y12 to Y15 are absent.

In some embodiments, Y1 to Y10 are present and Y11 to Y15 are absent.

In some embodiments, Y8 and Y15 are absent.

In some embodiments, Y3 and Y15 are absent

In some embodiments, Y3, Y14 and Y15 are absent.

In some embodiment Y5 is absent.

In some embodiments Y1, Y5, Y7, Y12, Y13, Y14 and Y15 are absent.

In some embodiments, the present invention provides a compound of formula (I'), wherein the compound comprises any one of the X'/Y' peptide sequence formula combinations presented in Table 2 below.

TABLE 2

Illustrative combinations of X' and Y' peptides of a compound of Formula (I')
Formula I' combinations

| Combination Number | X' Peptide Sequence Formula | Y' Peptide Sequence Formula |
| --- | --- | --- |
| 1 | Ia' | IIa' |
| 2 | Ia' | IIb' |
| 3 | Ia' | IIc' |
| 4 | Ia' | IId' |
| 5 | Ia' | IIe' |
| 6 | Ia' | IIf' |
| 7 | Ia' | IIg' |
| 8 | Ib' | IIa' |
| 9 | Ib' | IIb' |
| 10 | Ib' | IIc' |
| 11 | Ib' | IId' |
| 12 | Ib' | IIe' |
| 13 | Ib' | IIf' |
| 14 | Ib' | IIg' |
| 15 | Ic' | IIa' |
| 16 | Ic' | IIb' |
| 17 | Ic' | IIc' |
| 18 | Ic' | IId' |
| 19 | Ic' | IIe' |
| 20 | Ic' | IIf' |
| 21 | Ic' | IIg' |
| 22 | Id' | IIa' |
| 23 | Id' | IIb' |
| 24 | Id' | IIc' |
| 25 | Id' | IId' |
| 26 | Id' | IIe' |
| 27 | Id' | IIf' |
| 28 | Id' | IIg' |

In some embodiments, the invention provides peptides, which may be isolated and/or purified, comprising, consisting essentially of, or consisting of, the following structural formula:

$R^{1''}$-X''-Y''-$R^{2''}$    (I'') (SEQ ID NO:27)

or a pharmaceutically acceptable salt or solvate thereof, wherein $R^{1''}$ is hydrogen, an $C_1$-$C_6$ alkyl, $C_6$-$C_{12}$ aryl, $C_6$-$C_{12}$ aryl $C_1$-$C_6$ alkyl, $C_1$-$C_{20}$ alkanoyl (e.g., methyl, acetyl, formyl, benzoyl or trifluoroacetyl, isovaleric acid, isobutyric acid, octanoic acid, lauric acid and hexadecanoic acid), γ-Glu-hexadecanoic acid) or pGlu, appended to the N-terminus, and including PEGylated versions (e.g., PEG3 to PEG11), alone or as spacers of any of the foregoing;

$R^{2''}$ is —$NH_2$ or —OH;

X" is a peptide sequence having the formula (Ia")

X1-X2-X3-X4-X5-X6-X7-X8-X9-X10    (Ia") (SEQ ID NO:22)

wherein

X1 is Asp, Glu, Ala, Gly, Thr, Ida, pGlu, bhAsp, D-Asp, Tyr, Leu or absent;
X2 is Thr, Ala, Aib, D-Thr, Arg or absent;
X3 is His, Lys, Ala, D-His or Lys;
X4 is Phe, Ala, Dpa, bhPhe or D-Phe;
X5 is Pro, Glu, Ser, Gly, Arg, Lys, Val, Ala, D-Pro, bhPro, Sarc, Abu or absent;
X6 is Ile, Cys, Arg, Leu, Lys, His, Glu, D-Ile, D-Arg, D-Cys, Val, Ser or Ala;
X7 is Cys, Ile, Ala, Leu, Val, Ser, Phe, Dapa, D-Ile or D-Cys;
X8 is Ile, Lys, Arg, Ala, Gln, Phe, Glu, Asp, Tyr, Ser, Leu, Val, D-Ile, D-Lys, D-Arg, or Dapa;
X9 is Phe, Ala, Ile, Tyr, Lys, Arg, bhPhe or D-Phe; and
X10 is Lys, Phe or absent;
and provided that if Y" is absent, X7 is Ile;
wherein said compound of formula I" is optionally PEGylated on $R^{1''}$, X", or Y"; and
wherein when said compound of formula I" comprises two or more cysteine residues, at least two of said cysteine residues being linked via a disulfide bond.

In some embodiments, Y" is absent.

In some embodiments, $R^{1'''}$ is hydrogen, isovaleric acid, isobutyric acid or acetyl.

In some embodiments of the compound of formula (I"), X" is a peptide sequence according to formula (Ia"), wherein
X1 is Asp, Ala, Ida, pGlu, bhAsp, Leu, D-Asp or absent;
X2 is Thr, Ala, or D-Thr;
X3 is His, Lys, or D-His;
X4 is Phe, Ala, or Dpa;
X5 is Pro, Gly, Arg, Lys, Ala, D-Pro or bhPro;
X6 is Ile, Cys, Arg, Lys, D-Ile or D-Cys;
X7 is Cys, Ile, Leu, Val, Phe, D-Ile or D-Cys;
X8 is Ile, Arg, Phe, Gln, Lys, Glu, Val, Leu or D-Ile;
X9 is Phe or bhPhe; and
X10 is Lys or absent.

In some embodiments of the compound of formula (I"), X" is a peptide sequence having the formula (Ib")

X1-Thr-His-X4-X5-X6-X7-X8-Phe-X10    (Ib") (SEQ ID NO:23)

wherein
X1 is Asp, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile, Lys, Glu, Phe, Gln or Arg; and
X10 is Lys, Phe or absent.

In some embodiments of the compound of formula (I"), X" is a peptide sequence having the formula (Ic")

X1-Thr-His-X4-X5-Cys-Ile-X8-Phe-X10    (Ic") (SEQ ID NO:24)

wherein
X1 is Asp, Ida, pGlu, bhAsp or absent;
X4 is Phe or Dpa;
X5 is Pro or bhPro;
X8 is Ile, Lys, Glu, Phe, Gln or Arg; and
X10 is Lys or absent.

In some embodiments of the compound of formula (I"), X" is a peptide sequence having the formula (Id")

X1-Thr-His-Phe-X5-Cys-Ile-X8-Phe-X10    (Id") (SEQ ID NO:4)

wherein
X1 is Asp, Glu or Ida;
X4 is Phe;
X5 is Pro or bhPro;
X8 is Ile, Lys, or Phe; and
X10 is absent.

In some embodiments of the compound of formula (I"), Y" is a peptide having the formula (IIa")

Y1-Y2-Y3-Y4-Y5-Y6-Y7-Y8-Cys-Y10    (IIa") (SEQ ID NO:25)

wherein
Y1 is Gly, Ala, Lys, Pro or D-Pro;
Y2 is Pro, Ala or Gly;
Y3 is Arg, Ala, Lys or Trp;
Y4 is Ser, Gly or Ala;
Y5 is Lys, Met, Arg or Ala;
Y6 is Gly, Arg or Ala;
Y7 is Trp Ala or absent;
Y8 is Val, Thr, Lys, Ala, Glu or absent; and
Y10 is Met, Lys or absent.

In some embodiments of the compound of formula (I"), Y" is a peptide sequence according to formula (IIa") (SEQ ID NO:25)
wherein
Y1 is Gly, Glu, Val, or Lys
Y2 is Pro
Y3 is Arg or Lys;
Y4 is Ser
Y5 is Arg or Lys;
Y6 is Gly, Ser, Lys, Ile or Arg
Y7 is Trp or absent
Y8 is Val, Thr, Asp, Glu or absent;
Y10 is Lys or absent In some embodiments of the compound of formula (I"), Y" is a peptide sequence according to formula (IIa") (SEQ ID NO:25)
wherein
Y1 is Glu or Lys
Y2 is Pro
Y3 is Arg or Lys;
Y4 is Ser
Y5 is Arg or Lys;
Y6 is Gly, Ser, Lys, Ile or Arg;
Y7 is Trp or absent;
Y8 is Val or absent;
Y10 is Lys or absent In some embodiments of the compound of formula (I"), Y" is a peptide sequence according to formula (IIa") (SEQ ID NO:25)
wherein
Y1 is Gly, Pro or D-Pro;
Y2 is Pro or Gly;
Y3 is Arg or Lys;
Y4 is Ser;
Y5 is Lys;
Y6 is Gly;
Y7 is Trp;
Y8 is Val or Thr; and
Y10 is Met, Lys or absent.

In some embodiments of the compound of formula (I"), Y" is a peptide sequence having the formula (IIb")

Y1-Y2-Y3-Ser-Lys-Gly-Trp-Y8-Cys-Y10     (IIb") (SEQ ID NO:26)

wherein
Y1 is Gly, Pro or D-Pro;
Y2 is Pro or Gly;
Y3 is Arg or Lys;
Y8 is Val or Thr; and
Y10 is Met, Lys or absent.

In some embodiments, the present invention provides a compound of formula (I"), wherein the compound comprises any one of the X"/Y" peptide sequence formula combinations presented in Table 3 below.

TABLE 3

Illustrative combinations of X" and Y" peptides of a compound of Formula (I")
Formula I" combinations

| Combination Number | X" Peptide Sequence Formula | Y" Peptide Sequence Formula |
|---|---|---|
| 1 | Ia" | IIa" |
| 2 | Ia" | IIb" |
| 3 | Ib" | IIa" |
| 4 | Ib" | IIb" |
| 5 | Ic" | IIa" |
| 6 | Ic" | IIb" |
| 7 | Id" | IIa" |
| 8 | Id" | IIb" |

In some embodiments the peptide of formula (I") comprises at least three, at least four, at least five, at least six, at least seven, at least eight, at least nine, or at least ten Y residues in Y". In some embodiments, Y1 to Y3 are present and Y4 to Y10 are absent. In some embodiments Y5 is absent. In some embodiments Y1, Y5, and Y7 are absent. In some embodiments, Y8 is absent. In some embodiments, Y3 is absent.

In some embodiments, the present invention provides a compound of formula (I), (I'), or (I"), as described herein, each respectively comprising an X, X', or X" peptide sequence, according to the present disclosure, wherein X7 is Leu. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb", as described herein.

In some embodiments, the present invention provides a compound of formula (I), (I'), or (I"), as described herein, each respectively comprising an X, X', or X" peptide sequence, according to the present disclosure, wherein X7 is Val. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb", as described herein.

In some embodiments, the present invention provides a compound of formula (I), (I'), or (I"), as described herein, each respectively comprising an X, X', or X" peptide sequence, according to the present disclosure, wherein X6 is Cys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X7 is Cys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or lib', as described herein.

In some embodiments, the present invention provides a compound of formula (I), (I'), or (I"), as described herein, each respectively comprising an X, X', or X" peptide sequence, according to the present disclosure, wherein X6 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or lib', as described herein.

In some embodiments, the present invention provides a compound of formula (I), (I'), or (I"), as described herein, each respectively comprising an X, X', or X" peptide sequence, according to the present disclosure, wherein X7 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb", as described herein.

In some embodiments, the present invention provides a compound of formula (I), (I'), or (I"), as described herein, each respectively comprising an X, X', or X" peptide sequence, according to the present disclosure, wherein X8 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or lib', as described herein.

In some embodiments, the present invention provides a compound of formula (I), (I'), or (I"), as described herein, each respectively comprising an X, X', or X" peptide sequence, according to the present disclosure, wherein X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X6 is Cys and X7 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf′, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X6 is Cys and X8 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf′, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X6 is Cys, X7 is Ile, and X8 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf′, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X6 is Ile and X7 is Cys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf′, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X7 is Cys and X8 is Ile. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf′, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X6 is Ile, X7 is Cys, and X8 is Ile.

In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf′, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X6 is Cys and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf′, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X6 is Cys, X7 is Ile, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf′, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X6 is Cys and C7 is Leu. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf′, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X6 is Cys and C7 is Val. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa′, IIb′, IIc′, IId′, IIe′, IIf′, or IIg′, as described herein. In particular embodiments, formula (I″) comprises (i) Ia″, Ib″, Ic″, or Id″ and, optionally, (ii) IIa″ or IIb′, as described herein.

In some embodiments, the present invention provides a compound of formula (I), (I′), or (I″), as described herein, each respectively comprising an X, X′, or X″ peptide sequence, according to the present disclosure, wherein X7 is Ile and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I′) comprises (a) Ia′, Ib′, Ic′, or Id′ and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X7 is Leu and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X7 is Val and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Leu and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Ile, Leu, or Val. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is ASP or IDA, X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp or IDA, X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X2 is Thr, X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X3 is His, X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X4 is Phe, X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X5 is Pro, X6 is Cys, X7 is Ile, Leu, or Val, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Ile, Leu, or Val, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X2 is Thr, X6 is Cys, X7 is Ile and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X3 is His, X6 is Cys, X7 is Ile, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X4 is Phe, X6 is Cys, X7 Ile, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X5 is Pro, X6 is Cys, X7 Ile, and X8 is Lys. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X5 is Pro, X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X4 is Phe, X5 is Pro, X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X3 is His, X4 is Phe, X5 is Pro, X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X2 is Thr, X3 is His, X4 is Phe, X5 is Pro, X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp or IDA, X2 is Thr, X3 is His, X4 is Phe, X5 is Pro, X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, lie, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp or IDA, X2 is Thr, X3 is His, X4 is Phe, X5 is Pro, X6 is Cys, X7 is Ile, Leu, or Val, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp, X2 is Thr, X3 is His, X4 is Phe, X5 is Pro X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is IDA, X2 is Thr, X3 is His, X4 is Phe, X5 is Pro, X6 is Cys, X7 is Ile, X8 is Lys, and X9 is Phe. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, wherein the compound comprises an $R^1$ that is isovaleric acid.

In some embodiments, the present invention provides a compound of formula (I), (I'), or (I"), as described herein, each respectively comprising an X, X', or X" peptide sequence, according to the present disclosure, wherein X1 is Asp or IDA, X2 is Thr, X3 is His, X4 is Phe, X5 is Pro, X6 is Cys, X7 is Ile, Leu, or Val, X8 is Lys, and X9 is Phe; wherein said peptide further comprises an $R^1$ that is isovaleric acid. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp, X2 is Thr, X3 is His, X4 is Phe, X5 is Pro, X6 is Cys, X7 is Ile, Leu, or Val, and X8 is Lys; wherein said peptide further comprises an $R^1$ that is isovaleric acid. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp, X2 is Thr, X3 is His, X4 is Phe, X5 is Pro, X6 is Cys, X7 is Ile, Leu, or Val, X8 is Lys, and X9 is Phe; wherein said peptide further comprises an R group that is isovaleric acid. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, each respectively comprising an X, X', or X" peptide sequence, according to the present disclosure, wherein X1 is Asp, X2 is Thr, X3 is His, X4 is Phe, X5 is Pro, X6 is Cys, X7 is Ile, X8 is Lys, and X9 is Phe; wherein said peptide further comprises an R group that is isovaleric acid. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In some embodiments, the present invention provides a compound of formula (I), (I'), or (I"), as described herein, wherein the compound comprises a peptide sequence that is 85% or higher (e.g., 85%, 90%, 91%, 92%, 93%, 94%, 95%, 96%, 97%, 98%, 99%, or 99.5%) homologous to an amino acid sequence set forth in any one of Tables 5-15. In particular embodiments, formula (I) comprises (a) Ia, Ib, Ic, or Id and, optionally, (b) IIa, IIb, IIc, IId, IIe, IIf, or IIg, as described herein. In particular embodiments, formula (I') comprises (a) Ia', Ib', Ic', or Id' and, optionally, (b) IIa', IIb', IIc', IId', IIe', IIf', or IIg', as described herein. In particular embodiments, formula (I") comprises (i) Ia", Ib", Ic", or Id" and, optionally, (ii) IIa" or IIb', as described herein.

In certain embodiments, a peptide or a peptide dimer of the present invention comprises any one of the compounds shown in any one of Tables 5-15.

In certain embodiments, a peptide or a peptide dimer of the present invention comprises any one of the amino acid sequences provided as SEQ ID NOS: 1-334 and 338-375, or as shown in any one of Tables 5-15

In certain embodiments, a peptide or a peptide dimer of the present invention comprises an amino acid sequence set forth in any one of Tables 5-15.

In certain embodiments, a peptide or a peptide dimer of the present invention has a structure shown in any one of Tables 5-15, e.g., Tables 7 or 12-15. In one certain embodiment, a peptide or a peptide dimer of the present invention comprises an amino acid sequence set forth in any one of Tables 5-15, e.g., Tables 7 or 12-15. In some embodiments, a peptide of the present invention comprises an amino acid sequence having at least about 85% identical or at least about 90%, 95%, 97%, 98%, 99% identical to any amino acid sequence set forth in any one of Tables 5-15, e.g., Tables 7 or 12-15, or any one of SEQ ID NOS: 1-334 and 338-375. In one certain embodiment, a peptide or a peptide dimer of the present invention comprises an amino acid sequence having at least about 85% identical or at least about 90%, 95%, 97%, 98%, 99% identical to any amino acid sequence set forth in Table 7 or any one of Tables 5-15.

It is understood that in the context of the invention, a peptide or peptide dimer comprising a peptide sequence shown in one of the accompanying Tables or sequence listing may have certain minor alterations to one or more amino acid residues of the peptide sequence, as compared to the native amino acid, yet still be considered to comprises the peptide sequence shown in the Tables or sequence listing. For example, one or more side chains of one or more amino acid residues present in the peptide or peptide dimer may be slightly altered due to the attachment of a linker or dimerization via cysteine residues, or an N-terminal or C-terminal amino acid may be amidated.

In some embodiments, a peptide or a peptide dimer of the present invention exhibits hepcidin activity. In some embodiments, a peptide or a peptide dimer of the present invention exhibits at least about 50%, 60%, 70%, 80%, 90%, 95%, 97%, 98%, 99%, greater than 99%, greater than 100%, greater than 110%, greater than 120%, greater than 150%, greater than 200% greater than 500%, or greater than 1000% of the activity of a reference hepcidin, (e.g., any one of the hepcidin reference compounds provided in Table 4). In some embodiments, the activity is an in vitro or an in vivo activity as described herein.

In some embodiments, a peptide or a peptide dimer of the present invention exhibits at least about 50%, 60%, 70%, 80%, 90%, 95%, 97%, 98%, 99%, or greater than 99% of the in vitro activity for inducing the degradation of human ferroportin protein as that of a reference hepcidin, (e.g., any one of the hepcidin reference compounds provided in Table 4), wherein the activity is measured according to the methods described herein (e.g., according to Example 2).

In some embodiments, a peptide or a peptide dimer of the present invention exhibits at least about 50%, 60%, 70%, 80%, 90%, 95%, 97%, 98%, 99%, or greater than 99% of the in vivo activity for inducing the reduction of free plasma iron in an individual as does a reference hepcidin, (e.g., any one of the hepcidin reference compounds provided in Table 4), wherein the activity is measured according to the methods described herein (e.g., according to Example 8).

In some embodiments, a peptide or a peptide dimer of the present invention exhibits increased hepcidin activity as compared to a hepcidin reference peptide, (e.g., any one of the hepcidin reference compounds provided in Table 4). In certain embodiments, a peptide or a peptide dimer of the present invention exhibits 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, 500%, 700%, or 1000% greater activity than a reference hepcidin, (e.g., any one of the hepcidin reference compounds provided in Table 4). In some embodiments, a peptide or a peptide dimer of the present invention exhibits at least about 50%, 60%, 70%, 80%, 90%, 95%, 97%, 98%, 99%, or greater than 99% of the activity exhibited by a hepcidin reference compound. In some embodiments, the activity is an in vitro or an in vivo activity, e.g., an in vivo or an in vitro activity described herein. In certain embodiments, a peptide or a peptide dimer of the present invention exhibits 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, 500%, 700%, or 1000% greater activity than a reference hepcidin, (e.g., any one of the hepcidin reference compounds provided in Table 4), wherein the activity is an in vitro activity for inducing the degradation of ferropontin, e.g., as measured according to Example 2; or wherein the activity is an in vivo activity for reducing free plasma iron, e.g., as measured according to Example 8.

In some embodiments, a peptide or a peptide dimer of the present invention binds ferroportin, e.g., human ferroportin. In some embodiments, a peptide or a peptide dimer of the present invention exhibits at least about 50%, 60%, 70%, 80%, 90%, 95%, 97%, 98%, 99%, or greater than 99% of the ferroportin binding ability that is exhibited by a reference hepcidin (e.g., any one of the hepcidin reference compounds provided in Table 4). In some embodiments, a peptide or a peptide dimer of the present invention has a lower $IC_{50}$ (i.e., higher binding affinity) for binding to ferroportin, (e.g., human ferroportin) compared to a reference hepcidin, (e.g., any one of the hepcidin reference compounds provided in Table 4). In some embodiments, the peptide of the present invention has an $IC_{50}$ in a ferroportin competitive binding assay which is at least about 10%, 20%, 30%, 40%, 50%, 60%, 70%, 80%, 90%, 100%, 200%, 300%, 400%, 500%, 700%, or 1000% lower than a reference hepcidin, (e.g., any one of the hepcidin reference compounds provided in Table 4).

In some embodiments, the present invention provides a compound of formula I, I', or I", as described herein, wherein the peptide exhibits increased stability (e.g., as measured by half-life, rate of protein degradation) as compared to a reference hepcidin, (e.g., any one of the hepcidin reference compounds provided in Table 4). In some embodiments, the present invention provides a dimer of such a compound, and in certain embodiments the dimer is a homodimer. In certain embodiments, the stability of a peptide or a peptide dimer of the present invention is increased at least about 1.5, 2, 3, 4, 5, 6, 7, 8, 9, 10, 11, 12, 13, 14, 15, 16, 17, 18, 19, 20, 30, 40, 50, 60, 70, 80, 90, 100, 120, 140, 160, 180, or 200-fold greater or at least about 10%, 20%, 30%, 40%, 50%, 60%, 70%, 80%, 90%, 100%, 200%, 300%, 400%, or 500% greater than a reference hepcidin, (e.g., any one of the hepcidin reference compounds provided in Table 4). In some embodiments, the stability is a stability that is described herein. In some embodiments, the stability is a plasma stability, e.g., as optionally measured according to the method described in Example 7.

In particular embodiments, the present invention provides a compound of formula I, I', or I", as described herein, wherein the peptide exhibits a longer half-life than a reference hepcidin, (e.g., any one of the hepcidin reference compounds provided in Table 4). In some embodiments, the present invention provides a dimer of such a compound, and in certain embodiments the dimer is a homodimer. In particular embodiments, a peptide or a peptide dimer of the present invention has a half-life under a given set of conditions (e.g., temperature, pH) of at least about 5 minutes, at least about 10 minutes, at least about 20 minutes, at least about 30 minutes, at least about 45 minutes, at least about 1 hour, at least about 2 hour, at least about 3 hours, at least about 4 hours, at least about 5 hours, at least about 6 hours, at least about 12 hours, at least about 18 hours, at least about 1 day, at least about 2 days, at least about 4 days, at least about 7 days, at least about 10 days, at least about two weeks, at least about three weeks, at least about 1 month, at least about 2 months, at least about 3 months, or more, or any intervening half-life or range in between, about 5 minutes, about 10 minutes, about 20 minutes, about 30 minutes, about 45 minutes, about 1 hour, about 2 hour, about 3 hours, about 4 hours, about 5 hours, about 6 hours, about 12 hours, about 18 hours, about 1 day, about 2 days, about 4 days, about 7 days, about 10 days, about two weeks, about three weeks, about 1 month, about 2 months, about 3 months, or more, or any intervening half-life or range in between. In some embodiments, the half life of a peptide or a peptide dimer of the present invention is extended due to its conjugation to one or more lipophilic substituent, e.g., any of the lipophilic substituents disclosed herein. In some embodiments, the half life of a peptide or a peptide dimer of the present invention is extended due to its conjugation to one or more polymeric moieties, e.g., any of the polymeric moieties disclosed herein. In certain embodiments, the temperature is about 25° C., about 4° C., or about 37° C., and the pH is a physiological pH, or a pH about 7.4.

In some embodiments, the half-life is measured in vitro using any suitable method known in the art, e.g., in some embodiments, the stability of a peptide or a peptide dimer of the present invention is determined by incubating the peptide or the peptide dimer with pre-warmed human serum (Sigma) at 37° C. Samples are taken at various time points, typically up to 24 hours, and the stability of the sample is analyzed by separating the peptide or peptide dimer from the serum proteins and then analyzing for the presence of the peptide or peptide dimer of interest using LC-MS.

In some embodiments, the stability of the peptide is measured in vivo using any suitable method known in the art, e.g., in some embodiments, the stability of a peptide or a peptide dimer is determined in vivo by administering the peptide or peptide dimer to a subject such as a human or any mammal (e.g., mouse) and then samples are taken from the subject via blood draw at various time points, typically up to 24 hours. Samples are then analyzed as described above in regard to the in vitro method of measuring half-life. In some embodiments, in vivo stability of a peptide or a peptide dimer of the present invention is determined via the method disclosed in Example 7.

In some embodiments, the present invention provides a compound of formula I, I', or I", as described herein, or a dimer thereof, wherein the peptide or the dimer exhibits improved solubility or improved aggregation characteristics as compared to a reference hepcidin, (e.g., any one of the hepcidin reference compounds provided in Table 4). Solubility may be determined via any suitable method known in the art. In some embodiments, suitable methods known in the art for determining solubility include incubating peptides in various buffers (Acetate pH4.0, Acetate pH5.0, Phos/Citrate pH5.0, Phos Citrate pH6.0, Phos pH 6.0, Phos pH 7.0, Phos pH7.5, Strong PBS pH 7.5, Tris pH7.5, Tris pH 8.0, Glycine pH 9.0, Water, Acetic acid (pH 5.0 and other known in the art) and testing for aggregation or solubility using standard techniques. These include, but are not limited to, visual precipitation, dynamic light scattering, Circular Dichroism and fluorescent dyes to measure surface hydrophobicity, and detect aggregation or fibrillation, for example. In some embodiments, improved solubility means the peptide is more soluble in a given liquid than is a reference hepcidin (e.g., any one of the hepcidin reference compounds provided in Table 4).

In some embodiments, the present invention provides a compound of formula I, I', or I", as described herein, or a dimer thereof, wherein the peptide or the dimer exhibits less degradation (i.e., more degradation stability), e.g., greater than or about 10% less, greater than or about 20% less, greater than or about 30% less, greater than or about 40 less, or greater than or about 50% less than a reference hepcidin (e.g., any one of the hepcidin reference compounds provided in Table 4). In some embodiments, degradation stability is determined via any suitable method known in the art. In some embodiments, suitable methods known in the art for determining degradation stability include the method described in Hawe et al J Pharm Sci, VOL. 101, NO. 3, 2012, p 895-913, incorporated herein in its entirety. Such methods are in some embodiments used to select potent sequences with enhanced shelf lifes.

In some embodiments, the present invention provides compositions and medicaments comprising at least one peptide or peptide dimer as disclosed herein. In some embodiments, the present invention provides a method of manufacturing medicaments comprising at least one peptide or peptide dimer as disclosed herein for the treatment of diseases of iron metabolism, such as iron overload diseases. In some embodiments, the present invention provides a method of manufacturing medicaments comprising at least one peptide or pepitde dimer as disclosed herein for the treatment of diabetes (Type I or Type II), insulin resistance, or glucose intolerance. Also provided are methods of treating a disease of iron metabolism in a subject, such as a mammalian subject, and preferably a human subject, comprising administering at least one peptide, peptide dimer, or composition as disclosed herein to the subject. In some embodiments, the peptide, peptide dimer, or the composition is administered in a therapeutically effective amount. Also provided are methods of treating diabetes (Type I or Type II), insulin resistance, or glucose intolerance in a subject, such as a mammalian subject, and preferably a human subject, comprising administering at least one peptide, peptide dimer, or composition as disclosed herein to the subject. In some embodiments, the peptide, peptide dimer, or composition is administered in a therapeutically effective amount.

In some embodiments, thepeptide, or peptide dimer of this invention is synthetically manufactured. In other embodiments, the peptide or peptide dimer of this invention is recombinantly manufactured.

In some embodiments, the invention provides a process for manufacturing a compound, peptide, peptide analogue, peptide dimer, or pharmaceutical composition as disclosed herein.

In some embodiments, the invention provides a device comprising at least one peptide, peptide analogue, or peptide dimer of the present invention, or pharmaceutically acceptable salt or solvate thereof for delivery of the peptide analogue or the peptide dimer to a subject.

In some embodiments, the present invention provides methods of binding a ferroportin or inducing ferroportin internalization and degradation which comprises contacting the ferroportin with at least one peptide or peptide analogue, peptide dimer, or composition as disclosed herein.

In some embodiments, the present invention provides kits comprising at least one peptide, peptide analogue, peptide dimer, or composition as disclosed herein packaged together with a reagent, a device, instructional material, or a combination thereof.

In some embodiments, the present invention provides complexes which comprise at least one peptide or peptide dimer as disclosed herein bound to a ferroportin, preferably a human ferroportin, or an antibody, such as an antibody which specifically binds a peptide or a peptide dimer as disclosed herein, Hep25, or a combination thereof.

In some embodiments, the compound has a measurement (e.g., an EC50) of less than 500 nM within the Fpn internalization assay. As a skilled person will realize, the function of the peptide is dependent on the tertiary structure of the peptide and the binding surface presented. It is then possible to make minor changes of the sequence that do not affect the fold or are not on the binding surface and maintain function. In other embodiments, the compound of the invention is a peptide or peptidomimetic compound, or a dimer thereof having 85% or higher (e.g., 85%, 90%, 91%, 92%, 93%, 94%, 95%, 96%, 97%, 98%, 99%, or 99.5%) identity or homology to an amino acid sequence of any compound of formula I, I', or I" that exhibits an activity, or lessens a symptom of a disease or indication for which hepcidin is involved.

In some embodiments, the peptide, peptide analogue, or dimer thereof of the invention may comprise functional fragments or variants thereof that have at most 10, 9, 8, 7, 6, 5, 4, 3, 2, or 1 amino acid substitutions compared to one or more of the specific sequences recited below.

In addition to the methods disclosed herein in Example 1, the peptides and the peptide dimers of the present invention may be produced using methods known in the art including chemical synthesis, biosynthesis or in vitro synthesis using recombinant DNA methods, and solid phase synthesis. See e.g. Kelly & Winkler (1990) Genetic Engineering Principles and Methods, vol. 12, J. K. Setlow ed., Plenum Press, NY, pp. 1-19; Merrifield (1964) J Amer Chem Soc 85:2149; Houghten (1985) PNAS USA 82:5131-5135; and Stewart & Young (1984) Solid Phase Peptide Synthesis, 2ed. Pierce, Rockford, Ill., which are herein incorporated by reference. The peptides of the present invention may be purified using protein purification techniques known in the art such as reverse phase high-performance liquid chromatography (HPLC), ion-exchange or immunoaffinity chromatography, filtration or size exclusion, or electrophoresis. See Olsnes, S. and A. Pihl (1973) Biochem. 12(16):3121-3126; and Scopes (1982) Protein Purification, Springer-Verlag, NY, which are herein incorporated by reference. Alternatively, the peptides of the present invention may be made by recombinant DNA techniques known in the art. Thus, polynucleotides that encode the polypeptides of the present invention are contemplated herein. In preferred embodiments, the polynucleotides are isolated. As used herein "isolated polynucleotides" refers to polynucleotides that are in an environment different from that in which the polynucleotide naturally occurs.

In certain embodiments, peptides of the present invention bind ferroportin, preferably human ferroportin. Preferred peptides of the present invention specifically bind human ferroportin. As used herein, "specifically binds" refers to a specific binding agent's preferential interaction with a given ligand over other agents in a sample. For example, a specific binding agent that specifically binds a given ligand, binds the given ligand, under suitable conditions, in an amount or a degree that is observable over that of any nonspecific interaction with other components in the sample. Suitable conditions are those that allow interaction between a given specific binding agent and a given ligand. These conditions include pH, temperature, concentration, solvent, time of incubation, and the like, and may differ among given specific binding agent and ligand pairs, but may be readily determined by those skilled in the art.

The peptides of the present invention that mimic the hepcidin activity of Hep25, the bioactive human 25-amino acid form, are herein referred to as "mini-hepcidins". As used herein, in certain embodiments, a compound having "hepcidin activity" means that the compound has the ability to lower plasma iron concentrations in subjects (e.g. mice or humans), when administered thereto (e.g. parenterally injected or orally administered), in a dose-dependent and time-dependent manner. See e.g. as demonstrated in Rivera et al. (2005), Blood 106:2196-9. In some embodiments, the peptides of the present invention lower the plasma iron concentration in a subject by at least about 1.2, 1.5, 2, 3, 4, 5, 6, 7, 8, 9, or 10-fold, or at least about 5%, 10%, 20%, 25%, 30%, 40%, 50%, 60%, 70%, 80%, 90%, or about 99%.

In some embodiments, the peptides of the present invention have in vitro activity as assayed by the ability to cause the internalization and degradation of ferroportin in a ferroportin-expressing cell line as taught in Nemeth et al. (2006) Blood 107:328-33. In vitro activity may be measured by the dose-dependent loss of fluorescence of cells engineered to display ferroportin fused to green fluorescent protein as in Nemeth et al. (2006) Blood 107:328-33. Aliquots of cells are incubated for 24 hours with graded concentrations of a reference preparation of Hep25 or a mini-hepcidin. As provided herein, the EC50 values are provided as the concentration of a given compound (e.g. peptide) that elicits 50% of the maximal loss of fluorescence generated by the reference Hep25 preparation. EC50 of Hep25 preparations in this assay range from 5 to 15 nM and preferred mini-hepcidins have EC50 values in in vitro activity assays of about 1,000 nM or less. In certain embodiments, a peptide of the present invention has an EC50 in an in vitro activity assay (e.g., as described in Nemeth et al. (2006) Blood 107:328-33 or Example 2 herein) of less than about any one of 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90, 100, 200 or 500 nM. In some embodiments, a peptide analogue or biotherapeutic composition has an $EC_{50}$ value of about 1 nM or less.

Other methods known in the art for calculating the hepcidin activity and in vitro activity of peptides according to the present invention may be used. For example, the in vitro activity of compounds may be measured by their ability to internalize cellular ferroportin, which is determined by immunohistochemistry or flow cytometry using antibodies which recognizes extracellular epitopes of ferroportin. Alternatively, the in vitro activity of compounds may be measured by their dose-dependent ability to inhibit the efflux of iron from ferroportin-expressing cells that are preloaded with radioisotopes or stable isotopes of iron, as in Nemeth et al. (2006) Blood 107:328-33.

Conjugation

The skilled person will be well aware of suitable techniques for preparing the compounds employed in the context of the invention. For examples of suitable chemistry, see, e.g., WO98/08871, WO00/55184, WO00/55119, Madsen et al (*J. Med. Chem.* 2007, 50, 6126-32), and Knudsen et al. 2000 (*J. Med Chem.* 43, 1664-1669).

The side chains of one or more amino acid residues (e.g. Lys residues) in a compound of the invention may be further conjugated (i.e. covalently attached) to a lipophilic substituent. The lipophilic substituent may be covalently bonded to an atom in the amino acid side chain, or alternatively may be conjugated to the amino acid side chain via one or more spacers. The amino acid(s) in question may be part of the peptide moiety X, or a part of the peptide moiety Y.

Without wishing to be bound by any particular theory, it is believed that the lipophilic substituent binds to albumin in the blood stream, thereby shielding the peptide analogue of the invention from enzymatic degradation, and thus enhancing its half-life. The spacer, when present, may provide spacing between the peptide analogue and the lipophilic substituent.

In certain embodiments, the lipophilic substituent may comprise a hydrocarbon chain having from 4 to 30 C atoms, for example at least 8 or 12 C atoms, and preferably 24 C atoms or fewer, or 20 C atoms or fewer. The hydrocarbon chain may be linear or branched and may be saturated or unsaturated. In certain embodiments, the hydrocarbon chain is substituted with a moiety which forms part of the attachment to the amino acid side chain or the spacer, for example an acyl group, a sulfonyl group, an N atom, an O atom or an S atom. In some embodiments, the hydrocarbon chain is substituted with an acyl group, and accordingly the hydrocarbon chain may form part of an alkanoyl group, for example palmitoyl, caproyl, lauroyl, myristoyl or stearoyl.

A lipophilic substituent may be conjugated to any amino acid side chain in a compound of the invention. In certain embodiment, the amino acid side chain includes a carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gin, His, Lys, Arg, Ser, Thr, Tyr, Trp, Cys or Dbu, Dpr or Orn. In certain embodiments, the lipophilic substituent is conjugated to Lys. An amino acid shown as Lys in any of the formulae provided herein may be replaced by, e.g., Dbu, Dpr or Orn where a lipophilic substituent is added.

In further embodiments of the present invention, alternatively or additionally, the side-chains of one or more amino acid residues in the compound of the invention may be conjugated to a polymeric moiety, for example, in order to increase solubility and/or half-life in vivo (e.g. in plasma) and/or bioavailability. Such modifications are also known to reduce clearance (e.g. renal clearance) of therapeutic proteins and peptides.

As used herein, "Polyethylene glycol" or "PEG" is a polyether compound of general formula H—(O—CH2-CH2)n-OH. PEGs are also known as polyethylene oxides (PEOs) or polyoxyethylenes (POEs), depending on their molecular weight PEO, PEE, or POG, as used herein, refers to an oligomer or polymer of ethylene oxide. The three names are chemically synonymous, but PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. Throughout this disclosure, the 3 names are used indistinguishably. PEGs are prepared by polymerization of ethylene oxide and are commercially available over a wide range of molecular weights from 300 g/mol to 10,000,000 g/mol. While PEG and PEO with different molecular weights find use in different applications, and have different physical properties (e.g. viscosity) due to chain length effects, their chemical properties are nearly identical. The polymeric moiety is preferably water-soluble (amphiphilic or hydrophilic), non-toxic, and pharmaceutically inert. Suitable polymeric moieties include polyethylene glycols (PEG), homo- or co-polymers of PEG, a monomethyl-substituted polymer of PEG (mPEG), or polyoxyethylene glycerol (POG). See, for example, Int. J. Hematology 68:1 (1998); Bioconjugate Chem. 6:150 (1995); and Crit. Rev. Therap. Drug Carrier Sys. 9:249 (1992). Also encompassed are peptides that are prepared for purpose of half life extension, for example, mono-activated, alkoxy-terminated polyalkylene oxides (POA's) such as mono-methoxy-terminated polyethyelene glycols (mPEG's); bis activated polyethylene oxides (glycols) or other PEG derivatives are also contemplated. Suitable polymers will vary substantially by weights ranging from about 70 to about 40,000 or from about 200 to about 40,000 are usually selected for the purposes of the present invention. Molecular weights from 200 to 2,000 are preferred and 200 to 500 are particularly preferred. There are different forms of PEG are also available, depending on the initiator used for the polymerization process—the most common initiator is a monofunctional methyl ether PEG, or methoxypoly(ethylene glycol), abbreviated mPEG.

As used herein, lower-molecular-weight PEGs are also available as pure oligomers, referred to as monodisperse, uniform, or discrete. These are used in certain embodiments of the present invention.

PEGs are also available with different geometries: Branched PEGs have three to ten PEG chains emanating from a central core group; Star PEGs have 10 to 100 PEG chains emanating from a central core group; Comb PEGs have multiple PEG chains normally grafted onto a polymer backbone. PEGs can also be linear. The numbers that are often included in the names of PEGs indicate their average molecular weights (e.g. a PEG with n=9 would have an average molecular weight of approximately 400 daltons, and would be labeled PEG 400.

As used herein, "PEGylation" is the act of covalently coupling a PEG structure to the peptide of the invention, which is then referred to as a "PEGylated peptide". In some embodiments, the X moiety of formula I, the Y moiety of formula I, the $R^1$ moiety of formula I, the $R^2$ moiety of formula I, or any combination thereof, is PEGylated. In some embodiments, the X' moiety of formula I', the Y' moiety of formula I', the $R^{1'}$ moiety of formula I', the $R^{2'}$ moiety of formula I', or any combination thereof, is PEGylated. In some embodiments, the X" moiety of formula I", the Y" moiety of formula I", the $R^{1"}$ moiety of formula I", the $R^{2"}$ moiety of formula I", or any combination thereof, is PEGylated. In some embodiments, one or more side chains of an amino acid in the peptide of formula I, formula I', or formula I" is PEGylated. In certain embodiments, the PEG of the PEGylated side chain is a PEG with a molecular weight from about 200 to about 40,000. In some embodiments, a spacer of a peptide of formula I, formula I', or formula I" is PEGylated. In certain embodiments, the PEG of a PEGylated spacer is PEG3, PEG4, PEG5, PEG6, PEG7, PEG8, PEG9, PEG10, or PEG11. In certain embodiments, the PEG of a PEGylated spacer is PEG3 or PEG8. In certain embodiments, the PEG of a PEGylated spacer is PEG3 or PEG8.

Other suitable polymeric moieties include poly-amino acids such as poly-lysine, poly-aspartic acid and poly-glutamic acid (see for example Gombotz, et al. (1995), Bioconjugate Chem., vol. 6: 332-351; Hudecz, et al. (1992), Bioconjugate Chem., vol. 3, 49-57 and Tsukada, et al. (1984), J. Natl. Cancer Inst., vol. 73: 721-729. The polymeric moiety may be straight-chain or branched. In some embodiments, it has a molecular weight of 500-40,000 Da, for example 500-10,000 Da, 1000-5000 Da, 10,000-20,000 Da, or 20,000-40,000 Da.

In some embodiments, a compound of the invention may comprise two or more such polymeric moieties, in which case the total molecular weight of all such moieties will generally fall within the ranges provided above.

In some embodiments, the polymeric moiety may be coupled (by covalent linkage) to an amino, carboxyl or thiol group of an amino acid side chain. Preferred examples are the thiol group of Cys residues and the epsilon amino group of Lys residues, and the carboxyl groups of Asp and Glu residues may also be involved.

The skilled worker will be well aware of suitable techniques which can be used to perform the coupling reaction. For example, a PEG moiety bearing a methoxy group can be coupled to a Cys thiol group by a maleimido linkage using reagents commercially available from Nektar Therapeutics AL. See also WO 2008/101017, and the references cited above, for details of suitable chemistry. A maleimide-functionalised PEG may also be conjugated to the side-chain sulfhydryl group of a Cys residue.

As used herein, disulfide bond oxidation can occur within a single step or is a two step process. As used herein, for a single oxidation step the trityl protecting group is often employed during assembly, allowing deprotection during cleavage, followed by solution oxidation. When a second disulfide bond is required one has the option of native or selective oxidation. For selective oxidation requiring orthogonal protecting groups Acm and Trityl is used as the protecting groups for cysteine. Cleavage results in the removal of one protecting pair of cysteine allowing oxidation of this pair. The second oxidative deprotection step of the cysteine protected Acm group is then performed. For native oxidation the trityl protecting group is used for all cysteines, allowing for natural folding of the peptide.

A skilled worker will be well aware of suitable techniques which can be used to perform the oxidation step.

Peptide Dimers

The term "dimer," as in a peptide dimer, refers to compounds in which two peptide chains are linked, either identical (homo-dimer) or non-identical (hetero-dimer) through a linking moiety. A cysteine dimer is then two peptides chains linked through the amino acid cysteine disulfide bond.

In some embodiments, the peptides of the present invention may be active in a dimer conformation or a hetero-dimer conformation, in particular when free cysteine residues are present in the peptide. In certain embodiments, this occurs either as a synthesized dimer or, in particular, when a free cysteine monomer peptide is present and under oxidizing conditions, dimerizes. In some embodiments, the dimer is a homodimer. In other embodiments, the dimer is a heterodimer.

In certain embodiments, a peptide analogue of the present invention is a peptide dimer comprising a peptide of the invention. In particular embodiments, the peptide dimers comprise a peptide of formula I, a peptide of formula I', or a peptide of formula I". In particular embodiments, the peptide dimers comprise two peptides of formula I, two peptides of formula I', or two peptides of formula I". In certain embodiments, the peptide dimers are homodimers. In particular embodiments wherein the peptide dimer comprises a peptide of formula I, X has the formula Ia, Ib, Ic, or Id. In particular embodiments wherein the peptide dimer comprises a peptide of formula I, Y has the formula IIa, IIb, IIc, IId, IIe, IIf, or IIg. In particular embodiments wherein the peptide dimer comprises a peptide of formula I', X' has the formula Ia', Ib', Ic', or Id'. In particular embodiments wherein the peptide dimer comprises a peptide of formula I', Y' has the formula IIa', IIb', IIc', IId', IIe', IIf', or IIg'. In particular embodiments wherein the peptide dimer comprises a peptide of formula I", X" has the formula Ia", Ib", Ic", or Id". In particular embodiments wherein the peptide dimer comprises a peptide of formula I", Y" has the formula IIa" or IIb".

In some embodiments, the dimer is between two X groups of formula I, two X' groups of formula I', or two X" groups of formula I", e.g., the two peptides of the dimer are linked through two X groups of formula I, two X' groups of formula I', or two X" groups of formula I". In some embodiments, the dimer comprises two X groups of formula I, two X' groups of formula I', or two X" groups of formula I". In some embodiments, the two X groups, X' groups, or X" groups in the dimers comprise the same amino acid residues. In some embodiments, the two X groups, X' groups, or X" groups in the dimers comprise different amino acid residues (i.e., each amino acid in each of the two X, X' or X" groups is independently selected). In some embodiments, the dimer is between two Y groups of formula I, two Y groups of formula I', or two Y" groups of formula I", e.g., the two peptides of the dimer are linked through two Y groups of formula I, two Y' groups of formula I', or two Y" groups of formula I". In some embodiments, the dimer comprises two Y groups of formula I, two Y groups of formula I', or two Y" groups of formula I". In some embodiments, the two Y groups, Y' groups, or Y" groups in the dimer comprise the same amino acid residues. In some embodiments, the two Y groups, Y' groups or Y" groups in the dimer comprise different amino acid residues (i.e., each amino acid in each of the Y, Y' or Y" groups is independently selected). In some embodiments, a dimer is between an X group of formula I and a Y group of formula I (e.g., the two peptides of the dimer are linked through an X group of formula I and a Y group of formula I), an X' group of formula I' and a Y' group of formula I (e.g., the two peptides of the dimer are linked through an X' group of formula I' and a Y' group of formula I'), or an X" group of formula I" and a Y" group of formula I" (e.g., the two peptides of the dimer are linked through an X" group of formula I" and a Y" group of formula I").

In particular embodiments, a peptide dimer of the present invention comprises a peptide comprising: a peptide sequence set forth in any one of Tables 5-15 or SEQ ID NOs: 1-334 and 338-375; or a peptide sequence having at least 85%, at least 90%, at least 91%, at least 92%, at least 93%, at least 94%, at least 95%, at least 96%, at least 97%, at least 98%, or at least 99% identity to a peptide sequence set forth in any one of Tables 5-15 or SEQ ID NOs: 1-334 and 338-375. In particular embodiments, a peptide dimer of the present invention is a homodimer comprising two peptides, each comprising: a peptide sequence set forth in any one of Tables 5-15 or SEQ ID NOs: 1-334 and 338-375; or a peptide sequence having at least 85%, at least 90%, at least 91%, at least 92%, at least 93%, at least 94%, at least 95%, at least 96%, at least 97%, at least 98%, or at least 99% identity to a peptide sequence set forth in any one of Tables 5-15 or SEQ ID NOs: 1-334 and 338-375. In particular embodiments, a peptide dimer of the present invention comprises a compound set forth in any one of Tables 5-15. In particular embodiments, a peptide dimer of the present invention is a homodimer comprising two peptides, each comprising a compound set forth in any one of Tables 5-15.

In certain embodiments, the peptide dimers comprise two peptides dimerized via a disulfide linkage between a cysteine residue present in one of the peptides and a cysteine residue present in the second peptide, i.e., an intermolecular disulfide bond between these cysteine residues.

In certain embodiments, the peptide dimers comprise two peptides dimerized by covalent attachment of each peptide to a common linking moeity, i.e., a linker. A variety of linkers suitable for dimerizing two peptides are known in the art and commercially available, including, e.g., diethylene glycol (DIG), iminodiacetic acid (IDA), f3-Ala-IDA, PEG13, and PEG25. In particular embodiments, peptide dimers include any of the linking moieties shown below or have any of the structures shown below. In particular embodiments, peptide dimers are dimerized via both a linking moiety and a disulphide bond between a cysteine residue in one peptide and a cysteine residue in the other peptide of the dimer.

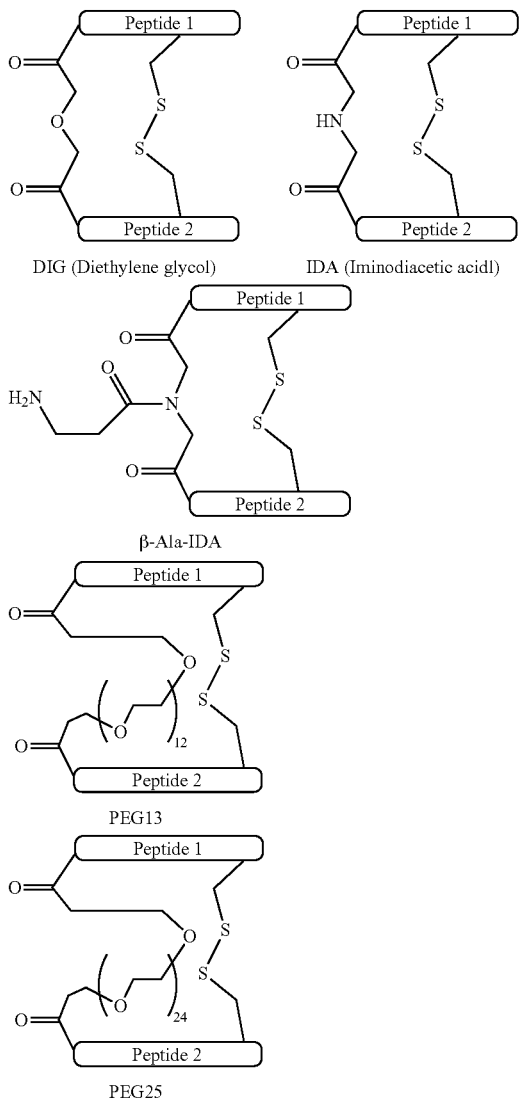

In certain embodiments, the linking moiety comprises the formula: —NH—$R_{20}$—NH—, wherein $R_{20}$ is a lower ($C_{1-20}$) alkyl. In certain embodiments, the linking moiety comprises the formula: —CO—$(CH_2)_n$-(X—$(CH_2)_m$)o- X—$(CH_2)_p$CO—, wherein n is 1-3, m is 1-3, p is 1-3, o is 0-24, and X is O or NH. In one embodiment, n, m and p are each 2, o is 1-25, X is O.

In certain embodiments, the linking moiety comprises the formula: —NH—$(CH2)\alpha$-[O—$(CH_2)_\beta]_\gamma$-O—$(CH_2)_\epsilon$—Y—, wherein $\alpha$, $\beta$ and $\epsilon$ are each integers whose values are independently selected from 1 to 6, $\delta$ is 0 or 1, $\gamma$ is an integer selected from 0 to 10, and y is selected from NH or CO, provided that 3 is 2 when y is greater than 1.

In various embodiments, the linker is attached to the N-terminal amino acid of one or both peptides of the dimer, the linker is attached to the C-terminal amino acid of one or both peptides of the dimer, or the linker is attached to an internal amino acid of one or both peptides of the dimer. In one embodiment, the linker is attached to lysine residues in each of the peptides of the dimer. In particular embodiments, the linker is not attached to the N-terminal amino acid of one or both peptides of the dimer.

In particular embodiments, one or both peptides present in a dimer comprise an amino acid residue that is conjugated (i.e., covalently attached) to a lipophilic substituent, including any of those described herein. In certain embodiments, one or both peptides present in a dimer comprise an amino acid residue that is conjugated to a polymeric moiety, including any of those described herein. In certain embodiments, one or both of the peptides present in the peptide dimers is conjugated to an acidic compound, e.g., isovaleric acid, isobutyric acid, valeric acid, or the like.

In particular embodiments, a linking moiety present in a dimer is conjugated (i.e., covalently attached) to a lipophilic substituent, including any of those described herein. In certain embodiments, a linking moiety present in a dimer is conjugated to a polymeric moiety, including any of those described herein. In certain embodiments, a linking moiety present in a peptide dimer is conjugated to an acidic compound, e.g., isovaleric acid, isobutyric acid, valeric acid, or the like.

Pharmaceutical Compositions

It is to be understood that the inclusion of a peptide analogue or a dimer thereof of the invention (i.e., one or more peptide analogues of the invention or one or more peptide dimers of the present invention) in a pharmaceutical composition also encompasses inclusion of a pharmaceutically acceptable salt or solvate of a peptide analogue or a peptide dimer of the invention.

The invention also provides a pharmaceutical composition comprising a peptide analogue, or a pharmaceutically acceptable salt or solvate thereof, according to the invention. In particular embodiments, the invention provides a pharmaceutical composition comprising a peptide dimer, or a pharmaceutically acceptable salt or solvate thereof, according to the invention. In particular embodiments, the pharmaceutical compositions further comprise one or more pharmaceutically acceptable carrier, ecxcipient, or vehicle.

The invention also provides a pharmaceutical composition comprising a peptide analogue, or a pharmaceutically acceptable salt or solvate thereof, for treating a variety of conditions, diseases, or disorders as disclosed herein elsewhere (see, e.g., therapeutic uses, supra). In particular embodiments, the invention provides a pharmaceutical composition comprising a peptide dimer, or a pharmaceutically acceptable salt or solvate thereof, for treating a variety of conditions, diseases, or disorders as disclosed herein elsewhere (see, e.g., therapeutic uses, supra).

The peptide analogues, including the peptide dimers, of the present invention may be formulated as pharmaceutical compositions which are suited for administration with or without storage, and which typically comprise a therapeutically effective amount of at least one peptide analogue of the invention, together with a pharmaceutically acceptable carrier, excipient or vehicle.

The term "pharmaceutically acceptable carrier" includes any of the standard pharmaceutical carriers. Pharmaceutically acceptable carriers for therapeutic use are well known in the pharmaceutical art and are described, for example, in "Remington's Pharmaceutical Sciences", 17th edition, Alfonso R. Gennaro (Ed.), Mark Publishing Company, Easton, Pa., USA, 1985. For example, sterile saline and phosphate-buffered saline at slightly acidic or physiological pH may be used. Suitable pH-buffering agents may, e.g., be phosphate, citrate, acetate, tris(hydroxymethyl)aminomethane (TRIS), N-tris(hydroxymethyl)methyl-3-aminopropanesulfonic acid (TAPS), ammonium bicarbonate, diethanolamine, histidine, arginine, lysine or acetate (e.g. as sodium acetate), or mixtures thereof. The term further encompasses any carrier agents listed in the US Pharmacopeia for use in animals, including humans.

A pharmaceutical composition of the invention may be in unit dosage form. In such form, the composition is divided into unit doses containing appropriate quantities of the active component or components. The unit dosage form may be presented as a packaged preparation, the package containing discrete quantities of the preparation, for example, packaged tablets, capsules or powders in vials or ampoules. The unit dosage form may also be, e.g., a capsule, cachet or tablet in itself, or it may be an appropriate number of any of these packaged forms. A unit dosage form may also be provided in single-dose injectable form, for example in the form of a pen device containing a liquid-phase (typically aqueous) composition. Compositions may be formulated for any suitable route and means of administration. Pharmaceutically acceptable carriers or diluents include those used in formulations suitable for e.g. oral, intravitreal, rectal, vaginal, nasal, topical, enteral or parenteral (including subcutaneous (SC), intramuscular (IM), intravenous (IV), intradermal and transdermal) administration or administration by inhalation. The formulations may conveniently be presented in unit dosage form and may be prepared by any of the methods well known in the art of pharmaceutical formulation.

Subcutaneous or transdermal modes of administration may be particularly suitable for the peptide analogues of the invention.

Further embodiments of the invention relate to devices, dosage forms and packages used to deliver the pharmaceutical formulations of the present invention. Thus, at least one peptide analogue or specified portion or variant in either the stable or preserved formulations or solutions described herein, can be administered to a patient in accordance with the present invention via a variety of delivery methods, including SC or IM injection; transdermal, pulmonary, transmucosal, implant, osmotic pump, cartridge, micro pump, or other means appreciated by the skilled artisan as well-known in the art.

Still further embodiments of the invention relate to oral formulations and oral administration. Formulations for oral administration may rely on the co-administration of adjuvants (e.g. resorcinols and/or nonionic surfactants such as polyoxyethylene oleyl ether and n-hexadecylpolyethylene ether) to artificially increase the permeability of the intestinal walls, and/or the co-administration of enzymatic inhibitors (e.g. pancreatic trypsin inhibitors, diisopropylfluorophosphate (DFF) or trasylol) to inhibit enzymatic degradation. The active constituent compound of a solid-type dosage form for oral administration can be mixed with at least one additive, such as sucrose, lactose, cellulose, mannitol, trehalose, raffinose, maltitol, dextran, starches, agar, alginates, chitins, chitosans, pectins, gum tragacanth, gum arabic, gelatin, collagen, casein, albumin, synthetic or semisynthetic polymer, or glyceride. These dosage forms can also contain other type(s) of additives, e.g., inactive diluting agent, lubricant such as magnesium stearate, paraben, preserving agent such as sorbic acid, ascorbic acid, alpha-tocopherol, antioxidants such as cysteine, disintegrators, binders, thickeners, buffering agents, pH adjusting agents, sweetening agents, flavoring agents or perfuming agents.

Dosages

A typical dosage of a peptide analogue, e.g., a peptide or a dimer of the invention, as employed in the context of the present invention may be in the range from about 0.0001 to about 100 mg/kg body weight per day, such as from about 0.0005 to about 50 mg/kg body weight per day, such as from about 0.001 to about 10 mg/kg body weight per day, e.g. from about 0.01 to about 1 mg/kg body weight per day, administered in one or more doses, such as from one to three doses. As already indicated to some extent above, the exact dosage employed will depend, inter alia, on: the nature and severity of the disease or disorder to be treated; the sex, age, body weight and general condition of the subject to be treated; possible other, concomitant, disease or disorder that is undergoing or is to undergo treatment; as well as other factors that will be known to a medical practitioner of skill in the art.

A peptide analogue, e.g., a peptide or a dimer, of the invention may be administered continuously (e.g. by intravenous administration or another continuous drug administration method), or may be administered to a subject at intervals, typically at regular time intervals, depending on the desired dosage and the pharmaceutical composition selected by the skilled practitioner for the particular subject. Regular administration dosing intervals include, e.g., once daily, twice daily, once every two, three, four, five or six days, once or twice weekly, once or twice monthly, and the like.

Such regular peptide analogue, peptide, or dimer administration regimens of the invention may, in certain circumstances such as, e.g., during chronic long-term administration, be advantageously interrupted for a period of time so that the medicated subject reduces the level of or stops taking the medication, often referred to as taking a "drug holiday." Drug holidays are useful for, e.g., maintaining or regaining sensitivity to a drug especially during long-term chronic treatment, or to reduce unwanted side-effects of long-term chronic treatment of the subject with the drug. The timing of a drug holiday depends on the timing of the regular dosing regimen and the purpose for taking the drug holiday (e.g., to regain drug sensitivity and/or to reduce unwanted side effects of continuous, long-term administration). In some embodiments, the drug holiday may be a reduction in the dosage of the drug (e.g. to below the therapeutically effective amount for a certain interval of time). In other embodiments, administration of the drug is stopped for a certain interval of time before administration is started again using the same or a different dosing regimen (e.g. at a lower or higher dose and/or frequency of administration). A drug holiday of the invention may thus be selected from a wide range of time-periods and dosage regimens. An exemplary drug holiday is two or more days, one or more weeks, or one or more months, up to about 24 months of drug holiday. So, for example, a regular daily dosing regimen with a peptide, a peptide analogue, or a dimer of the invention may, for example, be interrupted by a drug holiday of a week, or two weeks, or four weeks, after which time the preceding, regular dosage regimen (e.g. a daily or a weekly dosing regimen) is resumed. A variety of other drug holiday regimens are envisioned to be useful for administering the peptides, the dimers, and the peptide analogues of the invention.

Thus, the peptide analogue, peptide, or dimer may be delivered via an administration regime which comprises two or more administration phases separated by respective drug holiday phases.

During each administration phase, the peptide analogue, peptide, or dimer is administered to the recipient subject in a therapeutically effective amount according to a pre-determined administration pattern. The administration pattern may comprise continuous administration of the drug to the recipient subject over the duration of the administration phase. Alternatively, the administration pattern may comprise administration of a plurality of doses of the peptide analogue to the recipient subject, wherein said doses are spaced by dosing intervals.

A dosing pattern may comprise at least two doses per administration phase, at least five doses per administration phase, at least 10 doses per administration phase, at least 20 doses per administration phase, at least 30 doses per administration phase, or more.

Said dosing intervals may be regular dosing intervals, which may be as set out above, including once daily, twice daily, once every two, three, four, five or six days, once or twice weekly, once or twice monthly, or a regular and even less frequent dosing interval, depending on the particular dosage formulation, bioavailability, and pharmacokinetic profile of the peptide analogue the peptide, or the peptide dimer of the present invention.

An administration phase may have a duration of at least two days, at least a week, at least 2 weeks, at least 4 weeks, at least a month, at least 2 months, at least 3 months, at least 6 months, or more.

Where an administration pattern comprises a plurality of doses, the duration of the following drug holiday phase is longer than the dosing interval used in that administration pattern. Where the dosing interval is irregular, the duration of the drug holiday phase may be greater than the mean interval between doses over the course of the administration phase. Alternatively the duration of the drug holiday may be longer than the longest interval between consecutive doses during the administration phase.

The duration of the drug holiday phase may be at least twice that of the relevant dosing interval (or mean thereof), at least 3 times, at least 4 times, at least 5 times, at least 10 times, or at least 20 times that of the relevant dosing interval or mean thereof.

Within these constraints, a drug holiday phase may have a duration of at least two days, at least a week, at least 2 weeks, at least 4 weeks, at least a month, at least 2 months, at least 3 months, at least 6 months, or more, depending on the administration pattern during the previous administration phase.

An administration regime comprises at least 2 administration phases. Consecutive administration phases are separated by respective drug holiday phases. Thus the administration regime may comprise at least 3, at least 4, at least 5, at least 10, at least 15, at least 20, at least 25, or at least 30 administration phases, or more, each separated by respective drug holiday phases.

Consecutive administration phases may utilise the same administration pattern, although this may not always be desirable or necessary. However, if other drugs or active agents are administered in combination with a peptide analogue, a peptide or a peptide dimer of the invention, then typically the same combination of drugs or active agents is given in consecutive administration phases. In certain embodiments, the recipient subject is human.

Devices and Kits

In some embodiments, the invention relates to a device comprising one or more peptides, peptide analogues, peptide dimersor pharmaceutically acceptable salts or solvates thereof of the invention, for delivery of the compound of the present invention to a subject. Thus, one or more peptide analogues, peptides, dimers, or pharmaceutically acceptable salts or solvates thereof can be administered to a patient in accordance with the present invention via a variety of delivery methods including intravenous, subcutaneous, intramuscular, or intraperitoneal injection; oral administration, transdermally, by pulmonary or transmucosal administration, by implant or osmotic pump, by cartridge or micro pump, or by other means appreciated by the skilled artisan, as well-known in the art.

In some embodiments, the invention relates to a kit comprising one or more peptide analogues or pharmaceutically acceptable salts or solvates thereof of the invention. In some embodiments, the invention relates to a kit comprising one or more peptide dimer of the present invention, or pharmaceutically acceptable salts or solvates thereof. In other embodiments, the kit comprises one or more pharmaceutical compositions comprising one or more peptide analogues or pharmaceutically acceptable salts or solvates thereof. In certain embodiments, the kit further comprises packaging or instructions for use. In other embodiments, the kit comprises one or more pharmaceutical compositions comprising one or more peptide dimer of the present invention, or pharmaceutically acceptable salts or solvates thereof. In certain embodiments, the kit further comprises packaging or instructions for use.

Combination Therapy

As noted above, it will be understood that reference in the following to a peptide analogue of the invention (e.g., the compounds listed in any one of Tables 5-15, for example compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 66, 67, 68, 69, 70, 71, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 105, 106, 107, 108, 109, 110, 111, 112, 113, 114, 115, 117, 118, 119, 120, 121, 122, 123, 124, 125, 126, 127, 128, 129, 130, 131, 132, 133, 134, 135, 136, 137, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 293, 297, 298, 299, 300, 301, 302, 303, 304, 305, 306, 307, 308, 309, 310, 355, 356, 357, 358, 359, 360, 361 or dimers thereof, e.g., any one of the peptide dimers disclosed in Tables 12-15, for example compounds 311-353 also extends to a pharmaceutically acceptable salt or solvate thereof, as well as to a composition comprising more than one different peptide, peptide analogue, or peptide dimer of the invention.

In certain embodiments, a peptide analogue or a peptide dimer of the invention may have some benefit if administered in combination with an iron chelator, such as Deferoxamine and Deferasirox (Exjade™)

EXAMPLES

The following examples demonstrate certain specific embodiments of the present invention. The following examples were carried out using standard techniques that are well known and routine to those of skill in the art, except where otherwise described in detail. It is to be understood that these examples are for illustrative purposes only and do not purport to be wholly definitive as to conditions or scope of the invention. As such, they should not be construed in any way as limiting the scope of the present invention.

Abbreviations

DCM: dichloromethane
DMF: N,N-dimethylformamide
NMP: N-methylpyrolidone
HBTU: O-(Benzotriazol-1-yl)-N,N,N',N'-tetramethyluronium hexafluorophosphate
HATU: 2-(7-aza-1H-benzotriazole-1-yl)-1,1,3,3-tetramethyluronium hexafluorophosphate
DCC: Dicyclohexylcarbodiimide
NHS: N-hydoxysuccinimide
DIPEA: diisopropylethylamine
EtOH: ethanol
Et2O: diethyl ether
Hy: hydrogen
TFA: trifluoroacetic acid
TIS: triisopropylsilane
ACN: acetonitrile
HPLC: high performance liquid chromatography
ESI-MS: electron spray ionization mass spectrometry
PBS: phosphate-buffered saline
Boc: t-butoxycarbonyl
Fmoc: F luorenylmethyloxycarbonyl
Acm: acetamidomethyl
IVA: Isovaleric acid (or Isovaleryl)
K( ): In the peptide sequences provided herein, wherein a compound or chemical group is presented in parentheses directly after a Lysine residue, it is to be understood that the compound or chemical group in the parentheses is a side chain conjugated to the Lysine residue. So, e.g., but not to be limited in any way, K(PEG8) indicates that a PEG8 moiety is conjugated to a side chain of this Lysine. For a few non-limiting examples of such a conjugated Lysines, please see, e.g., compounds 54 and 90.
Palm: Indicates conjugation of a palmitic acid (palmitoyl).
As used herein "C( )" refers to a cysteine residue involved in a particular disulfide bridge. For example, in Hepcidin, there are four disulfide bridges: the first between the two C(1) residues; the second between the two C(2) residues; the third between the two C(3) residues; and the fourth between the two C(4) residues. Accordingly, in some embodiments, the sequence for Hepcidin is written as follows: Hy-DTH-FPIC(1)IFC(2)C(3)GC(2)C(4)HRSKC(3)GMC(4)C(1)KT-OH (SEQ ID NO:335); and the sequence for other peptides may also optionally be written in the same manner.

The following examples are provided to illustrate certain embodiments of the invention and are not intended to limit the scope of the invention.

Example 1

Synthesis of Compounds

Unless otherwise specified, reagents and solvents employed in the following were available commercially in standard laboratory reagent or analytical grade, and were used without further purification.

Procedure for Solid-Phase Synthesis of Peptides

Illustrative compounds of the invention (e.g., Compound No. 2) were chemically synthesized using optimized 9-fluorenylmethoxy carbonyl (Fmoc) solid phase peptide synthesis protocols. For C-terminal amides, rink-amide resin was used, although wang and trityl resins were also used to produce C-terminal acids. The side chain protecting groups were as follows: Glu, Thr and Tyr: O-tButyl; Trp and Lys: t-Boc (t-butyloxycarbonyl); Arg: N-gamma-2,2,4,6,7-pentamethyldihydrobenzofuran-5-sulfonyl; His, Gln, Asn, Cys: Trityl. For selective disulfide bridge formation, Acm (acetamidomethyl) was also used as a Cys protecting group. For coupling, a four to ten-fold excess of a solution containing Fmoc amino acid, HBTU and DIPEA (1:1:1.1) in DMF was added to swelled resin [HBTU: O-(Benzotriazol-1-yl)-N,N,N',N'-tetramethyluronium hexafluorophosphate; DIPEA: diisopropylethylamine; DMF: dimethylformamide]. HATU (O-(7-azabenzotriazol-1-yl)-1,1,3,3,-tetramethyluronium hexafluorophosphate) was used instead of HBTU to improve coupling efficiency in difficult regions. Fmoc protecting group removal was achieved by treatment with a DMF, piperidine (2:1) solution.

Procedure for Cleavage of Peptides Off Resin

Side chain deprotection and cleavage of the peptides of the invention (e.g., Compound No. 2) was achieved by stirring dry resin in a solution containing trifluoroacetic acid, water, ethanedithiol and tri-isopropylsilane (90:5:2.5:2.5) for 2 to 4 hours. Following TFA removal, peptide was precipitated using ice-cold diethyl ether. The solution was centrifuged and the ether was decanted, followed by a second diethyl ether wash. The peptide was dissolved in an acetonitrile, water solution (1:1) containing 0.1% TFA (trifluoroacetic acid) and the resulting solution was filtered. The linear peptide quality was assessed using electrospray ionisation mass spectrometry (ESI-MS).

Procedure for Purification of Peptides

Purification of the peptides of the invention (e.g., Compound No. 2) was achieved using reverse-phase high performance liquid chromatography (RP-HPLC). Analysis was performed using a C18 column (3 μm, 50×2 mm) with a flow rate of 1 mL/min. Purification of the linear peptides was achieved using preparative RP-HPLC with a C18 column (5 μm, 250×21.2 mm) with a flow rate of 20 mL/min. Separation was achieved using linear gradients of buffer B in A (Buffer A: Aqueous 0.05% TFA; Buffer B: 0.043% TFA, 90% acetonitrile in water).

Procedure for Oxidation of Peptides

Method a (Single Disulfide Oxidation).

Oxidation of the unprotected peptides of the invention (e.g., Compound No. 2) was achieved by adding drop-wise iodine in MeOH (1 mg per 1 mL) to the peptide in a solution (ACN: $H_2O$, 7: 3, 0.5% TFA). After stirring for 2 min, ascorbic acid portion wise was added until the solution was clear and the sample was immediately loaded onto the HPLC for purification.

Method B (Selective Oxidation of Two Disulfides).

When more than one disulfide was present (e.g., Compound 30), selective oxidation was often performed. Oxidation of the free cysteines was achieved at pH 7.6 $NH_4CO_3$ solution at 1 mg/10 mL of peptide. After 24 h stirring and prior to purification the solution was acidified to pH 3 with TFA followed by lyophilization. The resulting single oxidized peptides (with ACM protected cysteines) were then oxidized/selective deprotection using iodine solution. The peptide (1 mg per 2 mL) was dissolved in $MeOH/H_2O$, 80:20 iodine dissolved in the reaction solvent was added to the reaction (final concentration: 5 mg/mL) at room temperature. The solution was stirred for 7 minutes before ascorbic acid was added portion wise until the solution is clear. The solution was then loaded directly onto the HPLC.

Method C (Native Oxidation).

When more than one disulfide was present and when not performing selective oxidations, native oxidation was performed (e.g., this method was used for Compound 19). Native oxidation was achieved with 100 mM $NH4CO3$ (pH7.4) solution in the presence of oxidized and reduced glutathione (peptide/GSH/GSSG, 1:100:10 molar ratio) of (peptide: GSSG: GSH, 1:10, 100). After 24 h stirring and prior to RP-HPLC purification the solution was acidified to pH 3 with TFA followed by lyophilization.

Procedure of Cysteine Oxidation to Produce Dimers.

Oxidation of the unprotected peptides of the invention (e.g., Compound No. 1) was achieved by adding drop-wise iodine in MeOH (1 mg per 1 mL) to the peptide in a solution (ACN: H2O, 7: 3, 0.5% TFA). After stirring for 2 min, ascorbic acid portion wise was added until the solution was clear and the sample was immediately loaded onto the HPLC for purification.

Procedure for Dimerization.

Glyxoylic acid, IDA, or Fmoc-3-Ala-IDA was pre-activated as the N-hydoxysuccinimide ester by treating the acid (1 equiv) with 2.2 eq of both N-hydroxysuccinimide (NHS) and dicyclohexyl carbodiimide (DCC) in NMP (N-methyl pyrolidone) at a 0.1 M final concentration. For the PEG13 and PEG25 linkers, these chemical entities were purchased pre-formed as the activated succinimide ester. The activated ester ~0.4 eq was added slowly to the peptide in NMP (1 mg/mL) portionwise. The solution was left stirring for 10 min before 2-3 additional aliquots of the linker ~0.05 eq were slowly added. The solution was left stirring for a further 3 h before the solvent was removed under vaccuo and the residue was purified by reverse phase HPLC. An additional step of stirring the peptide in 20% piperidine in DMF (2×10 min) before an additional reverse phase HPLC purification was performed.

One of skill in the art will appreciate that standard methods of peptide synthesis may be used to generate the compounds of the invention.

Example 2

Activity Assays Methodology

The designed peptides were tested in vitro for induction of degradation of the human ferroportin protein.

The cDNA encoding the human ferroportin (SLC40A1) was cloned from a cDNA clone from Origene (NM_014585). The DNA encoding the ferroportin was amplified by PCR using primers also encoding terminal restriction sites for subcloning, but without the termination codon. The ferroportin receptor was subcloned into a mammalian GFP expression vector containing a neomycin (G418) resistance marker in such that the reading frame of the ferroportin was fused in frame with the GFP protein. The fidelity of the DNA encoding the protein was confirmed by DNA sequencing. HEK293 cells were used for transfection of the ferroportin-GFP receptor expression plasmid. The cells were grown according to standard protocol in growth medium and transfected with the plasmids using Lipofectamine (manufacturer's protocol, Invitrogen). The cells stably expressing ferroportin-GFP were selected using G418 in the growth medium (in that only cells that have taken up and incorporated the cDNA expression plasmid survive) and sorted several times on a Cytomation MoFlo™ cell sorter to obtain the GFP-positive cells (488 nm/530 nm). The cells were propagated and frozen in aliquots.

To determine compound activity on the human ferroportin, the cells were incubated in 96 well plates in standard media, without phenol red. Compound was added to desired final concentration for at least 18 hours in the incubator. Following incubation, the remaining GFP-fluorescence was determined either by whole cell GFP fluorescence (Envision plate reader, 485/535 filter pair), or by Beckman Coulter Quanta™ flow cytometer (express as Geometric mean of fluorescence intensity at 485 nm/525 nm). Compound was added to desired final concentration for at least 18 hours but no more than 24 hours in the incubator.

Reference compounds included native Hepcidin, Mini-Hepcidin, and R1-Mini-Hepcidin, which is an analog of mini-hepcidin. The "RI" in RI-Mini-Hepcidin refers to Retro Inverse. A retro inverse peptide is a peptide with a reversed sequence in all D amino acids. An example is that Hy-Glu-Thr-His-NH2 becomes Hy-DHis-DThr-Dglu-NH2. The EC50 of these reference compounds for ferroportin degradation was determined according to the activity assay described above. These peptides served as control standards for many of the subsequence studies.

TABLE 4

| | Reference compounds | | |
|---|---|---|---|
| Name | Sequence | SEQ ID No. | EC50 (nM) |
| Hepcidin | Hy-DTHFPIC(1)IFC(2)C(3)GC(2)C(4)HRSKC(3)GMC(4)C(1)KT-OH | 335 | 169 |
| Mini-Hepcidin 1-9 | Hy-DTHFPICIF-NH$_2$ | 336 | 712 |
| RI-Mini Hepcidin | Hy-DPhe-DIle-DCys-DIle-DPro-DPhe-DHis-DThr-DAsp-NH$_2$ | 337 | >10 μM |

To determine whether a given peptide modifies the internalization and degradation of endogenous ferroportin, the protein levels and cellular distribution of ferroportin in hepatocytes and macrophages treated with the peptide may be assayed using Western blotting, immunohistochemistry and ferroportin antibodies known in the art.

Example 3

Cysteine Replacement Scan of Mini-Hepcidin

Previous studies indicate that the N-terminal segment of Hep25 is important for its hepcidin activity and is likely to form the interface with ferroportin. Furthermore, it was thought that Cys in the 7$^{th}$ position is critical for activity. Disulfide bonds can act by structural, catalytic or by functional means. It is postulated that Hepcidin binds to Ferroportin through a disulphide linkage which subsequently internalizes the receptor. A closer inspection of hepcidin reveled that there are 4 disulfides present and that, any one of these cysteine might be responsible for binding to ferroportin. As such, the free thiol of ferroportin possesses a "functional, allosteric bond" equivalent. In order to more thoroughly understand the structure activity relationship with respect to the position of the cysteines within Hepcidin, we performed a cysteine scan up to the 15$^{th}$ residue of a mini-hepcidin peptide and we analyzed the peptides for their ability to exhibit hepcidin activity. Peptides were synthesized using the methods described in Example 1, and their potency for ferroportin degradation was tested as described in Example 2. Results of this study are shown in Table 5, with potency indicated by EC50 values.

TABLE 5

Cysteine replacement scan of Mini-Hepcidin derivatives

| Compound Number | SEQ ID No. | Sequence | EC50 (nM) (n > 3) |
|---|---|---|---|
| 269 | 292 | DTHFPIAIFAAGIC̱I-NH$_2$ | Not active |
| 270 | 293 | DTHFPIAIFAAIC̱I-NH$_2$ | Not active |
| 271 | 294 | DTHFPIAIFAIC̱I-NH$_2$ | Not active |
| 272 | 295 | DTHFPIAIFIC̱I-NH$_2$ | Not active |
| 273 | 296 | DTHFPIAIIC̱I-NH$_2$ | Not active |
| 274 | 297 | DTHFPIAIC̱I-NH$_2$ | Not active |
| 275 | 298 | DTHFPIIC̱I-NH$_2$ | Not active |
| Mini-Hepcidin 1-9 | 336 | Hy-DTHFPIC̱IF-NH$_2$ | 712 nM |
| 1 | 28 | DTHFPC̱IIF-NH$_2$ | 133 nM |
| 276 | 299 | DTHIC̱IAIF-NH$_2$ | Not active |
| 277 | 300 | DTHC̱PIAIF-NH$_2$ | Not active |

Inactive = Not active at 30 µM and/or lowest dose

Altering the position of the cysteine ablated activity for most of the peptides that were tested; however these data surprisingly demonstrated that Compound 1 is active despite having a Cysteine at the 6$^{th}$ position. FIG. 1 shows a comparison of the dose response curves for Compound 1, as compared to Hepcidin, and the Mini-Hepcidin control. These data clearly demonstrate that Compound 1 has similar in-vitro potency as Hepcidin.

Example 4

Ala Scans of Compound 1 Identified in Cysteine Scan

To validate the results from Example 3, an Ala scan was performed on Compound 1. Peptides were synthesized as described in Example 1, and they were tested for activity as described in Example 2. The results of this study are shown in Table 6. By comparing this result with known structure activity relationships with hepcidin and other mini-hepcidin analogs, we have increased potency. Moreover, these data clearly demonstrate the importance of several residues for activity. Conversely, these date also identify a number of residues that can be modified without ablating activity.

TABLE 6

Alanine scan of Compound 1

| Compound Number | SEQ ID No. | Sequence | EC50 (nM) (n > 3) |
|---|---|---|---|
| 1 | 28 | DTHFPCIIF-NH$_2$ | 133 nM |
| 278 | 301 | DTHFPCIIA-NH$_2$ | >1 µM |
| 51 | 78 | DTHFPCIAF-NH$_2$ | 382 nM |
| 279 | 302 | DTHFPCAIF-NH$_2$ | >1 µM |
| 280 | 303 | DTHFACIIF-NH$_2$ | >1 µM |
| 282 | 305 | DTHAPCIIF-NH$_2$ | Not active |
| 283 | 306 | DTAFPCIIF-NH$_2$ | 739 nM |
| 52 | 79 | DAHFPCIIF-NH$_2$ | 388 nM |
| 284 | 307 | ATHFPCIIF-NH$_2$ | >1 µM |
| 281 | 304 | DTHF-[(D)-Ala]-CIIF-NH$_2$ | Not active |

Example 5

Analysis of Peptide Activities In Vitro

Based in part on the structure activity relationships (SAR) determined from the results of the experiments described in Examples 3 and 4, a variety of Hepcidin-like peptides of the present invention were synthesized using the method described in Example 1, and in vitro activity was tested as described in Example 2. Reference compounds (shown in Table 4) included native Hepcidin, Mini-Hepcidin, and R1-Mini-Hepcidin. EC50 values of the peptides are shown in summary Table 7.

TABLE 7

In vitro activity of Hepcidin analog peptides

| No. | SEQ ID No. | Sequence | Potency EC$_{50}$ (nM) |
|---|---|---|---|
| 1 | 28 | Hy-DTHFPCIIF-NH$_2$ | 133 |
| 2 | 29 | Isovaleric acid-DTHFPICIFGPRSKGWVC-NH$_2$ | 5 |
| 3 | 30 | Isovaleric acid-DTHFPCIIFGPRSRGWVCK-NH$_2$ | 15 |
| 4 | 31 | Isovaleric acid-DTHFPCIIFGPRSKGWVC-NH$_2$ | 19 |

TABLE 7-continued

In vitro activity of Hepcidin analog peptides

| No. | SEQ ID No. | Sequence | Potency EC$_{50}$ (nM) |
|---|---|---|---|
| 5 | 32 | [Ida]-TH-[Dpa]-[bhPro]-ICIFGPRSKGWVCM-NH$_2$ | 17 |
| 6 | 33 | Isovaleric acid-DTHFPCIFFGPRSKGWVCK-NH$_2$ | 23 |
| 7 | 34 | Isovaleric acid-DTHFPCIIFGPRSKGWTCK-NH$_2$ | 24 |
| 8 | 35 | [Ida]-TH-[Dpa]-[bh-Pro]-CIIFGPRSRGWVCK-NH$_2$ | 29 |
| 9 | 36 | Isovaleric acid-DTHFPCIKFGPRSKGWVCK-NH$_2$ | 32 |
| 10 | 37 | Isovaleric acid-DTHFPCIQFGPRSKGWVCK-NH$_2$ | 35 |
| 11 | 38 | Isovaleric acid-DTHFPCIIFGPRSKGWVCK-NH$_2$ | 9 |
| 12 | 39 | Hy-DTHFPIC$_1$IFVC$_2$GHRSIC$_2$YRRC$_1$R-NH$_2$ | 77 |
| 13 | 40 | Isobutyric acid-DTHFPIC$_1$IFVC$_2$HRSKGC$_2$YRRC$_1$R-NH$_2$ | 63 |
| 14 | 41 | Hy-DTHFPIC$_1$IFVC$_2$HRSKGC$_2$YRAC$_1$-NH$_2$ | 69 |
| 15 | 42 | Isovaleric acid-DTHFPCIEFGPRSKGWVCK-NH$_2$ | 79 |
| 16 | 43 | Hy-DTHFPICIFGPRAKGWVCM-NH$_2$ | 88 |
| 17 | 44 | Isobutyric acid-DTHFPIC$_1$IFVC$_2$HRSKGC$_2$YRRC$_1$R-NH$_2$ | 93 |
| 18 | 45 | Hy-DTHFPICIFGPRSKGWVCM-NH$_2$ | 125 |
| 19 | 46 | Hy-DTHFPIC$_1$IFVC$_2$HRSKGC$_2$YRRC$_1$R-NH$_2$ | 140 |
| 20 | 47 | Hy-DTHFPICIFGPRSRGWVCK-NH$_2$ | 101 |
| 21 | 48 | Hy-DTHFPCIIFGPRSKGWVCM-NH$_2$ | 46 |
| 22 | 49 | Hy-DTHFPICIFAPRSKGWVCM-NH$_2$ | 9430 |
| 23 | 50 | Hy-DTHFPICIFGPRSKGWVCM-OH | 131 |
| 24 | 51 | Hy-DTHFPCIQF-NH$_2$ | 138 |
| 25 | 52 | Hy-DTHFPIC$_1$IFVC$_2$GHRSKGC$_2$YRRC$_1$R-NH$_2$ | 144 |
| 26 | 53 | Hy-DTHFAICIFGPRSKGWVCM-NH$_2$ | 147 |
| 27 | 54 | Hy-DTHFPICIFGPHRSKGWVCM-NH$_2$ | 149 |
| 28 | 55 | Hy-DTHFPICIFGPRAKGWVCM-NH$_2$ | 88 |
| 29 | 56 | Hy-DTHFPACIFGPRSKGWVCM-NH$_2$ | 157 |
| 30 | 57 | Hy-DTHFPC$_1$IIFVC$_2$HRPKGC$_2$YRRVC$_1$R-NH$_2$ | 173 |
| 31 | 58 | Hy-DTHFPICIFGPRSKAWVCM-NH$_2$ | 175 |
| 32 | 59 | Hy-DTHFPIC$_1$IFVC$_2$GHRGKGC$_2$YRRC$_1$R-NH$_2$ | 182 |
| 33 | 60 | Hy-ATHFPICIFGPRSKGWVCM-NH$_2$ | 184 |
| 34 | 61 | Hy-DTHFPICIFGPASKGWVCM-NH$_2$ | 206 |
| 35 | 62 | Hy-DTHFPIC$_1$IFVC$_2$HRSKGC$_2$YARC$_1$-NH$_2$ | 214 |
| 36 | 63 | Ac-DTHFPICIFGPRSKGWVCM-NH$_2$ | 239 |
| 37 | 64 | Hy-DTHFPICIFGPRSAGWVCM-NH$_2$ | 239 |
| 38 | 65 | Hy-DTHAPICIFGPRSKGWVCM-NH$_2$ | 254 |
| 39 | 66 | Hy-DTHFPIC$_1$IFVC$_2$HRSKGC$_2$YRRC$_1$-NH$_2$ | 256 |
| 40 | 67 | pGlu-THFPIC$_1$IFVC$_2$HRSKGC$_2$YRRC$_1$R-NH$_2$ | 260 |
| 41 | 68 | Ac-DTHFPICIFKPRSKGWVCM-NH$_2$ | 262 |
| 42 | 69 | Hy-DTHFPIC$_1$IFVC$_2$GHRSKGC$_2$YMRC$_1$KT-NH$_2$ | 265 |

TABLE 7-continued

In vitro activity of Hepcidin analog peptides

| No. | SEQ ID No. | Sequence | Potency $EC_{50}$ (nM) |
|---|---|---|---|
| 43 | 70 | Hy-DAHFPICIFGPRSKGWVCM-NH$_2$ | 265 |
| 44 | 71 | Hy-DTHFPIC$_1$IFVC$_2$YRGIC$_2$YRRC$_1$R-NH$_2$ | 269 |
| 45 | 72 | Ac-DTHFPICIFGPRSKGWVCM-NH$_2$ | 272 |
| 46 | 73 | Hy-[bhAsp]-THFPICIFGPRSKGWVC-NH$_2$ | 274 |
| 47 | 74 | Hy-DTHFPICIFGPRSKGWACM-NH$_2$ | 313 |
| 48 | 75 | [Ida]-TH-[Dpa]-[bhPro]-RCR-[bhPhe]-GPRSKGWVCM-NH$_2$ | 331 |
| 49 | 76 | Hy-DTHFPCIRF-NH$_2$ | 334 |
| 50 | 77 | Isovaleric acid-THFPCIIFGPRSKGWVCM-NH$_2$ | 345 |
| 51 | 78 | Hy-DTHFPCIAF-NH$_2$ | 382 |
| 52 | 79 | Hy-DAHFPCIIF-NH$_2$ | 388 |
| 53 | 80 | Hy-DTHFPIC$_1$IFVC$_2$HRPKGC$_2$YRRC$_1$P-NH2 | 393 |
| 54 | 81 | Ac-DTHFPICIFKPRS-K(PEG8)-GWVCM-NH$_2$ | 479 |
| 55 | 82 | Hy-DTHFPCIIFK-NH$_2$ | 419 |
| 56 | 83 | Hy-DTHFPCIFF-NH$_2$ | 441 |
| 57 | 84 | Hy-DTHFPICIFGPRSK-K(PEG8)-WVCM-NH$_2$ | 462 |
| 58 | 85 | Ac-DTHFPICIFGPRSKKWVCM-NH$_2$ | 472 |
| 59 | 86 | Hy-DTHFPIC$_1$IFC$_2$PWGMC$_2$C$_1$K-NH2 | 495 |
| 60 | 87 | Hy-DTAFPICIFGPRSKGWVCM-NH$_2$ | 498 |
| 65 | 88 | Hy-DTHFPIC$_1$IFVC$_2$YRGIC$_1$YMRC$_2$KT-NH$_2$ | 763 |
| 66 | 89 | Hy-DTHFPICIFGPRSKGAVCM-NH$_2$ | 520 |
| 67 | 90 | Hy-DTHFPICIAGPRSKGWVCM-NH$_2$ | 2466 |
| 68 | 91 | Hy-DTHFPICAFGPRSKGWVCM-NH$_2$ | >10 µM |
| 69 | 92 | Hy-DTHFPIAIFGPRSKGWVAM-NH$_2$ | Inactive |
| 70 | 93 | Hy-DTHFPCRRFGPRSKGWVC-NH$_2$ | Inactive |
| 71 | 94 | [Ida]-THF-[bh-Pro]-CRR-[bh-Phe]-GPRSKGWVC-NH$_2$ | N/A |
| 73 | 96 | Hy-DTHFPC$_1$IIFVC$_2$HRSKGC$_2$YWAVC$_1$-NH$_2$ | 2640 |
| 74 | 97 | Hy-DTHFP-(D)Cys$_1$-IIFVC$_2$HRSKGC$_2$YWAV-(D)Cys$_1$-F-NH$_2$ | 356 |
| 75 | 98 | Hy-DTHFPC$_1$IIFVC$_2$HRSKGC$_2$YWAVC$_1$FW-NH$_2$ | Not Tested |
| 76 | 99 | Ac-DTHFPICIF-K(PEG8)-PRSKGWVCM-NH$_2$ | 610 |
| 78 | 101 | Hy-DTH-[Dpa]-PCIIFGPRSRGWVCK-NH$_2$ | >1 µM |
| 79 | 102 | Hy-DTHF-[bh-Pro]-CIIFGPRSRGWVCK-NH$_2$ | >1 µM |
| 80 | 103 | Hy-DTHFPCIIFGPRSRGWRCK-NH$_2$ | >1 µM |
| 81 | 104 | Hy-DTHFPCIRFGPRSRGWVCK-NH$_2$ | >1 µM |
| 82 | 105 | Hy-DTHFPCIRFGPRSRGWRCK-NH$_2$ | >1 µM |
| 83 | 106 | Hy-DTHFPCIIFGPRSRGWVCK-NH$_2$ | >1 µM |
| 84 | 107 | Hy-DTHFPCIIFGPRSRGVCK-NH$_2$ | >1 µM |

TABLE 7-continued

In vitro activity of Hepcidin analog peptides

| No. | SEQ ID No. | Sequence | Potency EC$_{50}$ (nM) |
|---|---|---|---|
| 85 | 108 | Hy-DTHFPCIYFGPRSKGWVCK-NH$_2$ | 705 |
| 86 | 109 | Hy-DTHFPCIIFGPRSKGWVCK-NH$_2$ | >1 μM |
| 87 | 110 | Hy-DTHFPCIIFGPRARGWVCK-NH$_2$ | >1 μM |
| 88 | 111 | Octanoic acid-DTHFPCIIFGPRSRGWVCK-NH$_2$ | >1 μM |
| 89 | 112 | Palm-PEG11-DTHFPCIIFGPRSRGWVCK-NH$_2$ | >1 μM |
| 90 | 113 | Ac-DTHFPICIF-K(2K PEG)-PRSKGWVCK-NH$_2$ | 107 |
| 91 | 114 | Hy-DTHFPCIIFGPRSKGWKCK-NH$_2$ | Not Tested |
| 92 | 115 | Hy-DTHFPCIKFGPRSKGWKCK-NH$_2$ | Not Tested |
| 93 | 116 | Isovaleric acid-DTHFPCLIFGPRSKGWVCK-NH$_2$ | 19 |
| 94 | 117 | Isovaleric acid-DTHFPCVIFGPRSKGWVCK-NH$_2$ | 41 |
| 95 | 118 | Isovaleric acid-DTHFPCSIFGPRSKGWVCK-NH$_2$ | 78 |
| 96 | 119 | Isovaleric acid-DTHFPCQIFGPRSKGWVCK-NH$_2$ | 157 |
| 97 | 120 | Hy-THFPCIIFGPRSKGWVCK-NH$_2$ | Inactive |
| 98 | 121 | Isovaleric acid-THFPCIIFGPRSKGWVCK-NH$_2$ | Inactive |
| 99 | 122 | Hy-HFPCIIFGPRSKGWVCK-NH$_2$ | Inactive |
| 100 | 123 | Isovaleric acid-HFPCIIFGPRSKGWVCK-NH$_2$ | Inactive |
| 101 | 124 | Hy-DTHFPCISFGPRSKGWVCK-NH$_2$ | >1 μM |
| 102 | 125 | Hy-DTHFPCIKFGPRSKGWVCK-NH$_2$ | >1 μM |
| 103 | 126 | Hy-EDTHFPCIIFGPRSKGWVCK-NH$_2$ | >1 μM |
| 105 | 128 | Isovaleric acid-DTHFPCIIFEPRSKGWVCK-NH$_2$ | 10 |
| 106 | 129 | Isovaleric acid-DTHFPCIIFSPRSKGWVCK-NH$_2$ | 44 |
| 107 | 130 | Isovaleric acid-DTHFSCIIFGPRSKGWVCK-NH$_2$ | 50 |
| 108 | 131 | Octanoic acid-PEG11-DTHFPCIIFGPRSRGWVCK-NH$_2$ | >1 μM |
| 109 | 132 | Isobutyric acid-PEG11-DTHFPCIIFGPRSRGWVCK-NH$_2$ | >1 μM |
| 110 | 133 | [Ida]-THFPCIIFGPRSRGWVCK-NH$_2$ | >300 nM |
| 111 | 134 | Isovaleric acid-DTHFPCIIFGPKSKGWVCK-NH$_2$ | 12 |
| 112 | 135 | Isovaleric acid-DTHFPCIKFGPKSKGWVCK-NH$_2$ | 15 |
| 113 | 136 | Isovaleric acid-DTHFPCIIFGPRSKGWCK-NH$_2$ | 15 |
| 114 | 137 | Isovaleric acid-DTHFPCIIFGPRSKGVC-NH$_2$ | 18 |
| 115 | 138 | Isovaleric acid-DTHFPCIIFGPRSKGCK-NH$_2$ | 21 |
| 117 | 140 | Isovaleric acid-DTHFPC-[Dapa]-IFGPRSKGWDCK-NH$_2$ | 65 |
| 118 | 141 | Isovaleric acid-DTHFPCI-[Dapa]-FGPRSKGWDCK-NH$_2$ | 17 |
| 119 | 142 | Isovaleric acid-DTHFPC-[Dapa]-IFGPRSKGWECK-NH$_2$ | 151 |
| 120 | 143 | Isovaleric acid-DTHFPCI-[Dapa]-FGPRSKGWECK-NH$_2$ | 15 |
| 121 | 144 | Isovaleric acid-DTHFPCIKFGPRSKGWECK-NH$_2$ | 14 |
| 122 | 145 | Isovaleric acid-DTHFGCIIFGPRSKGWVCK-NH$_2$ | 57 |
| 123 | 146 | Hy-DTHFGCIIFGPRSKGWVCK-NH$_2$ | Inactive |
| 124 | 147 | Isovaleric acid-DTHFRCIIFGPRSKGWVCK-NH$_2$ | 106 |

TABLE 7-continued

In vitro activity of Hepcidin analog peptides

| No. | SEQ ID No. | Sequence | Potency EC$_{50}$ (nM) |
|---|---|---|---|
| 125 | 148 | Hy-DTHFRCIIFGPRSKGWVCK-NH$_2$ | Inactive |
| 126 | 149 | Isovaleric acid-DTHF-[Sarc]-CIIFGPRSKGWVCK-NH$_2$ | 31 |
| 127 | 150 | Hy-DTHF-[Sarc]-CIIFGPRSKGWVCK-NH$_2$ | Inactive |
| 128 | 151 | Isovaleric acid-DTHF-[β-Ala]-CIIFGPRSKGWVCK-NH$_2$ | 264 |
| 129 | 152 | Hy-DTHF-[β-Ala]-CIIFGPRSKGWVCK-NH$_2$ | Inactive |
| 130 | 153 | Isovaleric acid-DTHFKCIIFGPRSKGWVCK-NH$_2$ | 150 |
| 131 | 154 | Hy-DTHFKCIIFGPRSKGWVCK-NH$_2$ | Inactive |
| 132 | 155 | Hy-THFPCIIFGPRSKGWVCM-NH$_2$ | >1 μM |
| 133 | 156 | Hy-HFPCIIFGPRSKGWVCM-NH$_2$ | >1 μM |
| 134 | 157 | Isovaleric acid-HFPCIIFGPRSKGWVCM-NH$_2$ | >1 μM |
| 135 | 158 | Hy-DTHFPCISFGPRSKGWVCM-NH$_2$ | 545 |
| 136 | 159 | Hy-DTHFPCIKFGPRSKGWVCM-NH$_2$ | 669 |
| 137 | 160 | Hy-EDTHFPCIIFGPRSKGWVCM-NH$_2$ | 873 |
| 139 | 162 | Hy-DTHFPCIIFEPRSKGWVCM-NH$_2$ | N/A |
| 140 | 163 | Isovaleric acid-DTHFKCIEFGPRSKGWVCK-NH$_2$ | >1 μM |
| 141 | 164 | Isovaleric acid-DTHFPCIIFGPRSKGWACK-NH$_2$ | 11 |
| 142 | 165 | Isovaleric acid-DTHFPCIIFEPRSKGWVCK-NH$_2$ | 9 |
| 143 | 166 | Isovaleric acid-DTHFPCIIFGPRSKGWVCKKKK-NH$_2$ | 24 |
| 144 | 167 | Isovaleric acid-DTHFPCIIFEPRSKGWVCKKKK-NH$_2$ | 15 |
| 145 | 168 | Isovaleric acid-DTHFPCIIFGPRSKGWVCKK-NH$_2$ | 9 |
| 146 | 169 | Isovaleric acid-DTAFPCIIFGPRSKGWVCK-NH$_2$ | 24 |
| 147 | 170 | Isovaleric acid-DTKFPCIIFGPRSKGWVCK-NH$_2$ | 20 |
| 148 | 171 | Isovaleric acid-DTHFPC$_1$IIFVC$_2$HRPKGC$_2$YRRVC$_1$R-NH$_2$ | 2.2 |
| 149 | 172 | Isovaleric acid-DTHFPCI-K(PEG8)-FGPRSKGWVCK-NH$_2$ | 9 |
| 150 | 173 | Isovaleric acid-DTHFPCIKF-K(PEG8)-PRSKGWVCK-NH$_2$ | 7 |
| 151 | 174 | Isovaleric acid-DTHFPCIKFGP-K(PEG8)-SKGWVCK-NH$_2$ | 13 |
| 152 | 175 | Isovaleric acid-DTHFPCIKFGPRS-K(PEG8)-GWVCK-NH$_2$ | 16 |
| 153 | 176 | Isovaleric acid-DTHFPCIKFGPRSKGWVC-K(PEG8)-NH$_2$ | 18 |
| 154 | 177 | Isovaleric acid-DTHFPCIKFGPRSKGWTCK-NH$_2$ | 18 |
| 155 | 178 | Isovaleric acid-DTHFPCIEFGPRSKGWTCK-NH$_2$ | 38 |
| 156 | 179 | Isovaleric acid-DTHFPICIFGPRS-K(Betaine)-GWVC-NH$_2$ | Not Tested |
| 157 | 180 | Isovaleric acid-DTHFPCIKFGPRS-K(Betaine)-GWVCK-NH$_2$ | 18 |
| 158 | 181 | Isovaleric acid-DTHFPCI-K(Betaine)-FGPRSKGWVCK-NH$_2$ | 16 |

TABLE 7-continued

In vitro activity of Hepcidin analog peptides

| No. | SEQ ID No. | Sequence | Potency EC$_{50}$ (nM) |
|---|---|---|---|
| 159 | 182 | Isovaleric acid-DTHFPCIKFGPRSKGWVC-K(Betaine)-NH$_2$ | 17 |
| 160 | 183 | Ac-DTHFPCIKFGPRSKGWVCK-NH$_2$ | 464 |
| 161 | 184 | Isovaleric acid-PEG3-DTHFPCIKFGPRSKGWVCK-NH$_2$ | 666 |
| 162 | 185 | Isobutyric acid-DTHFPCIKFGPRSKGWVCK-NH$_2$ | 41 |
| 163 | 186 | Valeric acid-DTHFPCIKFGPRSKGWVCK-NH$_2$ | 64 |
| 164 | 187 | Hy-VDTHFPCIKFGPRSKGWVCK-NH$_2$ | 146 |
| 165 | 188 | Hy-LDTHFPCIKFGPRSKGWVCK-NH$_2$ | 107 |
| 166 | 189 | Hexanoic acid-DTHFPCIKFGPRSKGWVCK-NH$_2$ | 36 |
| 167 | 190 | 5-Methylpentanoic acid-DTHFPCIKFGPRSKGWVCK-NH$_2$ | 99 |
| 168 | 191 | Cyclohexanoic acid-DTHFPCIKFGPRSKGWVCK-NH$_2$ | 30 |
| 169 | 192 | Heptanoic acid-DTHFPCIKFGPRSKGWVCK-NH$_2$ | 91 |
| 170 | 193 | Octanoic acid-DTHFPCIKFGPRSKGWVCK-NH$_2$ | 183 |
| 171 | 194 | Isovaleric acid-DTHFPCIIFGPRSKGWKCK-NH$_2$ | 48 |
| 172 | 195 | Isovaleric acid-DTHFPCIIFGPRSKGWECK-NH$_2$ | 15 |
| 173 | 196 | Isovaleric acid-DTHFPCRRFGPRSKGWVCK-NH$_2$ | Not Tested |
| 176 | 199 | Isovaleric acid-DTHFPICIFGPRS-K(PEG8)-GWVC-NH$_2$ | 6 |
| 177 | 200 | Isovaleric acid-DTHFPICIFGPRS-K(PEG4)-GWVC-NH$_2$ | 6 |
| 178 | 201 | Isovaleric acid-DTHFPCIIFGPRSRGWVC-K(PEG8)-NH$_2$ | 3 |
| 179 | 202 | Isovaleric acid-DTHFPCIIFGPRSRGWVC-K(PEG4)-NH$_2$ | 4 |
| 180 | 203 | Isovaleric acid-DTHFPCIIFGPRSRGWVC-K(PEG2)-NH$_2$ | 9 |
| 181 | 204 | Isovaleric acid-DTHFPCIKFEPRSKGWVCK-NH2 | 15 |
| 182 | 205 | Isovaleric acid-DTHFPCIKFEPRSKGWTCK-NH$_2$ | 13 |
| 183 | 206 | Isovaleric acid-DTHFPCIKFEPRSKGWCK-NH$_2$ | 17 |
| 184 | 207 | Isovaleric acid-DTHFPCIKFEPRSKGCK-NH$_2$ | 23 |
| 185 | 208 | Isovaleric acid-DTHFPCIFEPRSKGCK-NH$_2$ | 54 |
| 186 | 209 | Isovaleric acid-DTHFPCIFEPRSKGWCK-NH$_2$ | 12 |
| 187 | 210 | Isovaleric acid-DTHFPCIKFGPRSKCK-NH$_2$ | 21 |
| 188 | 211 | Isovaleric acid-DTHFPCIKFGPRSCK-NH$_2$ | 30 |
| 189 | 212 | Isovaleric acid-DTHFPCIKFGPRCK-NH$_2$ | 36 |
| 190 | 213 | Isovaleric acid-DTHFPCIKFGPCK-NH$_2$ | 55 |
| 191 | 214 | Isovaleric acid-DTHFPCIKFGCK-NH$_2$ | 97 |
| 192 | 215 | Isovaleric acid-DTHFPCIKFCK-NH$_2$ | 48 |
| 193 | 216 | Isovaleric acid-DTHFPCIKFC-NH$_2$ | 80 |
| 194 | 217 | Isovaleric acid-DTHFPCI-K(Palm)-FGPRSKGWVCK-NH$_2$ | 4 |

TABLE 7-continued

In vitro activity of Hepcidin analog peptides

| No. | SEQ ID No. | Sequence | Potency EC$_{50}$ (nM) |
|---|---|---|---|
| 195 | 218 | Isovaleric acid-DTHFPCIKF-K(Palm)-PRSKGWVCK-NH$_2$ | 9 |
| 196 | 219 | Isovaleric acid-DTHFPCIKFGP-K(Palm)-SKGWVCK-NH$_2$ | 2 |
| 197 | 220 | Isovaleric acid-DTHFPCIKFGPRS-K(Palm)-GWVCK-NH$_2$ | 1 |
| 198 | 221 | Isovaleric acid-DTHFPCIKFGPRSKGWVC-K(Palm)-NH$_2$ | 7 |
| 199 | 222 | Isovaleric acid-DTHFPCI-K(PEG3-Palm)-FGPRSKGWVCK-NH$_2$ | 7 |
| 200 | 223 | Isovaleric acid-DTHFPCIKF-K(PEG3-Palm)-PRSKGWVCK-NH$_2$ | 6 |
| 201 | 224 | Isovaleric acid-DTHFPCIKFGP-K(PEG3-Palm)-SKGWVCK-NH$_2$ | 4 |
| 202 | 225 | Isovaleric acid-DTHFPCIKFGPRS-K(PEG3-Palm)-GWVCK-NH$_2$ | 3 |
| 203 | 226 | Isovaleric acid-DTHFPCIKFGPRSKGWVC-K(PEG3-Palm)-NH$_2$ | 4 |
| 204 | 227 | Hy-DTHFPCI-K(IVA)-FGPRSKGWVCK-NH$_2$ | >300 nM |
| 205 | 228 | Hy-DTHFPCIKF-K(IVA)-PRSKGWVCK-NH$_2$ | >300 nM |
| 206 | 229 | Hy-DTHFPCIKFGP-K(IVA)-SKGWVCK-NH$_2$ | 624 |
| 207 | 230 | Hy-DTHFPCIKFGPRS-K(IVA)-GWVCK-NH$_2$ | 318 |
| 208 | 231 | Hy-DTHFPCIKFGPRSKGWVC-K(IVA)-NH$_2$ | 109 |
| 209 | 232 | Hy-DTHFPCI-K(PEG3-IVA)-FGPRSKGWVCK-NH$_2$ | 342 |
| 210 | 233 | Hy-DTHFPCIKF-K(PEG3-IVA)-PRSKGWVCK-NH$_2$ | 457 |
| 211 | 234 | Hy-DTHFPCIKFGP-K(PEG3-IVA)-SKGWVCK-NH$_2$ | >300 nM |
| 212 | 235 | Hy-DTHFPCIKFGPRS-K(PEG3-IVA)-GWVCK-NH$_2$ | >300 nM |
| 213 | 236 | Hy-DTHFPCIKFGPRSKGWVC-K(PEG3-IVA)-NH$_2$ | 233 |
| 214 | 237 | Isovaleric acid-DTHFPCIKFEPRSKKWVCK-NH$_2$ | 15 |
| 215 | 238 | Hy-DTHFPCIKFGPRSKGWVCK-NH$_2$ | >1 µM |
| 216 | 239 | Palm-DTHFPCIKFGPRSKGWVCK-NH$_2$ | >1 µM |
| 217 | 240 | Palm-PEG3-DTHFPCIKFGPRSKGWVCK-NH$_2$ | >1 µM |
| 218 | 241 | Isovaleric acid-DTHFPCI-K(isoglu-Palm)-FEPRSKGCK-NH$_2$ | 10 |
| 219 | 242 | Isovaleric acid-DTHFPCIKF-K(isoglu-Palm)-PRSKGCK-NH$_2$ | 9 |
| 220 | 243 | Isovaleric acid-DTHFPCIKFEP-K(isoglu-Palm)-SKGCK-NH$_2$ | 5 |
| 221 | 244 | Isovaleric acid-DTHFPCIKFEPRS-K(isoglu-Palm)-GCK-NH$_2$ | 4 |
| 222 | 245 | Isovaleric acid-DTHFPCIKFEPRSK-K(isoglu-Palm)-CK-NH$_2$ | 4 |
| 223 | 246 | Isovaleric acid-DTHFPCIKFEPRSKGC-K(isoglu-Palm)-NH$_2$ | 5 |
| 224 | 247 | Isovaleric acid-DTHFPCIKFEPRSKGCK-K(isoglu-Palm)-NH$_2$ | 4 |

TABLE 7-continued

In vitro activity of Hepcidin analog peptides

| No. | SEQ ID No. | Sequence | Potency EC$_{50}$ (nM) |
|---|---|---|---|
| 225 | 248 | Isovaleric acid-DTHFPCI-K(dapa-Palm)-FEPRSKGCK-NH$_2$ | 17 |
| 226 | 249 | Isovaleric acid-DTHFPCIKF-K(dapa-Palm)-PRSKGCK-NH$_2$ | 14 |
| 227 | 250 | Isovaleric acid-DTHFPCIKFEP-K(dapa-Palm)-SKGCK-NH$_2$ | 10 |
| 228 | 251 | Isovaleric acid-DTHFPCIKFEPRS-K(dapa-Palm)-GCK-NH$_2$ | 7 |
| 229 | 252 | Isovaleric acid-DTHFPCIKFEPRSK-K(dapa-Palm)-CK-NH$_2$ | 13 |
| 230 | 253 | Isovaleric acid-DTHFPCIKFEPRSKGC-K(dapa-Palm)-K-NH$_2$ | 10 |
| 231 | 254 | Isovaleric acid-DTHFPCIKFEPRSKGCK-K(dapa-Palm)-NH2 | 11 |
| 232 | 255 | Isovaleric acid-DTHFPCIKFGPRSKGWVCK-NH$_2$ | Not Tested |
| 233 | 256 | Isovaleric acid-AAHFPCIKFGPRSKGWVCK-NH$_2$ | 320 |
| 234 | 257 | Isovaleric acid-ATHFPCIKFGPRSKGWVCK-NH$_2$ | 60 |
| 235 | 258 | Isovaleric acid-DAHFPCIKFGPRSKGWVCK-NH$_2$ | 203 |
| 236 | 259 | Isovaleric acid-DTHAPCIKFGPRSKGWVCK-NH$_2$ | >500 nM |
| 237 | 260 | Isovaleric acid-DTHFPCIKAGPRSKGWVCK-NH$_2$ | 50 |
| 238 | 261 | Isovaleric acid-DTHFPCIKFEPRSKGWVCK-OH | 47 |
| 239 | 262 | Isovaleric acid-DTHFPCIKFEPRSKGWECK-OH | 101 |
| 240 | 263 | Isovaleric acid-DTHFPCIIFEPRSKGWEC-OH | 139 |
| 241 | 264 | Isovaleric acid-DTHFPCIKFK(isoGlu-Palm)-PRSKGWECK-NH$_2$ | 6 |
| 242 | 265 | Isovaleric acid-DTHFPCIKFEPK(isoGlu-Palm)-SKGWECK-NH$_2$ | 8 |
| 243 | 266 | Isovaleric acid-DTHAPCIKFEPRSKGWECK-NH$_2$ | Inactive |
| 244 | 267 | Ida-THFPCIKFEPRSK-K(isoGlu-Palm)CK-NH$_2$ | 25 |
| 245 | 268 | Isovaleric acid-DTHFPCI-K(isoGlu-Palm)-FEPRSKGWEC-OH | 131 |
| 246 | 269 | 4,4-5,5-6,6,6-Heptafluorohexanoic acid-DTHFPCIKFGPRSKGWVCK-NH$_2$ | 480 |
| 247 | 270 | Isovaleric acid-DTHFPCIKF-K(mysteric acid)-PRSKGWVC-NH$_2$ | 7 |
| 248 | 271 | Isovaleric acid-DTHFPCIKF-K(lauric acid)-PRSKGWVC-NH$_2$ | 10 |
| 249 | 272 | Isovaleric acid-DTHFPCIKF-K(decanoic acid)-PRSKGWVC-NH$_2$ | 22 |
| 250 | 273 | Isovaleric acid-DTHFPCIKF-K(octanoic acid)-PRSKGWVC-NH$_2$ | 30 |
| 251 | 274 | Isovaleric acid-DTHFPCIKF-K(hexanoic acid)-PRSKGWVC-NH$_2$ | 21 |
| 252 | 275 | Isovaleric acid-DTHFPCIKF-K(butyric acid)-PRSKGWVC-NH$_2$ | 37 |
| 253 | 276 | Isovaleric acid-DTHFPCIKF-K(Ac)-PRSKGWVC-NH$_2$ | 29 |

TABLE 7-continued

In vitro activity of Hepcidin analog peptides

| No. | SEQ ID No. | Sequence | Potency EC$_{50}$ (nM) |
|---|---|---|---|
| 254 | 277 | Ida-THFPCIKFEPRSKGWVC-K(mysteric acid)-NH$_2$ | 20 |
| 255 | 278 | [Ida]-THFPCIKFEPRSKGWVC-K(lauric acid)-NH$_2$ | 52 |
| 256 | 279 | [Ida]-THFPCIKFEPRSKGWVC-K(decanoic acid)-NH$_2$ | 116 |
| 257 | 280 | [Ida]-THFPCIKFEPRSKGWVC-K(octanoic acid)-NH$_2$ | 129 |
| 258 | 281 | [Ida]-THFPCIKFEPRSKGWVC-K(hexanoic acid)-NH$_2$ | 191 |
| 259 | 282 | [Ida]-THFPCIKFEPRSKGWVC-K(butyric acid)-NH$_2$ | 355 |
| 260 | 283 | [Ida]-THFPCIKFEPRSKGWVC-K(Ac)-NH$_2$ | 502 |
| 261 | 284 | Isovaleric acid-HFPCIKFEPRSKGWVC-K(octanoic acid)-NH$_2$ | >300 nM |
| 262 | 285 | Isovaleric acid-HFPCIKFEPRSKGWVC-K(lauric acid)-NH$_2$ | 77 |
| 263 | 286 | Isovaleric acid-DTHFPCIKFEPHSKGCK-NH2 | 62 |
| 264 | 287 | Isovaleric acid-DTHFPCIHFEPHSKGC-NH$_2$ | 118 |
| 265 | 288 | Isovaleric acid-DTHFPCIKFEPHS-K(Albu)-GCK-NH$_2$ | 6 |
| 266 | 289 | Isovaleric acid-DTHFPCIKFEPREKEC-NH$_2$ | 183 |
| 267 | 290 | Isovaleric acid-DTAFPCIKFEPRSKEC-NH$_2$ | >1 µM |
| 268 | 291 | Isovaleric acid-DTHFPCIKFECK-NH$_2$ | 107 |
| 269 | 292 | Hy-DTHFPIAIFAAGICI-NH$_2$ | Inactive |
| 270 | 293 | Hy-DTHFPIAIFAAICI-NH$_2$ | Inactive |
| 271 | 294 | Hy-DTHFPIAIFAICI-NH$_2$ | Inactive |
| 272 | 295 | Hy-DTHFPIAIFICI-NH$_2$ | Inactive |
| 273 | 296 | Hy-DTHFPIAIICI-NH$_2$ | Inactive |
| 274 | 297 | Hy-DTHFPIAICI-NH$_2$ | Inactive |
| 275 | 298 | Hy-DTHFPIICI-NH$_2$ | Inactive |
| 276 | 299 | Hy-DTHICIAIF-NH$_2$ | Inactive |
| 277 | 300 | Hy-DTHCPIAIF-NH$_2$ | Inactive |
| 278 | 301 | Hy-DTHFPCIIA-NH$_2$ | >1 µM |
| 279 | 302 | Hy-DTHFPCAIF-NH$_2$ | >1 µM |
| 280 | 303 | Hy-DTHFACIIF-NH$_2$ | >1 µM |
| 281 | 304 | Hy-DTHF-(D)--Ala-CIIF-NH$_2$ | Inactive |
| 282 | 305 | Hy-DTHAPCIIF-NH$_2$ | Inactive |
| 283 | 306 | Hy-DTAFPCIIF-NH$_2$ | 739 nM |
| 284 | 307 | Hy-ATHFPCIIF-NH2 | >1 µM |
| 285 | 308 | [Ida]-THF-[bh-Pro]-CIIF-NH$_2$ | >1 µM |
| 287 | 310 | Hy-DTHFPCIEF-NH$_2$ | >1 µM |
| 288 | 311 | Isovaleric acid-DTHFPCIIF-NH$_2$ | 16 nM |
| 289 | 312 | Isovaleric acid-DTHFPAIIF-NH2 | Inactive |
| 290 | 313 | Isovaleric acid-DTHFPSIIF-NH2 | Inactive |

TABLE 7-continued

In vitro activity of Hepcidin analog peptides

| No. | SEQ ID No. | Sequence | Potency EC$_{50}$ (nM) |
|---|---|---|---|
| 291 | 314 | Isovaleric acid-DTHFPCIKF-NH$_2$ | 7 nM |
| 293 | 316 | Hy-DTHFPCIF-NH$_2$ | 52% at 1 μM |
| 297 | 320 | Hy-DTHFPCIKFF-NH$_2$ | 64% at 1 μM |
| 298 | 321 | Hy-YTHFPCIIF-NH$_2$ | Not Tested |
| 299 | 322 | Hy-LTHFPCIIF-NH$_2$ | 64% at 1 μM |
| 300 | 323 | Hy-ETHFPCIIF-NH$_2$ | 77% at 1 μM |
| 301 | 324 | Hy-DRHFPCIIF-NH$_2$ | Not Tested |
| 302 | 325 | Hy-DTKFPCIIF-NH$_2$ | 60% at 1 μM |
| 303 | 326 | Hy-DTHFECIIF-NH$_2$ | Not Tested |
| 304 | 327 | Hy-DTHFPCIIK-NH$_2$ | 55% at 1 μM |
| 305 | 328 | Hy-DTHFPCIIR-NH$_2$ | 62% at 1 μM |
| 306 | 329 | Hy-DTHFPCIEF-NH$_2$ | Not Tested |
| 307 | 330 | Hy-DTHFPCIVF-NH$_2$ | 75% at 1 μM |
| 308 | 331 | Hy-DTHFPCILF-NH$_2$ | 89% at 1 μM |
| 309 | 332 | Hy-DTHFPCILK-NH$_2$ | 55% at 1 μM |
| 310 | 333 | Hy-DTHFPCIEK-NH$_2$ | 0% at 1 μM |
| 355 | 369 | Isovaleric acid-DTHFPCIKFEPRSKECK-NH$_2$ | 48 |
| 356 | 370 | Isovaleric acid-DTHFPCIKFEPHSKECK-NH$_2$ | 181 |
| 357 | 371 | Isovaleric acid-DTHFPCIKKEPHSKECK-NH$_2$ | >1 μM |
| 358 | 372 | Isovaleric acid-DTHFPCIKF-K(isoglu-Palm)-PHSKECK-NH$_2$ | 6 |
| 359 | 373 | Isovaleric acid-DTHFPCIKFEPRECK-NH$_2$ | 64 |
| 360 | 374 | Isovaleric acid-DTHFPCIKFEPHECK-NH$_2$ | 138 |
| 361 | 375 | Isovaleric acid-DTHFPCIKFEPRCK-NH$_2$ | 29 |

Inactive = Not active at 30 μM and/or lowest dose.
For Table 7, parentheticals, e.g., (_), represent side chain conjugations and brackets, e.g., [ ], represent unnatural amino acid substitutions.

For certain compounds comprising an N-terminal PEG11 moiety (e.g., compounds 89, 108, and 109), the following was used in their synthesis:

Fmoc-Amino PEG Propionic Acid

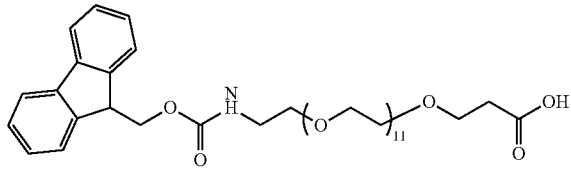

Example 6

Alanine Scan of Compound 18

To further understand Hepcidin's structure activity relationship, an alanine scan was performed on Compound 18, which is a Hepcidin analogue of the present invention that comprises a cysteine in the 7 position. Peptides were synthesized as described in Example 1 and tested for activity as described in Example 2; results are shown in Table 8 herein.

TABLE 8

Alanine scan of Coupound 18

| Compound Number | SEQ ID No. | Sequence | EC50 (nM) (n > 3) |
|---|---|---|---|
| 18 | 45 | DTHFPICIFGPRSKGWVCM-NH$_2$ | 125 |
| 47 | 74 | DTHFPICIFGPRSKGWACM-NH$_2$ | 313 |
| 66 | 89 | DTHFPICIFGPRSKGAVCM-NH$_2$ | 520 |
| 31 | 58 | DTHFPICIFGPRSKAWVCM-NH$_2$ | 175 |
| 37 | 64 | DTHFPICIFGPRSAGWVCM-NH$_2$ | 239 |
| 16 | 43 | DTHFPICIFGPRAKGWVCM-NH$_2$ | 88 |
| 34 | 61 | DTHFPICIFGPASKGWVCM-NH$_2$ | 206 |
| 354 | 334 | DTHFPICIFGARSKGWVCM-NH$_2$ | 153 |
| 22 | 49 | DTHFPICIFAPRSKGWVCM-NH$_2$ | 9430 |
| 67 | 90 | DTHFPICIAGPRSKGWVCM-NH$_2$ | 2466 |
| 68 | 91 | DTHFPICAFGPRSKGWVCM-NH$_2$ | >10 μM |
| 69 | 92 | DTHFPIAIFGPRSKGWVAM-NH$_2$ | Inactive |
| 29 | 56 | DTHFPACIFGPRSKGWVCM-NH$_2$ | 157 |
| 26 | 53 | DTHFAICIFGPRSKGWVCM-NH$_2$ | 147 |
| 38 | 65 | DTHAPICIFGPRSKGWVCM-NH$_2$ | 254 |
| 60 | 87 | DTAFPICIFGPRSKGWVCM-NH$_2$ | 498 |
| 43 | 70 | DAHFPICIFGPRSKGWVCM-NH$_2$ | 265 |
| 33 | 60 | ATHFPICIFGPRSKGWVCM-NH$_2$ | 184 |

Inactive = Not active at 30 μM and/or lowest dose

As was the case with the alanine scan of compound 1 (cysteine in position 6) this scan identified residues within compound 18 (cysteine in position 7) that are important for activity, as well as several residues that appear to be less important for activity and thus may modified without ablating activity.

Example 7

Plasma Stability

Serum stability experiments were undertaken to complement the in vivo results and assist in the design of potent, stable Ferroportin agonists. In order to predict the stability in humans, ex vivo stability studies were initially performed in human serum.

Key peptides (10 μM) were incubated with pre-warmed human serum (Sigma) at 37 degrees C. Samples were taken at various time points up to 24 hours. The samples were separated from serum proteins and analysed for the presence of the peptide of interest using LC-MS. The amount of intact peptide in each sample was calculated using the analyte peak area in relation to the zero time point. Table 9 shows the results of this study.

TABLE 9

Stability of key compounds in human serum

| Compound No. | t½ (h) |
|---|---|
| Hepcidin | 2.76 |
| Mini Hepcidin 1-9 | 0.10 |
| 1 | 0.18 |
| 18 | 2.32 |
| 46 | 2.10 |
| 2 | 1.99 |
| 47 | ~40 |
| 8 | 0.51 |
| 3 | 0.51 |

Example 8

Reduction of Free Plasma Iron in Rats

To investigate whether the hepcidin mimetic Compound No. 2 was effective in decreasing free $Fe^{2+}$ in serum, Retro Inverse mini Hepcidin was used as a reference peptide. Although RI mini-Hep has a very low potency in vitro it is highly active in vivo as reported by Presza et al. J Clin Invest. 2011.

At Day 1, the animals were monitored for free $Fe^{2+}$ in serum. In order to reach a homogenous serum level, $Fe^{2+}$ was analyzed and a homogenous cohort of 7 or 8 animals randomized to each treatment group. At Day 2, an acute experiment where the animals were subjected to i.p. dosing of test compound and subsequent tail vein blood samples. Prior to dosing, the animals were put under a heating lamp for 3-5 minutes. Blood samples were drawn from the tail vein from all animals in order to determine serum iron levels prior to vehicle or compound dosing. Animals were dosed i.p. with 1 ml of test substance in vehicle or just vehicle and blood samples of 250 μl was drawn from each animal at t=0, 60, 120, 240, 360 min and 24 hours in the study of the reference compound. The dose response study performed with Retro Inverse (RI) mini-Hepcidin (Reference compound), and the efficacy study performed with Compound No. 2 were performed as two separate experiments.

Analysis of $Fe^{2+}$ from Day 0 and 1 was done at a later time point not later than 10 days after. The chemicals and equipment used in this example are shown in Table 10.

TABLE 10

| Drug Name | Cmpd. No. | SEQ ID No. | MW (g/mol) | Peptide Content Calculated % | Peptide Content Determined % | Purity % | Solvent |
|---|---|---|---|---|---|---|---|
| Chemicals and equipment used in this example | | | | | | | |
| Isovaleric acid-DTHFPICIFGPRSKGWVC-$NH_2$ | 2 | 29 | 2144.52 | 86.2 | 86.2 | 90 | Na-Acetate buffer |
| RI-Hepcidin1-9 | | 337 | 1091.3 | 82.7 | 82.7 | 94.2 | Strong PBS |

Initially, all peptides were solubilized in acidic $H_2O$ in pH=2.5 and to a concentration of 3 mg/ml API. Compounds were thereafter either dissolved in Na-Acetate buffer (50 mM Acetic Acid, 125 mM NaCl, pH 5.0) or strong PBS, (25 mM sodium phosphate, 125 mM NaCl, pH 7.4).

Male Sprague-Dawley rats weighing 200-250 g were used in the study. They were housed in groups for n=2 in a light-, temperature- and humidity-controlled room (12-hour light: 12-hour dark cycle, lights on/off at 0600/1800 hour; 23 degrees Celcius; 50% relative humidity). Humane endpoints were applied, according to OECD's 'Guidelines for Endpoints in Animal Study Proposals." The animals were monitored daily. In case of significantly affected condition (based on signs such as weight loss >30% (obese animals); abnormal posture; rough hair coat; exudate around eyes and/or nose; skin lesions; abnormal breathing; difficulty with ambulation; abnormal food or water intake; or self mutilation), or other conditions causing significant pain or distress, the animals were euthanized immediately.

Iron content in plasma/serum is measured for iron content using a colorimetric assay on the Cobas c 111 according to instructions from the manufacturer of the assay (assay: IRON2: ACN 661).

The data obtained from the cobas Iron2 analysis are presented as mean values +/−SEM.

Figure 2:
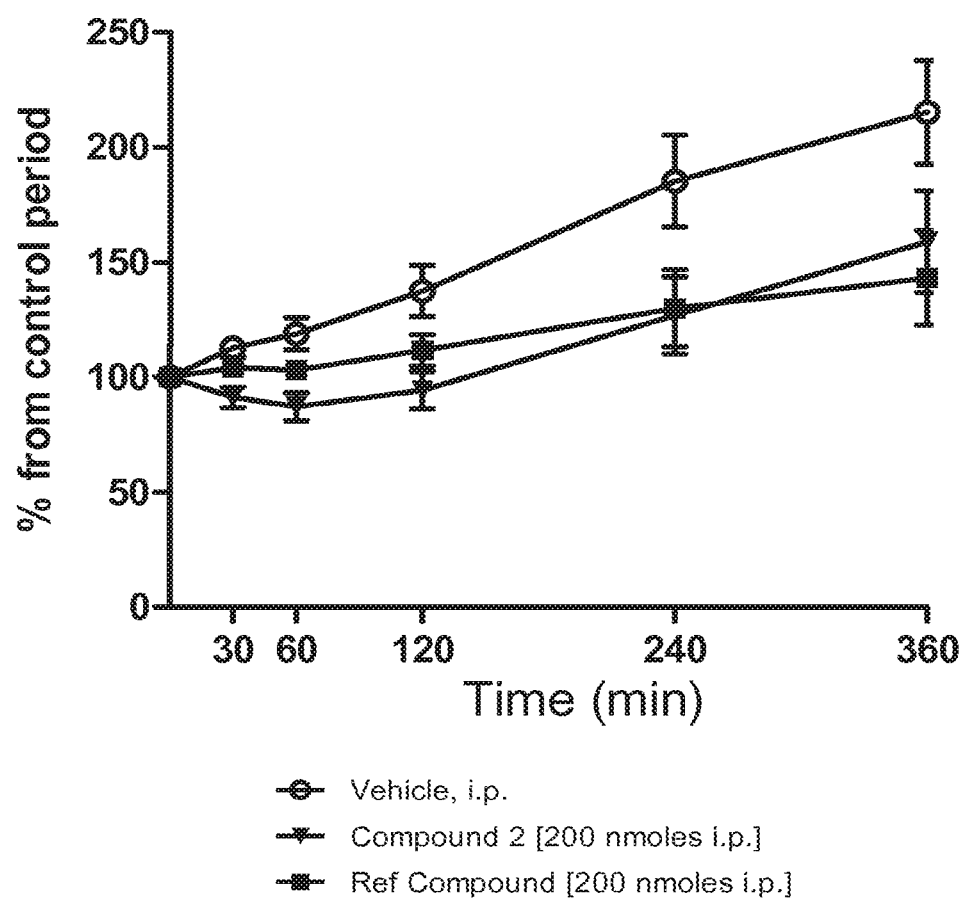
FIG. 2 shows time dependent changes in serum iron following animal exposure to vehicle, Compound No. 2 and reference compound RI Mini-Hepcidin. The responses are normalized to the initial (t=0) levels.
Figure 3:
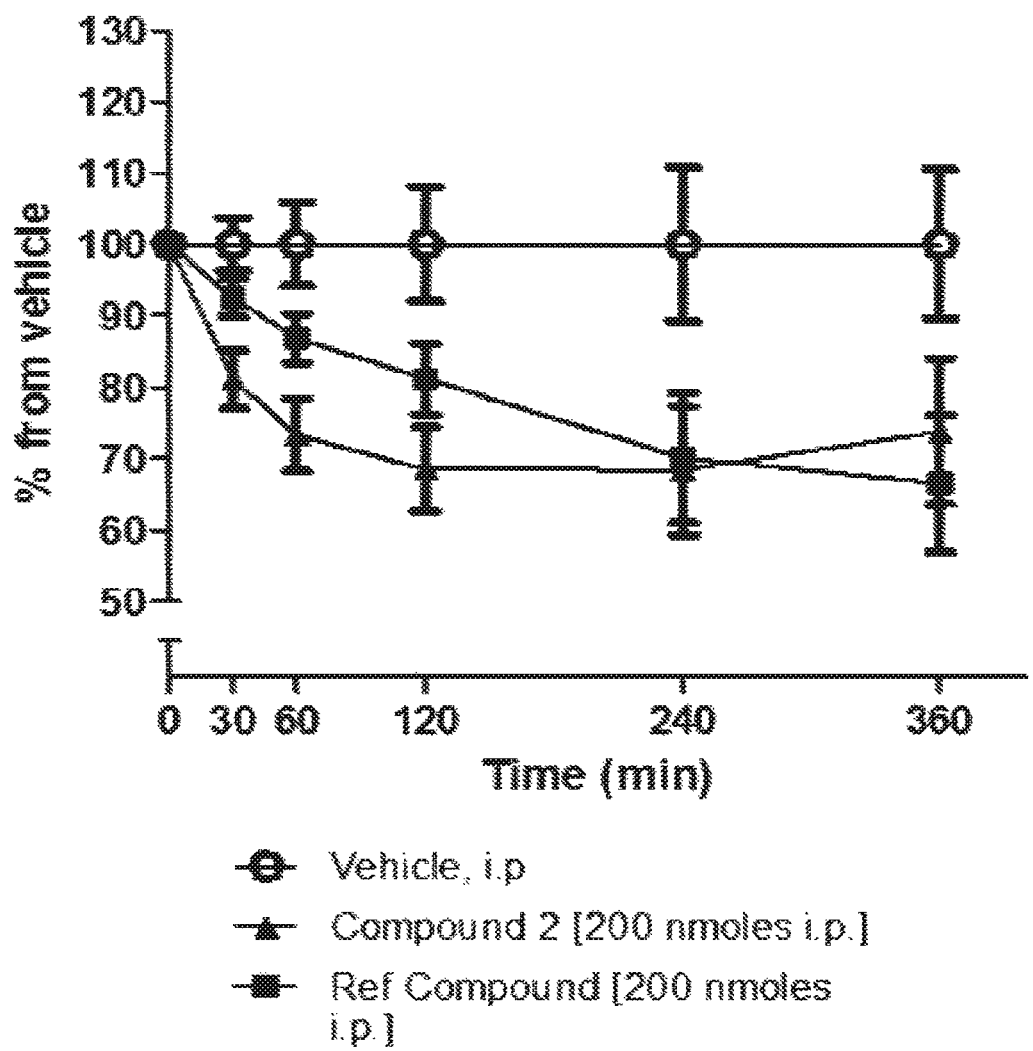
FIG. 3 shows relative decrease of serum iron relative to vehicle control measured with Compound No. 2 as well as the reference compound RI-Mini-Hepcidin at timepoints 0, 30, 60, 120, 240 and 360 minutes. 100% represents the measured average level of serum iron in the vehicle treated animals.

As shown in FIGS. 2 and 3, IP dosing of compound 2 resulted in a decrease in serum iron level that was comparable to that observed after injection of the positive control Retro Inverse mini Hepcidin (RI-Mini-Hepcidin). The decrease induced by RI-Mini-Hepcidin and compound 2 was in neither case significant, which was probably due to a large intergroup variance in the measurements.

Example 9

In Vivo Validation of Selected Peptides

Figure 4:
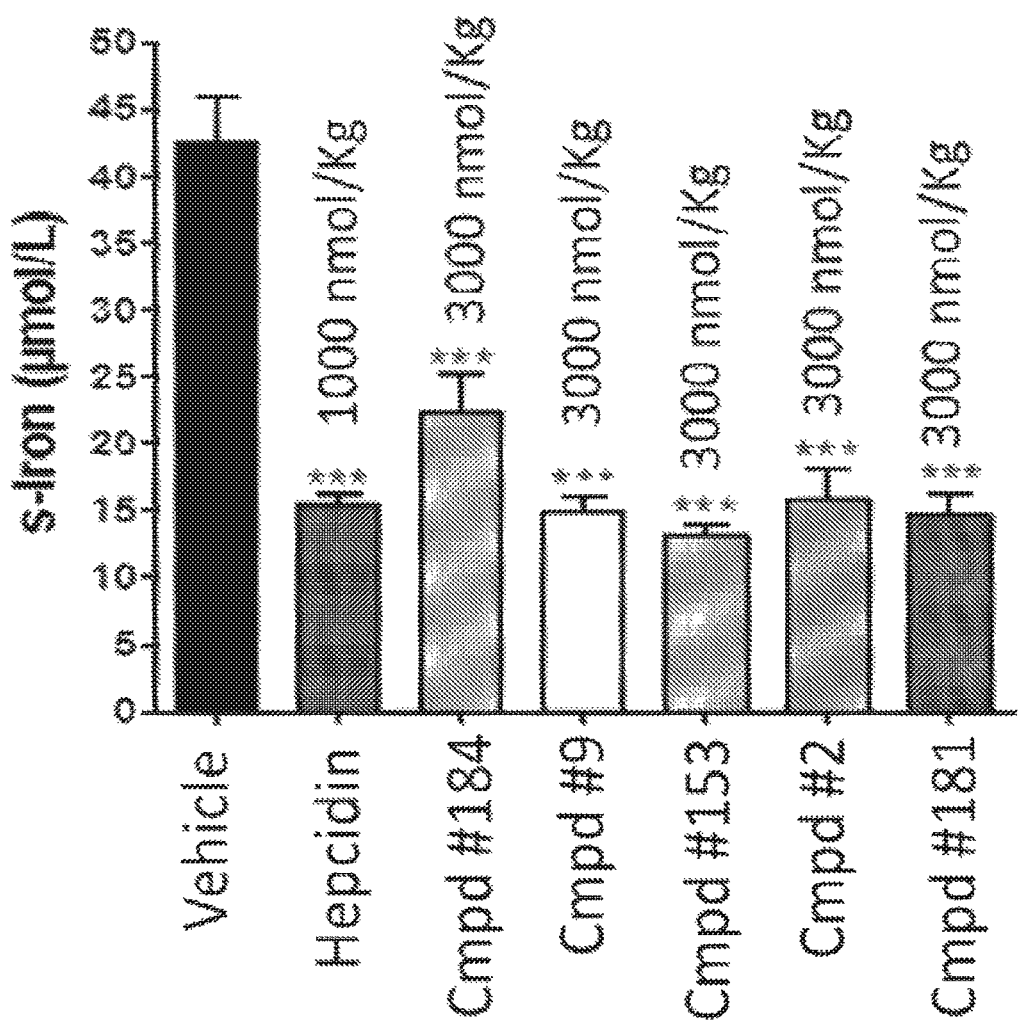
FIG. 4 shows the in vivo serum iron reducing abilities of selected peptides of the present invention and Hepcidin.

Selected peptides of the present invention were tested for in vivo activity, as described in Example 8, with the following changes. Instead of rats, mice (C57-BL6) were tested. Peptides or vehicle controls were administered to the mice (n=8/group) with the compounds of the present invention dosed at 3000 nmol/kg, and a hepcidin control administered via subcutaneous injection at 1000 nmol/kg. The primary goal of this experiment was to validate, in a mouse model, the activity of several peptides that were shown to be active in rat. Serum iron levels were assessed as in Example 8 two hours after peptide or vehicle administration. As shown in FIG. 4, at these doses, a significant reduction in serum iron was observed in compound-treated animals as compared to the vehicle control. Furthermore, the max-dose responses of the compounds of the invention were very similar to the max-dose response achieved with Hepcidin.

Figure 5:
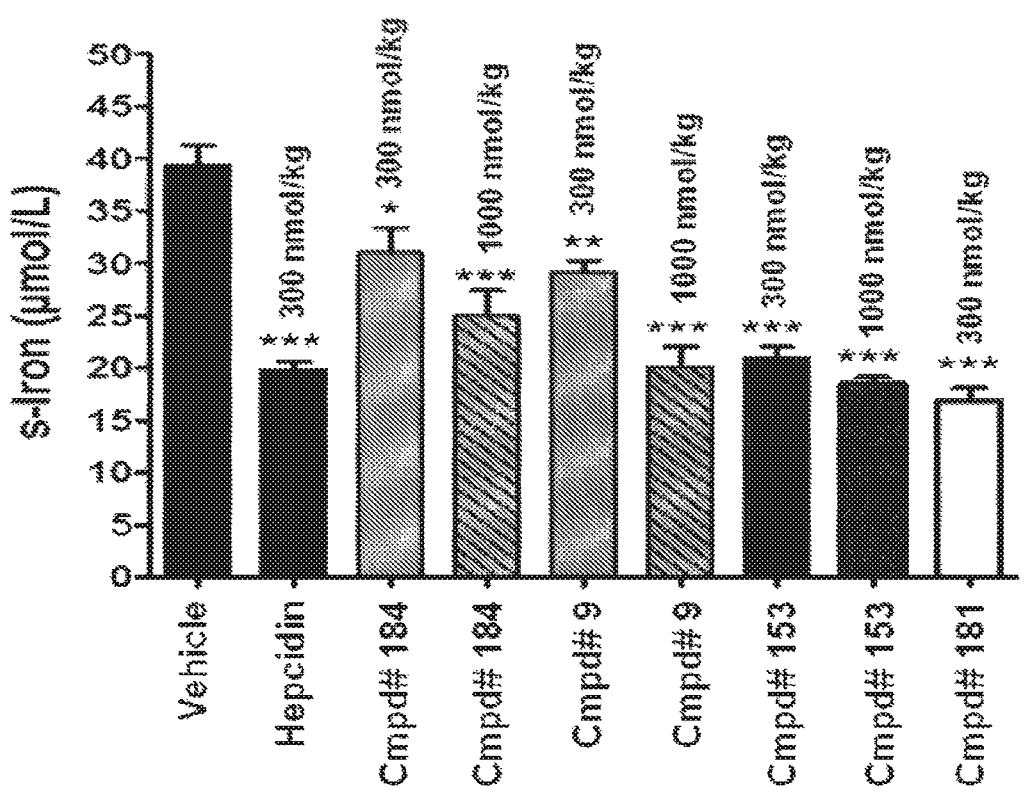
FIG. 5 shows a dose response of the in vivo serum iron reducing abilities of selected peptides of the present invention and Hepcidin.

A similar experiment was performed with lower doses to assess the dose response of these compounds for inducing serum iron reduction. Methods were as described above in this Example, except for the following parameters: n=4 mice/group, however n=8 for the vehicle, as two groups were pooled. Mice were administered test compounds at two separate dosages (300 nmol/kg or 1000 nmol/kg), via subcutaneous injection. Serum iron levels were assessed as in Example 8 two hours after peptide or vehicle injection. As shown in FIG. 5, these peptides induced similar iron reductions as did native hepcidin in vivo. Moreover, it was clear that several of the compounds were able to induce maximum effects at dosages as low as 300 nmol/kg.

Other peptides were tested similarly, either in rats as described in Example 8, or in mice as described above in the present Example, and the results of these tests are presented in Table 11, herein, in the column having the heading "in vivo activity." In this table, dosing is indicated in the sub-headings listed in the first row of the "in vivo activity" column; in vivo activity data is reported as a "yes" or "no" determination, with yes indicating that in vivo activity for serum iron reduction was observed, and with "no" indicating that no such activity was observed. The route of peptide administration was via subcutaneous injection, unless otherwise indicated as having been via intraperitoneal injection (this is noted on the table by "i.p." in parentheses following the "yes" or "no" determination).

Figure 6:
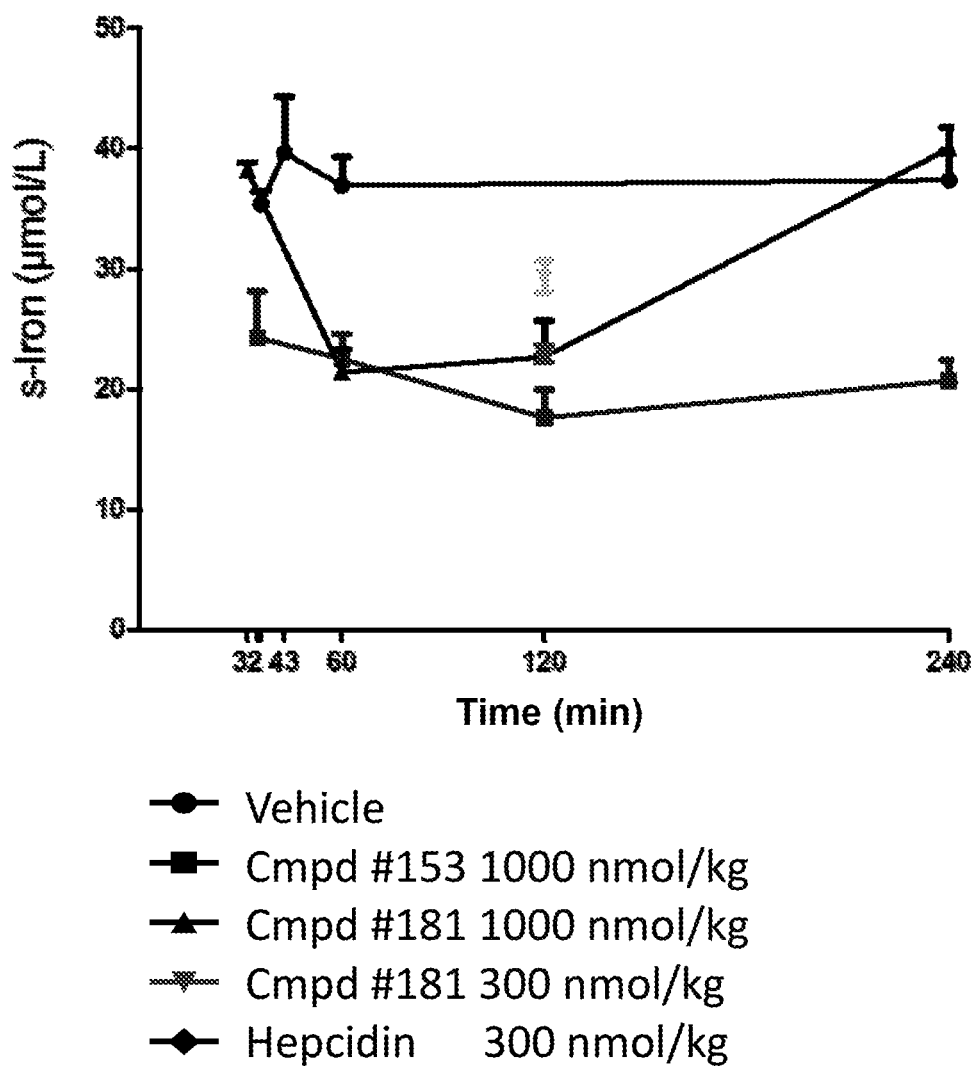
FIG. 6 shows the PK/PD effects for the in vivo serum iron reducing abilities of selected peptides of the present invention and Hepcidin. For Hepcidin and the 300 nmol/kg treatment with compound #181, only one timepoint was taken at t=120 min. The Hepcidin response is not clearly visible on this graph, as it overlapped with the Cmpd #181 1000 nmol/kg plot at the t-120 min point. The single data point for compound #181 300 nmol/kg is located directly above the Hepcidin point.

The peptides were also tested for other pharmacokinetic/pharmacodynamic (PK/PD) parameters using methods commonly know by the skilled artisan. The results of these tests are also indicated on Table 11. These parameters included determinations regarding stability (hours stable in plasma from the indicated human or rat subject), half-life in mice, and in vitro activity ($EC_{50}$), tested as described in Example 2. One example of such a study is presented in FIG. 6, wherein the PK/PD properties of two compounds of the present invention (#153 and #181) were compared with hepcidin to determine their PK/PD effects in C57BL6 mice. Each of these compounds produced a rapid decrease in serum iron, which was transient in the case of Cmpd #181, and sustained in the case of Cmpd #153.

These data, in addition to the data presented herein in Table 11, demonstrated the activity and beneficial PK/PD properties of the peptides of the present invention, a plurality of which show similar or improved PK/PD profiles as compared to hepcidin.

TABLE 11

Peptide activities in vivo

| Cmpd No. | Sequence | Stability Rat | Stability Human | Mouse PK T$_{1/2}$ (min) | In Vivo Activity EC50 (nM) | In Vivo Activity (s.c.) 300 nmol/kg | In Vivo Activity (s.c.) 1000 nmol/kg |
|---|---|---|---|---|---|---|---|
| | HepcidinHy-DTHFPICIFCCGCCHRSKCGMCCKT-OH SEQ ID NO: 335 | Var | 2.76 | | 34 | Yes | Yes |
| 2 | Isovaleric acid-DTHFPICIFGPRSKGWVC-NH$_2$ (SEQ ID NO: 29) | 0.15 | 1.99 | 17.4 | 5 | Yes | Yes |
| 3 | Isovaleric acid-DTHFPCIIFGPRSRGWVCK-NH$_2$ (SEQ ID NO: 30) | 0.08 | 0.43 | | 15 | No (i.p.) | No (i.p.) |
| 105 | Isovaleric acid-DTHFPCIIFEPRSKGWVCK-NH$_2$ (SEQ ID NO: 128) | 0.68 | 2.22 | 36.9 | 10 | Yes | Yes |
| 9 | Isovaleric acid-DTHFPCIKFGPRSKGWVCK-NH$_2$ (SEQ ID NO: 36) | 0.14 | 0.57 | 22.5 | 32 | Yes | Yes |
| 10 | Isovaleric acid-DTHFPCIQFGPRSKGWVCK-NH$_2$ (SEQ ID NO: 37) | 0.12 | | | 35 | — | Minor |
| 15 | Isovaleric acid-DTHFPCIEFGPRSKGWVCK-NH$_2$ (SEQ ID NO: 42) | 0.15 | | | 79 | — | Minor |
| 115 | Isovaleric acid-DTHFPCIIFGPRSKGCK-NH$_2$ (SEQ ID NO: 138) | | | | 21 | — | No |
| 150 | Isovaleric acid-DTHFPCIKFK(PEG8)PRSKGWVCK-NH$_2$ (SEQ ID NO: 173) | 0.42 | 1.35 | 31.6 | 7 | Yes | |
| 153 | Isovaleric acid-DTHFPCIKFGPRSKGWVCK(PEG8)-NH$_2$ (SEQ ID NO: 176) | 0.41 | 3.36 | | 18 | Yes | Yes |
| 176 | Isovaleric acid-DTHFPICIFGPRSK(PEG8)GWVC-NH$_2$ (SEQ ID NO: 199) | 1.62 | 15 | | 6 | Yes | |
| 184 | Isovaleric acid-DTHFPCIKFEPRSKGCK-NH$_2$ (SEQ ID NO: 207) | 2.12 | 8.16 | 36.9 | 16 | Yes | Yes |
| 181 | Isovaleric acid-DTHFPCIKFEPRSKGWVCK-NH$_2$ (SEQ ID NO: 204) | | | | 15 | Yes | |

Unless otherwise stated all compounds were injected s.c. Note Compound 2 was injected I.P.

Example 10

In Vitro Activity of Selected Peptide Dimers

Selected peptide dimers of the present invention were tested for in vitro activity, as described in Example 2. The EC$_{50}$ and % activity at 1 µM were determined for the peptide monomers and peptide dimers shown in Table 12. These peptide dimers were dimerized via a single disulphide linkage between a cysteine residue present in each peptide monomer. The results of these experiments are shown in Table 12.

TABLE 12

In vitro activity of peptides dimerized through a single disulphide linkage between cysteine residues

| Cmpd # | Sequence | EC$_{50}$ (nM) (n = 3) | % Activity At 1 uM | Cmpd # | Sequence | EC$_{50}$ (nM) (n = 3) | % Activity At 1 uM |
| --- | --- | --- | --- | --- | --- | --- | --- |
| 1 | Hy-DTHFPCIIF-NH$_2$ (SEQ ID NO: 28) | 133 | 92 | 311 | (Hy-DTHFPCIIF-NH$_2$)$_2$ (SEQ ID NO: 338) | 35 | 96 |
| 293 | Hy-DTHFPCIF-NH$_2$ (SEQ ID NO: 316) | >1 µM | 52 | 312 | (Hy-DTHFPCI_F-NH$_2$)$_2$ (SEQ ID NO: 339) | >300 nM | 51 |
| 297 | Hy-DTHFPCIKFF-NH$_2$ (SEQ ID NO: 320) | >300 nM | 64 | 314 | (Hy-DTHFPCIKFF-NH$_2$)$_2$ (SEQ ID NO: 341) | 130 | 100 |
| 299 | Hy-LTHFPCIIF-NH$_2$ (SEQ ID NO: 322) | >300 nM | 64 | 315 | (Hy-LTHFPCIIF-NH$_2$)$_2$ (SEQ ID NO: 342) | 35 | 97 |
| 300 | Hy-ETHFPCIIF-NH$_2$ (SEQ ID NO: 323) | >300 nM | 77 | 316 | (Hy-ETHFPCIIF-NH$_2$)$_2$ (SEQ ID NO: 343) | 63 | 100 |
| 302 | Hy-DTKFPCIIF-NH2 (SEQ ID NO: 325) | >1 µM | 60 | 317 | (Hy-DTKFPCIIF-NH$_2$)$_2$ (SEQ ID NO: 344) | 137 | 87 |
| 304 | Hy-DTHFPCIIK-NH$_2$ (SEQ ID NO: 327) | >1 µM | 55 | 318 | (Hy-DTHFPCIIK-NH$_2$)$_2$ (SEQ ID NO: 345) | >300 nM | 49 |
| 305 | Hy-DTHFPCIIR-NH$_2$ (SEQ ID NO: 328) | >1 µM | 62 | 319 | (Hy-DTHFPCIIR-NH$_2$)$_2$ (SEQ ID NO: 346) | 268 | 79 |
| 307 | Hy-DTHFPCIVF-NH$_2$ (SEQ ID NO: 330) | >300 nM | 75 | 320 | (Hy-DTHFPCIVF-NH$_2$)$_2$ (SEQ ID NO: 347) | 50 | 93 |
| 308 | Hy-DTHFPCILF-NH$_2$ (SEQ ID NO: 331) | >300 nM | 89 | 321 | (Hy-DTHFPCILF-NH$_2$)$_2$ (SEQ ID NO: 348) | 83 | 94 |
| 309 | Hy-DTHFPCILK-NH$_2$ (SEQ ID NO: 332) | >300 nM | 55 | 322 | (Hy-DTHFPCILK-NH$_2$)$_2$ (SEQ ID NO: 349) | >300 nM | 47 |
| 310 | Hy-DTHFPCIEK-NH$_2$ (SEQ ID NO: 333) | >1 µM | 0 | 323 | (Hy-DTHFPCIEK-NH$_2$)$_2$ (SEQ ID NO: 350) | >1 µM | 0 |
| 288 | Isovaleric acid-DTHFPCIIF-NH$_2$ (SEQ ID NO: 311) | 16 | 100 | 325 | (Isovaleric acid-DTHFPCIIF-NH$_2$)$_2$ (SEQ ID NO: 351) | 4 | 100 |
| 291 | Isovaleric acid-DTHFPCIKF-NH$_2$ (SEQ ID NO: 314) | 7 | 100 | 326 | (Isovaleric acid-DTHFPCIKF-NH$_2$)$_2$ (SEQ ID NO: 352) | 3 | 100 |

EC$_{50}$ values were also determined for the peptide dimers having the sequences shown in Table 10. The activity of peptide dimers dimerized only through a disulphide linkage between the two peptide monomers was compared to the activity of peptide dimers of the same monomers dimerized through both the disulphide linkage and also a DIG linking moiety. In addition, the activity of peptide dimers dimerized through a DIG linking moiety coupled to the N-terminus of the monomers, the C-terminus of the monomers, or different internal lysine residues was examined. The results of these experiments are provided in Table 13.

TABLE 13

Dimer Position explored (DIG as the representative linker explored)

| Cmpd No. | Sequence | EC$_{50}$ (nM) (n>3) |
|---|---|---|
| 327 (SEQ ID NO:353) | (DTHFPCIKF-NH$_2$)$_2$ 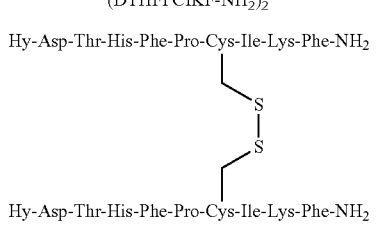 Hy-Asp-Thr-His-Phe-Pro-Cys-Ile-Lys-Phe-NH$_2$ / Hy-Asp-Thr-His-Phe-Pro-Cys-Ile-Lys-Phe-NH$_2$ | 193 |
| 328 (SEQ ID NO:354) | DIG-(DTHFPCIKF-NH$_2$)$_2$ DIG through N—terminus 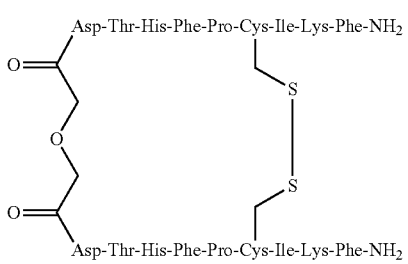 | >1000 |
| 329 (SEQ ID NO:355) | (Isovaleric acid-DTKFPCIRF-NH$_2$)$_2$ 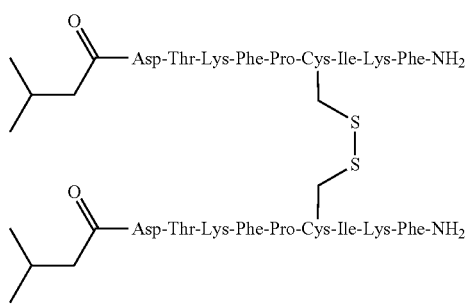 | 9 |
| 340 (SEQ ID NO:356) | (Isovaleric acid-DTKFPCIRF-NH$_2$)$_2$ DIG through K3 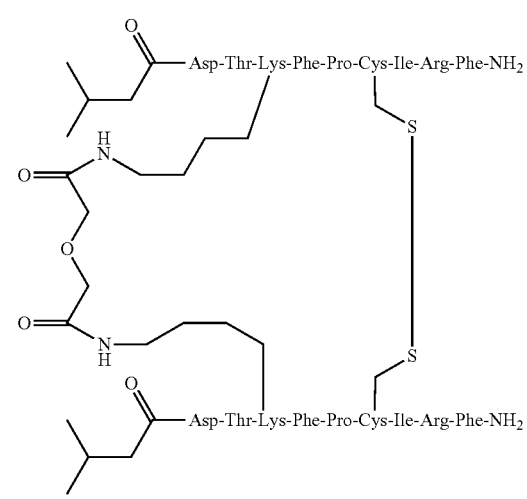 | 212 |

TABLE 13-continued
| Cmpd No. | Sequence | EC$_{50}$ (nM) (n>3) |
|---|---|---|
| 326 (SEQ ID NO:357) | (Isovaleric acid-DTHFPCIKF-NH$_2$)$_2$ 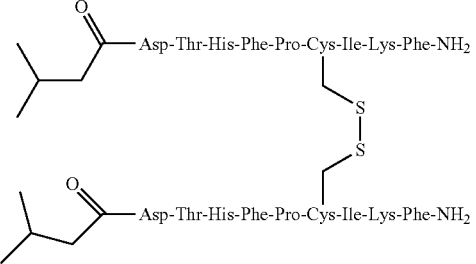 | 3 |
| 342 (SEQ ID NO:358) | (Isovaleric acid-DTHFPCIKF-NH$_2$)$_2$ DIG through K8 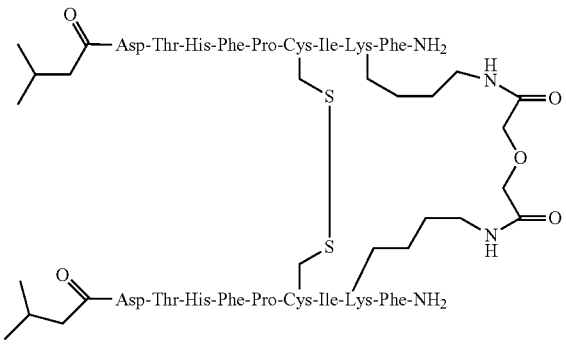 | 10 |
| 343 (SEQ ID NO:359) | (Isovaleric acid-DTHFPCIRK-NH$_2$)$_2$ 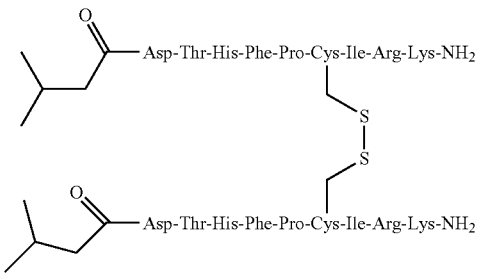 | 11 |
| 344 (SEQ ID NO:360) | (Isovaleric acid-DTHFPCIRK-NH$_2$)$_2$ DIG through K9 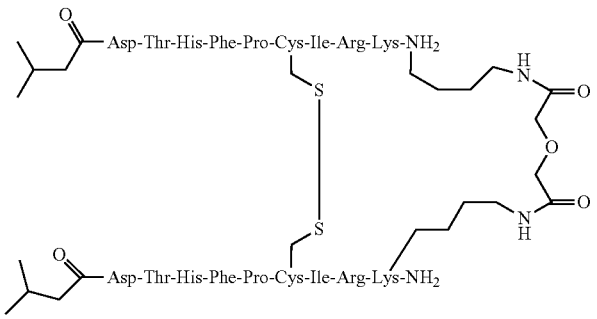 | 45 |

TABLE 13-continued

| | Dimer Position explored (DIG as the representative linker explored) | |
|---|---|---|
| Cmpd No. | Sequence | $EC_{50}$ (nM) (n>3) |
| 345 (SEQ ID NO:361) | (Isovaleric acid-DTHFPCIKFK-$NH_2$)$_2$ | 8 |

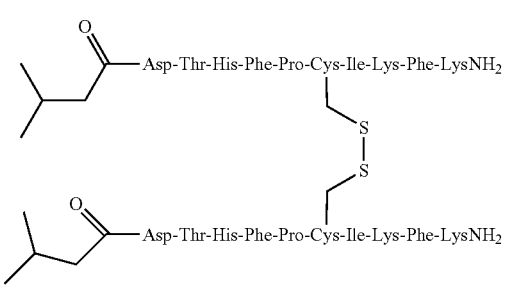

| 346 (SEQ ID NO:362) | (Isovaleric acid-DTHFPCIKFK-$NH_2$)$_2$ DIG through K10 | 15 |

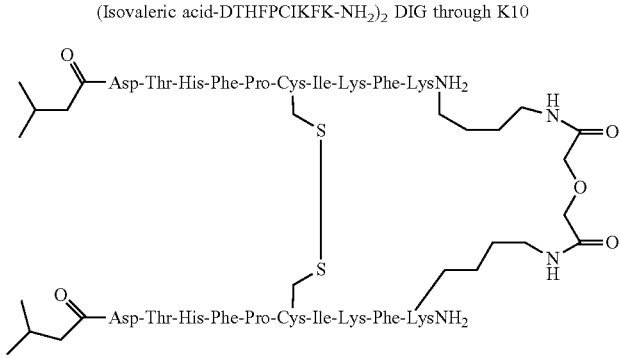

Figure 7:
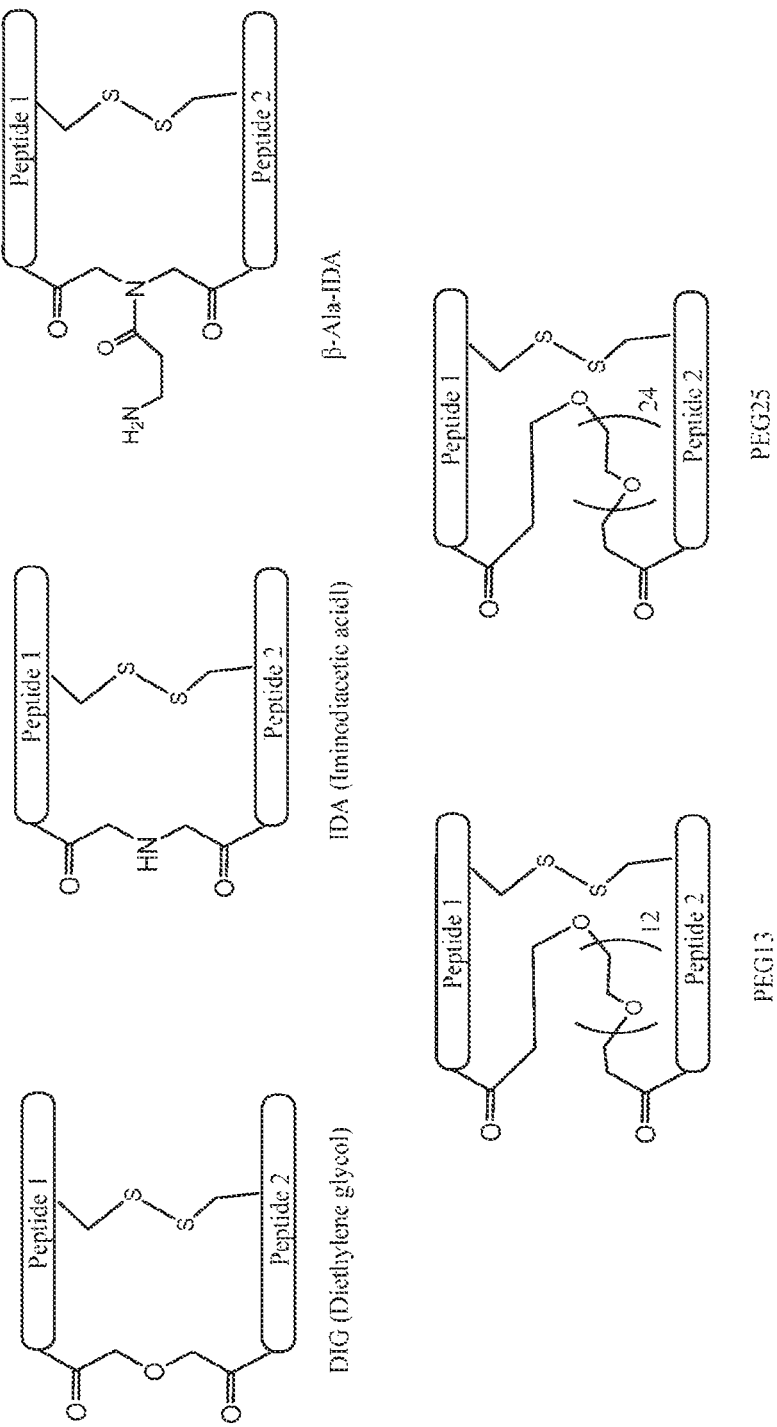
FIG. 7 shows selected examples of linkers that were used to dimerize the peptides.

$EC_{50}$ values were determined for peptide dimers comprising different linking moieties, and as compared to linkage via a disulphide bridge between the two peptide monomers, $EC_{50}$ values were determined for peptide dimers comprising different linking moieties, and as compared to linkage via a disulphide bridge between the two peptide monomers, including the peptide dimers shown in Table 14. Where a particular linking moiety is not indicated, the peptide dimer was dimerized via a disulphide bridge between cysteine residues present in each of the peptide monomers of the peptide dimer. The results of this experiment are shown in Table 14, and various linker types are shown as schematics in FIG. 7.

TABLE 14

| | Dimerization using various linkers at different positions | |
|---|---|---|
| Cmpd. No. | Sequence | Log dilutions $EC_{50}$ (nM) (n > 3) |
| 327 | (Hy-DTHFPCIKF-$NH_2$)$_2$ (SEQ ID NO: 353) | 193 |
| 348 | (Hy-DTHFPCIKF-$NH_2$)$_2$-[IDA-(β-Ala)] (SEQ ID NO: 363) | 18 |
| 326 | (Isovaleric acid-DTHFPCIKF-$NH_2$)$_2$ (SEQ ID NO: 357) | 6 |
| 349 | (Isovaleric acid-DTHFPCIKF-$NH_2$)$_2$-[IDA-(β-Ala)-Palm] (SEQ ID NO: 364) | 5 |
| 345 | (Isovaleric acid-DTHFPCIKFK-$NH_2$)$_2$ (SEQ ID NO: 361) | 8 |

TABLE 14-continued

| | Dimerization using various linkers at different positions | |
|---|---|---|
| Cmpd. No. | Sequence | Log dilutions $EC_{50}$ (nM) (n > 3) |
| 346 | (Isovaleric acid-DTHFPCIKFK-$NH_2$)$_2$-[DIG] DIG through K10 (SEQ ID NO: 362) | 15 |
| 327 | (Hy-DTHFPCIKF-$NH_2$)$_2$ (SEQ ID NO: 353) | 193 |
| 351 | [PEG25]-(DTHFPCIKF-$NH_2$)$_2$ (SEQ ID NO: 366) | >1000 |

In Table 14, brackets indicate linker and any linker conjugates (if present), e.g., [linker].

$EC_{50}$ values were determined for peptide dimers dimerized via a glycol linker attached to the εN of lysine residues within the peptide chains, as compared to the peptide monomers. As shown in Table 15, the peptide dimers had lower $EC_{50}$s than their corresponding peptide monomers. In this case, the disulphide bond exists intramolecularly within each peptide (e.g., cmpd #2 and cmpd#3) moiety before dimerization through using DIG through acylation of the Nε of lysine.

TABLE 15

Dimerization through a glycol linker attached to the ε$_N$ of lysine within the peptide chain

| Cmpd No. | Sequence | Log dilutions EC$_{50}$ (nM) (n > 3) |
|---|---|---|
| 3 | Isovaleric acid-DTHFPCIIFGPRSRGWVCK-NH$_2$ (SEQ ID NO: 30) | 15 |
| 352 | (Isovaleric acid-DTHFPCIIFGPRSRGWVCK-NH$_2$)$_2$-[DIG] (SEQ ID NO: 367) | 5 |
| 2 | Isovaleric acid-DTHFPICIFGPRSKGWVC-NH$_2$ (SEQ ID NO: 29) | 4.1 |
| 353 | (Isovaleric acid-DTHFPICIFGPRSKGWVC-NH$_2$)$_2$-[DIG] (SEQ ID NO: 368) | 2.2 |

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A peptide having the following structural formula I'

$$R^{1'}-X'-Y'-R^{2'} \quad (I') \text{ (SEQ ID NO:21)}$$

or a pharmaceutically acceptable salt or solvate thereof, wherein $R^{1'}$ is hydrogen, $C_1$-$C_6$ alkyl, $C_6$-$C_{12}$ aryl, $C_6$-$C_{12}$ aryl $C_1$-$C_6$ alkyl, $C_1$-$C_{20}$ alkanoyl or pGlu;

$R^{2'}$ is —$NH_2$ or —OH;

X' is a peptide sequence having the formula Ia'

$$X1-X2-X3-X4-X5-X6-X7-X8-X9-X10 \quad (Ia') \text{ (SEQ ID NO:13)}$$

wherein

X1 is Asp, Glu, Ala, Gly, Thr, Ida, pGlu, bhAsp, D-Asp, Tyr, Leu or absent;

X2 is Thr, Ala, Aib, D-Thr, Arg or absent;

X3 is His, Ala, D-His or Lys;

X4 is Phe, Ala, Dpa, bhPhe or D-Phe;

X5 is Pro, Glu, Ser, Gly, Arg, Lys, Val, Ala, D-Pro, Sarc, Abu or absent;

X6 is Ile, Cys, Arg, Leu, Lys, His, Glu, D-Ile, D-Arg, D-Cys, Val, Ser or Ala;

X7 is Cys, Ile, Ala, Leu, Val, Ser, Phe, Dapa, D-Ile or D-Cys;

X8 is Ile, Lys, Arg, Ala, Gln, Phe, Glu, Asp, Tyr, Ser, Leu, Val, D-Ile, D-Lys, D-Arg, or Dapa;

X9 is Phe, Ala, Ile, Tyr, Lys, Arg, bhPhe or D-Phe; and

X10 is Lys, Phe or absent;

Y' is a peptide having the formula IIa'

$$Y1-Y2-Y3-Y4-Y5-Y6-Y7-Y8-Y9-Y10-Y11-Y12-Y13-Y14-Y15 \quad (IIa') \text{ (SEQ ID NO:16)}$$

wherein

Y1 is Gly, Cys, Ala, Phe, Pro, Glu, Lys, D-Pro, Val, Ser or absent;

Y2 is Pro, Ala, Cys, Gly or absent;

Y3 is Arg, Lys, Pro, Gly, His, Ala, Trp or absent;

Y4 is Ser, Arg, Gly, Trp, Ala, His, Tyr or absent;

Y5 is Lys, Met, Arg, Ala or absent;

Y6 is Gly, Ser, Lys, Ile, Ala, Pro, Val or absent;

Y7 is Trp, Lys, Gly, Ala Ile, Val or absent;

Y8 is Val, Thr, Gly, Cys, Met, Tyr, Ala, Glu, Lys, Asp, Arg or absent;

Y9 is Cys, Tyr or absent;

Y10 is Met, Lys, Arg, Tyr or absent;

Y11 is Arg, Met, Cys, Lys or absent;

Y12 is Arg, Lys, Ala or absent;

Y13 is Arg, Cys, Lys, Val or absent;

Y14 is Arg, Lys, Pro, Cys, Thr or absent; and

Y15 is Thr, Arg or absent;

wherein at least one of Y1, Y2, Y8, Y9, Y11, Y13, or Y14 is Cys;

wherein said compound of formula I' is optionally PEGylated on X', or Y'; and wherein when said compound of formula I' comprises two or more cysteine residues, at least two of said cysteine residues being linked via a disulfide bond.

2. The peptide of formula I' or pharmaceutically acceptable salt or solvate thereof according to claim 1, wherein $R^{1'}$ is hydrogen, isovaleric acid, isobutyric acid or acetyl.

3. The peptide of formula I' or pharmaceutically acceptable salt or solvate thereof according to claim 1, wherein X' is a peptide having formula Ia' and wherein X1 is Asp, Ala, Ida, pGlu, bhAsp, Leu, D-Asp or absent;
X2 is Thr, Ala, or D-Thr;
X3 is His, D-His or Lys;
X4 is Phe, Ala, Dpa or D-Phe;
X5 is Pro, Gly, Arg, Lys, Ala, D-Pro or bhPro;
X6 is Ile, Cys, Arg, Lys, D-Ile or D-Cys;
X7 is Cys, Ile, Leu, Val, Phe, D-Ile or D-Cys;
X8 is Ile, Arg, Phe, Gln, Lys, Glu, Val, Leu or D-Ile;
X9 is Phe or bhPhe; and
X10 is Lys, Phe or absent.

4. The peptide of formula I' or pharmaceutically acceptable salt or solvate thereof according to claim 1, wherein X' is a peptide having formula Ib'

X1-Thr-His-X4-X5-X6-X7-X8-Phe-X10 (Ib') (SEQ ID NO:14)

wherein
X1 is Asp, Ida, pGlu, bhAsp or absent;
X4 is Phe or Dpa;
X5 is Pro or bhPro;
X6 is Ile, Cys or Arg;
X7 is Cys, Ile, Leu or Val;
X8 is Ile, Lys, Glu, Phe, Gln or Arg; and
X10 is Lys or absent.

5. The peptide of formula or I' pharmaceutically acceptable salt or solvate thereof according to claim h, wherein X' is a peptide having formula Ic'

X1-Thr-His-X4-X5-Cys-Ile-X8-Phe-X10 (Ic') (SEQ ID NO:15)

wherein
X1 is Asp, Ida, pGlu, bhAsp or absent;
X4 is Phe or Dpa;
X5 is Pro or bhPro;
X8 is Ile, Lys, Glu, Phe, Gln or Arg; and
X10 is Lys or absent.

6. The peptide of forumla I' pharmaceutically acceptable salt or solvate thereof according to claim 1, wherein Y' is a peptide having formula IIb'

Y1-Y2-Y3-Y4-Y5-Y6-Y7-Y8-Cys-Y10 (IIb') (SEQ ID NO:17)

wherein
Y1 is Gly, Ala, Lys, Pro or D-Pro;
Y2 is Pro, Ala or Gly;
Y3 is Arg, Ala, Lys or Trp;
Y4 is Ser, Gly or Ala;
Y5 is Lys, Met, Arg or Ala;
Y6 is Gly, Arg or Ala;
Y7 is Trp or Ala;
Y8 is Val, Thr, Ala or Glu; and
Y10 is Met, Lys or absent.

7. The peptide of formula I' or pharmaceutically acceptable salt or solvate thereof according to claim 1, wherein Y' is a peptide having formula IIc'

Y1-Y2-Y3-Ser-Lys-Gly-Trp-Y8-Cys-Y10 (IIc') (SEQ ID NO:18)

wherein
Y1 is Gly, Pro or D-Pro;
Y2 is Pro or Gly;
Y3 is Arg or Lys;
Y8 is Val or Thr; and
Y10 is Met, Lys or absent.

8. The peptide of formula I' or pharmaceutically acceptable salt or solvate thereof according to claim 1, wherein Y' is a peptide having the formula IId'

Y1-Cys-Y3-Y4-Arg-Y6-Y7-Y8-Cys-Y10-Y11-Y12-Y13-Y14-Y15 (IId') (SEQ ID NO:19)

wherein
Y1 is Val or Ala or absent;
Y3 is Gly, Pro or absent;
Y4 is His, Trp or Tyr;
Y6 is Ser, Gly or Pro;
Y7 is Ile, Gly or Lys;
Y8 is Gly, Met or absent;
Y10 is Tyr or Cys;
Y11 is Arg, Lys, Met or Ala;
Y12 is Arg or Ala;
Y13 is Cys or Val or absent;
Y14 is Cys, Lys, Pro, Arg, Thr or absent; and
Y15 is Arg, Thr or absent.

9. The peptide of formula I' or pharmaceutically acceptable salt or solvate thereof according to claim 1, wherein Y' is a peptide having the formula IIe'

Val-Cys-Y3-His-Arg-Y6-Y7-Y8-Cys-Tyr-Arg-Y12-Y13-Y14-Y15 (IIe') (SEQ ID NO:20)

wherein
Y3 is Gly or absent;
Y6 is Ser or Pro;
Y7 is Ile or Lys;
Y8 is Gly or absent;
Y12 is Arg or Ala;
Y13 is Cys or Val or absent;
Y14 is Cys, Arg, Thr or absent; and
Y15 is Arg or absent.

10. The peptide of formula I' or pharmaceutically acceptable salt or solvate thereof according to claim 1, wherein the peptide exhibits hepcidin activity.

11. The peptide of formula I' or pharmaceutically acceptable salt or solvate thereof according to claim 1, wherein the peptide binds ferroportin.

12. A composition which comprises at least one peptide of formula I' or pharmaceutically acceptable salt or solvate thereof according to claim 1.

13. A method of treating a disease of iron metabolism in a subject which comprises administering at least one peptide of formula I' or pharmaceutically acceptable salt or solvate thereof according to claim 1 or the composition according to claim 12 to the subject; wherein the disease of iron metabolism is hereditary hemochromatosis, iron hemochromatosis, HFE (High Iron Fe) mutation hemochromatosis, ferroportin mutation hemochromatosis, transferrin receptor 2 mutation hemochromatosis, hemojuvelin mutation hemochromatosis, hepicidin mutation hemochromatosis, juvenile hemochromatosis, neonatal hemochromatosis, hepcidin deficiency, transfusional iron overload, or thalassemia.

14. The method of claim 13, wherein the disease of iron metabolism is the transfusional iron overload disease.

15. The method of claim 13, wherein the disease of iron metabolism is hereditary hemochromatosis, iron hemochromatosis, HFE (High Iron Fe) mutation hemochromatosis, ferroportin mutation hemochromatosis, transferrin receptor 2 mutation hemochromatosis, hemojuvelin mutation hemochromatosis, hepcidin mutation hemochromatosis, juvenile hemochromatosis, or neonatal hemochromatosis.

16. The method of claim 13, wherein the disease of iron metabolism is the thalassemia.

17. The method of claim 16, wherein the thalassemia is thalassemia intermedia, alpha thalassemia, or β-thalassemia.

18. The method of claim 17, wherein the disease of iron metabolism is β-thalassemia.

19. The method of claim 15, wherein the disease of iron metabolism is hereditary hemochromatosis (HH).

* * * * *

SEQUENCE LISTING

```
<160> NUMBER OF SEQ ID NOS: 375

<210> SEQ ID NO 1
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Asp, Glu, Ala, Gly Thr, Tyr, Leu, D-Asp,
      Iminodiacetic acid, pyroglutamic acid, beta-homoaspartic acid or
      absent
<220> FEATURE:
<221> NAME/KEY: MISC_FEATURE
<222> LOCATION: (2)..(2)
<223> OTHER INFORMATION: Xaa = Thr, Ala, Arg, D-Thr, alpha-
      aminoisobutyric acid or absent
<220> FEATURE:
<221> NAME/KEY: MISC_FEATURE
<222> LOCATION: (3)..(3)
<223> OTHER INFORMATION: Xaa = His, Lys, Ala or D-His
<220> FEATURE:
<221> NAME/KEY: MISC_FEATURE
<222> LOCATION: (4)..(4)
<223> OTHER INFORMATION: Xaa = Phe, Ala, D-Phe, beta-beta-
      diphenylalanine or beta-homophenylalanine
<220> FEATURE:
<221> NAME/KEY: MISC_FEATURE
<222> LOCATION: (5)..(5)
<223> OTHER INFORMATION: Xaa = Pro, Glu, Ser, Gly, Arg, Lys, Val, Ala,
      D-Pro, beta-homoproline, 4-aminobutyric acid, sarcosine or absent
<220> FEATURE:
<221> NAME/KEY: MISC_FEATURE
<222> LOCATION: (6)..(6)
<223> OTHER INFORMATION: Xaa = Ile, Cys, Arg, Leu, Lys, His, Glu, D-Ile,
      D-Arg, D-Cys, Val, Ser or Ala
<220> FEATURE:
<221> NAME/KEY: MISC_FEATURE
<222> LOCATION: (7)..(7)
<223> OTHER INFORMATION: Xaa = Cys, Ile, Ala, Leu, Val, Ser, Phe, D-Ile,
      D-Cys or (2,3-diaminopropanoic acid)
<220> FEATURE:
<221> NAME/KEY: MISC_FEATURE
<222> LOCATION: (8)..(8)
<223> OTHER INFORMATION: Xaa = Ile, Lys, Arg, Ala, Gln, Phe, Glu, Asp,
      Tyr, Ser, Leu, Val, D-Ile, D-Lys, D-Arg or (2,3-diaminopropanoic
      acid)
<220> FEATURE:
<221> NAME/KEY: MISC_FEATURE
<222> LOCATION: (9)..(9)
<223> OTHER INFORMATION: Xaa = Phe, Ala, Ile, Tyr, Lys, Arg, beta-
      homoproline or D-Phe
<220> FEATURE:
```

```
<221> NAME/KEY: MISC_FEATURE
<222> LOCATION: (10)..(10)
<223> OTHER INFORMATION: Xaa = Lys, Phe or absent

<400> SEQUENCE: 1

Xaa Xaa Xaa Xaa Xaa Xaa Xaa Xaa Xaa Xaa
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Hepcidine peptide analogue motif
<220> FEATURE:
<221> NAME/KEY: MISC_FEATURE
<222> LOCATION: (1)..(1)
<223> OTHER INFORMATION: Xaa = Asp, Glu, iminodiacetic acid,
      pyroglutamic acid, beta-homoaspartic acid or absent
<220> FEATURE:
<221> NAME/KEY: MISC_FEATURE
<222> LOCATION: (4)..(4)
<223> OTHER INFORMATION: Xaa = Phe or (beta,beta diphenylalanine)
<220> FEATURE:
<221> NAME/KEY: MISC_FEATURE
<222> LOCATION: (5)..(5)
<223> OTHER INFORMATION: Xaa = Pro or beta-homoproline
<220> FEATURE:
<221> NAME/KEY: MISC_FEATURE
<222> LOCATION: (6)..(6)
<223> OTHER INFORMATION: Xaa = Ile, Cys or Arg
<220> FEATURE:
<221> NAME/KEY: MISC_FEATURE
<222> LOCATION: (7)..(7)
<223> OTHER INFORMATION: Xaa = Cys , Ile, Leu or Val
<220> FEATURE:
<221> NAME/KEY: MISC_FEATURE
<222> LOCATION: (8)..(8)
<223> OTHER INFORMATION: Xaa = Ile, Lys, Glu, Phe, Gln or Arg
<220> FEATURE:
<221> NAME/KEY: MISC_FEATURE
<222> LOCATION: (10)..(10)
<223> OTHER INFORMATION: Xaa = Lys, Phe or absent

<400> SEQUENCE: 2

Xaa Thr His Xaa Xaa Xaa Xaa Xaa Phe Xaa
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Asp, Glu, Iminodiacetic acid,
      pyroglutamic acid, beta-homoaspartic acid or absent
<220> FEATURE:
<221> NAME/KEY: MISC_FEATURE
<222> LOCATION: (4)..(4)
<223> OTHER INFORMATION: Xaa = Phe or (beta,beta diphenylalanine)
<220> FEATURE:
<221> NAME/KEY: MISC_FEATURE
<222> LOCATION: (5)..(5)
<223> OTHER INFORMATION: Xaa = Pro or beta-homoproline
<220> FEATURE:
<221> NAME/KEY: MISC_FEATURE
<222> LOCATION: (8)..(8)
<223> OTHER INFORMATION: Xaa = Ile, Lys, Glu, Phe, Gln or Arg
<220> FEATURE:
<221> NAME/KEY: MISC_FEATURE
<222> LOCATION: (10)..(10)
<223> OTHER INFORMATION: Xaa = Lys or absent
```

<400> SEQUENCE: 3

Xaa Thr His Xaa Xaa Cys Ile Xaa Phe Xaa
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Asp, Glu or Iminodiacetic acid
<220> FEATURE:
<221> NAME/KEY: MISC_FEATURE
<222> LOCATION: (5)..(5)
<223> OTHER INFORMATION: Xaa = Pro or beta-homoproline
<220> FEATURE:
<221> NAME/KEY: MISC_FEATURE
<222> LOCATION: (8)..(8)
<223> OTHER INFORMATION: Xaa = Ile Lys or Phe
<220> FEATURE:
<221> NAME/KEY: MISC_FEATURE
<222> LOCATION: (10)..(10)
<223> OTHER INFORMATION: Xaa = absent

<400> SEQUENCE: 4

Xaa Thr His Phe Xaa Cys Ile Xaa Phe Xaa
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Gly, Cys, Ala, Phe, Pro, Glu, Lys, D-Pro,
      Val, Ser or absent
<220> FEATURE:
<221> NAME/KEY: MISC_FEATURE
<222> LOCATION: (2)..(2)
<223> OTHER INFORMATION: Xaa = Pro, Ala, Cys, Gly or absent
<220> FEATURE:
<221> NAME/KEY: MISC_FEATURE
<222> LOCATION: (3)..(3)
<223> OTHER INFORMATION: Xaa = Arg, Lys, Pro, Gly, His, Ala, Trp or
      absent
<220> FEATURE:
<221> NAME/KEY: MISC_FEATURE
<222> LOCATION: (4)..(4)
<223> OTHER INFORMATION: Xaa = Ser, Arg, Gly, Trp, Ala, His, Tyr or
      absent
<220> FEATURE:
<221> NAME/KEY: MISC_FEATURE
<222> LOCATION: (5)..(5)
<223> OTHER INFORMATION: Xaa = Lys, Met, Arg, Ala or absent
<220> FEATURE:
<221> NAME/KEY: MISC_FEATURE
<222> LOCATION: (6)..(6)
<223> OTHER INFORMATION: Xaa = Gly, Ser, Lys, Ile, Arg, Ala, Pro, Val or
      absent
<220> FEATURE:
<221> NAME/KEY: MISC_FEATURE
<222> LOCATION: (7)..(7)
<223> OTHER INFORMATION: Xaa = Trp, Lys, Gly, Ala Ile, Val or absent
<220> FEATURE:
<221> NAME/KEY: MISC_FEATURE
<222> LOCATION: (8)..(8)
<223> OTHER INFORMATION: Xaa = Val, Thr, Gly, Cys, Met, Tyr, Ala, Glu,
      Lys, Asp, Arg or absent

```
<220> FEATURE:
<221> NAME/KEY: MISC_FEATURE
<222> LOCATION: (9)..(9)
<223> OTHER INFORMATION: Xaa = Cys, Tyr or absent
<220> FEATURE:
<221> NAME/KEY: MISC_FEATURE
<222> LOCATION: (10)..(10)
<223> OTHER INFORMATION: Xaa = Met, Lys, Arg, Tyr or absent
<220> FEATURE:
<221> NAME/KEY: MISC_FEATURE
<222> LOCATION: (11)..(11)
<223> OTHER INFORMATION: Xaa = Arg, Met, Cys, Lys or absent
<220> FEATURE:
<221> NAME/KEY: MISC_FEATURE
<222> LOCATION: (12)..(12)
<223> OTHER INFORMATION: Xaa = Arg, Lys, Ala or absent
<220> FEATURE:
<221> NAME/KEY: MISC_FEATURE
<222> LOCATION: (13)..(13)
<223> OTHER INFORMATION: Xaa = Arg, Cys, Lys, Val or absent
<220> FEATURE:
<221> NAME/KEY: MISC_FEATURE
<222> LOCATION: (14)..(14)
<223> OTHER INFORMATION: Xaa = Arg, Lys, Pro, Cys, Thr or absent
<220> FEATURE:
<221> NAME/KEY: MISC_FEATURE
<222> LOCATION: (15)..(15)
<223> OTHER INFORMATION: Xaa = Thr, Arg or absent

<400> SEQUENCE: 5

Xaa Xaa Xaa Xaa Xaa Xaa Xaa Xaa Xaa Xaa Xaa Xaa Xaa Xaa Xaa
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Gly, Ala, Lys, Pro or D-Pro
<220> FEATURE:
<221> NAME/KEY: MISC_FEATURE
<222> LOCATION: (2)..(2)
<223> OTHER INFORMATION: Xaa = Pro, Ala or Gly
<220> FEATURE:
<221> NAME/KEY: MISC_FEATURE
<222> LOCATION: (3)..(3)
<223> OTHER INFORMATION: Xaa = Arg, Ala, Lys or Trp
<220> FEATURE:
<221> NAME/KEY: MISC_FEATURE
<222> LOCATION: (4)..(4)
<223> OTHER INFORMATION: Xaa = Ser, Gly or Ala
<220> FEATURE:
<221> NAME/KEY: MISC_FEATURE
<222> LOCATION: (5)..(5)
<223> OTHER INFORMATION: Xaa = Lys, Met, Arg or Ala
<220> FEATURE:
<221> NAME/KEY: MISC_FEATURE
<222> LOCATION: (6)..(6)
<223> OTHER INFORMATION: Xaa = Gly, Arg or Ala
<220> FEATURE:
<221> NAME/KEY: MISC_FEATURE
<222> LOCATION: (7)..(7)
<223> OTHER INFORMATION: Xaa = Trp, Ala or absent
<220> FEATURE:
<221> NAME/KEY: MISC_FEATURE
<222> LOCATION: (8)..(8)
<223> OTHER INFORMATION: Xaa = Val, Thr, Lys, Ala, Glu or absent
<220> FEATURE:
<221> NAME/KEY: MISC_FEATURE
<222> LOCATION: (10)..(10)
<223> OTHER INFORMATION: Xaa = Met, Lys or absent

<400> SEQUENCE: 6
```

```
Xaa Xaa Xaa Xaa Xaa Xaa Xaa Xaa Cys Xaa
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Gly, Pro or D-Pro
<220> FEATURE:
<221> NAME/KEY: MISC_FEATURE
<222> LOCATION: (2)..(2)
<223> OTHER INFORMATION: Xaa = Pro or Gly
<220> FEATURE:
<221> NAME/KEY: MISC_FEATURE
<222> LOCATION: (3)..(3)
<223> OTHER INFORMATION: Xaa = Arg or Lys
<220> FEATURE:
<221> NAME/KEY: MISC_FEATURE
<222> LOCATION: (8)..(8)
<223> OTHER INFORMATION: Xaa = Val or Thr
<220> FEATURE:
<221> NAME/KEY: MISC_FEATURE
<222> LOCATION: (10)..(10)
<223> OTHER INFORMATION: Xaa = Met, Lys or absent

<400> SEQUENCE: 7

Xaa Xaa Xaa Ser Lys Gly Trp Xaa Cys Xaa
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Val, Ala or absent
<220> FEATURE:
<221> NAME/KEY: MISC_FEATURE
<222> LOCATION: (3)..(3)
<223> OTHER INFORMATION: Xaa = Gly, Pro or absent
<220> FEATURE:
<221> NAME/KEY: MISC_FEATURE
<222> LOCATION: (4)..(4)
<223> OTHER INFORMATION: Xaa = His, Trp or Tyr
<220> FEATURE:
<221> NAME/KEY: MISC_FEATURE
<222> LOCATION: (6)..(6)
<223> OTHER INFORMATION: Xaa = Ser, Gly or Pro
<220> FEATURE:
<221> NAME/KEY: MISC_FEATURE
<222> LOCATION: (7)..(7)
<223> OTHER INFORMATION: Xaa = Ile, Gly or Lys
<220> FEATURE:
<221> NAME/KEY: MISC_FEATURE
<222> LOCATION: (8)..(8)
<223> OTHER INFORMATION: Xaa = Gly, Met or absent
<220> FEATURE:
<221> NAME/KEY: MISC_FEATURE
<222> LOCATION: (10)..(10)
<223> OTHER INFORMATION: Xaa = Tyr or Cys
<220> FEATURE:
<221> NAME/KEY: MISC_FEATURE
<222> LOCATION: (11)..(11)
<223> OTHER INFORMATION: Xaa = Arg, Lys, Met or Ala
<220> FEATURE:
<221> NAME/KEY: MISC_FEATURE
<222> LOCATION: (12)..(12)
```

```
<223> OTHER INFORMATION: Xaa = Arg or Ala
<220> FEATURE:
<221> NAME/KEY: MISC_FEATURE
<222> LOCATION: (13)..(13)
<223> OTHER INFORMATION: Xaa = Cys or Val or absent
<220> FEATURE:
<221> NAME/KEY: MISC_FEATURE
<222> LOCATION: (14)..(14)
<223> OTHER INFORMATION: Xaa = Cys, Lys, Pro, Arg, Thr or absent
<220> FEATURE:
<221> NAME/KEY: MISC_FEATURE
<222> LOCATION: (15)..(15)
<223> OTHER INFORMATION: Xaa = Arg, Thr or absent

<400> SEQUENCE: 8

Xaa Cys Xaa Xaa Arg Xaa Xaa Xaa Cys Xaa Xaa Xaa Xaa Xaa Xaa
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (3)..(3)
<223> OTHER INFORMATION: Xaa = Gly or absent
<220> FEATURE:
<221> NAME/KEY: MISC_FEATURE
<222> LOCATION: (6)..(6)
<223> OTHER INFORMATION: Xaa = Ser or Pro;
<220> FEATURE:
<221> NAME/KEY: MISC_FEATURE
<222> LOCATION: (7)..(7)
<223> OTHER INFORMATION: Xaa = Ile or Lys
<220> FEATURE:
<221> NAME/KEY: MISC_FEATURE
<222> LOCATION: (8)..(8)
<223> OTHER INFORMATION: Xaa = Gly or absent
<220> FEATURE:
<221> NAME/KEY: MISC_FEATURE
<222> LOCATION: (12)..(12)
<223> OTHER INFORMATION: Xaa = Arg or Ala
<220> FEATURE:
<221> NAME/KEY: MISC_FEATURE
<222> LOCATION: (13)..(13)
<223> OTHER INFORMATION: Xaa = Cys or Val or absent
<220> FEATURE:
<221> NAME/KEY: MISC_FEATURE
<222> LOCATION: (14)..(14)
<223> OTHER INFORMATION: Xaa = Cys, Arg, Thr or absent
<220> FEATURE:
<221> NAME/KEY: MISC_FEATURE
<222> LOCATION: (15)..(15)
<223> OTHER INFORMATION: Xaa = Arg or absent

<400> SEQUENCE: 9

Val Cys Xaa His Arg Xaa Xaa Xaa Cys Tyr Arg Xaa Xaa Xaa Xaa
1               5                   10                  15

<210> SEQ ID NO 10
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Gly, Glu, Val or Lys
<220> FEATURE:
<221> NAME/KEY: MISC_FEATURE
<222> LOCATION: (3)..(3)
<223> OTHER INFORMATION: Xaa = Arg or Lys
```

```
-continued

<220> FEATURE:
<221> NAME/KEY: MISC_FEATURE
<222> LOCATION: (5)..(5)
<223> OTHER INFORMATION: Xaa = Arg or Lys
<220> FEATURE:
<221> NAME/KEY: MISC_FEATURE
<222> LOCATION: (6)..(6)
<223> OTHER INFORMATION: Xaa = Gly, Ser, Lys, Ile or Arg
<220> FEATURE:
<221> NAME/KEY: MISC_FEATURE
<222> LOCATION: (7)..(7)
<223> OTHER INFORMATION: Xaa = Trp or absent
<220> FEATURE:
<221> NAME/KEY: MISC_FEATURE
<222> LOCATION: (8)..(8)
<223> OTHER INFORMATION: Xaa = Val, Thr, Asp, Glu or absent
<220> FEATURE:
<221> NAME/KEY: MISC_FEATURE
<222> LOCATION: (10)..(10)
<223> OTHER INFORMATION: Xaa = Lys or absent

<400> SEQUENCE: 10

Xaa Pro Xaa Ser Xaa Xaa Xaa Xaa Cys Xaa
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Glu or Lys
<220> FEATURE:
<221> NAME/KEY: MISC_FEATURE
<222> LOCATION: (3)..(3)
<223> OTHER INFORMATION: Xaa = Arg or Lys
<220> FEATURE:
<221> NAME/KEY: MISC_FEATURE
<222> LOCATION: (5)..(5)
<223> OTHER INFORMATION: Xaa = Arg or Lys
<220> FEATURE:
<221> NAME/KEY: MISC_FEATURE
<222> LOCATION: (6)..(6)
<223> OTHER INFORMATION: Xaa = Gly, Ser, Lys, Ile or Arg
<220> FEATURE:
<221> NAME/KEY: MISC_FEATURE
<222> LOCATION: (7)..(7)
<223> OTHER INFORMATION: Xaa = Trp or absent
<220> FEATURE:
<221> NAME/KEY: MISC_FEATURE
<222> LOCATION: (8)..(8)
<223> OTHER INFORMATION: Xaa = Val, or absent
<220> FEATURE:
<221> NAME/KEY: MISC_FEATURE
<222> LOCATION: (10)..(10)
<223> OTHER INFORMATION: Xaa = Lys or absent

<400> SEQUENCE: 11

Xaa Pro Xaa Ser Xaa Xaa Xaa Xaa Cys Xaa
 1               5                  10

<210> SEQ ID NO 12
<211> LENGTH: 25
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Asp, Glu, Ala, Gly Thr, Tyr, Leu, D-Asp,
     Iminodiacetic acid, pyroglutamic acid, beta-homoaspartic acid or
```

```
      absent
<220> FEATURE:
<221> NAME/KEY: MISC_FEATURE
<222> LOCATION: (2)..(2)
<223> OTHER INFORMATION: Xaa = Thr, Ala, Arg, D-Thr, alpha-
      aminoisobutyric acid or absent
<220> FEATURE:
<221> NAME/KEY: MISC_FEATURE
<222> LOCATION: (3)..(3)
<223> OTHER INFORMATION: Xaa = His, Lys, Ala or D-His
<220> FEATURE:
<221> NAME/KEY: MISC_FEATURE
<222> LOCATION: (4)..(4)
<223> OTHER INFORMATION: Xaa = Phe, Ala, D-Phe, beta-beta-
      diphenylalanine or beta-homophenylalanine
<220> FEATURE:
<221> NAME/KEY: MISC_FEATURE
<222> LOCATION: (5)..(5)
<223> OTHER INFORMATION: Xaa = Pro, Glu, Ser, Gly, Arg, Lys, Val, Ala,
      D-Pro, beta-homoproline, 4-aminobutyric acid, sarcosine or absent
<220> FEATURE:
<221> NAME/KEY: MISC_FEATURE
<222> LOCATION: (6)..(6)
<223> OTHER INFORMATION: Xaa = Ile, Cys, Arg, Leu, Lys, His, Glu, D-Ile,
      D-Arg, D-Cys, Val, Ser or Ala
<220> FEATURE:
<221> NAME/KEY: MISC_FEATURE
<222> LOCATION: (7)..(7)
<223> OTHER INFORMATION: Xaa = Cys, Ile, Ala, Leu, Val, Ser, Phe, D-Ile,
      D-Cys or (2,3-diaminopropanoic acid)
<220> FEATURE:
<221> NAME/KEY: MISC_FEATURE
<222> LOCATION: (8)..(8)
<223> OTHER INFORMATION: Xaa = Ile, Lys, Arg, Ala, Gln, Phe, Glu, Asp,
      Tyr, Ser, Leu, Val, D-Ile, D-Lys, D-Arg or (2,3-diaminopropanoic
      acid)
<220> FEATURE:
<221> NAME/KEY: MISC_FEATURE
<222> LOCATION: (9)..(9)
<223> OTHER INFORMATION: Xaa = Phe, Ala, Ile, Tyr, Lys, Arg, beta-
      homoproline or D-Phe
<220> FEATURE:
<221> NAME/KEY: MISC_FEATURE
<222> LOCATION: (10)..(10)
<223> OTHER INFORMATION: Xaa = Lys, Phe or absent
<220> FEATURE:
<221> NAME/KEY: MISC_FEATURE
<222> LOCATION: (11)..(11)
<223> OTHER INFORMATION: Xaa = Gly, Cys, Ala, Phe, Pro, Glu, Lys, D-Pro,
      Val, Ser or absent
<220> FEATURE:
<221> NAME/KEY: MISC_FEATURE
<222> LOCATION: (12)..(12)
<223> OTHER INFORMATION: Xaa = Pro, Ala, Cys, Gly or absent
<220> FEATURE:
<221> NAME/KEY: MISC_FEATURE
<222> LOCATION: (13)..(13)
<223> OTHER INFORMATION: Xaa = Arg, Lys, Pro, Gly, His, Ala, Trp or
      absent
<220> FEATURE:
<221> NAME/KEY: MISC_FEATURE
<222> LOCATION: (14)..(14)
<223> OTHER INFORMATION: Xaa = Ser, Arg, Gly, Trp, Ala, His, Tyr or
      absent
<220> FEATURE:
<221> NAME/KEY: MISC_FEATURE
<222> LOCATION: (15)..(15)
<223> OTHER INFORMATION: Xaa = Lys, Met, Arg, Ala or absent
<220> FEATURE:
<221> NAME/KEY: MISC_FEATURE
<222> LOCATION: (16)..(16)
<223> OTHER INFORMATION: Xaa = Gly, Ser, Lys, Ile, Arg, Ala, Pro, Val or
      absent
<220> FEATURE:
<221> NAME/KEY: MISC_FEATURE
<222> LOCATION: (17)..(17)
<223> OTHER INFORMATION: Xaa = Trp, Lys, Gly, Ala Ile, Val or absent
<220> FEATURE:
<221> NAME/KEY: MISC_FEATURE
```

```
<222> LOCATION: (18)..(18)
<223> OTHER INFORMATION: Xaa = Val, Thr, Gly, Cys, Met, Tyr, Ala, Glu,
      Lys, Asp, Arg or absent
<220> FEATURE:
<221> NAME/KEY: MISC_FEATURE
<222> LOCATION: (19)..(19)
<223> OTHER INFORMATION: Xaa = Cys, Tyr or absent
<220> FEATURE:
<221> NAME/KEY: MISC_FEATURE
<222> LOCATION: (20)..(20)
<223> OTHER INFORMATION: Xaa = Met, Lys, Arg, Tyr or absent
<220> FEATURE:
<221> NAME/KEY: MISC_FEATURE
<222> LOCATION: (21)..(21)
<223> OTHER INFORMATION: Xaa = Arg, Met, Cys, Lys or absent
<220> FEATURE:
<221> NAME/KEY: MISC_FEATURE
<222> LOCATION: (22)..(22)
<223> OTHER INFORMATION: Xaa = Arg, Lys, Ala or absent
<220> FEATURE:
<221> NAME/KEY: MISC_FEATURE
<222> LOCATION: (23)..(23)
<223> OTHER INFORMATION: Xaa = Arg, Cys, Lys, Val or absent
<220> FEATURE:
<221> NAME/KEY: MISC_FEATURE
<222> LOCATION: (24)..(24)
<223> OTHER INFORMATION: Xaa = Arg, Lys, Pro, Cys, Thr or absent
<220> FEATURE:
<221> NAME/KEY: MISC_FEATURE
<222> LOCATION: (25)..(25)
<223> OTHER INFORMATION: Xaa = Thr, Arg or absent

<400> SEQUENCE: 12

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 13
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Asp, Glu, Ala, Gly Thr, Tyr, Leu, D-Asp,
      Iminodiacetic acid, pyroglutamic acid, beta-homoaspartic acid or
      absent
<220> FEATURE:
<221> NAME/KEY: MISC_FEATURE
<222> LOCATION: (2)..(2)
<223> OTHER INFORMATION: Xaa = Thr, Ala, Arg, D-Thr, alpha-
      aminoisobutyric acid or absent
<220> FEATURE:
<221> NAME/KEY: MISC_FEATURE
<222> LOCATION: (3)..(3)
<223> OTHER INFORMATION: Xaa = His, Lys, Ala or D-His
<220> FEATURE:
<221> NAME/KEY: MISC_FEATURE
<222> LOCATION: (4)..(4)
<223> OTHER INFORMATION: Xaa = Phe, Ala, D-Phe, beta-beta-
      diphenylalanine or beta-homophenylalanine
<220> FEATURE:
<221> NAME/KEY: MISC_FEATURE
<222> LOCATION: (5)..(5)
<223> OTHER INFORMATION: Xaa = Pro, Glu, Ser, Gly, Arg, Lys, Val, Ala,
      D-Pro, beta-homoproline, 4-aminobutyric acid, sarcosine or absent
<220> FEATURE:
<221> NAME/KEY: MISC_FEATURE
<222> LOCATION: (6)..(6)
<223> OTHER INFORMATION: Xaa = Ile, Cys, Arg, Leu, Lys, His, Glu, D-Ile,
      D-Arg, D-Cys, Val, Ser or Ala
<220> FEATURE:
<221> NAME/KEY: MISC_FEATURE
```

```
<222> LOCATION: (7)..(7)
<223> OTHER INFORMATION: Xaa = Cys, Ile, Ala, Leu, Val, Ser, Phe, D-Ile,
      D-Cys or (2,3-diaminopropanoic acid)
<220> FEATURE:
<221> NAME/KEY: MISC_FEATURE
<222> LOCATION: (8)..(8)
<223> OTHER INFORMATION: Xaa = Ile, Lys, Arg, Ala, Gln, Phe, Glu, Asp,
      Tyr, Ser, Leu, Val, D-Ile, D-Lys, D-Arg or (2,3-diaminopropanoic
      acid)
<220> FEATURE:
<221> NAME/KEY: MISC_FEATURE
<222> LOCATION: (9)..(9)
<223> OTHER INFORMATION: Xaa = Phe, Ala, Ile, Tyr, Lys, Arg, beta-
      homoproline or D-Phe
<220> FEATURE:
<221> NAME/KEY: MISC_FEATURE
<222> LOCATION: (10)..(10)
<223> OTHER INFORMATION: Xaa = Lys, Phe or absent

<400> SEQUENCE: 13

Xaa Xaa Xaa Xaa Xaa Xaa Xaa Xaa Xaa Xaa
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Hepcidine peptide analogue motif
<220> FEATURE:
<221> NAME/KEY: MISC_FEATURE
<222> LOCATION: (1)..(1)
<223> OTHER INFORMATION: Xaa = Asp, iminodiacetic acid, pyroglutamic
      acid, beta-homoaspartic acid or absent
<220> FEATURE:
<221> NAME/KEY: MISC_FEATURE
<222> LOCATION: (4)..(4)
<223> OTHER INFORMATION: Xaa = Phe or (beta,beta diphenylalanine)
<220> FEATURE:
<221> NAME/KEY: MISC_FEATURE
<222> LOCATION: (5)..(5)
<223> OTHER INFORMATION: Xaa = Pro or beta-homoproline
<220> FEATURE:
<221> NAME/KEY: MISC_FEATURE
<222> LOCATION: (6)..(6)
<223> OTHER INFORMATION: Xaa = Ile, Cys or Arg
<220> FEATURE:
<221> NAME/KEY: MISC_FEATURE
<222> LOCATION: (7)..(7)
<223> OTHER INFORMATION: Xaa = Cys , Ile, Leu or Val
<220> FEATURE:
<221> NAME/KEY: MISC_FEATURE
<222> LOCATION: (8)..(8)
<223> OTHER INFORMATION: Xaa = Ile, Lys, Glu, Phe, Gln or Arg
<220> FEATURE:
<221> NAME/KEY: MISC_FEATURE
<222> LOCATION: (10)..(10)
<223> OTHER INFORMATION: Xaa = Lys or absent

<400> SEQUENCE: 14

Xaa Thr His Xaa Xaa Xaa Xaa Xaa Phe Xaa
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Asp, Iminodiacetic acid, pyroglutamic
      acid, beta-homoaspartic acid or absent
<220> FEATURE:
```

```
<221> NAME/KEY: MISC_FEATURE
<222> LOCATION: (4)..(4)
<223> OTHER INFORMATION: Xaa = Phe or (beta,beta diphenylalanine)
<220> FEATURE:
<221> NAME/KEY: MISC_FEATURE
<222> LOCATION: (5)..(5)
<223> OTHER INFORMATION: Xaa = Pro or beta-homoproline
<220> FEATURE:
<221> NAME/KEY: MISC_FEATURE
<222> LOCATION: (8)..(8)
<223> OTHER INFORMATION: Xaa = Ile, Lys, Glu, Phe, Gln or Arg
<220> FEATURE:
<221> NAME/KEY: MISC_FEATURE
<222> LOCATION: (10)..(10)
<223> OTHER INFORMATION: Xaa = Lys or absent

<400> SEQUENCE: 15

Xaa Thr His Xaa Xaa Cys Ile Xaa Phe Xaa
 1               5                  10

<210> SEQ ID NO 16
<211> LENGTH: 15
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Gly, Cys, Ala, Phe, Pro, Glu, Lys, D-Pro,
      Val, Ser or absent
<220> FEATURE:
<221> NAME/KEY: MISC_FEATURE
<222> LOCATION: (2)..(2)
<223> OTHER INFORMATION: Xaa = Pro, Ala, Cys, Gly or absent
<220> FEATURE:
<221> NAME/KEY: MISC_FEATURE
<222> LOCATION: (3)..(3)
<223> OTHER INFORMATION: Xaa = Arg, Lys, Pro, Gly, His, Ala, Trp or
      absent
<220> FEATURE:
<221> NAME/KEY: MISC_FEATURE
<222> LOCATION: (4)..(4)
<223> OTHER INFORMATION: Xaa = Ser, Arg, Gly, Trp, Ala, His, Tyr or
      absent
<220> FEATURE:
<221> NAME/KEY: MISC_FEATURE
<222> LOCATION: (5)..(5)
<223> OTHER INFORMATION: Xaa = Lys, Met, Arg, Ala or absent
<220> FEATURE:
<221> NAME/KEY: MISC_FEATURE
<222> LOCATION: (6)..(6)
<223> OTHER INFORMATION: Xaa = Gly, Ser, Lys, Ile, Arg, Ala, Pro, Val or
      absent
<220> FEATURE:
<221> NAME/KEY: MISC_FEATURE
<222> LOCATION: (7)..(7)
<223> OTHER INFORMATION: Xaa = Trp, Lys, Gly, Ala Ile, Val or absent
<220> FEATURE:
<221> NAME/KEY: MISC_FEATURE
<222> LOCATION: (8)..(8)
<223> OTHER INFORMATION: Xaa = Val, Thr, Gly, Cys, Met, Tyr, Ala, Glu,
      Lys, Asp, Arg or absent
<220> FEATURE:
<221> NAME/KEY: MISC_FEATURE
<222> LOCATION: (9)..(9)
<223> OTHER INFORMATION: Xaa = Cys, Tyr or absent
<220> FEATURE:
<221> NAME/KEY: MISC_FEATURE
<222> LOCATION: (10)..(10)
<223> OTHER INFORMATION: Xaa = Met, Lys, Arg, Tyr or absent
<220> FEATURE:
<221> NAME/KEY: MISC_FEATURE
<222> LOCATION: (11)..(11)
<223> OTHER INFORMATION: Xaa = Arg, Met, Cys, Lys or absent
<220> FEATURE:
<221> NAME/KEY: MISC_FEATURE
```

```
<222> LOCATION: (12)..(12)
<223> OTHER INFORMATION: Xaa = Arg, Lys, Ala or absent
<220> FEATURE:
<221> NAME/KEY: MISC_FEATURE
<222> LOCATION: (13)..(13)
<223> OTHER INFORMATION: Xaa = Arg, Cys, Lys, Val or absent
<220> FEATURE:
<221> NAME/KEY: MISC_FEATURE
<222> LOCATION: (14)..(14)
<223> OTHER INFORMATION: Xaa = Arg, Lys, Pro, Cys, Thr or absent
<220> FEATURE:
<221> NAME/KEY: MISC_FEATURE
<222> LOCATION: (15)..(15)
<223> OTHER INFORMATION: Xaa = Thr, Arg or absent

<400> SEQUENCE: 16

Xaa Xaa Xaa Xaa Xaa Xaa Xaa Xaa Xaa Xaa Xaa Xaa Xaa Xaa Xaa
1               5                   10                  15

<210> SEQ ID NO 17
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Gly, Ala, Lys, Pro or D-Pro
<220> FEATURE:
<221> NAME/KEY: MISC_FEATURE
<222> LOCATION: (2)..(2)
<223> OTHER INFORMATION: Xaa = Pro, Ala or Gly
<220> FEATURE:
<221> NAME/KEY: MISC_FEATURE
<222> LOCATION: (3)..(3)
<223> OTHER INFORMATION: Xaa = Arg, Ala, Lys or Trp
<220> FEATURE:
<221> NAME/KEY: MISC_FEATURE
<222> LOCATION: (4)..(4)
<223> OTHER INFORMATION: Xaa = Ser, Gly or Ala
<220> FEATURE:
<221> NAME/KEY: MISC_FEATURE
<222> LOCATION: (5)..(5)
<223> OTHER INFORMATION: Xaa = Lys, Met, Arg or Ala
<220> FEATURE:
<221> NAME/KEY: MISC_FEATURE
<222> LOCATION: (6)..(6)
<223> OTHER INFORMATION: Xaa = Gly, Arg or Ala
<220> FEATURE:
<221> NAME/KEY: MISC_FEATURE
<222> LOCATION: (7)..(7)
<223> OTHER INFORMATION: Xaa = Trp or Ala
<220> FEATURE:
<221> NAME/KEY: MISC_FEATURE
<222> LOCATION: (8)..(8)
<223> OTHER INFORMATION: Xaa = Val, Thr, Lys, Ala or Glu
<220> FEATURE:
<221> NAME/KEY: MISC_FEATURE
<222> LOCATION: (10)..(10)
<223> OTHER INFORMATION: Xaa = Met, Lys or absent

<400> SEQUENCE: 17

Xaa Xaa Xaa Xaa Xaa Xaa Xaa Xaa Cys Xaa
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
```

```
<223> OTHER INFORMATION: Xaa = Gly, Pro or D-Pro
<220> FEATURE:
<221> NAME/KEY: MISC_FEATURE
<222> LOCATION: (2)..(2)
<223> OTHER INFORMATION: Xaa = Pro or Gly
<220> FEATURE:
<221> NAME/KEY: MISC_FEATURE
<222> LOCATION: (3)..(3)
<223> OTHER INFORMATION: Xaa = Arg or Lys
<220> FEATURE:
<221> NAME/KEY: MISC_FEATURE
<222> LOCATION: (8)..(8)
<223> OTHER INFORMATION: Xaa = Val or Thr
<220> FEATURE:
<221> NAME/KEY: MISC_FEATURE
<222> LOCATION: (10)..(10)
<223> OTHER INFORMATION: Xaa = Met, Lys or absent

<400> SEQUENCE: 18

Xaa Xaa Xaa Ser Lys Gly Trp Xaa Cys Xaa
1               5                   10

<210> SEQ ID NO 19
<211> LENGTH: 15
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Val, Ala or absent
<220> FEATURE:
<221> NAME/KEY: MISC_FEATURE
<222> LOCATION: (3)..(3)
<223> OTHER INFORMATION: Xaa = Gly, Pro or absent
<220> FEATURE:
<221> NAME/KEY: MISC_FEATURE
<222> LOCATION: (4)..(4)
<223> OTHER INFORMATION: Xaa = His, Trp or Tyr
<220> FEATURE:
<221> NAME/KEY: MISC_FEATURE
<222> LOCATION: (6)..(6)
<223> OTHER INFORMATION: Xaa = Ser, Gly or Pro
<220> FEATURE:
<221> NAME/KEY: MISC_FEATURE
<222> LOCATION: (7)..(7)
<223> OTHER INFORMATION: Xaa = Ile, Gly or Lys
<220> FEATURE:
<221> NAME/KEY: MISC_FEATURE
<222> LOCATION: (8)..(8)
<223> OTHER INFORMATION: Xaa = Gly, Met or absent
<220> FEATURE:
<221> NAME/KEY: MISC_FEATURE
<222> LOCATION: (10)..(10)
<223> OTHER INFORMATION: Xaa = Tyr or Cys
<220> FEATURE:
<221> NAME/KEY: MISC_FEATURE
<222> LOCATION: (11)..(11)
<223> OTHER INFORMATION: Xaa = Arg, Lys, Met or Ala
<220> FEATURE:
<221> NAME/KEY: MISC_FEATURE
<222> LOCATION: (12)..(12)
<223> OTHER INFORMATION: Xaa = Arg or Ala
<220> FEATURE:
<221> NAME/KEY: MISC_FEATURE
<222> LOCATION: (13)..(13)
<223> OTHER INFORMATION: Xaa = Cys or Val or absent
<220> FEATURE:
<221> NAME/KEY: MISC_FEATURE
<222> LOCATION: (14)..(14)
<223> OTHER INFORMATION: Xaa = Cys, Lys, Pro, Arg, Thr or absent
<220> FEATURE:
<221> NAME/KEY: MISC_FEATURE
<222> LOCATION: (15)..(15)
<223> OTHER INFORMATION: Xaa = Arg, Thr or absent
```

```
<400> SEQUENCE: 19

Xaa Cys Xaa Xaa Arg Xaa Xaa Xaa Cys Xaa Xaa Xaa Xaa Xaa
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (3)..(3)
<223> OTHER INFORMATION: Xaa = Gly or absent
<220> FEATURE:
<221> NAME/KEY: MISC_FEATURE
<222> LOCATION: (6)..(6)
<223> OTHER INFORMATION: Xaa = Ser or Pro;
<220> FEATURE:
<221> NAME/KEY: MISC_FEATURE
<222> LOCATION: (7)..(7)
<223> OTHER INFORMATION: Xaa = Ile or Lys
<220> FEATURE:
<221> NAME/KEY: MISC_FEATURE
<222> LOCATION: (8)..(8)
<223> OTHER INFORMATION: Xaa = Gly or absent
<220> FEATURE:
<221> NAME/KEY: MISC_FEATURE
<222> LOCATION: (12)..(12)
<223> OTHER INFORMATION: Xaa = Arg or Ala
<220> FEATURE:
<221> NAME/KEY: MISC_FEATURE
<222> LOCATION: (13)..(13)
<223> OTHER INFORMATION: Xaa = Cys or Val or absent
<220> FEATURE:
<221> NAME/KEY: MISC_FEATURE
<222> LOCATION: (14)..(14)
<223> OTHER INFORMATION: Xaa = Cys, Arg, Thr or absent
<220> FEATURE:
<221> NAME/KEY: MISC_FEATURE
<222> LOCATION: (15)..(15)
<223> OTHER INFORMATION: Xaa = Arg or absent

<400> SEQUENCE: 20

Val Cys Xaa His Arg Xaa Xaa Xaa Cys Tyr Arg Xaa Xaa Xaa Xaa
1               5                   10                  15

<210> SEQ ID NO 21
<211> LENGTH: 25
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Asp, Glu, Ala, Gly Thr, Tyr, Leu, D-Asp,
      Iminodiacetic acid, pyroglutamic acid, beta-homoaspartic acid or
      absent
<220> FEATURE:
<221> NAME/KEY: MISC_FEATURE
<222> LOCATION: (2)..(2)
<223> OTHER INFORMATION: Xaa = Thr, Ala, Arg, D-Thr, alpha-
      aminoisobutyric acid or absent
<220> FEATURE:
<221> NAME/KEY: MISC_FEATURE
<222> LOCATION: (3)..(3)
<223> OTHER INFORMATION: Xaa = His, Lys, Ala or D-His
<220> FEATURE:
<221> NAME/KEY: MISC_FEATURE
<222> LOCATION: (4)..(4)
<223> OTHER INFORMATION: Xaa = Phe, Ala, D-Phe, beta-beta-
      diphenylalanine or beta-homophenylalanine
<220> FEATURE:
<221> NAME/KEY: MISC_FEATURE
```

-continued

```
<222> LOCATION: (5)..(5)
<223> OTHER INFORMATION: Xaa = Pro, Glu, Ser, Gly, Arg, Lys, Val, Ala,
      D-Pro, beta-homoproline, 4-aminobutyric acid, sarcosine or absent
<220> FEATURE:
<221> NAME/KEY: MISC_FEATURE
<222> LOCATION: (6)..(6)
<223> OTHER INFORMATION: Xaa = Ile, Cys, Arg, Leu, Lys, His, Glu, D-Ile,
      D-Arg, D-Cys, Val, Ser or Ala
<220> FEATURE:
<221> NAME/KEY: MISC_FEATURE
<222> LOCATION: (7)..(7)
<223> OTHER INFORMATION: Xaa = Cys, Ile, Ala, Leu, Val, Ser, Phe, D-Ile,
      D-Cys or (2,3-diaminopropanoic acid)
<220> FEATURE:
<221> NAME/KEY: MISC_FEATURE
<222> LOCATION: (8)..(8)
<223> OTHER INFORMATION: Xaa = Ile, Lys, Arg, Ala, Gln, Phe, Glu, Asp,
      Tyr, Ser, Leu, Val, D-Ile, D-Lys, D-Arg or (2,3-diaminopropanoic
      acid)
<220> FEATURE:
<221> NAME/KEY: MISC_FEATURE
<222> LOCATION: (9)..(9)
<223> OTHER INFORMATION: Xaa = Phe, Ala, Ile, Tyr, Lys, Arg, beta-
      homoproline or D-Phe
<220> FEATURE:
<221> NAME/KEY: MISC_FEATURE
<222> LOCATION: (10)..(10)
<223> OTHER INFORMATION: Xaa = Lys, Phe or absent
<220> FEATURE:
<221> NAME/KEY: MISC_FEATURE
<222> LOCATION: (11)..(11)
<223> OTHER INFORMATION: Xaa = Gly, Cys, Ala, Phe, Pro, Glu, Lys, D-Pro,
      Val, Ser or absent
<220> FEATURE:
<221> NAME/KEY: MISC_FEATURE
<222> LOCATION: (12)..(12)
<223> OTHER INFORMATION: Xaa = Pro, Ala, Cys, Gly or absent
<220> FEATURE:
<221> NAME/KEY: MISC_FEATURE
<222> LOCATION: (13)..(13)
<223> OTHER INFORMATION: Xaa = Arg, Lys, Pro, Gly, His, Ala, Trp or
      absent
<220> FEATURE:
<221> NAME/KEY: MISC_FEATURE
<222> LOCATION: (14)..(14)
<223> OTHER INFORMATION: Xaa = Ser, Arg, Gly, Trp, Ala, His, Tyr or
      absent
<220> FEATURE:
<221> NAME/KEY: MISC_FEATURE
<222> LOCATION: (15)..(15)
<223> OTHER INFORMATION: Xaa = Lys, Met, Arg, Ala or absent
<220> FEATURE:
<221> NAME/KEY: MISC_FEATURE
<222> LOCATION: (16)..(16)
<223> OTHER INFORMATION: Xaa = Gly, Ser, Lys, Ile, Arg, Ala, Pro, Val or
      absent
<220> FEATURE:
<221> NAME/KEY: MISC_FEATURE
<222> LOCATION: (17)..(17)
<223> OTHER INFORMATION: Xaa = Trp, Lys, Gly, Ala Ile, Val or absent
<220> FEATURE:
<221> NAME/KEY: MISC_FEATURE
<222> LOCATION: (18)..(18)
<223> OTHER INFORMATION: Xaa = Val, Thr, Gly, Cys, Met, Tyr, Ala, Glu,
      Lys, Asp, Arg or absent
<220> FEATURE:
<221> NAME/KEY: MISC_FEATURE
<222> LOCATION: (19)..(19)
<223> OTHER INFORMATION: Xaa = Cys, Tyr or absent
<220> FEATURE:
<221> NAME/KEY: MISC_FEATURE
<222> LOCATION: (20)..(20)
<223> OTHER INFORMATION: Xaa = Met, Lys, Arg, Tyr or absent
<220> FEATURE:
<221> NAME/KEY: MISC_FEATURE
<222> LOCATION: (21)..(21)
<223> OTHER INFORMATION: Xaa = Arg, Met, Cys, Lys or absent
<220> FEATURE:
<221> NAME/KEY: MISC_FEATURE
```

```
<222> LOCATION: (22)..(22)
<223> OTHER INFORMATION: Xaa = Arg, Lys, Ala or absent
<220> FEATURE:
<221> NAME/KEY: MISC_FEATURE
<222> LOCATION: (23)..(23)
<223> OTHER INFORMATION: Xaa = Arg, Cys, Lys, Val or absent
<220> FEATURE:
<221> NAME/KEY: MISC_FEATURE
<222> LOCATION: (24)..(24)
<223> OTHER INFORMATION: Xaa = Arg, Lys, Pro, Cys, Thr or absent
<220> FEATURE:
<221> NAME/KEY: MISC_FEATURE
<222> LOCATION: (25)..(25)
<223> OTHER INFORMATION: Xaa = Thr, Arg or absent

<400> SEQUENCE: 21

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25

<210> SEQ ID NO 22
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Asp, Glu, Ala, Gly Thr, Tyr, Leu, D-Asp,
      Iminodiacetic acid, pyroglutamic acid, beta-homoaspartic acid or
      absent
<220> FEATURE:
<221> NAME/KEY: MISC_FEATURE
<222> LOCATION: (2)..(2)
<223> OTHER INFORMATION: Xaa = Thr, Ala, Arg, D-Thr, alpha-
      aminoisobutyric acid or absent
<220> FEATURE:
<221> NAME/KEY: MISC_FEATURE
<222> LOCATION: (3)..(3)
<223> OTHER INFORMATION: Xaa = His, Lys, Ala or D-His
<220> FEATURE:
<221> NAME/KEY: MISC_FEATURE
<222> LOCATION: (4)..(4)
<223> OTHER INFORMATION: Xaa = Phe, Ala, D-Phe, beta-beta-
      diphenylalanine or beta-homophenylalanine
<220> FEATURE:
<221> NAME/KEY: MISC_FEATURE
<222> LOCATION: (5)..(5)
<223> OTHER INFORMATION: Xaa = Pro, Glu, Ser, Gly, Arg, Lys, Val, Ala,
      D-Pro, beta-homoproline, 4-aminobutyric acid, sarcosine or absent
<220> FEATURE:
<221> NAME/KEY: MISC_FEATURE
<222> LOCATION: (6)..(6)
<223> OTHER INFORMATION: Xaa = Ile, Cys, Arg, Leu, Lys, His, Glu, D-Ile,
      D-Arg, D-Cys, Val, Ser or Ala
<220> FEATURE:
<221> NAME/KEY: MISC_FEATURE
<222> LOCATION: (7)..(7)
<223> OTHER INFORMATION: Xaa = Cys, Ile, Ala, Leu, Val, Ser, Phe, D-Ile,
      D-Cys or (2,3-diaminopropanoic acid)
<220> FEATURE:
<221> NAME/KEY: MISC_FEATURE
<222> LOCATION: (8)..(8)
<223> OTHER INFORMATION: Xaa = Ile, Lys, Arg, Ala, Gln, Phe, Glu, Asp,
      Tyr, Ser, Leu, Val, D-Ile, D-Lys, D-Arg or (2,3-diaminopropanoic
      acid)
<220> FEATURE:
<221> NAME/KEY: MISC_FEATURE
<222> LOCATION: (9)..(9)
<223> OTHER INFORMATION: Xaa = Phe, Ala, Ile, Tyr, Lys, Arg, beta-
      homoproline or D-Phe
<220> FEATURE:
<221> NAME/KEY: MISC_FEATURE
<222> LOCATION: (10)..(10)
```

-continued

```
<223> OTHER INFORMATION: Xaa = Lys, Phe or absent

<400> SEQUENCE: 22

Xaa Xaa Xaa Xaa Xaa Xaa Xaa Xaa Xaa Xaa
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Hepcidine peptide analogue motif
<220> FEATURE:
<221> NAME/KEY: MISC_FEATURE
<222> LOCATION: (1)..(1)
<223> OTHER INFORMATION: Xaa = Asp, iminodiacetic acid, pyroglutamic
      acid, beta-homoaspartic acid or absent
<220> FEATURE:
<221> NAME/KEY: MISC_FEATURE
<222> LOCATION: (4)..(4)
<223> OTHER INFORMATION: Xaa = Phe or (beta,beta diphenylalanine)
<220> FEATURE:
<221> NAME/KEY: MISC_FEATURE
<222> LOCATION: (5)..(5)
<223> OTHER INFORMATION: Xaa = Pro or beta-homoproline
<220> FEATURE:
<221> NAME/KEY: MISC_FEATURE
<222> LOCATION: (6)..(6)
<223> OTHER INFORMATION: Xaa = Ile, Cys or Arg
<220> FEATURE:
<221> NAME/KEY: MISC_FEATURE
<222> LOCATION: (7)..(7)
<223> OTHER INFORMATION: Xaa = Cys , Ile, Leu or Val
<220> FEATURE:
<221> NAME/KEY: MISC_FEATURE
<222> LOCATION: (8)..(8)
<223> OTHER INFORMATION: Xaa = Ile, Lys, Glu, Phe, Gln or Arg
<220> FEATURE:
<221> NAME/KEY: MISC_FEATURE
<222> LOCATION: (10)..(10)
<223> OTHER INFORMATION: Xaa = Lys, Phe or absent

<400> SEQUENCE: 23

Xaa Thr His Xaa Xaa Xaa Xaa Xaa Phe Xaa
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Asp, Iminodiacetic acid, pyroglutamic
      acid, beta-homoaspartic acid or absent
<220> FEATURE:
<221> NAME/KEY: MISC_FEATURE
<222> LOCATION: (4)..(4)
<223> OTHER INFORMATION: Xaa = Phe or (beta,beta diphenylalanine)
<220> FEATURE:
<221> NAME/KEY: MISC_FEATURE
<222> LOCATION: (5)..(5)
<223> OTHER INFORMATION: Xaa = Pro or beta-homoproline
<220> FEATURE:
<221> NAME/KEY: MISC_FEATURE
<222> LOCATION: (8)..(8)
<223> OTHER INFORMATION: Xaa = Ile, Lys, Glu, Phe, Gln or Arg
<220> FEATURE:
<221> NAME/KEY: MISC_FEATURE
<222> LOCATION: (10)..(10)
<223> OTHER INFORMATION: Xaa = Lys or absent

<400> SEQUENCE: 24
```

```
Xaa Thr His Xaa Xaa Cys Ile Xaa Phe Xaa
1               5                   10
```

<210> SEQ ID NO 25
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Gly, Ala, Pro, Lys or D-Pro
<220> FEATURE:
<221> NAME/KEY: MISC_FEATURE
<222> LOCATION: (2)..(2)
<223> OTHER INFORMATION: Xaa = Pro, Ala or Gly
<220> FEATURE:
<221> NAME/KEY: MISC_FEATURE
<222> LOCATION: (3)..(3)
<223> OTHER INFORMATION: Xaa = Arg, Lys, Ala or Trp
<220> FEATURE:
<221> NAME/KEY: MISC_FEATURE
<222> LOCATION: (4)..(4)
<223> OTHER INFORMATION: Xaa = Ser, Gly or Ala
<220> FEATURE:
<221> NAME/KEY: MISC_FEATURE
<222> LOCATION: (5)..(5)
<223> OTHER INFORMATION: Xaa = Lys, Met, Arg or Ala
<220> FEATURE:
<221> NAME/KEY: MISC_FEATURE
<222> LOCATION: (6)..(6)
<223> OTHER INFORMATION: Xaa = Gly, Arg or Ala
<220> FEATURE:
<221> NAME/KEY: MISC_FEATURE
<222> LOCATION: (7)..(7)
<223> OTHER INFORMATION: Xaa = Trp, Ala or absent
<220> FEATURE:
<221> NAME/KEY: MISC_FEATURE
<222> LOCATION: (8)..(8)
<223> OTHER INFORMATION: Xaa = Val, Thr, Ala, Glu, Lys or absent
<220> FEATURE:
<221> NAME/KEY: MISC_FEATURE
<222> LOCATION: (10)..(10)
<223> OTHER INFORMATION: Xaa = Met, Lys or absent

<400> SEQUENCE: 25

```
Xaa Xaa Xaa Xaa Xaa Xaa Xaa Xaa Cys Xaa
1               5                   10
```

<210> SEQ ID NO 26
<211> LENGTH: 10
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Gly, Pro or D-Pro
<220> FEATURE:
<221> NAME/KEY: MISC_FEATURE
<222> LOCATION: (2)..(2)
<223> OTHER INFORMATION: Xaa = Pro or Gly
<220> FEATURE:
<221> NAME/KEY: MISC_FEATURE
<222> LOCATION: (3)..(3)
<223> OTHER INFORMATION: Xaa = Arg or Lys
<220> FEATURE:
<221> NAME/KEY: MISC_FEATURE
<222> LOCATION: (8)..(8)
<223> OTHER INFORMATION: Xaa = Val or Thr
<220> FEATURE:
<221> NAME/KEY: MISC_FEATURE
<222> LOCATION: (10)..(10)

<223> OTHER INFORMATION: Xaa = Met, Lys or absent

<400> SEQUENCE: 26

Xaa Xaa Xaa Ser Lys Gly Trp Xaa Cys Xaa
1               5                   10

<210> SEQ ID NO 27
<211> LENGTH: 20
<212> TYPE: PRT
<213> ORGANISM: Artificial Sequence
<220> FEATURE:
<223> OTHER INFORMATION: Hepcidin peptide analogue motif
<220> FEATURE:
<221> NAME/KEY: MISC_FEATURE
<222> LOCATION: (1)..(1)
<223> OTHER INFORMATION: Xaa = Asp, Glu, Ala, Gly Thr, Tyr, Leu, D-Asp,
      Iminodiacetic acid, pyroglutamic acid, beta-homoaspartic acid or
      absent
<220> FEATURE:
<221> NAME/KEY: MISC_FEATURE
<222> LOCATION: (2)..(2)
<223> OTHER INFORMATION: Xaa = Thr, Ala, Arg, D-Thr, alpha-
      aminoisobutyric acid or absent
<220> FEATURE:
<221> NAME/KEY: MISC_FEATURE
<222> LOCATION: (3)..(3)
<223> OTHER INFORMATION: Xaa = His, Lys, Ala or D-His
<220> FEATURE:
<221> NAME/KEY: MISC_FEATURE
<222> LOCATION: (4)..(4)
<223> OTHER INFORMATION: Xaa = Phe, Ala, D-Phe, beta-beta-
      diphenylalanine or beta-homophenylalanine
<220> FEATURE:
<221> NAME/KEY: MISC_FEATURE
<222> LOCATION: (5)..(5)
<223> OTHER INFORMATION: Xaa = Pro, Glu, Ser, Gly, Arg, Lys, Val, Ala,
      D-Pro, beta-homoproline, 4-aminobutyric acid, sarcosine or absent
<220> FEATURE:
<221> NAME/KEY: MISC_FEATURE
<222> LOCATION: (6)..(6)
<223> OTHER INFORMATION: Xaa = Ile, Cys, Arg, Leu, Lys, His, Glu, D-Ile,
      D-Arg, D-Cys, Val, Ser or Ala
<220> FEATURE:
<221> NAME/KEY: MISC_FEATURE
<222> LOCATION: (7)..(7)
<223> OTHER INFORMATION: Xaa = Cys, Ile, Ala, Leu, Val, Ser, Phe, D-Ile,
      D-Cys or (2,3-diaminopropanoic acid)
<220> FEATURE:
<221> NAME/KEY: MISC_FEATURE
<222> LOCATION: (8)..(8)
<223> OTHER INFORMATION: Xaa = Ile, Lys, Arg, Ala, Gln, Phe, Glu, Asp,
      Tyr, Ser, Leu, Val, D-Ile, D-Lys, D-Arg or (2,3-diaminopropanoic
      acid)
<220> FEATURE:
<221> NAME/KEY: MISC_FEATURE
<222> LOCATION: (9)..(9)
<223> OTHER INFORMATION: Xaa = Phe, Ala, Ile, Tyr, Lys, Arg, beta-
      homoproline or D-Phe
<220> FEATURE:
<221> NAME/KEY: MISC_FEATURE
<222> LOCATION: (10)..(10)
<223> OTHER INFORMATION: Xaa = Lys, Phe or absent
<220> FEATURE:
<221> NAME/KEY: MISC_FEATURE
<222> LOCATION: (11)..(11)
<223> OTHER INFORMATION: Xaa = Gly, Ala, Pro, Lys or D-Pro
<220> FEATURE:
<221> NAME/KEY: MISC_FEATURE
<222> LOCATION: (12)..(12)
<223> OTHER INFORMATION: Xaa = Pro, Ala or Gly
<220> FEATURE:
<221> NAME/KEY: MISC_FEATURE
<222> LOCATION: (13)..(13)
<223> OTHER INFORMATION: Xaa = Arg, Lys, Ala or Trp
<220> FEATURE:
<221> NAME/KEY: MISC_FEATURE
<222> LOCATION: (14)..(14)

```
<223> OTHER INFORMATION: Xaa = Ser, Gly or Ala
<220> FEATURE:
<221> NAME/KEY: MISC_FEATURE
<222> LOCATION: (15)..(15)
<223> OTHER INFORMATION: Xaa = Lys, Met, Arg or Ala
<220> FEATURE:
<221> NAME/KEY: MISC_FEATURE
<222> LOCATION: (16)..(16)
<223> OTHER INFORMATION: Xaa = Gly, Arg or Ala
<220> FEATURE:
<221> NAME/KEY: MISC_FEATURE
<222> LOCATION: (17)..(17)
<223> OTHER INFORMATION: Xaa = Trp, Ala or absent
<220> FEATURE:
<221> NAME/KEY: MISC_FEATURE
<222> LOCATION: (18)..(18)
<223> OTHER INFORMATION: Xaa = Val, Thr, Ala, Glu, Lys or absent
<220> FEATURE:
<221> NAME/KEY: MISC_FEATURE
<222> LOCATION: (20)..(20)
<223> OTHER INFORMATION: Xaa = Met, Lys or absent

<400> SEQUENCE: 27

Xaa Xaa Xaa Xaa Xaa Xaa Xaa Xaa Xaa Xaa Xaa Xaa Xaa Xaa Xaa
1               5                   10                  15

Xaa Xaa Cys Xaa
            20

<210> SEQ ID NO 28
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 28

Asp Thr His Phe Pro Cys Ile Ile Phe
1               5

<210> SEQ ID NO 29
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 29

Asp Thr His Phe Pro Ile Cys Ile Phe Gly Pro Arg Ser Lys Gly Trp
1               5                   10                  15

Val Cys

<210> SEQ ID NO 30
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 30

Asp Thr His Phe Pro Cys Ile Ile Phe Gly Pro Arg Ser Arg Gly Trp
1               5                   10                  15

Val Cys Lys

<210> SEQ ID NO 31
<211> LENGTH: 18
<212> TYPE: PRT
<213> ORGANISM: Artificial Sequence
<220> FEATURE:
```

```
<223> OTHER INFORMATION: Hepcidin peptide analogue

<400> SEQUENCE: 31

Asp Thr His Phe Pro Cys Ile Ile Phe Gly Pro Arg Ser Lys Gly Trp
1               5                   10                  15

Val Cys

<210> SEQ ID NO 32
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid
<220> FEATURE:
<221> NAME/KEY: MOD_RES
<222> LOCATION: (4)..(4)
<223> OTHER INFORMATION: Xaa is beta,beta diphenylalanine
<220> FEATURE:
<221> NAME/KEY: MOD_RES
<222> LOCATION: (5)..(5)
<223> OTHER INFORMATION: Xaa is beta-homoproline

<400> SEQUENCE: 32

Xaa Thr His Xaa Xaa Ile Cys Ile Phe Gly Pro Arg Ser Lys Gly Trp
1               5                   10                  15

Val Cys Met

<210> SEQ ID NO 33
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 33

Asp Thr His Phe Pro Cys Ile Phe Phe Gly Pro Arg Ser Lys Gly Trp
1               5                   10                  15

Val Cys Lys

<210> SEQ ID NO 34
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 34

Asp Thr His Phe Pro Cys Ile Ile Phe Gly Pro Arg Ser Lys Gly Trp
1               5                   10                  15

Thr Cys Lys

<210> SEQ ID NO 35
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<220> FEATURE:
<221> NAME/KEY: MOD_RES
<222> LOCATION: (4)..(4)
```

<223> OTHER INFORMATION: Xaa is beta,beta diphenylalanine
<220> FEATURE:
<221> NAME/KEY: MOD_RES
<222> LOCATION: (5)..(5)
<223> OTHER INFORMATION: Xaa is beta-homoproline

<400> SEQUENCE: 35

Xaa Thr His Xaa Xaa Cys Ile Ile Phe Gly Pro Arg Ser Arg Gly Trp
1               5                   10                  15

Val Cys Lys

<210> SEQ ID NO 36
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 36

Asp Thr His Phe Pro Cys Ile Lys Phe Gly Pro Arg Ser Lys Gly Trp
1               5                   10                  15

Val Cys Lys

<210> SEQ ID NO 37
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 37

Asp Thr His Phe Pro Cys Ile Gln Phe Gly Pro Arg Ser Lys Gly Trp
1               5                   10                  15

Val Cys Lys

<210> SEQ ID NO 38
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 38

Asp Thr His Phe Pro Cys Ile Ile Phe Gly Pro Arg Ser Lys Gly Trp
1               5                   10                  15

Val Cys Lys

<210> SEQ ID NO 39
<211> LENGTH: 22
<212> TYPE: PRT
<213> ORGANISM: Artificial Sequence
<220> FEATURE:
<223> OTHER INFORMATION: Hepcidin peptide analogue

<400> SEQUENCE: 39

Asp Thr His Phe Pro Ile Cys Ile Phe Val Cys Gly His Arg Ser Ile
1               5                   10                  15

Cys Tyr Arg Arg Cys Arg
            20

<210> SEQ ID NO 40
<211> LENGTH: 23
<212> TYPE: PRT
<213> ORGANISM: Artificial Sequence

```
<220> FEATURE:
<223> OTHER INFORMATION: Hepcidin peptide analogue

<400> SEQUENCE: 40

Ala Asp Thr His Phe Pro Ile Cys Ile Phe Val Cys His Arg Ser Lys
1               5                   10                  15

Gly Cys Tyr Arg Arg Cys Arg
            20

<210> SEQ ID NO 41
<211> LENGTH: 21
<212> TYPE: PRT
<213> ORGANISM: Artificial Sequence
<220> FEATURE:
<223> OTHER INFORMATION: Hepcidin peptide analogue

<400> SEQUENCE: 41

Asp Thr His Phe Pro Ile Cys Ile Phe Val Cys His Arg Ser Lys Gly
1               5                   10                  15

Cys Tyr Arg Ala Cys
            20

<210> SEQ ID NO 42
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 42

Asp Thr His Phe Pro Cys Ile Glu Phe Gly Pro Arg Ser Lys Gly Trp
1               5                   10                  15

Val Cys Lys

<210> SEQ ID NO 43
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 43

Asp Thr His Phe Pro Ile Cys Ile Phe Gly Pro Arg Ala Lys Gly Trp
1               5                   10                  15

Val Cys Met

<210> SEQ ID NO 44
<211> LENGTH: 23
<212> TYPE: PRT
<213> ORGANISM: Artificial Sequence
<220> FEATURE:
<223> OTHER INFORMATION: Hepcidin peptide analogue

<400> SEQUENCE: 44

Ala Asp Thr His Phe Pro Ile Cys Ile Phe Val Cys His Arg Ser Lys
1               5                   10                  15

Gly Cys Tyr Arg Arg Cys Arg
            20

<210> SEQ ID NO 45
<211> LENGTH: 19
<212> TYPE: PRT
<213> ORGANISM: Artificial Sequence
<220> FEATURE:
```

<223> OTHER INFORMATION: Hepcidin peptide analogue

<400> SEQUENCE: 45

Asp Thr His Phe Pro Ile Cys Ile Phe Gly Pro Arg Ser Lys Gly Trp
1               5                   10                  15

Val Cys Met

<210> SEQ ID NO 46
<211> LENGTH: 22
<212> TYPE: PRT
<213> ORGANISM: Artificial Sequence
<220> FEATURE:
<223> OTHER INFORMATION: Hepcidin peptide analogue

<400> SEQUENCE: 46

Asp Thr His Phe Pro Ile Cys Ile Phe Val Cys His Arg Ser Lys Gly
1               5                   10                  15

Cys Tyr Arg Arg Cys Arg
            20

<210> SEQ ID NO 47
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 47

Asp Thr His Phe Pro Ile Cys Ile Phe Gly Pro Arg Ser Arg Gly Trp
1               5                   10                  15

Val Cys Lys

<210> SEQ ID NO 48
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 48

Asp Thr His Phe Pro Cys Ile Ile Phe Gly Pro Arg Ser Lys Gly Trp
1               5                   10                  15

Val Cys Met

<210> SEQ ID NO 49
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 49

Asp Thr His Phe Pro Ile Cys Ile Phe Ala Pro Arg Ser Lys Gly Trp
1               5                   10                  15

Val Cys Met

<210> SEQ ID NO 50
<211> LENGTH: 20
<212> TYPE: PRT
<213> ORGANISM: Artificial Sequence
<220> FEATURE:
<223> OTHER INFORMATION: Hepcidin peptide analogue

<400> SEQUENCE: 50

```
Asp Thr His Phe Pro Ile Cys Ile Phe Gly Pro Arg Ser Lys Gly Trp
1               5                   10                  15

Val Cys Met His
            20

<210> SEQ ID NO 51
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 51

Asp Thr His Phe Pro Cys Ile Gln Phe
1               5

<210> SEQ ID NO 52
<211> LENGTH: 23
<212> TYPE: PRT
<213> ORGANISM: Artificial Sequence
<220> FEATURE:
<223> OTHER INFORMATION: Hepcidin peptide analogue

<400> SEQUENCE: 52

Asp Thr His Phe Pro Ile Cys Ile Phe Val Cys Gly His Arg Ser Lys
1               5                   10                  15

Gly Cys Tyr Arg Arg Cys Arg
            20

<210> SEQ ID NO 53
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 53

Asp Thr His Phe Ala Ile Cys Ile Phe Gly Pro Arg Ser Lys Gly Trp
1               5                   10                  15

Val Cys Met

<210> SEQ ID NO 54
<211> LENGTH: 20
<212> TYPE: PRT
<213> ORGANISM: Artificial Sequence
<220> FEATURE:
<223> OTHER INFORMATION: Hepcidin peptide analogue

<400> SEQUENCE: 54

Asp Thr His Phe Pro Ile Cys Ile Phe Gly Pro His Arg Ser Lys Gly
1               5                   10                  15

Trp Val Cys Met
            20

<210> SEQ ID NO 55
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 55

Asp Thr His Phe Pro Ile Cys Ile Phe Gly Pro Arg Ala Lys Gly Trp
1               5                   10                  15
```

Val Cys Met

<210> SEQ ID NO 56
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 56

Asp Thr His Phe Pro Ala Cys Ile Phe Gly Pro Arg Ser Lys Gly Trp
1               5                   10                  15

Val Cys Met

<210> SEQ ID NO 57
<211> LENGTH: 23
<212> TYPE: PRT
<213> ORGANISM: Artificial Sequence
<220> FEATURE:
<223> OTHER INFORMATION: Hepcidin peptide analogue

<400> SEQUENCE: 57

Asp Thr His Phe Pro Cys Ile Ile Phe Val Cys His Arg Pro Lys Gly
1               5                   10                  15

Cys Tyr Arg Arg Val Cys Arg
            20

<210> SEQ ID NO 58
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 58

Asp Thr His Phe Pro Ile Cys Ile Phe Gly Pro Arg Ser Lys Ala Trp
1               5                   10                  15

Val Cys Met

<210> SEQ ID NO 59
<211> LENGTH: 23
<212> TYPE: PRT
<213> ORGANISM: Artificial Sequence
<220> FEATURE:
<223> OTHER INFORMATION: Hepcidin peptide analogue

<400> SEQUENCE: 59

Asp Thr His Phe Pro Ile Cys Ile Phe Val Cys Gly His Arg Gly Lys
1               5                   10                  15

Gly Cys Tyr Arg Arg Cys Arg
            20

<210> SEQ ID NO 60
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 60

Ala Thr His Phe Pro Ile Cys Ile Phe Gly Pro Arg Ser Lys Gly Trp
1               5                   10                  15

Val Cys Met

```
<210> SEQ ID NO 61
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 61

Asp Thr His Phe Pro Ile Cys Ile Phe Gly Pro Ala Ser Lys Gly Trp
1               5                   10                  15

Val Cys Met

<210> SEQ ID NO 62
<211> LENGTH: 21
<212> TYPE: PRT
<213> ORGANISM: Artificial Sequence
<220> FEATURE:
<223> OTHER INFORMATION: Hepcidin peptide analogue

<400> SEQUENCE: 62

Asp Thr His Phe Pro Ile Cys Ile Phe Val Cys His Arg Ser Lys Gly
1               5                   10                  15

Cys Tyr Ala Arg Cys
            20

<210> SEQ ID NO 63
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 63

Asp Thr His Phe Pro Ile Cys Ile Phe Gly Pro Arg Ser Lys Gly Trp
1               5                   10                  15

Val Cys Met

<210> SEQ ID NO 64
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 64

Asp Thr His Phe Pro Ile Cys Ile Phe Gly Pro Arg Ser Ala Gly Trp
1               5                   10                  15

Val Cys Met

<210> SEQ ID NO 65
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 65

Asp Thr His Ala Pro Ile Cys Ile Phe Gly Pro Arg Ser Lys Gly Trp
1               5                   10                  15

Val Cys Met

<210> SEQ ID NO 66
```

```
<211> LENGTH: 21
<212> TYPE: PRT
<213> ORGANISM: Artificial Sequence
<220> FEATURE:
<223> OTHER INFORMATION: Hepcidin peptide analogue

<400> SEQUENCE: 66

Asp Thr His Phe Pro Ile Cys Ile Phe Val Cys His Arg Ser Lys Gly
1               5                   10                  15

Cys Tyr Arg Arg Cys
            20

<210> SEQ ID NO 67
<211> LENGTH: 22
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is pyroglutamic acid

<400> SEQUENCE: 67

Xaa Thr His Phe Pro Ile Cys Ile Phe Val Cys His Arg Ser Lys Gly
1               5                   10                  15

Cys Tyr Arg Arg Cys Arg
            20

<210> SEQ ID NO 68
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 68

Asp Thr His Phe Pro Ile Cys Ile Phe Lys Pro Arg Ser Lys Gly Trp
1               5                   10                  15

Val Cys Met

<210> SEQ ID NO 69
<211> LENGTH: 24
<212> TYPE: PRT
<213> ORGANISM: Artificial Sequence
<220> FEATURE:
<223> OTHER INFORMATION: Hepcidin peptide analogue

<400> SEQUENCE: 69

Asp Thr His Phe Pro Ile Cys Ile Phe Val Cys Gly His Arg Ser Lys
1               5                   10                  15

Gly Cys Tyr Met Arg Cys Lys Thr
            20

<210> SEQ ID NO 70
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 70

Asp Ala His Phe Pro Ile Cys Ile Phe Gly Pro Arg Ser Lys Gly Trp
1               5                   10                  15

Val Cys Met
```

```
<210> SEQ ID NO 71
<211> LENGTH: 21
<212> TYPE: PRT
<213> ORGANISM: Artificial Sequence
<220> FEATURE:
<223> OTHER INFORMATION: Hepcidin peptide analogue

<400> SEQUENCE: 71

Asp Thr His Phe Pro Ile Cys Ile Phe Val Cys Tyr Arg Gly Ile Cys
1               5                   10                  15

Tyr Arg Arg Cys Arg
            20

<210> SEQ ID NO 72
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 72

Asp Thr His Phe Pro Ile Cys Ile Phe Gly Pro Arg Ser Lys Gly Trp
1               5                   10                  15

Val Cys Met

<210> SEQ ID NO 73
<211> LENGTH: 18
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is beta-homoaspartic acid

<400> SEQUENCE: 73

Xaa Thr His Phe Pro Ile Cys Ile Phe Gly Pro Arg Ser Lys Gly Trp
1               5                   10                  15

Val Cys

<210> SEQ ID NO 74
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 74

Asp Thr His Phe Pro Ile Cys Ile Phe Gly Pro Arg Ser Lys Gly Trp
1               5                   10                  15

Ala Cys Met

<210> SEQ ID NO 75
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid
<220> FEATURE:
<221> NAME/KEY: MOD_RES
```

```
<222> LOCATION: (4)..(4)
<223> OTHER INFORMATION: Xaa is beta,beta diphenylalanine
<220> FEATURE:
<221> NAME/KEY: MOD_RES
<222> LOCATION: (5)..(5)
<223> OTHER INFORMATION: Xaa is beta-homoproline
<220> FEATURE:
<221> NAME/KEY: MOD_RES
<222> LOCATION: (9)..(9)
<223> OTHER INFORMATION: Xaa is beta homophenylalanine

<400> SEQUENCE: 75

Xaa Thr His Xaa Xaa Arg Cys Arg Xaa Gly Pro Arg Ser Lys Gly Trp
1               5                   10                  15

Val Cys Met

<210> SEQ ID NO 76
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 76

Asp Thr His Phe Pro Cys Ile Arg Phe
1               5

<210> SEQ ID NO 77
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 77

Thr His Phe Pro Cys Ile Ile Phe Gly Pro Arg Ser Lys Gly Trp Val
1               5                   10                  15

Cys Met

<210> SEQ ID NO 78
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 78

Asp Thr His Phe Pro Cys Ile Ala Phe
1               5

<210> SEQ ID NO 79
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 79

Asp Ala His Phe Pro Cys Ile Ile Phe
1               5

<210> SEQ ID NO 80
<211> LENGTH: 22
<212> TYPE: PRT
<213> ORGANISM: Artificial Sequence
<220> FEATURE:
<223> OTHER INFORMATION: Hepcidin peptide analogue
```

<400> SEQUENCE: 80

Asp Thr His Phe Pro Ile Cys Ile Phe Val Cys His Arg Pro Lys Gly
1               5                   10                  15
Cys Tyr Arg Arg Cys Pro
            20

<210> SEQ ID NO 81
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 81

Asp Thr His Phe Pro Ile Cys Ile Phe Lys Pro Arg Ser Lys Gly Trp
1               5                   10                  15
Val Cys Met

<210> SEQ ID NO 82
<211> LENGTH: 10
<212> TYPE: PRT
<213> ORGANISM: Artificial Sequence
<220> FEATURE:
<223> OTHER INFORMATION: Hepcidin peptide analogue

<400> SEQUENCE: 82

Asp Thr His Phe Pro Cys Ile Ile Phe Lys
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 83

Asp Thr His Phe Pro Cys Ile Phe Phe
1               5

<210> SEQ ID NO 84
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 84

Asp Thr His Phe Pro Ile Cys Ile Phe Gly Pro Arg Ser Lys Lys Trp
1               5                   10                  15
Val Cys Met

<210> SEQ ID NO 85
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 85

Asp Thr His Phe Pro Ile Cys Ile Phe Gly Pro Arg Ser Lys Lys Trp
1               5                   10                  15
Val Cys Met

```
<210> SEQ ID NO 86
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 86

Asp Thr His Phe Pro Ile Cys Ile Phe Cys Pro Trp Gly Met Cys Cys
1               5                   10                  15

Lys

<210> SEQ ID NO 87
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 87

Asp Thr Ala Phe Pro Ile Cys Ile Phe Gly Pro Arg Ser Lys Gly Trp
1               5                   10                  15

Val Cys Met

<210> SEQ ID NO 88
<211> LENGTH: 22
<212> TYPE: PRT
<213> ORGANISM: Artificial Sequence
<220> FEATURE:
<223> OTHER INFORMATION: Hepcidin peptide analogue

<400> SEQUENCE: 88

Asp Thr His Phe Pro Ile Cys Ile Phe Val Cys Tyr Arg Gly Ile Cys
1               5                   10                  15

Tyr Met Arg Cys Lys Thr
            20

<210> SEQ ID NO 89
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 89

Asp Thr His Phe Pro Ile Cys Ile Phe Gly Pro Arg Ser Lys Gly Ala
1               5                   10                  15

Val Cys Met

<210> SEQ ID NO 90
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 90

Asp Thr His Phe Pro Ile Cys Ile Ala Gly Pro Arg Ser Lys Gly Trp
1               5                   10                  15

Val Cys Met

<210> SEQ ID NO 91
```

```
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 91

Asp Thr His Phe Pro Ile Cys Ala Phe Gly Pro Arg Ser Lys Gly Trp
1               5                   10                  15

Val Cys Met

<210> SEQ ID NO 92
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 92

Asp Thr His Phe Pro Ile Ala Ile Phe Gly Pro Arg Ser Lys Gly Trp
1               5                   10                  15

Val Ala Met

<210> SEQ ID NO 93
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 93

Asp Thr His Phe Pro Cys Arg Arg Phe Gly Pro Arg Ser Lys Gly Trp
1               5                   10                  15

Val Cys

<210> SEQ ID NO 94
<211> LENGTH: 18
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid
<220> FEATURE:
<221> NAME/KEY: MOD_RES
<222> LOCATION: (5)..(5)
<223> OTHER INFORMATION: Xaa is beta-homoproline
<220> FEATURE:
<221> NAME/KEY: MOD_RES
<222> LOCATION: (9)..(9)
<223> OTHER INFORMATION: Xaa is beta-homophenylalanine

<400> SEQUENCE: 94

Xaa Thr His Phe Xaa Cys Arg Arg Xaa Gly Pro Arg Ser Lys Gly Trp
1               5                   10                  15

Val Cys

<210> SEQ ID NO 95

<400> SEQUENCE: 95

000

<210> SEQ ID NO 96
```

<211> LENGTH: 22
<212> TYPE: PRT
<213> ORGANISM: Artificial Sequence
<220> FEATURE:
<223> OTHER INFORMATION: Hepcidin peptide analogue

<400> SEQUENCE: 96

Asp Thr His Phe Pro Cys Ile Ile Phe Val Cys His Arg Ser Lys Gly
1               5                   10                  15

Cys Tyr Trp Ala Val Cys
            20

<210> SEQ ID NO 97
<211> LENGTH: 23
<212> TYPE: PRT
<213> ORGANISM: Artificial Sequence
<220> FEATURE:
<223> OTHER INFORMATION: Hepcidin peptide analogue

<400> SEQUENCE: 97

Asp Thr His Phe Pro Cys Ile Ile Phe Val Cys His Arg Ser Lys Gly
1               5                   10                  15

Cys Tyr Trp Ala Val Cys Phe
            20

<210> SEQ ID NO 98
<211> LENGTH: 24
<212> TYPE: PRT
<213> ORGANISM: Artificial Sequence
<220> FEATURE:
<223> OTHER INFORMATION: Hepcidin peptide analogue

<400> SEQUENCE: 98

Asp Thr His Phe Pro Cys Ile Ile Phe Val Cys His Arg Ser Lys Gly
1               5                   10                  15

Cys Tyr Trp Ala Val Cys Phe Trp
            20

<210> SEQ ID NO 99
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 99

Asp Thr His Phe Pro Ile Cys Ile Phe Lys Pro Arg Ser Lys Gly Trp
1               5                   10                  15

Val Cys Met

<210> SEQ ID NO 100

<400> SEQUENCE: 100

000

<210> SEQ ID NO 101
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (4)..(4)
<223> OTHER INFORMATION: Xaa is beta,beta diphenylalanine

```
<400> SEQUENCE: 101

Asp Thr His Xaa Pro Cys Ile Ile Phe Gly Pro Arg Ser Arg Gly Trp
1               5                   10                  15

Val Cys Lys

<210> SEQ ID NO 102
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (5)..(5)
<223> OTHER INFORMATION: Xaa is beta-homoproline

<400> SEQUENCE: 102

Asp Thr His Phe Xaa Cys Ile Ile Phe Gly Pro Arg Ser Arg Gly Trp
1               5                   10                  15

Val Cys Lys

<210> SEQ ID NO 103
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 103

Asp Thr His Phe Pro Cys Ile Ile Phe Gly Pro Arg Ser Arg Gly Trp
1               5                   10                  15

Arg Cys Lys

<210> SEQ ID NO 104
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 104

Asp Thr His Phe Pro Cys Ile Arg Phe Gly Pro Arg Ser Arg Gly Trp
1               5                   10                  15

Val Cys Lys

<210> SEQ ID NO 105
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 105

Asp Thr His Phe Pro Cys Ile Arg Phe Gly Pro Arg Ser Arg Gly Trp
1               5                   10                  15

Arg Cys Lys

<210> SEQ ID NO 106
<211> LENGTH: 19
<212> TYPE: PRT
<213> ORGANISM: Artificial Sequence
<220> FEATURE:
<223> OTHER INFORMATION: Hepcidin peptide analogue
```

<400> SEQUENCE: 106

Asp Thr His Phe Pro Cys Ile Ile Phe Gly Pro Arg Ser Arg Gly Trp
1               5                   10                  15

Val Cys Lys

<210> SEQ ID NO 107
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 107

Asp Thr His Phe Pro Cys Ile Ile Phe Gly Pro Arg Ser Arg Gly Val
1               5                   10                  15

Cys Lys

<210> SEQ ID NO 108
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 108

Asp Thr His Phe Pro Cys Ile Tyr Phe Gly Pro Arg Ser Lys Gly Trp
1               5                   10                  15

Val Cys Lys

<210> SEQ ID NO 109
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 109

Asp Thr His Phe Pro Cys Ile Ile Phe Gly Pro Arg Ser Lys Gly Trp
1               5                   10                  15

Val Cys Lys

<210> SEQ ID NO 110
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 110

Asp Thr His Phe Pro Cys Ile Ile Phe Gly Pro Arg Ala Arg Gly Trp
1               5                   10                  15

Val Cys Lys

<210> SEQ ID NO 111
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 111

Asp Thr His Phe Pro Cys Ile Ile Phe Gly Pro Arg Ser Arg Gly Trp

```
1               5                  10                  15
Val Cys Lys

<210> SEQ ID NO 112
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 112

Asp Thr His Phe Pro Cys Ile Ile Phe Gly Pro Arg Ser Arg Gly Trp
1               5                  10                  15

Val Cys Lys

<210> SEQ ID NO 113
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 113

Asp Thr His Phe Pro Ile Cys Ile Phe Lys Pro Arg Ser Lys Gly Trp
1               5                  10                  15

Val Cys Lys

<210> SEQ ID NO 114
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 114

Asp Thr His Phe Pro Cys Ile Ile Phe Gly Pro Arg Ser Lys Gly Trp
1               5                  10                  15

Lys Cys Lys

<210> SEQ ID NO 115
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 115

Asp Thr His Phe Pro Cys Ile Lys Phe Gly Pro Arg Ser Lys Gly Trp
1               5                  10                  15

Lys Cys Lys

<210> SEQ ID NO 116
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 116

Asp Thr His Phe Pro Cys Leu Ile Phe Gly Pro Arg Ser Lys Gly Trp
1               5                  10                  15

Val Cys Lys
```

```
<210> SEQ ID NO 117
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 117

Asp Thr His Phe Pro Cys Val Ile Phe Gly Pro Arg Ser Lys Gly Trp
1               5                   10                  15

Val Cys Lys

<210> SEQ ID NO 118
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 118

Asp Thr His Phe Pro Cys Ser Ile Phe Gly Pro Arg Ser Lys Gly Trp
1               5                   10                  15

Val Cys Lys

<210> SEQ ID NO 119
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 119

Asp Thr His Phe Pro Cys Gln Ile Phe Gly Pro Arg Ser Lys Gly Trp
1               5                   10                  15

Val Cys Lys

<210> SEQ ID NO 120
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 120

Thr His Phe Pro Cys Ile Ile Phe Gly Pro Arg Ser Lys Gly Trp Val
1               5                   10                  15

Cys Lys

<210> SEQ ID NO 121
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 121

Thr His Phe Pro Cys Ile Ile Phe Gly Pro Arg Ser Lys Gly Trp Val
1               5                   10                  15

Cys Lys

<210> SEQ ID NO 122
<211> LENGTH: 17
<212> TYPE: PRT
```

```
<213> ORGANISM: Artificial Sequence
<220> FEATURE:
<223> OTHER INFORMATION: Hepcidin peptide analogue

<400> SEQUENCE: 122

His Phe Pro Cys Ile Ile Phe Gly Pro Arg Ser Lys Gly Trp Val Cys
1               5                   10                  15

Lys

<210> SEQ ID NO 123
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 123

His Phe Pro Cys Ile Ile Phe Gly Pro Arg Ser Lys Gly Trp Val Cys
1               5                   10                  15

Lys

<210> SEQ ID NO 124
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 124

Asp Thr His Phe Pro Cys Ile Ser Phe Gly Pro Arg Ser Lys Gly Trp
1               5                   10                  15

Val Cys Lys

<210> SEQ ID NO 125
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 125

Asp Thr His Phe Pro Cys Ile Lys Phe Gly Pro Arg Ser Lys Gly Trp
1               5                   10                  15

Val Cys Lys

<210> SEQ ID NO 126
<211> LENGTH: 20
<212> TYPE: PRT
<213> ORGANISM: Artificial Sequence
<220> FEATURE:
<223> OTHER INFORMATION: Hepcidin peptide analogue

<400> SEQUENCE: 126

Glu Asp Thr His Phe Pro Cys Ile Ile Phe Gly Pro Arg Ser Lys Gly
1               5                   10                  15

Trp Val Cys Lys
            20

<210> SEQ ID NO 127

<400> SEQUENCE: 127

000
```

```
<210> SEQ ID NO 128
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 128

Asp Thr His Phe Pro Cys Ile Ile Phe Glu Pro Arg Ser Lys Gly Trp
1               5                   10                  15

Val Cys Lys

<210> SEQ ID NO 129
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 129

Asp Thr His Phe Pro Cys Ile Ile Phe Ser Pro Arg Ser Lys Gly Trp
1               5                   10                  15

Val Cys Lys

<210> SEQ ID NO 130
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 130

Asp Thr His Phe Ser Cys Ile Ile Phe Gly Pro Arg Ser Lys Gly Trp
1               5                   10                  15

Val Cys Lys

<210> SEQ ID NO 131
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 131

Asp Thr His Phe Pro Cys Ile Ile Phe Gly Pro Arg Ser Arg Gly Trp
1               5                   10                  15

Val Cys Lys

<210> SEQ ID NO 132
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 132

Asp Thr His Phe Pro Cys Ile Ile Phe Gly Pro Arg Ser Arg Gly Trp
1               5                   10                  15

Val Cys Lys

<210> SEQ ID NO 133
<211> LENGTH: 19
<212> TYPE: PRT
```

```
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid

<400> SEQUENCE: 133

Xaa Thr His Phe Pro Cys Ile Ile Phe Gly Pro Arg Ser Arg Gly Trp
1               5                   10                  15

Val Cys Lys

<210> SEQ ID NO 134
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 134

Asp Thr His Phe Pro Cys Ile Ile Phe Gly Pro Lys Ser Lys Gly Trp
1               5                   10                  15

Val Cys Lys

<210> SEQ ID NO 135
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 135

Asp Thr His Phe Pro Cys Ile Lys Phe Gly Pro Lys Ser Lys Gly Trp
1               5                   10                  15

Val Cys Lys

<210> SEQ ID NO 136
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 136

Asp Thr His Phe Pro Cys Ile Ile Phe Gly Pro Arg Ser Lys Gly Trp
1               5                   10                  15

Cys Lys

<210> SEQ ID NO 137
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 137

Asp Thr His Phe Pro Cys Ile Ile Phe Gly Pro Arg Ser Lys Gly Val
1               5                   10                  15

Cys

<210> SEQ ID NO 138
<211> LENGTH: 17
<212> TYPE: PRT
```

```
<213> ORGANISM: Artificial Sequence
<220> FEATURE:
<223> OTHER INFORMATION: Hepcidin peptide analogue

<400> SEQUENCE: 138

Asp Thr His Phe Pro Cys Ile Ile Phe Gly Pro Arg Ser Lys Gly Cys
1               5                   10                  15

Lys

<210> SEQ ID NO 139

<400> SEQUENCE: 139

000

<210> SEQ ID NO 140
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (7)..(7)
<223> OTHER INFORMATION: Xaa is 2,3 diaminopropanoic acid

<400> SEQUENCE: 140

Asp Thr His Phe Pro Cys Xaa Ile Phe Gly Pro Arg Ser Lys Gly Trp
1               5                   10                  15

Asp Cys Lys

<210> SEQ ID NO 141
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (8)..(8)
<223> OTHER INFORMATION: Xaa is 2,3 diaminopropanoic acid

<400> SEQUENCE: 141

Asp Thr His Phe Pro Cys Ile Xaa Phe Gly Pro Arg Ser Lys Gly Trp
1               5                   10                  15

Asp Cys Lys

<210> SEQ ID NO 142
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (7)..(7)
<223> OTHER INFORMATION: Xaa is 2,3 diaminopropanoic acid

<400> SEQUENCE: 142

Asp Thr His Phe Pro Cys Xaa Ile Phe Gly Pro Arg Ser Lys Gly Trp
1               5                   10                  15

Glu Cys Lys

<210> SEQ ID NO 143
<211> LENGTH: 19
<212> TYPE: PRT
```

```
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (8)..(8)
<223> OTHER INFORMATION: Xaa is 2,3 diaminopropanoic acid

<400> SEQUENCE: 143

Asp Thr His Phe Pro Cys Ile Xaa Phe Gly Pro Arg Ser Lys Gly Trp
1               5                   10                  15

Glu Cys Lys

<210> SEQ ID NO 144
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 144

Asp Thr His Phe Pro Cys Ile Lys Phe Gly Pro Arg Ser Lys Gly Trp
1               5                   10                  15

Glu Cys Lys

<210> SEQ ID NO 145
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 145

Asp Thr His Phe Gly Cys Ile Ile Phe Gly Pro Arg Ser Lys Gly Trp
1               5                   10                  15

Val Cys Lys

<210> SEQ ID NO 146
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 146

Asp Thr His Phe Gly Cys Ile Ile Phe Gly Pro Arg Ser Lys Gly Trp
1               5                   10                  15

Val Cys Lys

<210> SEQ ID NO 147
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 147

Asp Thr His Phe Arg Cys Ile Ile Phe Gly Pro Arg Ser Lys Gly Trp
1               5                   10                  15

Val Cys Lys

<210> SEQ ID NO 148
<211> LENGTH: 19
<212> TYPE: PRT
```

```
<213> ORGANISM: Artificial Sequence
<220> FEATURE:
<223> OTHER INFORMATION: Hepcidin peptide analogue

<400> SEQUENCE: 148

Asp Thr His Phe Arg Cys Ile Ile Phe Gly Pro Arg Ser Lys Gly Trp
1               5                   10                  15

Val Cys Lys

<210> SEQ ID NO 149
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (5)..(5)
<223> OTHER INFORMATION: Xaa is sarcosine

<400> SEQUENCE: 149

Asp Thr His Phe Xaa Cys Ile Ile Phe Gly Pro Arg Ser Lys Gly Trp
1               5                   10                  15

Val Cys Lys

<210> SEQ ID NO 150
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (5)..(5)
<223> OTHER INFORMATION: Xaa is sarcosine

<400> SEQUENCE: 150

Asp Thr His Phe Xaa Cys Ile Ile Phe Gly Pro Arg Ser Lys Gly Trp
1               5                   10                  15

Val Cys Lys

<210> SEQ ID NO 151
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (5)..(5)
<223> OTHER INFORMATION: Xaa is beta-alanine

<400> SEQUENCE: 151

Asp Thr His Phe Xaa Cys Ile Ile Phe Gly Pro Arg Ser Lys Gly Trp
1               5                   10                  15

Val Cys Lys

<210> SEQ ID NO 152
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (5)..(5)
<223> OTHER INFORMATION: Xaa is beta-alanine
```

<400> SEQUENCE: 152

Asp Thr His Phe Xaa Cys Ile Ile Phe Gly Pro Arg Ser Lys Gly Trp
1               5                   10                  15

Val Cys Lys

<210> SEQ ID NO 153
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 153

Asp Thr His Phe Lys Cys Ile Ile Phe Gly Pro Arg Ser Lys Gly Trp
1               5                   10                  15

Val Cys Lys

<210> SEQ ID NO 154
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 154

Asp Thr His Phe Lys Cys Ile Ile Phe Gly Pro Arg Ser Lys Gly Trp
1               5                   10                  15

Val Cys Lys

<210> SEQ ID NO 155
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 155

Thr His Phe Pro Cys Ile Ile Phe Gly Pro Arg Ser Lys Gly Trp Val
1               5                   10                  15

Cys Met

<210> SEQ ID NO 156
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 156

His Phe Pro Cys Ile Ile Phe Gly Pro Arg Ser Lys Gly Trp Val Cys
1               5                   10                  15

Met

<210> SEQ ID NO 157
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 157

His Phe Pro Cys Ile Ile Phe Gly Pro Arg Ser Lys Gly Trp Val Cys

Met

<210> SEQ ID NO 158
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 158

Asp Thr His Phe Pro Cys Ile Ser Phe Gly Pro Arg Ser Lys Gly Trp
1               5                   10                  15

Val Cys Met

<210> SEQ ID NO 159
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 159

Asp Thr His Phe Pro Cys Ile Lys Phe Gly Pro Arg Ser Lys Gly Trp
1               5                   10                  15

Val Cys Met

<210> SEQ ID NO 160
<211> LENGTH: 20
<212> TYPE: PRT
<213> ORGANISM: Artificial Sequence
<220> FEATURE:
<223> OTHER INFORMATION: Hepcidin peptide analogue

<400> SEQUENCE: 160

Glu Asp Thr His Phe Pro Cys Ile Ile Phe Gly Pro Arg Ser Lys Gly
1               5                   10                  15

Trp Val Cys Met
            20

<210> SEQ ID NO 161

<400> SEQUENCE: 161

000

<210> SEQ ID NO 162
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 162

Asp Thr His Phe Pro Cys Ile Ile Phe Glu Pro Arg Ser Lys Gly Trp
1               5                   10                  15

Val Cys Met

<210> SEQ ID NO 163
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 163

Asp Thr His Phe Lys Cys Ile Glu Phe Gly Pro Arg Ser Lys Gly Trp
1               5                   10                  15

Val Cys Lys

<210> SEQ ID NO 164
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 164

Asp Thr His Phe Pro Cys Ile Ile Phe Gly Pro Arg Ser Lys Gly Trp
1               5                   10                  15

Ala Cys Lys

<210> SEQ ID NO 165
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 165

Asp Thr His Phe Pro Cys Ile Ile Phe Glu Pro Arg Ser Lys Gly Trp
1               5                   10                  15

Val Cys Lys

<210> SEQ ID NO 166
<211> LENGTH: 22
<212> TYPE: PRT
<213> ORGANISM: Artificial Sequence
<220> FEATURE:
<223> OTHER INFORMATION: Hepcidin peptide analogue

<400> SEQUENCE: 166

Asp Thr His Phe Pro Cys Ile Ile Phe Gly Pro Arg Ser Lys Gly Trp
1               5                   10                  15

Val Cys Lys Lys Lys Lys
            20

<210> SEQ ID NO 167
<211> LENGTH: 22
<212> TYPE: PRT
<213> ORGANISM: Artificial Sequence
<220> FEATURE:
<223> OTHER INFORMATION: Hepcidin peptide analogue

<400> SEQUENCE: 167

Asp Thr His Phe Pro Cys Ile Ile Phe Glu Pro Arg Ser Lys Gly Trp
1               5                   10                  15

Val Cys Lys Lys Lys Lys
            20

<210> SEQ ID NO 168
<211> LENGTH: 20
<212> TYPE: PRT
<213> ORGANISM: Artificial Sequence
<220> FEATURE:
<223> OTHER INFORMATION: Hepcidin peptide analogue

<400> SEQUENCE: 168

Asp Thr His Phe Pro Cys Ile Ile Phe Gly Pro Arg Ser Lys Gly Trp
1               5                   10                  15

Val Cys Lys Lys
            20

<210> SEQ ID NO 169
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 169

Asp Thr Ala Phe Pro Cys Ile Ile Phe Gly Pro Arg Ser Lys Gly Trp
1               5                   10                  15

Val Cys Lys

<210> SEQ ID NO 170
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 170

Asp Thr Lys Phe Pro Cys Ile Ile Phe Gly Pro Arg Ser Lys Gly Trp
1               5                   10                  15

Val Cys Lys

<210> SEQ ID NO 171
<211> LENGTH: 23
<212> TYPE: PRT
<213> ORGANISM: Artificial Sequence
<220> FEATURE:
<223> OTHER INFORMATION: Hepcidin peptide analogue

<400> SEQUENCE: 171

Asp Thr His Phe Pro Cys Ile Ile Phe Val Cys His Arg Pro Lys Gly
1               5                   10                  15

Cys Tyr Arg Arg Val Cys Arg
            20

<210> SEQ ID NO 172
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 172

Asp Thr His Phe Pro Cys Ile Lys Phe Gly Pro Arg Ser Lys Gly Trp
1               5                   10                  15

Val Cys Lys

<210> SEQ ID NO 173
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 173

Asp Thr His Phe Pro Cys Ile Lys Phe Lys Pro Arg Ser Lys Gly Trp

```
1               5                  10                 15

Val Cys Lys

<210> SEQ ID NO 174
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 174

Asp Thr His Phe Pro Cys Ile Lys Phe Gly Pro Lys Ser Lys Gly Trp
1               5                  10                 15

Val Cys Lys

<210> SEQ ID NO 175
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 175

Asp Thr His Phe Pro Cys Ile Lys Phe Gly Pro Arg Ser Lys Gly Trp
1               5                  10                 15

Val Cys Lys

<210> SEQ ID NO 176
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 176

Asp Thr His Phe Pro Cys Ile Lys Phe Gly Pro Arg Ser Lys Gly Trp
1               5                  10                 15

Val Cys Lys

<210> SEQ ID NO 177
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 177

Asp Thr His Phe Pro Cys Ile Lys Phe Gly Pro Arg Ser Lys Gly Trp
1               5                  10                 15

Thr Cys Lys

<210> SEQ ID NO 178
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 178

Asp Thr His Phe Pro Cys Ile Glu Phe Gly Pro Arg Ser Lys Gly Trp
1               5                  10                 15

Thr Cys Lys
```

<210> SEQ ID NO 179
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 179

Asp Thr His Phe Pro Ile Cys Ile Phe Gly Pro Arg Ser Lys Gly Trp
1               5                   10                  15

Val Cys

<210> SEQ ID NO 180
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 180

Asp Thr His Phe Pro Cys Ile Lys Phe Gly Pro Arg Ser Lys Gly Trp
1               5                   10                  15

Val Cys Lys

<210> SEQ ID NO 181
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 181

Asp Thr His Phe Pro Cys Ile Lys Phe Gly Pro Arg Ser Lys Gly Trp
1               5                   10                  15

Val Cys Lys

<210> SEQ ID NO 182
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 182

Asp Thr His Phe Pro Cys Ile Lys Phe Gly Pro Arg Ser Lys Gly Trp
1               5                   10                  15

Val Cys Lys

<210> SEQ ID NO 183
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 183

Asp Thr His Phe Pro Cys Ile Lys Phe Gly Pro Arg Ser Lys Gly Trp
1               5                   10                  15

Val Cys Lys

<210> SEQ ID NO 184
<211> LENGTH: 19
<212> TYPE: PRT

```
<213> ORGANISM: Artificial Sequence
<220> FEATURE:
<223> OTHER INFORMATION: Hepcidin peptide analogue

<400> SEQUENCE: 184

Asp Thr His Phe Pro Cys Ile Lys Phe Gly Pro Arg Ser Lys Gly Trp
1               5                   10                  15

Val Cys Lys

<210> SEQ ID NO 185
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 185

Asp Thr His Phe Pro Cys Ile Lys Phe Gly Pro Arg Ser Lys Gly Trp
1               5                   10                  15

Val Cys Lys

<210> SEQ ID NO 186
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 186

Asp Thr His Phe Pro Cys Ile Lys Phe Gly Pro Arg Ser Lys Gly Trp
1               5                   10                  15

Val Cys Lys

<210> SEQ ID NO 187
<211> LENGTH: 20
<212> TYPE: PRT
<213> ORGANISM: Artificial Sequence
<220> FEATURE:
<223> OTHER INFORMATION: Hepcidin peptide analogue

<400> SEQUENCE: 187

Val Asp Thr His Phe Pro Cys Ile Lys Phe Gly Pro Arg Ser Lys Gly
1               5                   10                  15

Trp Val Cys Lys
            20

<210> SEQ ID NO 188
<211> LENGTH: 20
<212> TYPE: PRT
<213> ORGANISM: Artificial Sequence
<220> FEATURE:
<223> OTHER INFORMATION: Hepcidin peptide analogue

<400> SEQUENCE: 188

Leu Asp Thr His Phe Pro Cys Ile Lys Phe Gly Pro Arg Ser Lys Gly
1               5                   10                  15

Trp Val Cys Lys
            20

<210> SEQ ID NO 189
<211> LENGTH: 19
<212> TYPE: PRT
<213> ORGANISM: Artificial Sequence
<220> FEATURE:
```

<223> OTHER INFORMATION: Hepcidin peptide analogue

<400> SEQUENCE: 189

Asp Thr His Phe Pro Cys Ile Lys Phe Gly Pro Arg Ser Lys Gly Trp
1               5                   10                  15

Val Cys Lys

<210> SEQ ID NO 190
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 190

Asp Thr His Phe Pro Cys Ile Lys Phe Gly Pro Arg Ser Lys Gly Trp
1               5                   10                  15

Val Cys Lys

<210> SEQ ID NO 191
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 191

Asp Thr His Phe Pro Cys Ile Lys Phe Gly Pro Arg Ser Lys Gly Trp
1               5                   10                  15

Val Cys Lys

<210> SEQ ID NO 192
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 192

Asp Thr His Phe Pro Cys Ile Lys Phe Gly Pro Arg Ser Lys Gly Trp
1               5                   10                  15

Val Cys Lys

<210> SEQ ID NO 193
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 193

Asp Thr His Phe Pro Cys Ile Lys Phe Gly Pro Arg Ser Lys Gly Trp
1               5                   10                  15

Val Cys Lys

<210> SEQ ID NO 194
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 194

Asp Thr His Phe Pro Cys Ile Ile Phe Gly Pro Arg Ser Lys Gly Trp
1               5                   10                  15

Lys Cys Lys

<210> SEQ ID NO 195
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 195

Asp Thr His Phe Pro Cys Ile Ile Phe Gly Pro Arg Ser Lys Gly Trp
1               5                   10                  15

Glu Cys Lys

<210> SEQ ID NO 196
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 196

Asp Thr His Phe Pro Cys Arg Arg Phe Gly Pro Arg Ser Lys Gly Trp
1               5                   10                  15

Val Cys Lys

<210> SEQ ID NO 197

<400> SEQUENCE: 197

000

<210> SEQ ID NO 198

<400> SEQUENCE: 198

000

<210> SEQ ID NO 199
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 199

Asp Thr His Phe Pro Ile Cys Ile Phe Gly Pro Arg Ser Lys Gly Trp
1               5                   10                  15

Val Cys

<210> SEQ ID NO 200
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 200

Asp Thr His Phe Pro Ile Cys Ile Phe Gly Pro Arg Ser Lys Gly Trp
1               5                   10                  15

Val Cys

<210> SEQ ID NO 201
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 201

Asp Thr His Phe Pro Cys Ile Ile Phe Gly Pro Arg Ser Arg Gly Trp
1               5                   10                  15

Val Cys Lys

<210> SEQ ID NO 202
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 202

Asp Thr His Phe Pro Cys Ile Ile Phe Gly Pro Arg Ser Arg Gly Trp
1               5                   10                  15

Val Cys Lys

<210> SEQ ID NO 203
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 203

Asp Thr His Phe Pro Cys Ile Ile Phe Gly Pro Arg Ser Arg Gly Trp
1               5                   10                  15

Val Cys Lys

<210> SEQ ID NO 204
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 204

Asp Thr His Phe Pro Cys Ile Lys Phe Glu Pro Arg Ser Lys Gly Trp
1               5                   10                  15

Val Cys Lys

<210> SEQ ID NO 205
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 205

Asp Thr His Phe Pro Cys Ile Lys Phe Glu Pro Arg Ser Lys Gly Trp
1               5                   10                  15

Thr Cys Lys

<210> SEQ ID NO 206
<211> LENGTH: 18
<212> TYPE: PRT

-continued

```
<213> ORGANISM: Artificial Sequence
<220> FEATURE:
<223> OTHER INFORMATION: Hepcidin peptide analogue

<400> SEQUENCE: 206

Asp Thr His Phe Pro Cys Ile Lys Phe Glu Pro Arg Ser Lys Gly Trp
1               5                   10                  15

Cys Lys

<210> SEQ ID NO 207
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 207

Asp Thr His Phe Pro Cys Ile Lys Phe Glu Pro Arg Ser Lys Gly Cys
1               5                   10                  15

Lys

<210> SEQ ID NO 208
<211> LENGTH: 16
<212> TYPE: PRT
<213> ORGANISM: Artificial Sequence
<220> FEATURE:
<223> OTHER INFORMATION: Hepcidin peptide analogue

<400> SEQUENCE: 208

Asp Thr His Phe Pro Cys Ile Phe Glu Pro Arg Ser Lys Gly Cys Lys
1               5                   10                  15

<210> SEQ ID NO 209
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 209

Asp Thr His Phe Pro Cys Ile Phe Glu Pro Arg Ser Lys Gly Trp Cys
1               5                   10                  15

Lys

<210> SEQ ID NO 210
<211> LENGTH: 16
<212> TYPE: PRT
<213> ORGANISM: Artificial Sequence
<220> FEATURE:
<223> OTHER INFORMATION: Hepcidin peptide analogue

<400> SEQUENCE: 210

Asp Thr His Phe Pro Cys Ile Lys Phe Gly Pro Arg Ser Lys Cys Lys
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Hepcidin peptide analogue

<400> SEQUENCE: 211

Asp Thr His Phe Pro Cys Ile Lys Phe Gly Pro Arg Ser Cys Lys
1               5                   10                  15
```

<210> SEQ ID NO 212
<211> LENGTH: 14
<212> TYPE: PRT
<213> ORGANISM: Artificial Sequence
<220> FEATURE:
<223> OTHER INFORMATION: Hepcidin peptide analogue

<400> SEQUENCE: 212

Asp Thr His Phe Pro Cys Ile Lys Phe Gly Pro Arg Cys Lys
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Hepcidin peptide analogue

<400> SEQUENCE: 213

Asp Thr His Phe Pro Cys Ile Lys Phe Gly Pro Cys Lys
1               5                   10

<210> SEQ ID NO 214
<211> LENGTH: 12
<212> TYPE: PRT
<213> ORGANISM: Artificial Sequence
<220> FEATURE:
<223> OTHER INFORMATION: Hepcidin peptide analogue

<400> SEQUENCE: 214

Asp Thr His Phe Pro Cys Ile Lys Phe Gly Cys Lys
1               5                   10

<210> SEQ ID NO 215
<211> LENGTH: 11
<212> TYPE: PRT
<213> ORGANISM: Artificial Sequence
<220> FEATURE:
<223> OTHER INFORMATION: Hepcidin peptide analogue

<400> SEQUENCE: 215

Asp Thr His Phe Pro Cys Ile Lys Phe Cys Lys
1               5                   10

<210> SEQ ID NO 216
<211> LENGTH: 10
<212> TYPE: PRT
<213> ORGANISM: Artificial Sequence
<220> FEATURE:
<223> OTHER INFORMATION: Hepcidin peptide analogue

<400> SEQUENCE: 216

Asp Thr His Phe Pro Cys Ile Lys Phe Cys
1               5                   10

<210> SEQ ID NO 217
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 217

Asp Thr His Phe Pro Cys Ile Lys Phe Gly Pro Arg Ser Lys Gly Trp
1               5                   10                  15

Val Cys Lys

<210> SEQ ID NO 218
<211> LENGTH: 20
<212> TYPE: PRT
<213> ORGANISM: Artificial Sequence
<220> FEATURE:
<223> OTHER INFORMATION: Hepcidin peptide analogue

<400> SEQUENCE: 218

Asp Thr His Phe Pro Cys Ile Lys Phe Lys Ala Pro Arg Ser Lys Gly
1               5                   10                  15

Trp Val Cys Lys
            20

<210> SEQ ID NO 219
<211> LENGTH: 20
<212> TYPE: PRT
<213> ORGANISM: Artificial Sequence
<220> FEATURE:
<223> OTHER INFORMATION: Hepcidin peptide analogue

<400> SEQUENCE: 219

Asp Thr His Phe Pro Cys Ile Lys Phe Gly Pro Lys Ala Ser Lys Gly
1               5                   10                  15

Trp Val Cys Lys
            20

<210> SEQ ID NO 220
<211> LENGTH: 20
<212> TYPE: PRT
<213> ORGANISM: Artificial Sequence
<220> FEATURE:
<223> OTHER INFORMATION: Hepcidin peptide analogue

<400> SEQUENCE: 220

Asp Thr His Phe Pro Cys Ile Lys Phe Gly Pro Arg Ser Lys Ala Gly
1               5                   10                  15

Trp Val Cys Lys
            20

<210> SEQ ID NO 221
<211> LENGTH: 20
<212> TYPE: PRT
<213> ORGANISM: Artificial Sequence
<220> FEATURE:
<223> OTHER INFORMATION: Hepcidin peptide analogue

<400> SEQUENCE: 221

Asp Thr His Phe Pro Cys Ile Lys Phe Gly Pro Arg Ser Lys Gly Trp
1               5                   10                  15

Val Cys Lys Ala
            20

<210> SEQ ID NO 222
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 222

Asp Thr His Phe Pro Cys Ile Lys Phe Gly Pro Arg Ser Lys Gly Trp
1               5                   10                  15

Val Cys Lys

<210> SEQ ID NO 223
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 223

Asp Thr His Phe Pro Cys Ile Lys Phe Lys Pro Arg Ser Lys Gly Trp
1               5                   10                  15

Val Cys Lys

<210> SEQ ID NO 224
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 224

Asp Thr His Phe Pro Cys Ile Lys Phe Gly Pro Lys Ser Lys Gly Trp
1               5                   10                  15

Val Cys Lys

<210> SEQ ID NO 225
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 225

Asp Thr His Phe Pro Cys Ile Lys Phe Gly Pro Arg Ser Lys Gly Trp
1               5                   10                  15

Val Cys Lys

<210> SEQ ID NO 226
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 226

Asp Thr His Phe Pro Cys Ile Lys Phe Gly Pro Arg Ser Lys Gly Trp
1               5                   10                  15

Val Cys Lys

<210> SEQ ID NO 227
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 227

Asp Thr His Phe Pro Cys Ile Lys Phe Gly Pro Arg Ser Lys Gly Trp
1               5                   10                  15

Val Cys Lys

<210> SEQ ID NO 228

```
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 228

Asp Thr His Phe Pro Cys Ile Lys Phe Lys Pro Arg Ser Lys Gly Trp
1               5                   10                  15

Val Cys Lys

<210> SEQ ID NO 229
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 229

Asp Thr His Phe Pro Cys Ile Lys Phe Gly Pro Lys Ser Lys Gly Trp
1               5                   10                  15

Val Cys Lys

<210> SEQ ID NO 230
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 230

Asp Thr His Phe Pro Cys Ile Lys Phe Gly Pro Arg Ser Lys Gly Trp
1               5                   10                  15

Val Cys Lys

<210> SEQ ID NO 231
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 231

Asp Thr His Phe Pro Cys Ile Lys Phe Gly Pro Arg Ser Lys Gly Trp
1               5                   10                  15

Val Cys Lys

<210> SEQ ID NO 232
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 232

Asp Thr His Phe Pro Cys Ile Lys Phe Gly Pro Arg Ser Lys Gly Trp
1               5                   10                  15

Val Cys Lys

<210> SEQ ID NO 233
<211> LENGTH: 19
<212> TYPE: PRT
<213> ORGANISM: Artificial Sequence
<220> FEATURE:
```

<223> OTHER INFORMATION: Hepcidin peptide analogue

<400> SEQUENCE: 233

Asp Thr His Phe Pro Cys Ile Lys Phe Lys Pro Arg Ser Lys Gly Trp
1               5                   10                  15

Val Cys Lys

<210> SEQ ID NO 234
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 234

Asp Thr His Phe Pro Cys Ile Lys Phe Gly Pro Lys Ser Lys Gly Trp
1               5                   10                  15

Val Cys Lys

<210> SEQ ID NO 235
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 235

Asp Thr His Phe Pro Cys Ile Lys Phe Gly Pro Arg Ser Lys Gly Trp
1               5                   10                  15

Val Cys Lys

<210> SEQ ID NO 236
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 236

Asp Thr His Phe Pro Cys Ile Lys Phe Gly Pro Arg Ser Lys Gly Trp
1               5                   10                  15

Val Cys Lys

<210> SEQ ID NO 237
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 237

Asp Thr His Phe Pro Cys Ile Lys Phe Glu Pro Arg Ser Lys Lys Trp
1               5                   10                  15

Val Cys Lys

<210> SEQ ID NO 238
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 238

```
Asp Thr His Phe Pro Cys Ile Lys Phe Gly Pro Arg Ser Lys Gly Trp
1               5                   10                  15

Val Cys Lys

<210> SEQ ID NO 239
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 239

Asp Thr His Phe Pro Cys Ile Lys Phe Gly Pro Arg Ser Lys Gly Trp
1               5                   10                  15

Val Cys Lys

<210> SEQ ID NO 240
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 240

Asp Thr His Phe Pro Cys Ile Lys Phe Gly Pro Arg Ser Lys Gly Trp
1               5                   10                  15

Val Cys Lys

<210> SEQ ID NO 241
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 241

Asp Thr His Phe Pro Cys Ile Lys Phe Glu Pro Arg Ser Lys Gly Cys
1               5                   10                  15

Lys

<210> SEQ ID NO 242
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 242

Asp Thr His Phe Pro Cys Ile Lys Phe Lys Pro Arg Ser Lys Gly Cys
1               5                   10                  15

Lys

<210> SEQ ID NO 243
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 243

Asp Thr His Phe Pro Cys Ile Lys Phe Glu Pro Lys Ser Lys Gly Cys
1               5                   10                  15

Lys
```

```
<210> SEQ ID NO 244
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 244

Asp Thr His Phe Pro Cys Ile Lys Phe Glu Pro Arg Ser Lys Gly Cys
1               5                   10                  15

Lys

<210> SEQ ID NO 245
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 245

Asp Thr His Phe Pro Cys Ile Lys Phe Glu Pro Arg Ser Lys Lys Cys
1               5                   10                  15

Lys

<210> SEQ ID NO 246
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 246

Asp Thr His Phe Pro Cys Ile Lys Phe Glu Pro Arg Ser Lys Gly Cys
1               5                   10                  15

Lys

<210> SEQ ID NO 247
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 247

Asp Thr His Phe Pro Cys Ile Lys Phe Glu Pro Arg Ser Lys Gly Cys
1               5                   10                  15

Lys Lys

<210> SEQ ID NO 248
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 248

Asp Thr His Phe Pro Cys Ile Lys Phe Glu Pro Arg Ser Lys Gly Cys
1               5                   10                  15

Lys

<210> SEQ ID NO 249
<211> LENGTH: 17
```

```
<212> TYPE: PRT
<213> ORGANISM: Artificial Sequence
<220> FEATURE:
<223> OTHER INFORMATION: Hepcidin peptide analogue

<400> SEQUENCE: 249

Asp Thr His Phe Pro Cys Ile Lys Phe Lys Pro Arg Ser Lys Gly Cys
1               5                   10                  15
Lys

<210> SEQ ID NO 250
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 250

Asp Thr His Phe Pro Cys Ile Lys Phe Glu Pro Lys Ser Lys Gly Cys
1               5                   10                  15
Lys

<210> SEQ ID NO 251
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 251

Asp Thr His Phe Pro Cys Ile Lys Phe Glu Pro Arg Ser Lys Gly Cys
1               5                   10                  15
Lys

<210> SEQ ID NO 252
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 252

Asp Thr His Phe Pro Cys Ile Lys Phe Glu Pro Arg Ser Lys Lys Cys
1               5                   10                  15
Lys

<210> SEQ ID NO 253
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 253

Asp Thr His Phe Pro Cys Ile Lys Phe Glu Pro Arg Ser Lys Gly Cys
1               5                   10                  15
Lys Lys

<210> SEQ ID NO 254
<211> LENGTH: 18
<212> TYPE: PRT
<213> ORGANISM: Artificial Sequence
<220> FEATURE:
<223> OTHER INFORMATION: Hepcidin peptide analogue
```

<400> SEQUENCE: 254

Asp Thr His Phe Pro Cys Ile Lys Phe Glu Pro Arg Ser Lys Gly Cys
1               5                   10                  15

Lys Lys

<210> SEQ ID NO 255
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 255

Asp Thr His Phe Pro Cys Ile Lys Phe Gly Pro Arg Ser Lys Gly Trp
1               5                   10                  15

Val Cys Lys

<210> SEQ ID NO 256
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 256

Ala Ala His Phe Pro Cys Ile Lys Phe Gly Pro Arg Ser Lys Gly Trp
1               5                   10                  15

Val Cys Lys

<210> SEQ ID NO 257
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 257

Ala Thr His Phe Pro Cys Ile Lys Phe Gly Pro Arg Ser Lys Gly Trp
1               5                   10                  15

Val Cys Lys

<210> SEQ ID NO 258
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 258

Asp Ala His Phe Pro Cys Ile Lys Phe Gly Pro Arg Ser Lys Gly Trp
1               5                   10                  15

Val Cys Lys

<210> SEQ ID NO 259
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 259

Asp Thr His Ala Pro Cys Ile Lys Phe Gly Pro Arg Ser Lys Gly Trp

-continued

```
                1               5                   10                  15

Val Cys Lys

<210> SEQ ID NO 260
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 260

Asp Thr His Phe Pro Cys Ile Lys Ala Gly Pro Arg Ser Lys Gly Trp
1               5                   10                  15

Val Cys Lys

<210> SEQ ID NO 261
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 261

Asp Thr His Phe Pro Cys Ile Lys Phe Glu Pro Arg Ser Lys Gly Trp
1               5                   10                  15

Val Cys Lys

<210> SEQ ID NO 262
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 262

Asp Thr His Phe Pro Cys Ile Lys Phe Glu Pro Arg Ser Lys Gly Trp
1               5                   10                  15

Glu Cys Lys

<210> SEQ ID NO 263
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 263

Asp Thr His Phe Pro Cys Ile Ile Phe Glu Pro Arg Ser Lys Gly Trp
1               5                   10                  15

Glu Cys

<210> SEQ ID NO 264
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 264

Asp Thr His Phe Pro Cys Ile Lys Phe Lys Pro Arg Ser Lys Gly Trp
1               5                   10                  15

Glu Cys Lys
```

```
<210> SEQ ID NO 265
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 265

Asp Thr His Phe Pro Cys Ile Lys Phe Glu Pro Lys Ser Lys Gly Trp
1               5                   10                  15

Glu Cys Lys

<210> SEQ ID NO 266
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 266

Asp Thr His Ala Pro Cys Ile Lys Phe Glu Pro Arg Ser Lys Gly Trp
1               5                   10                  15

Glu Cys Lys

<210> SEQ ID NO 267
<211> LENGTH: 17
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid

<400> SEQUENCE: 267

Xaa Thr His Phe Pro Cys Ile Lys Phe Glu Pro Arg Ser Lys Lys Cys
1               5                   10                  15

Lys

<210> SEQ ID NO 268
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 268

Asp Thr His Phe Pro Cys Ile Lys Phe Glu Pro Arg Ser Lys Gly Trp
1               5                   10                  15

Glu Cys

<210> SEQ ID NO 269
<211> LENGTH: 19
<212> TYPE: PRT
<213> ORGANISM: Artificial Sequence
<220> FEATURE:
<223> OTHER INFORMATION: Hepcidin peptide analogue

<400> SEQUENCE: 269

Asp Thr His Phe Pro Cys Ile Lys Phe Gly Pro Arg Ser Lys Gly Trp
1               5                   10                  15

Val Cys Lys
```

<210> SEQ ID NO 270
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 270

Asp Thr His Phe Pro Cys Ile Lys Phe Lys Pro Arg Ser Lys Gly Trp
1               5                   10                  15

Val Cys

<210> SEQ ID NO 271
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 271

Asp Thr His Phe Pro Cys Ile Lys Phe Lys Pro Arg Ser Lys Gly Trp
1               5                   10                  15

Val Cys

<210> SEQ ID NO 272
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 272

Asp Thr His Phe Pro Cys Ile Lys Phe Lys Pro Arg Ser Lys Gly Trp
1               5                   10                  15

Val Cys

<210> SEQ ID NO 273
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 273

Asp Thr His Phe Pro Cys Ile Lys Phe Lys Pro Arg Ser Lys Gly Trp
1               5                   10                  15

Val Cys

<210> SEQ ID NO 274
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 274

Asp Thr His Phe Pro Cys Ile Lys Phe Lys Pro Arg Ser Lys Gly Trp
1               5                   10                  15

Val Cys

<210> SEQ ID NO 275
<211> LENGTH: 18
<212> TYPE: PRT

```
<213> ORGANISM: Artificial Sequence
<220> FEATURE:
<223> OTHER INFORMATION: Hepcidin peptide analogue

<400> SEQUENCE: 275

Asp Thr His Phe Pro Cys Ile Lys Phe Lys Pro Arg Ser Lys Gly Trp
1               5                   10                  15

Val Cys

<210> SEQ ID NO 276
<211> LENGTH: 18
<212> TYPE: PRT
<213> ORGANISM: Artificial Sequence
<220> FEATURE:
<223> OTHER INFORMATION: Hepcidin peptide analogue

<400> SEQUENCE: 276

Asp Thr His Phe Pro Cys Ile Lys Phe Lys Pro Arg Ser Lys Gly Trp
1               5                   10                  15

Val Cys

<210> SEQ ID NO 277
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid

<400> SEQUENCE: 277

Xaa Thr His Phe Pro Cys Ile Lys Phe Glu Pro Arg Ser Lys Gly Trp
1               5                   10                  15

Val Cys Lys

<210> SEQ ID NO 278
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid

<400> SEQUENCE: 278

Xaa Thr His Phe Pro Cys Ile Lys Phe Glu Pro Arg Ser Lys Gly Trp
1               5                   10                  15

Val Cys Lys

<210> SEQ ID NO 279
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid

<400> SEQUENCE: 279

Xaa Thr His Phe Pro Cys Ile Lys Phe Glu Pro Arg Ser Lys Gly Trp
```

```
                1               5                   10                  15

Val Cys Lys

<210> SEQ ID NO 280
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid

<400> SEQUENCE: 280

Xaa Thr His Phe Pro Cys Ile Lys Phe Glu Pro Arg Ser Lys Gly Trp
1               5                   10                  15

Val Cys Lys

<210> SEQ ID NO 281
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid

<400> SEQUENCE: 281

Xaa Thr His Phe Pro Cys Ile Lys Phe Glu Pro Arg Ser Lys Gly Trp
1               5                   10                  15

Val Cys Lys

<210> SEQ ID NO 282
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid

<400> SEQUENCE: 282

Xaa Thr His Phe Pro Cys Ile Lys Phe Glu Pro Arg Ser Lys Gly Trp
1               5                   10                  15

Val Cys Lys

<210> SEQ ID NO 283
<211> LENGTH: 19
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid

<400> SEQUENCE: 283

Xaa Thr His Phe Pro Cys Ile Lys Phe Glu Pro Arg Ser Lys Gly Trp
1               5                   10                  15

Val Cys Lys
```

<210> SEQ ID NO 284
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 284

His Phe Pro Cys Ile Lys Phe Glu Pro Arg Ser Lys Gly Trp Val Cys
1               5                   10                  15

Lys

<210> SEQ ID NO 285
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 285

His Phe Pro Cys Ile Lys Phe Glu Pro Arg Ser Lys Gly Trp Val Cys
1               5                   10                  15

Lys

<210> SEQ ID NO 286
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 286

Asp Thr His Phe Pro Cys Ile Lys Phe Glu Pro His Ser Lys Gly Cys
1               5                   10                  15

Lys

<210> SEQ ID NO 287
<211> LENGTH: 16
<212> TYPE: PRT
<213> ORGANISM: Artificial Sequence
<220> FEATURE:
<223> OTHER INFORMATION: Hepcidin peptide analogue

<400> SEQUENCE: 287

Asp Thr His Phe Pro Cys Ile His Phe Glu Pro His Ser Lys Gly Cys
1               5                   10                  15

<210> SEQ ID NO 288
<211> LENGTH: 17
<212> TYPE: PRT
<213> ORGANISM: Artificial Sequence
<220> FEATURE:
<223> OTHER INFORMATION: Hepcidin peptide analogue

<400> SEQUENCE: 288

Asp Thr His Phe Pro Cys Ile Lys Phe Glu Pro His Ser Lys Gly Cys
1               5                   10                  15

Lys

<210> SEQ ID NO 289
<211> LENGTH: 16
<212> TYPE: PRT
<213> ORGANISM: Artificial Sequence

```
<220> FEATURE:
<223> OTHER INFORMATION: Hepcidin peptide analogue

<400> SEQUENCE: 289

Asp Thr His Phe Pro Cys Ile Lys Phe Glu Pro Arg Glu Lys Glu Cys
1               5                   10                  15

<210> SEQ ID NO 290
<211> LENGTH: 16
<212> TYPE: PRT
<213> ORGANISM: Artificial Sequence
<220> FEATURE:
<223> OTHER INFORMATION: Hepcidin peptide analogue

<400> SEQUENCE: 290

Asp Thr Ala Phe Pro Cys Ile Lys Phe Glu Pro Arg Ser Lys Glu Cys
1               5                   10                  15

<210> SEQ ID NO 291
<211> LENGTH: 12
<212> TYPE: PRT
<213> ORGANISM: Artificial Sequence
<220> FEATURE:
<223> OTHER INFORMATION: Hepcidin peptide analogue

<400> SEQUENCE: 291

Asp Thr His Phe Pro Cys Ile Lys Phe Glu Cys Lys
1               5                   10

<210> SEQ ID NO 292
<211> LENGTH: 15
<212> TYPE: PRT
<213> ORGANISM: Artificial Sequence
<220> FEATURE:
<223> OTHER INFORMATION: Hepcidin peptide analogue

<400> SEQUENCE: 292

Asp Thr His Phe Pro Ile Ala Ile Phe Ala Ala Gly Ile Cys Ile
1               5                   10                  15

<210> SEQ ID NO 293
<211> LENGTH: 14
<212> TYPE: PRT
<213> ORGANISM: Artificial Sequence
<220> FEATURE:
<223> OTHER INFORMATION: Hepcidin peptide analogue

<400> SEQUENCE: 293

Asp Thr His Phe Pro Ile Ala Ile Phe Ala Ala Ile Cys Ile
1               5                   10

<210> SEQ ID NO 294
<211> LENGTH: 13
<212> TYPE: PRT
<213> ORGANISM: Artificial Sequence
<220> FEATURE:
<223> OTHER INFORMATION: Hepcidin peptide analogue

<400> SEQUENCE: 294

Asp Thr His Phe Pro Ile Ala Ile Phe Ala Ile Cys Ile
1               5                   10

<210> SEQ ID NO 295
<211> LENGTH: 12
<212> TYPE: PRT
<213> ORGANISM: Artificial Sequence
<220> FEATURE:
```

<223> OTHER INFORMATION: Hepcidin peptide analogue

<400> SEQUENCE: 295

Asp Thr His Phe Pro Ile Ala Ile Phe Ile Cys Ile
1               5                   10

<210> SEQ ID NO 296
<211> LENGTH: 11
<212> TYPE: PRT
<213> ORGANISM: Artificial Sequence
<220> FEATURE:
<223> OTHER INFORMATION: Hepcidin peptide analogue

<400> SEQUENCE: 296

Asp Thr His Phe Pro Ile Ala Ile Ile Cys Ile
1               5                   10

<210> SEQ ID NO 297
<211> LENGTH: 10
<212> TYPE: PRT
<213> ORGANISM: Artificial Sequence
<220> FEATURE:
<223> OTHER INFORMATION: Hepcidin peptide analogue

<400> SEQUENCE: 297

Asp Thr His Phe Pro Ile Ala Ile Cys Ile
1               5                   10

<210> SEQ ID NO 298
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 298

Asp Thr His Phe Pro Ile Ile Cys Ile
1               5

<210> SEQ ID NO 299
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 299

Asp Thr His Ile Cys Ile Ala Ile Phe
1               5

<210> SEQ ID NO 300
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 300

Asp Thr His Cys Pro Ile Ala Ile Phe
1               5

<210> SEQ ID NO 301
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 301

Asp Thr His Phe Pro Cys Ile Ile Ala
1               5

<210> SEQ ID NO 302
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 302

Asp Thr His Phe Pro Cys Ala Ile Phe
1               5

<210> SEQ ID NO 303
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 303

Asp Thr His Phe Ala Cys Ile Ile Phe
1               5

<210> SEQ ID NO 304
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 304

Asp Thr His Phe Ala Cys Ile Ile Phe
1               5

<210> SEQ ID NO 305
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 305

Asp Thr His Ala Pro Cys Ile Ile Phe
1               5

<210> SEQ ID NO 306
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 306

Asp Thr Ala Phe Pro Cys Ile Ile Phe
1               5

<210> SEQ ID NO 307
<211> LENGTH: 9
<212> TYPE: PRT
<213> ORGANISM: Artificial Sequence
<220> FEATURE:
<223> OTHER INFORMATION: Hepcidin peptide analogue

```
<400> SEQUENCE: 307

Ala Thr His Phe Pro Cys Ile Ile Phe
1               5

<210> SEQ ID NO 308
<211> LENGTH: 9
<212> TYPE: PRT
<213> ORGANISM: Artificial Sequence
<220> FEATURE:
<223> OTHER INFORMATION: Hepcidin peptide analogue
<220> FEATURE:
<221> NAME/KEY: MOD_RES
<222> LOCATION: (1)..(1)
<223> OTHER INFORMATION: Xaa is iminodiacetic acid
<220> FEATURE:
<221> NAME/KEY: MOD_RES
<222> LOCATION: (5)..(5)
<223> OTHER INFORMATION: Xaa is beta-homoproline

<400> SEQUENCE: 308

Xaa Thr His Phe Xaa Cys Ile Ile Phe
1               5

<210> SEQ ID NO 309

<400> SEQUENCE: 309

000

<210> SEQ ID NO 310
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 310

Asp Thr His Phe Pro Cys Ile Glu Phe
1               5

<210> SEQ ID NO 311
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 311

Asp Thr His Phe Pro Cys Ile Ile Phe
1               5

<210> SEQ ID NO 312
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 312

Asp Thr His Phe Pro Ala Ile Ile Phe
1               5

<210> SEQ ID NO 313
<211> LENGTH: 9
<212> TYPE: PRT
<213> ORGANISM: Artificial Sequence
<220> FEATURE:
<223> OTHER INFORMATION: Hepcidin peptide analogue
```

<400> SEQUENCE: 313

Asp Thr His Phe Pro Ser Ile Ile Phe
1               5

<210> SEQ ID NO 314
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 314

Asp Thr His Phe Pro Cys Ile Lys Phe
1               5

<210> SEQ ID NO 315

<400> SEQUENCE: 315

000

<210> SEQ ID NO 316
<211> LENGTH: 8
<212> TYPE: PRT
<213> ORGANISM: Artificial Sequence
<220> FEATURE:
<223> OTHER INFORMATION: Hepcidin peptide analogue

<400> SEQUENCE: 316

Asp Thr His Phe Pro Cys Ile Phe
1               5

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320
<211> LENGTH: 10
<212> TYPE: PRT
<213> ORGANISM: Artificial Sequence
<220> FEATURE:
<223> OTHER INFORMATION: Hepcidin peptide analogue

<400> SEQUENCE: 320

Asp Thr His Phe Pro Cys Ile Lys Phe Phe
1               5                   10

<210> SEQ ID NO 321
<211> LENGTH: 9
<212> TYPE: PRT
<213> ORGANISM: Artificial Sequence
<220> FEATURE:

<223> OTHER INFORMATION: Hepcidin peptide analogue

<400> SEQUENCE: 321

Tyr Thr His Phe Pro Cys Ile Ile Phe
1               5

<210> SEQ ID NO 322
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 322

Leu Thr His Phe Pro Cys Ile Ile Phe
1               5

<210> SEQ ID NO 323
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 323

Glu Thr His Phe Pro Cys Ile Ile Phe
1               5

<210> SEQ ID NO 324
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 324

Asp Arg His Phe Pro Cys Ile Ile Phe
1               5

<210> SEQ ID NO 325
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 325

Asp Thr Lys Phe Pro Cys Ile Ile Phe
1               5

<210> SEQ ID NO 326
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 326

Asp Thr His Phe Glu Cys Ile Ile Phe
1               5

<210> SEQ ID NO 327
<211> LENGTH: 9
<212> TYPE: PRT
<213> ORGANISM: Artificial Sequence
<220> FEATURE:
<223> OTHER INFORMATION: Hepcidin peptide analogue

```
<400> SEQUENCE: 327

Asp Thr His Phe Pro Cys Ile Ile Lys
1               5

<210> SEQ ID NO 328
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 328

Asp Thr His Phe Pro Cys Ile Ile Arg
1               5

<210> SEQ ID NO 329
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 329

Asp Thr His Phe Pro Cys Ile Glu Phe
1               5

<210> SEQ ID NO 330
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 330

Asp Thr His Phe Pro Cys Ile Val Phe
1               5

<210> SEQ ID NO 331
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 331

Asp Thr His Phe Pro Cys Ile Leu Phe
1               5

<210> SEQ ID NO 332
<211> LENGTH: 9
<212> TYPE: PRT
<213> ORGANISM: Artificial Sequence
<220> FEATURE:
<223> OTHER INFORMATION: Hepcidin peptide analogue

<400> SEQUENCE: 332

Asp Thr His Phe Pro Cys Ile Leu Lys
1               5

<210> SEQ ID NO 333
<211> LENGTH: 9
<212> TYPE: PRT
<213> ORGANISM: Artificial Sequence
<220> FEATURE:
<223> OTHER INFORMATION: Hepcidin peptide analogue
```

```
<400> SEQUENCE: 333

Asp Thr His Phe Pro Cys Ile Glu Lys
1               5

<210> SEQ ID NO 334
<211> LENGTH: 19
<212> TYPE: PRT
<213> ORGANISM: Artificial Sequence
<220> FEATURE:
<223> OTHER INFORMATION: Hepcidine peptide analogue

<400> SEQUENCE: 334

Asp Thr His Phe Pro Ile Cys Ile Phe Gly Ala Arg Ser Lys Gly Trp
1               5                   10                  15

Val Met Cys

<210> SEQ ID NO 335
<211> LENGTH: 25
<212> TYPE: PRT
<213> ORGANISM: Homo sapiens

<400> SEQUENCE: 335

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 336
<211> LENGTH: 9
<212> TYPE: PRT
<213> ORGANISM: Homo sapiens

<400> SEQUENCE: 336

Asp Thr His Phe Pro Ile Cys Ile Phe
1               5

<210> SEQ ID NO 337
<211> LENGTH: 9
<212> TYPE: PRT
<213> ORGANISM: Artificial Sequence
<220> FEATURE:
<223> OTHER INFORMATION: Retro inverse of mini-hepcidin peptide
<220> FEATURE:
<221> NAME/KEY: MISC_FEATURE
<222> LOCATION: (1)..(9)
<223> OTHER INFORMATION: All amino acids are the D stereo isoform

<400> SEQUENCE: 337

Phe Ile Cys Ile Pro Phe His Thr Asp
1               5

<210> SEQ ID NO 338
<211> LENGTH: 9
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)
<223> OTHER INFORMATION: dimer linked through disulphide linkage

<400> SEQUENCE: 338

Asp Thr His Phe Pro Cys Ile Ile Phe
1               5
```

<210> SEQ ID NO 339
<211> LENGTH: 8
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 339

Asp Thr His Phe Pro Cys Ile Phe
1               5

<210> SEQ ID NO 340

<400> SEQUENCE: 340

000

<210> SEQ ID NO 341
<211> LENGTH: 10
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 341

Asp Thr His Phe Pro Cys Ile Lys Phe Phe
1               5                   10

<210> SEQ ID NO 342
<211> LENGTH: 9
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 342

Leu Thr His Phe Pro Cys Ile Ile Phe
1               5

<210> SEQ ID NO 343
<211> LENGTH: 9
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 343

Glu Thr His Phe Pro Cys Ile Ile Phe
1               5

<210> SEQ ID NO 344
<211> LENGTH: 9

```
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 344

Asp Thr Lys Phe Pro Cys Ile Ile Phe
1               5

<210> SEQ ID NO 345
<211> LENGTH: 9
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 345

Asp Thr His Phe Pro Cys Ile Ile Lys
1               5

<210> SEQ ID NO 346
<211> LENGTH: 9
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 346

Asp Thr His Phe Pro Cys Ile Ile Arg
1               5

<210> SEQ ID NO 347
<211> LENGTH: 9
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 347

Asp Thr His Phe Pro Cys Ile Val Phe
1               5

<210> SEQ ID NO 348
<211> LENGTH: 9
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 348
```

Asp Thr His Phe Pro Cys Ile Leu Phe
1               5

<210> SEQ ID NO 349
<211> LENGTH: 9
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 349

Asp Thr His Phe Pro Cys Ile Leu Lys
1               5

<210> SEQ ID NO 350
<211> LENGTH: 9
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 350

Asp Thr His Phe Pro Cys Ile Glu Lys
1               5

<210> SEQ ID NO 351
<211> LENGTH: 9
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 351

Asp Thr His Phe Pro Cys Ile Ile Phe
1               5

<210> SEQ ID NO 352
<211> LENGTH: 9
<212> TYPE: PRT
<213> ORGANISM: Artificial Sequence
<220> FEATURE:
<223> OTHER INFORMATION: Dimerized peptide through sing disulphide
      linkage between cysteine
<220> FEATURE:
<221> NAME/KEY: DISULFID
<222> LOCATION: (6)..(6)

<400> SEQUENCE: 352

Asp Thr His Phe Pro Cys Ile Lys Phe
1               5

<210> SEQ ID NO 353
<211> LENGTH: 9
<212> TYPE: PRT
<213> ORGANISM: Artificial Sequence
<220> FEATURE:
<223> OTHER INFORMATION: Dimerized peptide through sing disulphide
      linkage between cysteine

```
<220> FEATURE:
<221> NAME/KEY: DISULFID
<222> LOCATION: (6)..(6)

<400> SEQUENCE: 353

Asp Thr His Phe Pro Cys Ile Lys Phe
1               5

<210> SEQ ID NO 354
<211> LENGTH: 9
<212> TYPE: PRT
<213> ORGANISM: Artificial Sequence
<220> FEATURE:
<223> OTHER INFORMATION: Hepcidin dimerized peptide
<220> FEATURE:
<221> NAME/KEY: MISC_FEATURE
<222> LOCATION: (1)..(1)
<223> OTHER INFORMATION: Diethylene glycol linkage between Asp residues
<220> FEATURE:
<221> NAME/KEY: DISULFID
<222> LOCATION: (6)..(6)
<223> OTHER INFORMATION: Disulphide linkage between Cys residues

<400> SEQUENCE: 354

Asp Thr His Phe Pro Cys Ile Lys Phe
1               5

<210> SEQ ID NO 355
<211> LENGTH: 9
<212> TYPE: PRT
<213> ORGANISM: Artificial Sequence
<220> FEATURE:
<223> OTHER INFORMATION: Hepcidin dimerized peptide
<220> FEATURE:
<221> NAME/KEY: DISULFID
<222> LOCATION: (6)..(6)
<223> OTHER INFORMATION: disulphide linkage between Cys residues

<400> SEQUENCE: 355

Asp Thr Lys Phe Pro Cys Ile Arg Phe
1               5

<210> SEQ ID NO 356
<211> LENGTH: 9
<212> TYPE: PRT
<213> ORGANISM: Artificial Sequence
<220> FEATURE:
<223> OTHER INFORMATION: Hepcidin dimerized peptide
<220> FEATURE:
<221> NAME/KEY: MISC_FEATURE
<222> LOCATION: (3)..(3)
<223> OTHER INFORMATION: Diethylene glycol linkage
<220> FEATURE:
<221> NAME/KEY: DISULFID
<222> LOCATION: (6)..(6)

<400> SEQUENCE: 356

Asp Thr Lys Phe Pro Cys Ile Arg Phe
1               5

<210> SEQ ID NO 357
<211> LENGTH: 9
<212> TYPE: PRT
<213> ORGANISM: Artificial Sequence
<220> FEATURE:
<223> OTHER INFORMATION: Hepcidin dimerized peptide
<220> FEATURE:
<221> NAME/KEY: DISULFID
<222> LOCATION: (6)..(6)

<400> SEQUENCE: 357
```

Asp Thr His Phe Pro Cys Ile Lys Phe
1               5

<210> SEQ ID NO 358
<211> LENGTH: 9
<212> TYPE: PRT
<213> ORGANISM: Artificial Sequence
<220> FEATURE:
<223> OTHER INFORMATION: Hepcidin dimerized peptide
<220> FEATURE:
<221> NAME/KEY: DISULFID
<222> LOCATION: (6)..(6)
<220> FEATURE:
<221> NAME/KEY: MISC_FEATURE
<222> LOCATION: (8)..(8)
<223> OTHER INFORMATION: Diethylene glycol linkage

<400> SEQUENCE: 358

Asp Thr His Phe Pro Cys Ile Lys Phe
1               5

<210> SEQ ID NO 359
<211> LENGTH: 9
<212> TYPE: PRT
<213> ORGANISM: Artificial Sequence
<220> FEATURE:
<223> OTHER INFORMATION: Hepcidin dimerized peptide
<220> FEATURE:
<221> NAME/KEY: DISULFID
<222> LOCATION: (6)..(6)

<400> SEQUENCE: 359

Asp Thr His Phe Pro Cys Ile Arg Lys
1               5

<210> SEQ ID NO 360
<211> LENGTH: 9
<212> TYPE: PRT
<213> ORGANISM: Artificial Sequence
<220> FEATURE:
<223> OTHER INFORMATION: Hepcidin dimerized peptide
<220> FEATURE:
<221> NAME/KEY: DISULFID
<222> LOCATION: (6)..(6)
<220> FEATURE:
<221> NAME/KEY: MISC_FEATURE
<222> LOCATION: (9)..(9)
<223> OTHER INFORMATION: diethylene glycol linkage

<400> SEQUENCE: 360

Asp Thr His Phe Pro Cys Ile Arg Lys
1               5

<210> SEQ ID NO 361
<211> LENGTH: 10
<212> TYPE: PRT
<213> ORGANISM: Artificial Sequence
<220> FEATURE:
<223> OTHER INFORMATION: Hepcidin dimerized peptide
<220> FEATURE:
<221> NAME/KEY: DISULFID
<222> LOCATION: (6)..(6)

<400> SEQUENCE: 361

Asp Thr His Phe Pro Cys Ile Lys Phe Lys
1               5                   10

<210> SEQ ID NO 362
<211> LENGTH: 10

```
<212> TYPE: PRT
<213> ORGANISM: Artificial Sequence
<220> FEATURE:
<223> OTHER INFORMATION: Hepcidin dimerized peptide
<220> FEATURE:
<221> NAME/KEY: DISULFID
<222> LOCATION: (6)..(6)
<220> FEATURE:
<221> NAME/KEY: MISC_FEATURE
<222> LOCATION: (10)..(10)
<223> OTHER INFORMATION: diethylene glycol linkage

<400> SEQUENCE: 362

Asp Thr His Phe Pro Cys Ile Lys Phe Lys
1               5                   10

<210> SEQ ID NO 363
<211> LENGTH: 9
<212> TYPE: PRT
<213> ORGANISM: Artificial Sequence
<220> FEATURE:
<223> OTHER INFORMATION: Hepcidin dimerized peptide

<400> SEQUENCE: 363

Asp Thr His Phe Pro Cys Ile Lys Phe
1               5

<210> SEQ ID NO 364
<211> LENGTH: 9
<212> TYPE: PRT
<213> ORGANISM: Artificial Sequence
<220> FEATURE:
<223> OTHER INFORMATION: Hepcidin dimerized peptide

<400> SEQUENCE: 364

Asp Thr His Phe Pro Cys Ile Lys Phe
1               5

<210> SEQ ID NO 365
<211> LENGTH: 10
<212> TYPE: PRT
<213> ORGANISM: Artificial Sequence
<220> FEATURE:
<223> OTHER INFORMATION: Hepcidin dimerized peptide

<400> SEQUENCE: 365

Asp Thr His Phe Pro Cys Ile Lys Phe Lys
1               5                   10

<210> SEQ ID NO 366
<211> LENGTH: 9
<212> TYPE: PRT
<213> ORGANISM: Artificial Sequence
<220> FEATURE:
<223> OTHER INFORMATION: Hepcidin dimerized peptide

<400> SEQUENCE: 366

Asp Thr His Phe Pro Cys Ile Lys Phe
1               5

<210> SEQ ID NO 367
<211> LENGTH: 19
<212> TYPE: PRT
<213> ORGANISM: Artificial Sequence
<220> FEATURE:
<223> OTHER INFORMATION: Hepcidin dimerized peptide

<400> SEQUENCE: 367
```

```
Asp Thr His Phe Pro Cys Ile Ile Phe Gly Pro Arg Ser Arg Gly Trp
1               5                   10                  15

Val Cys Lys
```

<210> SEQ ID NO 368
<211> LENGTH: 18
<212> TYPE: PRT
<213> ORGANISM: Artificial Sequence
<220> FEATURE:
<223> OTHER INFORMATION: Hepcidin dimerized peptide

<400> SEQUENCE: 368

```
Asp Thr His Phe Pro Ile Cys Ile Phe Gly Pro Arg Ser Lys Gly Trp
1               5                   10                  15

Val Cys
```

<210> SEQ ID NO 369
<211> LENGTH: 17
<212> TYPE: PRT
<213> ORGANISM: Artificial Sequence
<220> FEATURE:
<223> OTHER INFORMATION: Hepciding analogue peptide

<400> SEQUENCE: 369

```
Asp Thr His Phe Pro Cys Ile Lys Phe Glu Pro Arg Ser Lys Glu Cys
1               5                   10                  15

Lys
```

<210> SEQ ID NO 370
<211> LENGTH: 17
<212> TYPE: PRT
<213> ORGANISM: Artificial Sequence
<220> FEATURE:
<223> OTHER INFORMATION: Hepcidin analogue peptide

<400> SEQUENCE: 370

```
Asp Thr His Phe Pro Cys Ile Lys Phe Glu Pro His Ser Lys Glu Cys
1               5                   10                  15

Lys
```

<210> SEQ ID NO 371
<211> LENGTH: 17
<212> TYPE: PRT
<213> ORGANISM: Artificial Sequence
<220> FEATURE:
<223> OTHER INFORMATION: Hepcidin analogue pepide

<400> SEQUENCE: 371

```
Asp Thr His Phe Pro Cys Ile Lys Lys Glu Pro His Ser Lys Glu Cys
1               5                   10                  15

Lys
```

<210> SEQ ID NO 372
<211> LENGTH: 17
<212> TYPE: PRT
<213> ORGANISM: Artificial Sequence
<220> FEATURE:
<223> OTHER INFORMATION: Hepcidin analogue peptide

<400> SEQUENCE: 372

```
Asp Thr His Phe Pro Cys Ile Lys Phe Lys Pro His Ser Lys Glu Cys
1               5                   10                  15

Lys
```

```
<210> SEQ ID NO 373
<211> LENGTH: 15
<212> TYPE: PRT
<213> ORGANISM: Artificial Sequence
<220> FEATURE:
<223> OTHER INFORMATION: Hepcidin analogue peptide

<400> SEQUENCE: 373

Asp Thr His Phe Pro Cys Ile Lys Phe Glu Pro Arg Glu Cys Lys
1               5                   10                  15

<210> SEQ ID NO 374
<211> LENGTH: 15
<212> TYPE: PRT
<213> ORGANISM: Artificial Sequence
<220> FEATURE:
<223> OTHER INFORMATION: Hepcidin analogue peptide

<400> SEQUENCE: 374

Asp Thr His Phe Pro Cys Ile Lys Phe Glu Pro His Glu Cys Lys
1               5                   10                  15

<210> SEQ ID NO 375
<211> LENGTH: 14
<212> TYPE: PRT
<213> ORGANISM: Artificial Sequence
<220> FEATURE:
<223> OTHER INFORMATION: Hepcidin analogue peptide

<400> SEQUENCE: 375

Asp Thr His Phe Pro Cys Ile Lys Phe Glu Pro Arg Cys Lys
1               5                   10
```